US006132973A

United States Patent [19]
Lal et al.

[11] Patent Number: 6,132,973
[45] Date of Patent: Oct. 17, 2000

[54] HUMAN REGULATORY MOLECULES

[75] Inventors: Preeti Lal, Santa Clara; Jennifer L. Hillman; Olga Bandman, both of Mountain View; Purvi Shah, Sunnyvale; Janice Au-Young, Berkeley; Henry Yue, Sunnyvale; Karl J. Guegler, Menlo Park; Neil C. Corley, Mountain View, all of Calif.

[73] Assignee: Incyte Pharmaceuticals, Inc., Palo Alto, Calif.

[21] Appl. No.: 09/234,613

[22] Filed: Jan. 20, 1999

Related U.S. Application Data

[62] Division of application No. 08/933,750, Sep. 23, 1997, Pat. No. 5,932,442.

[51] Int. Cl.$^7$ .............................. C12Q 1/68; C12P 21/06; C12P 19/34; C07H 21/04; C01N 33/50

[52] U.S. Cl. .................... 435/6; 435/69.1; 435/252.3; 435/91.2; 435/320.1; 536/23.5; 536/24.31; 436/86; 436/94

[58] Field of Search ...................... 435/6, 252.3, 320.1, 435/69.1, 91.2; 536/23.5, 24.31; 436/86, 94

[56] References Cited

PUBLICATIONS

Pabo, C.O. and Sauer, R.T., "Transcription Factors: Structural Families and Principles of DNA Recognition," *Annu.Rev.Biochem.* (1992) 61:1053–1095.

Faisst, S. and Meyer, S. "Compilation of vertebrate–encoded transcription factors," *Nucl.Acids Res.* (1992) 20(1):3–26.

Alberts, B. et al., *Molecular Biology of the Cell*, Garland Publishing Co., New York, NY, pp. 401–407.

Cleary, M.L., "Transcription Factors in Human Leukaemias" *Cancer Surv.* (1992) 15:89–104.

Groden, J. et al., "Response of Colon Cancer Cell Lines to the Introduction of APC, a Colon–specific Tumor Suppressor Gene", *Cancer Res.* (1995) 55: 1531–1539.

Nomura, N., (GI 285946) GenBank Sequence Database (Accession D14661), National Center for Biotechnology Information, National Library of Medicine, Bethesda, Maryland, 20894.

Liu, L.X., (GI 1518120), GenBank Sequence Database (Accession U66208), National Center for Biotechnology Information, National Library of Medicine, Bethesda, Maryland, 20894.

Coster, F. et al., (GI 1302210), GenBank Sequence Database (Accession Z71483; Y13139), National Center for Biotechnology Information, National Library of Medicine, Bethesda, Maryland, 20894.

Petroni, D. et al., (GI 1613851), GenBank Sequence Database (Accession U71598), National Center for Biotechnology Information, National Library of Medicine, Bethesda, Maryland, 20894.

Oliver, K. and Harris, D., (GI 755782), GenBank Sequence Database (Accession Z48784; Z71256), National Center for Biotechnology Information, National Library of Medicine, Bethesda, Maryland, 20894.

Borsani, G., (GI 895844), GenBank Sequence Database (Accession X87689), National Center for Biotechnology Information, National Library of Medicine, Bethesda, Maryland, 20894.

Andersson, B. et al., (GI 1710240), GenBank Sequence Database (Accession U79274), National Center for Biotechnology Information, National Library of Medicine, Bethesda, Maryland, 20894.

Rad, M.R. et al., (GI 1907116), GenBank Sequence Database (Accession X59720; S43845; S49180; S58084; S93798), National Center for Biotechnology Information, National Library of Medicine, Bethesda, Maryland, 20894.

Wilson, R. et al., (GI 1627696), GenBank Sequence Database (Accession Z81051), National Center for Biotechnology Information, National Library of Medicine, Bethesda, Maryland, 20894.

Hirashima, S. et al., (GI 220593), GenBank Sequence Database (Accession D00926), National Center for Biotechnology Information, National Library of Medicine, Bethesda, Maryland, 20894.

Wilson, R. et al., (GI 1086722), GenBank Sequence Database (Accession U41030), National Center for Biotechnology Information, National Library of Medicine, Bethesda, Maryland, 20894.

Johnston, M. et al., (GI 2258165), GenBank Sequence Database (Accession U20618; Y13138), National Center for Biotechnology Information, National Library of Medicine, Bethesda, Maryland, 20894.

Shi, S. and Yu, L., (GI 1698719), GenBank Sequence Database (Accession U68536), National Center for Biotechnology Information, National Library of Medicine, Bethesda, Maryland, 20894.

Schmiedeknecht, G. et al., (GI 1177434), GenBank Sequence Database (Accession X95384), National Center for Biotechnology Information, National Library of Medicine, Bethesda, Maryland, 20894.

Andersson, B. et al., (GI 1710201), GenBank Sequence Database (Accession U79252), National Center for Biotechnology Information, National Library of Medicine, Bethesda, Maryland, 20894.

Wilson, R. et al., (GI 506879), GenBank Sequence Database (Accession Z34533), National Center for Biotechnology Information, National Library of Medicine, Bethesda, Maryland, 20894.

(List continued on next page.)

*Primary Examiner*—Elizabeth Slobodyansky
*Attorney, Agent, or Firm*—Incyte Pharmaceuticals, Inc.; Lynn E. Murry

[57] ABSTRACT

The invention provides human regulatory molecules and polynucleotides (collectively designated HRM) which identify and encode them. The invention also provides expression vectors, host cells, agonists, antibodies and antagonists. The invention further provides methods for diagnosing, preventing, and treating disorders associated with expression of human regulatory molecules.

15 Claims, No Drawings

OTHER PUBLICATIONS

Ernoult–Lange, M. et al., (GI 1310668), GenBank Sequence Database (Accession X82126), National Center for Biotechnology Information, National Library of Medicine, Bethesda, Maryland, 20894.

Li, K. et al., (GI 309182), GenBank Sequence Database (Accession L08407), National Center for Biotechnology Information, National Library of Medicine, Bethesda, Maryland, 20894.

Wilson, R. et al., (GI 577541), GenBank Sequence Database (Accession Z46787), National Center for Biotechnology Information, National Library of Medicine, Bethesda, Maryland, 20894.

Wilson, R. et al., (GI 1418558), GenBank Sequence Database (Accession Z75545), National Center for Biotechnology Information, National Library of Medicine, Bethesda, Maryland, 20894.

Wilson, R. et al., (GI 458996), GenBank Sequence Database (Accession U00036), National Center for Biotechnology Information, National Library of Medicine, Bethesda, Maryland, 20894.

Rowen, L. et al., (GI 1841547), GenBank Sequence Database (Accession U89336), National Center for Biotechnology Information, National Library of Medicine, Bethesda, Maryland, 20894.

Wilson, R. et al., (GI 868261), GenBank Sequence Database (Accession U29536), National Center for Biotechnology Information, National Library of Medicine, Bethesda, Maryland, 20894.

Desseyn, J.L. et al., (GI 1834502), GenBank Sequence Database (Accession 272496), National Center for Biotechnology Information, National Library of Medicine, Bethesda, Maryland, 20894.

Dietrich, F.S. et al., (GI 603377), GenBank Sequence Database (Accession U18917; L10718; U00092), National Center for Biotechnology Information, National Library of Medicine, Bethesda, Maryland, 20894.

Ding, H., (GI 849184), GenBank Sequence Database (Accession U28373; Z71256), National Center for Biotechnology Information, National Library of Medicine, Bethesda, Maryland, 20894.

Devlin, K. and Churcher, C.M., (GI 728645), GenBank Sequence Database (Accession Z48613; Z71257), National Center for Biotechnology Information, National Library of Medicine, Bethesda, Maryland, 20894.

Wilson, R. et al., (GI 687818), GenBank Sequence Database (Accession U21317), National Center for Biotechnology Information, National Library of Medicine, Bethesda, Maryland, 20894.

Wilson, R. et al., (GI 1200032), GenBank Sequence Database (Accession Z69637), National Center for Biotechnology Information, National Library of Medicine, Bethesda, Maryland, 20894.

Nomura, N., (GI 286000), GenBank Sequence Database (Accession D13630), National Center for Biotechnology Information, National Library of Medicine, Bethesda, Maryland, 20894.

Wilson, R. et al., (GI 790397), GenBank Sequence Database (Accession Z49130), National Center for Biotechnology Information, National Library of Medicine, Bethesda, Maryland, 20894.

Fleischmann, R.D. et al., (GI 1574563), GenBank Sequence Database (Accession U32844; L42023), National Center for Biotechnology Information, National Library of Medicine, Bethesda, Maryland, 20894.

Wilson, R. et al., (GI 1055075), GenBank Sequence Database (Accession U39853), National Center for Biotechnology Information, National Library of Medicine, Bethesda, Maryland, 20894.

Scherens, B. et al., (GI 313733), GenBank Sequence Database (Accession Z23261), National Center for Biotechnology Information, National Library of Medicine, Bethesda, Maryland, 20894.

Wilson, R. et al., (GI 1006637), GenBank Sequence Database (Accession Z54281), National Center for Biotechnology Information, National Library of Medicine, Bethesda, Maryland, 20894.

Wu, R–Y. and Gill, G.N., (GI 561636), GenBank Sequence Database (Accession L35240), National Center for Biotechnology Information, National Library of Medicine, Bethesda, Maryland, 20894.

Rowley, N., (GI 558388), GenBank Sequence Database (Accession Z38113; Z47047), National Center for Biotechnology Information, National Library of Medicine, Bethesda, Maryland, 20894.

Das, N. and Dey, S.K., (GI 1066284), GenBank Sequence Database (Accession U38981), National Center for Biotechnology Information, National Library of Medicine, Bethesda, Maryland, 20894.

Wilson, R. et al., (GI 861301), GenBank Sequence Database (Accession U28928), National Center for Biotechnology Information, National Library of Medicine, Bethesda, Maryland, 20894.

Wilson, R. et al., (GI 868238), GenBank Sequence Database (Accession U29488), National Center for Biotechnology Information, National Library of Medicine, Bethesda, Maryland, 20894.

Wilson, R. et al., (GI 733597), GenBank Sequence Database (Accession U23484), National Center for Biotechnology Information, National Library of Medicine, Bethesda, Maryland, 20894.

Nagao, K. et al., (GI 1507664), GenBank Sequence Database (Accession D84656), National Center for Biotechnology Information, National Library of Medicine, Bethesda, Maryland, 20894.

Wilson, R. et al., (GI 1495329), GenBank Sequence Database (Accession Z78418), National Center for Biotechnology Information, National Library of Medicine, Bethesda, Maryland, 20894.

Nomura, N., (GI 1665790), GenBank Sequence Database (Accession D87451), National Center for Biotechnology Information, National Library of Medicine, Bethesda, Maryland, 20894.

Gatignol, A. et al., (GI 478989), GenBank Sequence Database (Accession U08998), National Center for Biotechnology Information, National Library of Medicine, Bethesda, Maryland, 20894.

SEQUENCE LISTING (1) GENERAL INFORMATION:

(iii) NUMBER OF SEQUENCES: 98

(2) INFORMATION FOR SEQ ID NO:     1:

(i) SEQUENCE CHARACTERISTICS:
      (A) LENGTH: 151 amino acids
      (B) TYPE: amino acid
      (C) STRANDEDNESS: single
      (D) TOPOLOGY: linear (vii) IMMEDIATE SOURCE:
      (A) LIBRARY: U937NOT01
      (B) CLONE: 133

(xi) SEQUENCE DESCRIPTION: SEQ ID NO: 1 :

```
Met Thr Asn Glu Glu Pro Leu Pro Lys Lys Val Arg Leu Ser Glu
              5                  10                  15

Thr Asp Phe Lys Val Met Ala Arg Asp Glu Leu Ile Leu Arg Trp
             20                  25                  30

Lys Gln Tyr Glu Ala Tyr Val Gln Ala Leu Glu Gly Lys Tyr Thr
             35                  40                  45

Asp Leu Asn Ser Asn Asp Val Thr Gly Leu Arg Glu Ser Glu Glu
             50                  55                  60

Lys Leu Lys Gln Gln Gln Glu Ser Ala Arg Arg Glu Asn Ile
             65                  70                  75

Leu Val Met Arg Leu Ala Thr Lys Glu Gln Glu Met Gln Glu Cys
             80                  85                  90
```

```
Thr Thr Gln Ile Gln Tyr Leu Lys Gln Val Gln Gln Pro Ser Val
                 95                 100                 105

Ala Gln Leu Arg Ser Thr Met Val Asp Pro Ala Ile Asn Leu Phe
            110                 115                 120

Phe Leu Lys Met Lys Gly Glu Leu Glu Gln Thr Lys Asp Lys Leu
            125                 130                 135

Glu Gln Ala Gln Asn Glu Leu Ser Ala Trp Lys Phe Thr Pro Asp
            140                 145                 150

Arg
```

(2) INFORMATION FOR SEQ ID NO: 2:

(i) SEQUENCE CHARACTERISTICS:
        (A) LENGTH: 185 amino acids
        (B) TYPE: amino acid
        (C) STRANDEDNESS: single
        (D) TOPOLOGY: linear (vii) IMMEDIATE SOURCE:
        (A) LIBRARY: U937NOT01
        (B) CLONE: 1762

(xi) SEQUENCE DESCRIPTION: SEQ ID NO: 2 :

```
Met Leu Thr Leu Ala Ser Lys Leu Lys Arg Asp Asp Gly Leu Lys
             5                  10                  15

Gly Ser Arg Thr Ala Ala Thr Ala Ser Asp Ser Thr Arg Arg Val
            20                  25                  30

Ser Val Arg Asp Lys Leu Leu Val Lys Glu Val Ala Glu Leu Glu
            35                  40                  45

Ala Asn Leu Pro Cys Thr Cys Lys Val His Phe Pro Asp Pro Asn
            50                  55                  60

Lys Leu His Cys Phe Gln Leu Thr Val Thr Pro Asp Glu Gly Tyr
            65                  70                  75

Tyr Gln Gly Gly Lys Phe Gln Phe Glu Thr Glu Val Pro Asp Ala
            80                  85                  90

Tyr Asn Met Val Pro Pro Lys Val Lys Cys Leu Thr Lys Ile Trp
            95                 100                 105

His Pro Asn Ile Thr Glu Thr Gly Glu Ile Cys Leu Ser Leu Leu
           110                 115                 120

Arg Glu His Ser Ile Asp Gly Thr Gly Trp Ala Pro Thr Arg Thr
           125                 130                 135

Leu Lys Asp Val Val Trp Gly Leu Asn Ser Leu Phe Thr Asp Leu
           140                 145                 150

Leu Asn Phe Asp Asp Pro Leu Asn Ile Glu Ala Ala Glu His His
           155                 160                 165

Leu Arg Asp Lys Glu Asp Phe Arg Asn Lys Val Asp Asp Tyr Ile
           170                 175                 180

Lys Arg Tyr Ala Arg
           185
```

(2) INFORMATION FOR SEQ ID NO: 3:

(i) SEQUENCE CHARACTERISTICS:
        (A) LENGTH: 59 amino acids
        (B) TYPE: amino acid
        (C) STRANDEDNESS: single
        (D) TOPOLOGY: linear (vii) IMMEDIATE SOURCE:

```
            (A) LIBRARY: U937NOT01
            (B) CLONE: 1847

(xi) SEQUENCE DESCRIPTION: SEQ ID NO: 3 :

Met Gly Lys Val Asn Val Ala Lys Leu Arg Tyr Met Ser Arg Asp
                5                  10                  15

Asp Phe Arg Val Leu Thr Ala Val Glu Met Gly Met Lys Asn His
               20                  25                  30

Glu Ile Val Pro Gly Ser Leu Ile Ala Ser Ile Ala Ser Leu Lys
               35                  40                  45

His Gly Gly Cys Asn Lys Val Leu Arg Glu Leu Val Lys His
               50                  55

(2) INFORMATION FOR SEQ ID NO:     4:

(i) SEQUENCE CHARACTERISTICS:
        (A) LENGTH: 338 amino acids
        (B) TYPE: amino acid
        (C) STRANDEDNESS: single
        (D) TOPOLOGY: linear (vii) IMMEDIATE SOURCE:
        (A) LIBRARY: HMC1NOT01
        (B) CLONE: 9337

(xi) SEQUENCE DESCRIPTION: SEQ ID NO: 4 :

Met Leu Glu Thr Phe Gly His Leu Val Ser Val Gly Trp Glu Thr
                5                  10                  15

Thr Leu Glu Asn Lys Glu Leu Ala Pro Asn Ser Asp Ile Pro Glu
               20                  25                  30

Glu Glu Pro Ala Pro Ser Leu Lys Val Gln Glu Ser Ser Arg Asp
               35                  40                  45

Cys Ala Leu Ser Ser Thr Leu Glu Asp Thr Leu Gln Gly Gly Val
               50                  55                  60

Gln Glu Val Gln Asp Thr Val Leu Lys Gln Met Glu Ser Ala Gln
               65                  70                  75

Glu Lys Asp Leu Pro Gln Lys Lys His Phe Asp Asn Arg Glu Ser
               80                  85                  90

Gln Ala Asn Ser Gly Ala Leu Asp Thr Asn Gln Val Ser Leu Gln
               95                 100                 105

Lys Ile Asp Asn Pro Glu Ser Gln Ala Asn Ser Gly Ala Leu Asp
              110                 115                 120

Thr Asn Gln Val Leu Leu His Lys Ile Pro Pro Arg Lys Arg Leu
              125                 130                 135

Arg Lys Arg Asp Ser Gln Val Lys Ser Met Lys His Asn Ser Arg
              140                 145                 150

Val Lys Ile His Gln Lys Ser Cys Glu Arg Gln Lys Ala Lys Glu
              155                 160                 165

Gly Asn Gly Cys Arg Lys Thr Phe Ser Arg Ser Thr Lys Gln Ile
              170                 175                 180

Thr Phe Ile Arg Ile His Lys Gly Ser Gln Val Cys Arg Cys Ser
              185                 190                 195

Glu Cys Gly Lys Ile Phe Arg Asn Pro Arg Tyr Phe Ser Val His
              200                 205                 210

Lys Lys Ile His Thr Gly Glu Arg Pro Tyr Val Cys Gln Asp Cys
              215                 220                 225

Gly Lys Gly Phe Val Gln Ser Ser Ser Leu Thr Gln His Gln Arg
              230                 235                 240
```

```
Val His Ser Gly Glu Arg Pro Phe Glu Cys Gln Glu Cys Gly Arg
            245                 250                 255

Thr Phe Asn Asp Arg Ser Ala Ile Ser Gln His Leu Arg Thr His
            260                 265                 270

Thr Gly Ala Lys Pro Tyr Lys Cys Gln Asp Cys Gly Lys Ala Phe
            275                 280                 285

Arg Gln Ser Ser His Leu Ile Arg His Gln Arg Thr His Thr Gly
            290                 295                 300

Glu Arg Pro Tyr Ala Cys Asn Lys Cys Gly Lys Ala Phe Thr Gln
            305                 310                 315

Ser Ser His Leu Ile Gly His Gln Arg Thr His Asn Arg Thr Lys
            320                 325                 330

Arg Lys Lys Lys Gln Pro Thr Ser
            335
```

(2) INFORMATION FOR SEQ ID NO: 5:

(i) SEQUENCE CHARACTERISTICS:
        (A) LENGTH: 456 amino acids
        (B) TYPE: amino acid
        (C) STRANDEDNESS: single
        (D) TOPOLOGY: linear (vii) IMMEDIATE SOURCE:
        (A) LIBRARY: HMC1NOT01
        (B) CLONE: 9476

(xi) SEQUENCE DESCRIPTION: SEQ ID NO: 5 :

```
Met Lys Ile Glu Glu Val Lys Ser Thr Thr Lys Thr Gln Arg Ile
              5                  10                  15

Ala Ser His Ser His Val Lys Gly Leu Gly Leu Asp Glu Ser Gly
             20                  25                  30

Leu Ala Lys Gln Ala Ala Ser Gly Leu Val Gly Gln Glu Asn Ala
             35                  40                  45

Arg Glu Ala Cys Gly Val Ile Val Glu Leu Ile Glu Ser Lys Lys
             50                  55                  60

Met Ala Gly Arg Ala Val Leu Leu Ala Gly Pro Pro Gly Thr Gly
             65                  70                  75

Lys Thr Ala Leu Ala Leu Ala Ile Ala Gln Glu Leu Gly Ser Lys
             80                  85                  90

Val Pro Phe Cys Pro Met Val Gly Ser Glu Val Tyr Ser Thr Glu
             95                 100                 105

Ile Lys Lys Thr Glu Val Leu Met Glu Asn Phe Arg Arg Ala Ile
            110                 115                 120

Gly Leu Arg Ile Lys Glu Thr Lys Glu Val Tyr Glu Gly Glu Val
            125                 130                 135

Thr Glu Leu Thr Pro Cys Glu Thr Glu Asn Pro Met Gly Gly Tyr
            140                 145                 150

Gly Lys Thr Ile Ser His Val Ile Ile Gly Leu Lys Thr Ala Lys
            155                 160                 165

Gly Thr Lys Gln Leu Lys Leu Asp Pro Ser Ile Phe Glu Ser Leu
            170                 175                 180

Gln Lys Glu Arg Val Glu Ala Gly Asp Val Ile Tyr Ile Glu Ala
            185                 190                 195

Asn Ser Gly Ala Val Lys Arg Gln Gly Arg Cys Asp Thr Tyr Ala
            200                 205                 210
```

```
Thr Glu Phe Asp Leu Glu Ala Glu Tyr Val Pro Leu Pro Lys
            215                 220                 225

Gly Asp Val His Lys Lys Glu Ile Ile Gln Asp Val Thr Leu
            230                 235                 240

His Asp Leu Asp Val Ala Asn Ala Arg Pro Gln Gly Gly Gln Asp
            245                 250                 255

Ile Leu Ser Met Met Gly Gln Leu Met Lys Pro Lys Lys Thr Glu
            260                 265                 270

Ile Thr Asp Lys Leu Arg Gly Glu Ile Asn Lys Val Val Asn Lys
            275                 280                 285

Tyr Ile Asp Gln Gly Ile Ala Glu Leu Val Pro Gly Val Leu Phe
            290                 295                 300

Val Asp Glu Val His Met Leu Asp Ile Glu Cys Phe Thr Tyr Leu
            305                 310                 315

His Arg Ala Leu Glu Ser Ser Ile Ala Pro Ile Val Ile Phe Ala
            320                 325                 330

Ser Asn Arg Gly Asn Cys Val Ile Arg Gly Thr Glu Asp Ile Thr
            335                 340                 345

Ser Pro His Gly Ile Pro Leu Asp Leu Leu Asp Arg Val Met Ile
            350                 355                 360

Ile Arg Thr Met Leu Tyr Thr Pro Gln Glu Met Lys Gln Ile Ile
            365                 370                 375

Lys Ile Arg Ala Gln Thr Glu Gly Ile Asn Ile Ser Glu Glu Ala
            380                 385                 390

Leu Asn His Leu Gly Glu Ile Gly Thr Lys Thr Thr Leu Arg Tyr
            395                 400                 405

Ser Val Gln Leu Leu Thr Pro Ala Asn Leu Leu Ala Lys Ile Asn
            410                 415                 420

Gly Lys Asp Ser Ile Glu Lys Glu His Val Glu Glu Ile Ser Glu
            425                 430                 435

Leu Phe Tyr Asp Ala Lys Ser Ser Ala Lys Ile Leu Ala Asp Gln
            440                 445                 450

Gln Asp Lys Tyr Met Lys
            455

(2) INFORMATION FOR SEQ ID NO:       6:

(i) SEQUENCE CHARACTERISTICS:
        (A) LENGTH: 210 amino acids
        (B) TYPE: amino acid
        (C) STRANDEDNESS: single
        (D) TOPOLOGY: linear (vii) IMMEDIATE SOURCE:
        (A) LIBRARY: THP1PLB01
        (B) CLONE: 10370

(xi) SEQUENCE DESCRIPTION: SEQ ID NO: 6 :

Met Val Leu Trp Leu Lys Gly Val Thr Phe Asn Val Thr Thr Val
            5                   10                  15

Asp Thr Lys Arg Arg Thr Glu Thr Val Gln Lys Leu Cys Pro Gly
            20                  25                  30

Gly Gln Leu Pro Phe Leu Leu Tyr Gly Thr Glu Val His Thr Asp
            35                  40                  45

Thr Asn Lys Ile Glu Glu Phe Leu Glu Ala Val Leu Cys Pro Pro
            50                  55                  60

Arg Tyr Pro Lys Leu Ala Ala Leu Asn Pro Glu Ser Asn Thr Ala
```

```
                65                  70                  75
Gly Leu Asp Ile Phe Ala Lys Phe Ser Ala Tyr Ile Lys Asn Ser
                80                  85                  90

Asn Pro Ala Leu Asn Asp Asn Leu Glu Lys Gly Leu Leu Lys Ala
                95                 100                 105

Leu Lys Val Leu Asp Asn Tyr Leu Thr Ser Pro Leu Pro Glu Glu
               110                 115                 120

Val Asp Glu Thr Ser Ala Glu Asp Glu Gly Val Ser Gln Arg Lys
               125                 130                 135

Phe Leu Asp Gly Asn Glu Leu Thr Leu Ala Asp Cys Asn Leu Leu
               140                 145                 150

Pro Lys Leu His Ile Val Gln Val Val Cys Lys Lys Tyr Arg Gly
               155                 160                 165

Phe Thr Ile Pro Glu Ala Phe Arg Gly Val His Arg Tyr Leu Ser
               170                 175                 180

Asn Ala Tyr Ala Arg Glu Glu Phe Ala Ser Thr Cys Pro Asp Asp
               185                 190                 195

Glu Glu Ile Glu Leu Ala Tyr Glu Gln Val Ala Lys Ala Leu Lys
               200                 205                 210

(2) INFORMATION FOR SEQ ID NO:       7:

(i) SEQUENCE CHARACTERISTICS:
        (A) LENGTH: 255 amino acids
        (B) TYPE: amino acid
        (C) STRANDEDNESS: single
        (D) TOPOLOGY: linear (vii) IMMEDIATE SOURCE:
        (A) LIBRARY: THP1NOB01
        (B) CLONE: 30137

(xi) SEQUENCE DESCRIPTION: SEQ ID NO: 7 :

Met Leu Gly Gln Leu Leu Pro His Thr Ala Arg Gly Leu Gly Ala
                 5                  10                  15

Ala Glu Met Pro Gly Gln Gly Pro Gly Ser Asp Trp Thr Glu Arg
                20                  25                  30

Ser Ser Ser Ala Glu Pro Pro Ala Val Ala Gly Thr Glu Gly Gly
                35                  40                  45

Gly Gly Gly Ser Ala Gly Tyr Ser Cys Tyr Gln Asn Ser Lys Gly
                50                  55                  60

Ser Asp Arg Ile Lys Asp Gly Tyr Lys Val Asn Ser His Ile Ala
                65                  70                  75

Lys Leu Gln Glu Leu Trp Lys Thr Pro Gln Asn Gln Thr Ile His
                80                  85                  90

Leu Ser Lys Ser Met Met Glu Ala Ser Phe Phe Lys His Pro Asp
                95                 100                 105

Leu Thr Thr Gly Gln Lys Arg Tyr Leu Cys Ser Ile Ala Lys Ile
               110                 115                 120

Tyr Asn Ala Asn Tyr Leu Lys Met Leu Met Lys Arg Gln Tyr Met
               125                 130                 135

His Val Leu Gln His Ser Ser Gln Lys Pro Gly Val Leu Thr His
               140                 145                 150

His Arg Ser Arg Leu Ser Ser Arg Tyr Ser Gln Lys Gln His Tyr
               155                 160                 165

Pro Cys Thr Thr Trp Arg His Gln Leu Glu Arg Glu Asp Ser Gly
               170                 175                 180
```

Ser Ser Asp Ile Ala Ala Ala Ser Ala Pro Glu Met Leu Ile Gln
                185                 190                 195

His Ser Leu Trp Arg Pro Val Arg Asn Lys Glu Gly Ile Lys Thr
                200                 205                 210

Gly Tyr Ala Ser Lys Thr Arg Cys Lys Ser Leu Lys Ile Phe Arg
                215                 220                 225

Arg Pro Arg Lys Leu Phe Met Gln Thr Val Ser Ser Asp Asp Ser
                230                 235                 240

Glu Ser His Met Ser Gly Glu Lys Lys Gly Arg Gly Phe Thr Thr
                245                 250                 255

(2) INFORMATION FOR SEQ ID NO:     8:

(i) SEQUENCE CHARACTERISTICS:
        (A) LENGTH: 188 amino acids
        (B) TYPE: amino acid
        (C) STRANDEDNESS: single
        (D) TOPOLOGY: linear (vii) IMMEDIATE SOURCE:
        (A) LIBRARY: SYNORAB01
        (B) CLONE: 77180

(xi) SEQUENCE DESCRIPTION: SEQ ID NO: 8 :

Met Ala Leu Ala Met Leu Val Leu Val Val Ser Pro Trp Ser Ala
                5                   10                  15

Ala Arg Gly Val Leu Arg Asn Tyr Trp Glu Arg Leu Leu Arg Lys
                20                  25                  30

Leu Pro Gln Ser Arg Pro Gly Phe Pro Ser Pro Pro Trp Gly Pro
                35                  40                  45

Ala Leu Ala Val Gln Gly Pro Ala Met Phe Thr Glu Pro Ala Asn
                50                  55                  60

Asp Thr Ser Gly Ser Lys Glu Asn Ser Ser Leu Leu Asp Ser Ile
                65                  70                  75

Phe Trp Met Ala Ala Pro Lys Asn Arg Arg Thr Ile Glu Val Asn
                80                  85                  90

Arg Cys Arg Arg Arg Asn Pro Gln Lys Leu Ile Lys Val Lys Asn
                95                  100                 105

Asn Ile Asp Val Cys Pro Glu Cys Gly His Leu Lys Gln Lys His
                110                 115                 120

Val Leu Cys Ala Tyr Cys Tyr Glu Lys Val Cys Lys Glu Thr Ala
                125                 130                 135

Glu Ile Arg Arg Gln Ile Gly Lys Gln Glu Gly Gly Pro Phe Lys
                140                 145                 150

Ala Pro Thr Ile Glu Thr Val Val Leu Tyr Thr Gly Glu Thr Pro
                155                 160                 165

Ser Glu Gln Asp Gln Gly Lys Arg Ile Ile Glu Arg Asp Arg Lys
                170                 175                 180

Arg Pro Ser Trp Phe Thr Gln Asn
                185

(2) INFORMATION FOR SEQ ID NO:     9:

(i) SEQUENCE CHARACTERISTICS:
        (A) LENGTH: 531 amino acids
        (B) TYPE: amino acid
        (C) STRANDEDNESS: single
        (D) TOPOLOGY: linear -continued

```
    (vii) IMMEDIATE SOURCE:
          (A) LIBRARY: PITUNOR01
          (B) CLONE: 98974

(xi) SEQUENCE DESCRIPTION: SEQ ID NO: 9 :

Met Ala Pro Thr Ile Gln Thr Gln Ala Gln Arg Glu Asp Gly His
                 5                  10                  15

Arg Pro Asn Ser His Arg Thr Leu Pro Glu Arg Ser Gly Val Val
             20                  25                  30

Cys Arg Val Lys Tyr Cys Asn Ser Leu Pro Asp Ile Pro Phe Asp
             35                  40                  45

Pro Lys Phe Ile Thr Tyr Pro Phe Asp Gln Asn Arg Phe Val Gln
             50                  55                  60

Tyr Lys Ala Thr Ser Leu Glu Lys Gln His Lys His Asp Leu Leu
             65                  70                  75

Thr Glu Pro Asp Leu Gly Val Thr Ile Asp Leu Ile Asn Pro Asp
             80                  85                  90

Thr Tyr Arg Ile Asp Pro Asn Val Leu Leu Asp Pro Ala Asp Glu
             95                 100                 105

Lys Leu Leu Glu Glu Glu Ile Gln Ala Pro Thr Ser Ser Lys Arg
            110                 115                 120

Ser Gln Gln His Ala Lys Val Val Pro Trp Met Arg Lys Thr Glu
            125                 130                 135

Tyr Ile Ser Thr Glu Phe Asn Arg Tyr Gly Ile Ser Asn Glu Lys
            140                 145                 150

Pro Glu Val Lys Ile Gly Val Ser Val Lys Gln Gln Phe Thr Glu
            155                 160                 165

Glu Glu Ile Tyr Lys Asp Arg Asp Ser Gln Ile Thr Ala Ile Glu
            170                 175                 180

Lys Thr Phe Glu Asp Ala Gln Lys Ser Ile Ser Gln His Tyr Ser
            185                 190                 195

Lys Pro Arg Val Thr Pro Val Glu Val Met Pro Val Phe Pro Asp
            200                 205                 210

Phe Lys Met Trp Ile Asn Pro Cys Ala Gln Val Ile Phe Asp Ser
            215                 220                 225

Asp Pro Ala Pro Lys Asp Thr Ser Gly Ala Ala Ala Leu Glu Met
            230                 235                 240

Met Ser Gln Ala Met Ile Arg Gly Met Met Asp Glu Glu Gly Asn
            245                 250                 255

Gln Phe Val Ala Tyr Phe Leu Pro Val Glu Glu Thr Leu Lys Lys
            260                 265                 270

Arg Lys Arg Asp Gln Glu Glu Met Asp Tyr Ala Pro Asp Asp
            275                 280                 285

Val Tyr Asp Tyr Lys Ile Ala Arg Glu Tyr Asn Trp Asn Val Lys
            290                 295                 300

Asn Lys Ala Ser Lys Gly Tyr Glu Glu Asn Tyr Phe Phe Ile Phe
            305                 310                 315

Arg Glu Gly Asp Gly Val Tyr Tyr Asn Glu Leu Glu Thr Arg Val
            320                 325                 330

Arg Leu Ser Lys Arg Arg Ala Lys Ala Gly Val Gln Ser Gly Thr
            335                 340                 345

Asn Ala Leu Leu Val Val Lys His Arg Asp Met Asn Glu Lys Glu
            350                 355                 360

Leu Glu Ala Gln Glu Ala Arg Lys Ala Gln Leu Glu Asn His Glu
```

-continued

```
                365                 370                 375
Pro Glu Glu Glu Glu Glu Glu Met Glu Thr Glu Lys Glu
                380                 385                 390
Ala Gly Gly Ser Asp Glu Gln Glu Lys Gly Ser Ser Glu
                395                 400                 405
Lys Glu Gly Ser Glu Asp Glu His Ser Gly Ser Glu Arg
                410                 415                 420
Glu Glu Gly Asp Arg Asp Glu Ala Ser Asp Lys Ser Gly Gly
                425                 430                 435
Glu Asp Glu Ser Ser Glu Asp Glu Ala Arg Ala Ala Arg Asp Lys
                440                 445                 450
Glu Glu Ile Phe Gly Ser Asp Ala Asp Ser Glu Asp Ala Asp
                455                 460                 465
Ser Asp Asp Glu Asp Arg Gly Gln Ala Gln Gly Gly Ser Asp Asn
                470                 475                 480
Asp Ser Asp Ser Gly Ser Asn Gly Gly Gly Gln Arg Ser Arg Ser
                485                 490                 495
His Ser Arg Ser Ala Ser Pro Phe Pro Ser Gly Ser Glu His Ser
                500                 505                 510
Ala Gln Glu Asp Gly Ser Glu Ala Ala Ala Ser Asp Ser Ser Glu
                515                 520                 525
Ala Asp Ser Asp Ser Asp
                530
```

(2) INFORMATION FOR SEQ ID NO: 10:

(i) SEQUENCE CHARACTERISTICS:
        (A) LENGTH: 348 amino acids
        (B) TYPE: amino acid
        (C) STRANDEDNESS: single
        (D) TOPOLOGY: linear (vii) IMMEDIATE SOURCE:
        (A) LIBRARY: MUSCNOT01
        (B) CLONE: 118160

(xi) SEQUENCE DESCRIPTION: SEQ ID NO: 10 :

```
Met Gly Gln Glu Glu Glu Leu Leu Arg Ile Ala Lys Lys Leu Glu
                  5                  10                  15
Lys Met Val Ala Arg Lys Asn Thr Glu Gly Ala Leu Asp Leu Leu
                 20                  25                  30
Lys Lys Leu His Ser Cys Gln Met Ser Ile Gln Leu Leu Gln Thr
                 35                  40                  45
Thr Arg Ile Gly Val Ala Val Asn Gly Val Arg Lys His Cys Ser
                 50                  55                  60
Asp Lys Glu Val Val Ser Leu Ala Lys Val Leu Ile Lys Asn Trp
                 65                  70                  75
Lys Arg Leu Leu Asp Ser Pro Gly Pro Lys Gly Glu Lys Gly
                 80                  85                  90
Glu Glu Arg Glu Lys Ala Lys Lys Glu Lys Gly Leu Glu Cys
                 95                 100                 105
Ser Asp Trp Lys Pro Glu Ala Gly Leu Ser Pro Pro Arg Lys Lys
                110                 115                 120
Arg Glu Asp Pro Lys Thr Arg Arg Asp Ser Val Asp Ser Lys Ser
                125                 130                 135
Ser Ala Ser Ser Ser Pro Lys Arg Pro Ser Val Glu Arg Ser Asn
                140                 145                 150
```

-continued

```
Ser Ser Lys Ser Lys Ala Glu Ser Pro Lys Thr Pro Ser Ser Pro
            155                 160                 165

Leu Thr Pro Thr Phe Ala Ser Ser Met Cys Leu Leu Ala Pro Cys
            170                 175                 180

Tyr Leu Thr Gly Asp Ser Val Arg Asp Lys Cys Val Glu Met Leu
            185                 190                 195

Ser Ala Ala Leu Lys Ala Asp Asp Tyr Lys Asp Tyr Gly Val
            200                 205                 210

Asn Cys Asp Lys Met Ala Ser Glu Ile Glu Asp His Ile Tyr Gln
            215                 220                 225

Glu Leu Lys Ser Thr Asp Met Lys Tyr Arg Asn Arg Val Arg Ser
            230                 235                 240

Arg Ile Ser Asn Leu Lys Asp Pro Arg Asn Pro Gly Leu Arg Arg
            245                 250                 255

Asn Val Leu Ser Gly Ala Ile Ser Ala Gly Leu Ile Ala Lys Met
            260                 265                 270

Thr Ala Glu Glu Met Ala Ser Asp Glu Leu Arg Glu Leu Arg Asn
            275                 280                 285

Ala Met Thr Gln Glu Ala Ile Arg Glu His Gln Met Ala Lys Thr
            290                 295                 300

Gly Gly Thr Thr Thr Asp Leu Phe Gln Cys Ser Lys Cys Lys Lys
            305                 310                 315

Lys Asn Cys Thr Tyr Asn Gln Val Gln Thr Arg Ser Ala Asp Glu
            320                 325                 330

Pro Met Thr Thr Phe Val Leu Cys Asn Glu Cys Gly Asn Arg Trp
            335                 340                 345

Lys Phe Cys (2) INFORMATION FOR SEQ ID NO:      11:

(i) SEQUENCE CHARACTERISTICS:
        (A) LENGTH: 393 amino acids
        (B) TYPE: amino acid
        (C) STRANDEDNESS: single
        (D) TOPOLOGY: linear (vii) IMMEDIATE SOURCE:
        (A) LIBRARY: TLYMNOR01
        (B) CLONE: 140516

(xi) SEQUENCE DESCRIPTION: SEQ ID NO: 11 :

Met Arg Thr Leu Phe Asn Leu Leu Trp Leu Ala Leu Ala Cys Ser
              5                  10                  15

Pro Val His Thr Thr Leu Ser Lys Ser Asp Ala Lys Lys Ala Ala
             20                  25                  30

Ser Lys Thr Leu Leu Glu Lys Ser Gln Phe Ser Asp Lys Pro Val
             35                  40                  45

Gln Asp Arg Gly Leu Val Val Thr Asp Leu Lys Ala Glu Ser Val
             50                  55                  60

Val Leu Glu His Arg Ser Tyr Cys Ser Ala Lys Ala Arg Asp Arg
             65                  70                  75

His Phe Ala Gly Asp Val Leu Gly Tyr Val Thr Pro Trp Asn Ser
             80                  85                  90

His Gly Tyr Asp Val Thr Lys Val Phe Gly Ser Lys Phe Thr Gln
             95                 100                 105

Ile Ser Pro Val Trp Leu Gln Leu Lys Arg Arg Gly Arg Glu Met
```

-continued

```
                    110                 115                 120
Phe Glu Val Thr Gly Leu His Asp Val Asp Gln Gly Trp Met Arg
                125                 130                 135
Ala Val Arg Lys His Ala Lys Gly Leu His Ile Val Pro Arg Leu
                140                 145                 150
Leu Phe Glu Asp Trp Thr Tyr Asp Asp Phe Arg Asn Val Leu Asp
                155                 160                 165
Ser Glu Asp Glu Ile Glu Leu Ser Lys Thr Val Val Gln Val
                170                 175                 180
Ala Lys Asn Gln His Phe Asp Gly Phe Val Glu Val Trp Asn
                185                 190                 195
Gln Leu Leu Ser Gln Lys Arg Val Gly Leu Ile His Met Leu Thr
                200                 205                 210
His Leu Ala Glu Ala Leu His Gln Ala Arg Leu Leu Ala Leu Leu
                215                 220                 225
Val Ile Pro Pro Ala Ile Thr Pro Gly Thr Asp Gln Leu Gly Met
                230                 235                 240
Phe Thr His Lys Glu Phe Glu Gln Leu Ala Pro Val Leu Asp Gly
                245                 250                 255
Phe Ser Leu Met Thr Tyr Asp Tyr Ser Thr Ala His Gln Pro Gly
                260                 265                 270
Pro Asn Ala Pro Leu Ser Trp Val Arg Ala Cys Val Gln Val Leu
                275                 280                 285
Asp Pro Lys Ser Lys Trp Arg Ser Lys Ile Leu Leu Gly Leu Asn
                290                 295                 300
Phe Tyr Gly Met Asp Tyr Ala Thr Ser Lys Asp Ala Arg Glu Pro
                305                 310                 315
Val Val Gly Ala Arg Tyr Ile Gln Thr Leu Lys Asp His Arg Pro
                320                 325                 330
Arg Met Val Trp Asp Ser Gln Ala Ser Glu His Phe Phe Glu Tyr
                335                 340                 345
Lys Lys Ser Arg Ser Gly Arg His Val Val Phe Tyr Pro Thr Leu
                350                 355                 360
Lys Ser Leu Gln Val Arg Leu Glu Leu Ala Arg Glu Leu Gly Val
                365                 370                 375
Gly Val Ser Ile Trp Glu Leu Gly Gln Gly Leu Asp Tyr Phe Tyr
                380                 385                 390
Asp Leu Leu
```

(2) INFORMATION FOR SEQ ID NO:    12:

(i) SEQUENCE CHARACTERISTICS:
        (A) LENGTH: 320 amino acids
        (B) TYPE: amino acid
        (C) STRANDEDNESS: single
        (D) TOPOLOGY: linear (vii) IMMEDIATE SOURCE:
        (A) LIBRARY: SPLNNOT02
        (B) CLONE: 207452

(xi) SEQUENCE DESCRIPTION: SEQ ID NO: 12 :

```
Met Val Gly Tyr Asp Pro Lys Pro Asp Gly Arg Asn Asn Thr Lys
                5                   10                  15
Phe Gln Val Ala Val Ala Gly Ser Val Ser Gly Leu Val Thr Arg
                20                  25                  30
```

-continued

```
Ala Leu Ile Ser Pro Phe Asp Val Ile Lys Ile Arg Phe Gln Leu
                 35                  40                  45

Gln His Glu Arg Leu Ser Arg Ser Asp Pro Ser Ala Lys Tyr His
                 50                  55                  60

Gly Ile Leu Gln Ala Ser Arg Gln Ile Leu Gln Glu Gly Pro
                 65                  70                  75

Thr Ala Phe Trp Lys Gly His Val Pro Ala Gln Ile Leu Ser Ile
                 80                  85                  90

Gly Tyr Gly Ala Val Gln Phe Leu Ser Phe Glu Met Leu Thr Glu
                 95                 100                 105

Leu Val His Arg Gly Ser Val Tyr Asp Ala Arg Glu Phe Ser Val
                110                 115                 120

His Phe Val Cys Gly Gly Leu Ala Ala Cys Met Ala Thr Leu Thr
                125                 130                 135

Val His Pro Val Asp Val Leu Arg Thr Arg Phe Ala Ala Gln Gly
                140                 145                 150

Glu Pro Lys Val Tyr Asn Thr Leu Arg His Ala Val Gly Thr Met
                155                 160                 165

Tyr Arg Ser Glu Gly Pro Gln Val Phe Tyr Lys Gly Leu Ala Pro
                170                 175                 180

Thr Leu Ile Ala Ile Phe Pro Tyr Ala Gly Leu Gln Phe Ser Cys
                185                 190                 195

Tyr Ser Ser Leu Lys His Leu Tyr Lys Trp Ala Ile Pro Ala Glu
                200                 205                 210

Gly Lys Lys Asn Glu Asn Leu Gln Asn Leu Leu Cys Gly Ser Gly
                215                 220                 225

Ala Gly Val Ile Ser Lys Thr Leu Thr Tyr Pro Leu Asp Leu Phe
                230                 235                 240

Lys Lys Arg Leu Gln Val Gly Gly Phe Glu His Ala Arg Ala Ala
                245                 250                 255

Phe Gly Gln Val Arg Arg Tyr Lys Gly Leu Met Asp Cys Ala Lys
                260                 265                 270

Gln Val Leu Gln Lys Glu Gly Ala Leu Gly Phe Phe Lys Gly Leu
                275                 280                 285

Ser Pro Ser Leu Leu Lys Ala Ala Leu Ser Thr Gly Phe Met Phe
                290                 295                 300

Phe Ser Tyr Glu Phe Phe Cys Asn Val Phe His Cys Met Asn Arg
                305                 310                 315

Thr Ala Ser Gln Arg
                320
```

(2) INFORMATION FOR SEQ ID NO:    13:

(i) SEQUENCE CHARACTERISTICS:
        (A) LENGTH: 343 amino acids
        (B) TYPE: amino acid
        (C) STRANDEDNESS: single
        (D) TOPOLOGY: linear (vii) IMMEDIATE SOURCE:
        (A) LIBRARY: SPLNNOT02
        (B) CLONE: 208836

(xi) SEQUENCE DESCRIPTION: SEQ ID NO: 13 :

```
Met Ala Glu Gln Leu Ser Pro Gly Lys Ala Val Asp Gln Val Cys
                  5                  10                  15

Thr Phe Leu Phe Lys Lys Pro Gly Arg Lys Gly Ala Ala Gly Arg
```

-continued

```
                  20                  25                  30
Arg Lys Arg Pro Ala Cys Asp Pro Glu Pro Gly Glu Ser Gly Ser
                  35                  40                  45
Ser Ser Asp Glu Gly Cys Thr Val Val Arg Pro Glu Lys Lys Arg
                  50                  55                  60
Val Thr His Asn Pro Met Met Gln Lys Thr Arg Asp Ser Gly Lys
                  65                  70                  75
Gln Lys Ala Ala Tyr Gly Asp Leu Ser Ser Glu Glu Glu Glu
                  80                  85                  90
Asn Glu Pro Glu Ser Leu Gly Val Val Tyr Lys Ser Thr Arg Ser
                  95                 100                 105
Ala Lys Pro Val Gly Pro Glu Asp Met Gly Ala Thr Ala Val Tyr
                 110                 115                 120
Glu Leu Asp Thr Glu Lys Glu Arg Asp Ala Gln Ala Ile Phe Glu
                 125                 130                 135
Arg Ser Gln Lys Ile Gln Glu Leu Arg Gly Lys Glu Asp Asp
                 140                 145                 150
Lys Ile Tyr Arg Gly Ile Asn Asn Tyr Gln Lys Tyr Met Lys Pro
                 155                 160                 165
Lys Asp Thr Ser Met Gly Asn Ala Ser Ser Gly Met Val Arg Lys
                 170                 175                 180
Gly Pro Ile Arg Ala Pro Glu His Leu Arg Ala Thr Val Arg Trp
                 185                 190                 195
Asp Tyr Gln Pro Asp Ile Cys Lys Asp Tyr Lys Glu Thr Gly Phe
                 200                 205                 210
Cys Gly Phe Gly Asp Ser Cys Lys Phe Leu His Asp Arg Ser Asp
                 215                 220                 225
Tyr Lys His Gly Trp Gln Ile Glu Arg Glu Leu Asp Glu Gly Arg
                 230                 235                 240
Tyr Gly Val Tyr Glu Asp Glu Asn Tyr Glu Val Gly Ser Asp Asp
                 245                 250                 255
Glu Glu Ile Pro Phe Lys Cys Phe Ile Cys Arg Gln Ser Phe Gln
                 260                 265                 270
Asn Pro Val Val Thr Lys Cys Arg His Tyr Phe Cys Glu Ser Cys
                 275                 280                 285
Ala Leu Gln His Phe Arg Thr Thr Pro Arg Cys Tyr Val Cys Asp
                 290                 295                 300
Gln Gln Thr Asn Gly Val Phe Asn Pro Ala Lys Glu Leu Ile Ala
                 305                 310                 315
Lys Leu Glu Lys His Arg Ala Thr Gly Glu Gly Ala Ser Asp
                 320                 325                 330
Leu Pro Glu Asp Pro Asp Glu Ala Ile Pro Ile Thr
                 335                 340
```

(2) INFORMATION FOR SEQ ID NO: 14:

(i) SEQUENCE CHARACTERISTICS:
        (A) LENGTH: 368 amino acids
        (B) TYPE: amino acid
        (C) STRANDEDNESS: single
        (D) TOPOLOGY: linear (vii) IMMEDIATE SOURCE:
        (A) LIBRARY: MMLR3DT01
        (B) CLONE: 569710

(xi) SEQUENCE DESCRIPTION: SEQ ID NO: 14 :

Met Ser Ala Gln Ser Val Glu Glu Asp Ser Ile Leu Ile Ile Pro
                  5                  10                  15

Thr Pro Asp Glu Glu Lys Ile Leu Arg Val Lys Leu Glu Glu
                 20                  25                  30

Asp Pro Asp Gly Glu Glu Gly Ser Ser Ile Pro Trp Asn His Leu
                 35                  40                  45

Pro Asp Pro Glu Ile Phe Arg Gln Arg Phe Arg Gln Phe Gly Tyr
                 50                  55                  60

Gln Asp Ser Pro Gly Pro Arg Glu Ala Val Ser Gln Leu Arg Glu
                 65                  70                  75

Leu Cys Arg Leu Trp Leu Arg Pro Glu Thr His Thr Lys Glu Gln
                 80                  85                  90

Ile Leu Glu Leu Val Val Leu Glu Gln Phe Val Ala Ile Leu Pro
                 95                 100                 105

Lys Glu Leu Gln Thr Trp Val Arg Asp His His Pro Glu Asn Gly
                110                 115                 120

Glu Glu Ala Val Thr Val Leu Glu Asp Leu Glu Ser Glu Leu Asp
                125                 130                 135

Asp Pro Gly Gln Pro Val Ser Leu Arg Arg Arg Lys Arg Glu Val
                140                 145                 150

Leu Val Glu Asp Met Val Ser Gln Glu Glu Ala Gln Gly Leu Pro
                155                 160                 165

Ser Ser Glu Leu Asp Ala Val Glu Asn Gln Leu Lys Trp Ala Ser
                170                 175                 180

Trp Glu Leu His Ser Leu Arg His Cys Asp Asp Gly Arg Thr
                185                 190                 195

Glu Asn Gly Ala Leu Ala Pro Lys Gln Glu Leu Pro Ser Ala Leu
                200                 205                 210

Glu Ser His Glu Val Pro Gly Thr Leu Ser Met Gly Val Pro Gln
                215                 220                 225

Ile Phe Lys Tyr Gly Glu Thr Cys Phe Pro Lys Gly Arg Phe Glu
                230                 235                 240

Arg Lys Arg Asn Pro Ser Arg Lys Lys Gln His Ile Cys Asp Glu
                245                 250                 255

Cys Gly Lys His Phe Ser Gln Gly Ser Ala Leu Ile Leu His Gln
                260                 265                 270

Arg Ile His Ser Gly Glu Lys Pro Tyr Gly Cys Val Glu Cys Gly
                275                 280                 285

Lys Ala Phe Ser Arg Ser Ser Ile Leu Val Gln His Gln Arg Val
                290                 295                 300

His Thr Gly Glu Lys Pro Tyr Lys Cys Leu Glu Cys Gly Lys Ala
                305                 310                 315

Phe Ser Gln Asn Ser Gly Leu Ile Asn His Gln Arg Ile His Thr
                320                 325                 330

Gly Glu Lys Pro Tyr Glu Cys Val Gln Cys Gly Lys Ser Tyr Ser
                335                 340                 345

Gln Ser Ser Asn Leu Phe Arg His Gln Arg Arg His Asn Ala Glu
                350                 355                 360

Lys Leu Leu Asn Val Val Lys Val
                365

(2) INFORMATION FOR SEQ ID NO:    15:

```
    (i) SEQUENCE CHARACTERISTICS:
        (A) LENGTH: 158 amino acids
        (B) TYPE: amino acid
        (C) STRANDEDNESS: single
        (D) TOPOLOGY: linear (vii) IMMEDIATE SOURCE:
        (A) LIBRARY: BRSTTUT01
        (B) CLONE: 606742

(xi) SEQUENCE DESCRIPTION: SEQ ID NO: 15 :

Met Glu Gly Pro Arg Arg Gly Pro Glu Val Gly Gly Phe Cys Lys
                 5                  10                  15

Tyr Arg Leu Leu Arg Val Ser Arg Ala Leu Cys His Asp Thr Ser
                20                  25                  30

Leu Gly Leu Thr Trp Leu Arg Thr Cys Ser Val Arg Gly Phe Val
                35                  40                  45

Arg Thr Leu Pro Phe Cys Leu Lys Leu Lys Ala Lys Glu Asn Asp
                50                  55                  60

Arg Arg Leu Arg Thr Glu Leu Thr Leu Ala Pro Gly Trp Glu Ala
                65                  70                  75

Ala Ala Leu Leu Asp Ala Thr Tyr Cys Lys Trp Pro Glu Tyr Gln
                80                  85                  90

Arg Gly Gly Phe His Gly Gln Met His Ser Arg Cys Leu Pro Leu
                95                 100                 105

His Leu Asp His Leu Val Val Phe Lys Phe Leu Val Pro Glu Ala
               110                 115                 120

Lys Ser Thr Thr Cys Leu Leu Val Thr Cys Leu Pro Ala Val Val
               125                 130                 135

Val Asp Val Leu Ala Gly Arg Phe Gly Ile Ser His Gln Ser Phe
               140                 145                 150

Cys Thr Val Leu Val Ser Ser Ile
               155

(2) INFORMATION FOR SEQ ID NO:      16:

(i) SEQUENCE CHARACTERISTICS:
        (A) LENGTH: 334 amino acids
        (B) TYPE: amino acid
        (C) STRANDEDNESS: single
        (D) TOPOLOGY: linear (vii) IMMEDIATE SOURCE:
        (A) LIBRARY: COLNNOT01
        (B) CLONE: 611135

(xi) SEQUENCE DESCRIPTION: SEQ ID NO: 16 :

Met Ala Thr Arg Gln Arg Glu Ser Ser Ile Thr Ser Cys Cys Ser
                 5                  10                  15

Thr Ser Ser Cys Asp Ala Asp Asp Glu Gly Val Arg Gly Thr Cys
                20                  25                  30

Glu Asp Ala Ser Leu Cys Lys Arg Phe Ala Val Ser Ile Gly Tyr
                35                  40                  45

Trp His Asp Pro Tyr Ile Gln His Phe Val Arg Leu Ser Lys Glu
                50                  55                  60

Arg Lys Ala Pro Glu Ile Asn Arg Gly Tyr Phe Ala Arg Val His
                65                  70                  75

Gly Val Ser Gln Leu Ile Lys Ala Phe Leu Arg Lys Thr Glu Cys
                80                  85                  90

His Cys Gln Ile Val Asn Leu Gly Ala Gly Met Asp Thr Thr Phe
```

```
                    95                  100                 105

Trp Arg Leu Lys Asp Glu Asp Leu Leu Pro Ser Lys Tyr Phe Glu
                110                 115                 120

Val Asp Phe Pro Met Ile Val Thr Arg Lys Leu His Ser Ile Lys
                125                 130                 135

Cys Lys Pro Pro Leu Ser Ser Pro Ile Leu Glu Leu His Ser Glu
                140                 145                 150

Asp Thr Leu Gln Met Asp Gly His Ile Leu Asp Ser Lys Arg Tyr
                155                 160                 165

Ala Val Ile Gly Ala Asp Leu Arg Asp Leu Ser Glu Leu Glu Glu
                170                 175                 180

Lys Leu Lys Lys Cys Asn Met Asn Thr Gln Leu Pro Thr Leu Leu
                185                 190                 195

Ile Ala Glu Cys Val Leu Val Tyr Met Thr Pro Glu Gln Ser Ala
                200                 205                 210

Asn Leu Lys Trp Ala Ala Asn Ser Phe Glu Arg Ala Met Phe
                215                 220                 225

Ile Asn Tyr Glu Gln Val Asn Met Gly Asp Arg Phe Gly Gln Ile
                230                 235                 240

Met Ile Glu Asn Leu Arg Arg Arg Gln Cys Asp Leu Ala Gly Val
                245                 250                 255

Glu Thr Cys Lys Ser Leu Glu Ser Gln Lys Glu Arg Leu Leu Ser
                260                 265                 270

Asn Gly Trp Glu Thr Ala Ser Ala Val Asp Met Met Glu Leu Tyr
                275                 280                 285

Asn Arg Leu Pro Arg Ala Glu Val Ser Arg Ile Glu Ser Leu Glu
                290                 295                 300

Phe Leu Asp Glu Met Glu Leu Leu Glu Gln Leu Met Arg His Tyr
                305                 310                 315

Cys Leu Cys Trp Ala Thr Lys Gly Gly Asn Glu Leu Gly Leu Lys
                320                 325                 330

Glu Ile Thr Tyr (2) INFORMATION FOR SEQ ID NO:    17:

(i) SEQUENCE CHARACTERISTICS:
        (A) LENGTH: 488 amino acids
        (B) TYPE: amino acid
        (C) STRANDEDNESS: single
        (D) TOPOLOGY: linear (vii) IMMEDIATE SOURCE:
        (A) LIBRARY: BRSTNOT03
        (B) CLONE: 641127

(xi) SEQUENCE DESCRIPTION: SEQ ID NO: 17 :

Met Ala Ser Thr Ile Thr Gly Ser Gln Asp Cys Ile Val Asn His
                 5                  10                  15

Arg Gly Glu Val Asp Gly Glu Pro Glu Leu Asp Ile Ser Pro Cys
                20                  25                  30

Gln Gln Trp Gly Glu Ala Ser Ser Pro Ile Ser Arg Asn Arg Asp
                35                  40                  45

Ser Val Met Thr Leu Gln Ser Gly Cys Phe Glu Asn Ile Glu Ser
                50                  55                  60

Glu Thr Tyr Leu Pro Leu Lys Val Ser Ser Gln Ile Asp Thr Gln
                65                  70                  75
```

-continued

```
Asp Ser Ser Val Lys Phe Cys Lys Asn Glu Pro Gln Asp His Gln
             80                  85                  90

Glu Ser Arg Arg Leu Phe Val Met Glu Glu Ser Thr Glu Arg Lys
             95                 100                 105

Val Ile Lys Gly Glu Ser Cys Ser Glu Asn Leu Gln Val Lys Leu
            110                 115                 120

Val Ser Asp Gly Gln Glu Leu Ala Ser Pro Leu Leu Asn Gly Glu
            125                 130                 135

Ala Thr Cys Gln Asn Gly Gln Leu Lys Glu Ser Leu Asp Pro Ile
            140                 145                 150

Asp Cys Asn Cys Lys Asp Ile His Gly Trp Lys Ser Gln Val Val
            155                 160                 165

Ser Cys Ser Gln Gln Arg Gly His Thr Glu Glu Lys Pro Cys Asp
            170                 175                 180

His Asn Asn Cys Gly Lys Ile Leu Asn Thr Ser Pro Asp Gly His
            185                 190                 195

Pro Tyr Glu Lys Ile His Thr Ala Glu Lys Gln Tyr Glu Gly Ser
            200                 205                 210

Gln Cys Gly Lys Asn Phe Ser Gln Ser Ser Glu Leu Leu Leu His
            215                 220                 225

Gln Arg Asp His Thr Glu Glu Lys Pro Tyr Lys Cys Glu Gln Cys
            230                 235                 240

Gly Lys Gly Phe Thr Arg Ser Ser Leu Leu Ile His Gln Ala
            245                 250                 255

Val His Thr Asp Glu Lys Pro Tyr Lys Cys Asp Lys Cys Gly Lys
            260                 265                 270

Gly Phe Thr Arg Ser Ser Leu Leu Ile His His Ala Val His
            275                 280                 285

Thr Gly Glu Lys Pro Tyr Lys Cys Asp Lys Cys Gly Lys Gly Phe
            290                 295                 300

Ser Gln Ser Ser Lys Leu His Ile His Gln Arg Val His Thr Gly
            305                 310                 315

Glu Lys Pro Tyr Glu Cys Glu Cys Gly Met Ser Phe Ser Gln
            320                 325                 330

Arg Ser Asn Leu His Ile His Gln Arg Val His Thr Gly Glu Arg
            335                 340                 345

Pro Tyr Lys Cys Gly Glu Cys Gly Lys Gly Phe Ser Gln Ser Ser
            350                 355                 360

Asn Leu His Ile His Arg Cys Ile His Thr Gly Glu Lys Pro Tyr
            365                 370                 375

Gln Cys Tyr Glu Cys Gly Lys Gly Phe Ser Gln Ser Ser Asp Leu
            380                 385                 390

Arg Ile His Leu Arg Val His Thr Gly Glu Lys Pro Tyr His Cys
            395                 400                 405

Gly Lys Cys Gly Lys Gly Phe Ser Gln Ser Ser Lys Leu Leu Ile
            410                 415                 420

His Gln Arg Val His Thr Gly Glu Lys Pro Tyr Glu Cys Ser Lys
            425                 430                 435

Cys Gly Lys Gly Phe Ser Gln Ser Ser Asn Leu His Ile His Gln
            440                 445                 450

Arg Val His Lys Arg Asp Pro Arg Ala His Pro Gly Leu His Ser
            455                 460                 465

Ala His Thr Val Asn Thr Val Lys Tyr Leu Val Ser Leu Leu Leu
```

-continued

```
                     470                 475                 480
Tyr Ile Leu Gln Arg Arg Glu Met
                485

(2) INFORMATION FOR SEQ ID NO:    18:

(i) SEQUENCE CHARACTERISTICS:
         (A) LENGTH: 255 amino acids
         (B) TYPE: amino acid
         (C) STRANDEDNESS: single
         (D) TOPOLOGY: linear (vii) IMMEDIATE SOURCE:
         (A) LIBRARY: LUNGTUT02
         (B) CLONE: 691768

(xi) SEQUENCE DESCRIPTION: SEQ ID NO: 18 :

Met Gly Arg Asn Lys Lys Lys Arg Asp Gly Asp Arg Arg
                 5                  10                  15

Pro Arg Leu Val Leu Ser Phe Asp Glu Glu Lys Arg Arg Glu Tyr
                20                  25                  30

Leu Thr Gly Phe His Lys Arg Lys Val Glu Arg Lys Lys Ala Ala
                35                  40                  45

Ile Glu Glu Ile Lys Gln Arg Leu Lys Glu Glu Gln Arg Lys Leu
                50                  55                  60

Arg Glu Glu Arg His Gln Glu Tyr Leu Lys Met Leu Ala Glu Arg
                65                  70                  75

Glu Glu Ala Leu Glu Glu Ala Asp Glu Leu Asp Arg Leu Val Thr
                80                  85                  90

Ala Lys Thr Glu Ser Val Gln Tyr Asp His Pro Asn His Thr Val
                95                 100                 105

Thr Val Thr Thr Ile Ser Asp Leu Asp Leu Ser Gly Ala Arg Leu
               110                 115                 120

Leu Gly Leu Thr Pro Pro Glu Gly Gly Ala Gly Asp Arg Ser Glu
               125                 130                 135

Glu Glu Ala Ser Ser Thr Glu Lys Pro Thr Lys Ala Leu Pro Arg
               140                 145                 150

Lys Ser Arg Asp Pro Leu Leu Ser Gln Arg Ile Ser Ser Leu Thr
               155                 160                 165

Ala Ser Leu His Ala His Ser Arg Lys Lys Val Lys Arg Lys His
               170                 175                 180

Ser Arg Arg Ala Gln Asp Ser Lys Lys Pro Pro Lys Gly Pro Ser
               185                 190                 195

Tyr Gln Gln Arg Pro Ser Gly Ala Val Phe Thr Gly Lys Ala Pro
               200                 205                 210

Ala Gln Arg Gly Asn Xaa Arg Xaa Glu Asn Glu Ala Gly Cys Pro
               215                 220                 225

His Ser Lys Ala Xaa Arg Gly Xaa Cys Ser Leu Gly Ser Ala Leu
               230                 235                 240

Ala Val Pro Leu Leu Xaa Pro Ala Leu Xaa Leu Lys Val Leu Pro
               245                 250                 255

(2) INFORMATION FOR SEQ ID NO:    19:

(i) SEQUENCE CHARACTERISTICS:
         (A) LENGTH: 351 amino acids
         (B) TYPE: amino acid
         (C) STRANDEDNESS: single
         (D) TOPOLOGY: linear
```

-continued

```
    (vii) IMMEDIATE SOURCE:
          (A) LIBRARY: SYNO0AT01
          (B) CLONE: 724157

(xi) SEQUENCE DESCRIPTION: SEQ ID NO: 19 :

Met Ala Asp Gln Asp Pro Ala Gly Ile Ser Pro Leu Gln Gln Met
                  5                  10                  15

Val Ala Ser Gly Thr Gly Ala Val Val Thr Ser Leu Phe Met Thr
                 20                  25                  30

Pro Leu Asp Val Val Lys Val Arg Leu Gln Ser Gln Arg Pro Ser
                 35                  40                  45

Met Ala Ser Glu Leu Met Pro Ser Ser Arg Leu Trp Ser Leu Ser
                 50                  55                  60

Tyr Thr Lys Trp Lys Cys Leu Leu Tyr Cys Asn Gly Val Leu Glu
                 65                  70                  75

Pro Leu Tyr Leu Cys Pro Asn Gly Ala Arg Cys Ala Thr Trp Phe
                 80                  85                  90

Gln Asp Pro Thr Arg Phe Thr Gly Thr Met Asp Ala Phe Val Lys
                 95                 100                 105

Ile Val Arg His Glu Gly Thr Arg Thr Leu Trp Ser Gly Leu Pro
                110                 115                 120

Ala Thr Leu Val Met Thr Val Pro Ala Thr Ala Ile Tyr Phe Thr
                125                 130                 135

Ala Tyr Asp Gln Leu Lys Ala Phe Leu Cys Gly Arg Ala Leu Thr
                140                 145                 150

Ser Asp Leu Tyr Ala Pro Met Val Ala Gly Ala Leu Ala Arg Leu
                155                 160                 165

Gly Thr Val Thr Val Ile Ser Pro Leu Glu Leu Met Arg Thr Lys
                170                 175                 180

Leu Gln Ala Gln His Val Ser Tyr Arg Glu Leu Gly Ala Cys Val
                185                 190                 195

Arg Thr Ala Val Ala Gln Gly Gly Trp Arg Ser Leu Trp Leu Gly
                200                 205                 210

Trp Gly Pro Thr Ala Leu Arg Asp Val Pro Phe Ser Ala Leu Tyr
                215                 220                 225

Trp Phe Asn Tyr Glu Leu Val Lys Ser Trp Leu Asn Gly Leu Arg
                230                 235                 240

Pro Lys Asp Gln Thr Ser Val Gly Met Ser Phe Val Ala Gly Gly
                245                 250                 255

Ile Ser Gly Thr Val Ala Ala Val Leu Thr Leu Pro Phe Asp Val
                260                 265                 270

Val Lys Thr Gln Arg Gln Val Ala Leu Gly Ala Met Glu Ala Val
                275                 280                 285

Arg Val Asn Pro Leu His Val Asp Ser Thr Trp Leu Leu Leu Arg
                290                 295                 300

Arg Ile Arg Ala Glu Ser Gly Thr Lys Gly Leu Phe Ala Gly Phe
                305                 310                 315

Leu Pro Arg Ile Ile Lys Ala Ala Pro Ser Cys Ala Ile Met Ile
                320                 325                 330

Ser Thr Tyr Glu Phe Gly Lys Ser Phe Phe Gln Arg Leu Asn Gln
                335                 340                 345

Asp Arg Leu Leu Gly Gly
                350
```

6,132,973

89                                                                  90

-continued (2) INFORMATION FOR SEQ ID NO:    20:

(i) SEQUENCE CHARACTERISTICS:
        (A) LENGTH: 535 amino acids
        (B) TYPE: amino acid
        (C) STRANDEDNESS: single
        (D) TOPOLOGY: linear (vii) IMMEDIATE SOURCE:
        (A) LIBRARY: BRAITUT03
        (B) CLONE: 864683

(xi) SEQUENCE DESCRIPTION: SEQ ID NO: 20 :

```
Met Ser Glu Gly Glu Ser Gln Thr Val Leu Ser Ser Gly Ser Asp
                 5                  10                  15

Pro Lys Val Glu Ser Ser Ser Ala Pro Gly Leu Thr Ser Val
                20                  25                  30

Ser Pro Pro Val Thr Ser Thr Thr Ser Ala Ala Ser Pro Glu Glu
                35                  40                  45

Glu Glu Glu Ser Glu Asp Glu Ser Glu Ile Leu Glu Glu Ser Pro
                50                  55                  60

Cys Gly Arg Trp Gln Lys Arg Arg Glu Glu Val Asn Gln Arg Asn
                65                  70                  75

Val Pro Gly Ile Asp Ser Ala Tyr Leu Ala Met Asp Thr Glu Glu
                80                  85                  90

Gly Val Glu Val Val Trp Asn Glu Val Gln Phe Ser Glu Arg Lys
                95                 100                 105

Asn Tyr Lys Leu Gln Glu Glu Lys Val Arg Ala Val Phe Asp Asn
               110                 115                 120

Leu Ile Gln Leu Glu His Leu Asn Ile Val Lys Phe His Lys Tyr
               125                 130                 135

Trp Ala Asp Ile Lys Glu Asn Lys Ala Arg Val Ile Phe Ile Thr
               140                 145                 150

Glu Tyr Met Ser Ser Gly Ser Leu Lys Gln Phe Leu Lys Lys Thr
               155                 160                 165

Lys Lys Asn His Lys Thr Met Asn Glu Lys Ala Trp Lys Arg Trp
               170                 175                 180

Cys Thr Gln Ile Leu Ser Ala Leu Ser Tyr Leu His Ser Cys Asp
               185                 190                 195

Pro Pro Ile Ile His Gly Asn Leu Thr Cys Asp Thr Ile Phe Ile
               200                 205                 210

Gln His Asn Gly Leu Ile Lys Ile Gly Ser Val Ala Pro Asp Thr
               215                 220                 225

Ile Asn Asn His Val Lys Thr Cys Arg Glu Glu Gln Lys Asn Leu
               230                 235                 240

His Phe Phe Ala Pro Glu Tyr Gly Glu Val Thr Asn Val Thr Thr
               245                 250                 255

Ala Val Asp Ile Tyr Ser Phe Gly Met Cys Ala Leu Glu Met Ala
               260                 265                 270

Val Leu Glu Ile Gln Gly Asn Gly Glu Ser Ser Tyr Val Pro Gln
               275                 280                 285

Glu Ala Ile Ser Ser Ala Ile Gln Leu Leu Glu Asp Pro Leu Gln
               290                 295                 300

Arg Glu Phe Ile Gln Lys Cys Leu Gln Ser Glu Pro Ala Arg Arg
               305                 310                 315

Pro Thr Ala Arg Glu Leu Leu Phe His Pro Ala Leu Phe Glu Val
```

```
                    320                 325                 330
Pro Ser Leu Lys Leu Leu Ala Ala His Cys Ile Val Gly His Gln
                335                 340                 345
His Met Ile Pro Glu Asn Ala Leu Glu Glu Ile Thr Lys Asn Met
                350                 355                 360
Asp Thr Ser Ala Val Leu Ala Glu Ile Pro Ala Gly Pro Gly Arg
                365                 370                 375
Glu Pro Val Gln Thr Leu Tyr Ser Gln Ser Pro Ala Leu Glu Leu
                380                 385                 390
Asp Lys Phe Leu Glu Asp Val Arg Asn Gly Ile Tyr Pro Leu Thr
                395                 400                 405
Ala Phe Gly Leu Pro Arg Pro Gln Gln Pro Gln Gln Glu Glu Val
                410                 415                 420
Thr Ser Pro Val Val Pro Pro Ser Val Lys Thr Pro Thr Pro Glu
                425                 430                 435
Pro Ala Glu Val Glu Thr Arg Lys Val Val Leu Met Gln Cys Asn
                440                 445                 450
Ile Glu Ser Val Glu Glu Gly Val Lys His His Leu Thr Leu Leu
                455                 460                 465
Leu Lys Leu Glu Asp Lys Leu Asn Arg His Leu Ser Cys Asp Leu
                470                 475                 480
Met Pro Asn Glu Asn Ile Pro Glu Leu Ala Ala Glu Leu Val Gln
                485                 490                 495
Leu Gly Phe Ile Ser Glu Ala Asp Gln Ser Arg Leu Thr Ser Leu
                500                 505                 510
Leu Glu Glu Thr Leu Asn Lys Phe Asn Phe Ala Arg Asn Ser Thr
                515                 520                 525
Leu Asn Ser Ala Ala Val Thr Val Ser Ser
                530                 535

(2) INFORMATION FOR SEQ ID NO:     21:

(i) SEQUENCE CHARACTERISTICS:
           (A) LENGTH: 201 amino acids
           (B) TYPE: amino acid
           (C) STRANDEDNESS: single
           (D) TOPOLOGY: linear (vii) IMMEDIATE SOURCE:
           (A) LIBRARY: CERVNOT01
           (B) CLONE: 933353

(xi) SEQUENCE DESCRIPTION: SEQ ID NO: 21 :

Met Ala Ala Thr Ala Leu Leu Glu Ala Gly Leu Ala Arg Val Leu
                  5                  10                  15
Phe Tyr Pro Thr Leu Leu Tyr Thr Leu Phe Arg Gly Lys Val Pro
                 20                  25                  30
Gly Arg Ala His Arg Asp Trp Tyr His Arg Ile Asp Pro Thr Val
                 35                  40                  45
Leu Leu Gly Ala Leu Pro Leu Arg Ser Leu Thr Arg Gln Leu Val
                 50                  55                  60
Gln Asp Glu Asn Val Arg Gly Val Ile Thr Met Asn Glu Glu Tyr
                 65                  70                  75
Glu Thr Arg Phe Leu Cys Asn Ser Ser Gln Glu Trp Lys Arg Leu
                 80                  85                  90
Gly Val Glu Gln Leu Arg Leu Ser Thr Val Asp Met Thr Gly Ile
                 95                 100                 105
```

```
Pro Thr Leu Asp Asn Leu Gln Lys Gly Val Gln Phe Ala Leu Lys
            110                 115                 120

Tyr Gln Ser Leu Gly Gln Cys Val Tyr Val His Cys Lys Ala Gly
            125                 130                 135

Arg Ser Arg Ser Ala Thr Met Val Ala Ala Tyr Leu Ile Gln Val
            140                 145                 150

His Lys Trp Ser Pro Glu Glu Ala Val Arg Ala Ile Ala Lys Ile
            155                 160                 165

Arg Ser Tyr Ile His Ile Arg Pro Gly Gln Leu Asp Val Leu Lys
            170                 175                 180

Glu Phe His Lys Gln Ile Thr Ala Arg Ala Thr Lys Asp Gly Thr
            185                 190                 195

Phe Val Ile Ser Lys Thr
            200
```

(2) INFORMATION FOR SEQ ID NO:    22:

(i) SEQUENCE CHARACTERISTICS:
        (A) LENGTH: 239 amino acids
        (B) TYPE: amino acid
        (C) STRANDEDNESS: single
        (D) TOPOLOGY: linear (vii) IMMEDIATE SOURCE:
        (A) LIBRARY: LATRTUT02
        (B) CLONE: 1404643

(xi) SEQUENCE DESCRIPTION: SEQ ID NO: 22 :

```
Met Ala Tyr Gln Ser Leu Arg Leu Glu Tyr Leu Gln Ile Pro Pro
              5                  10                  15

Val Ser Arg Ala Tyr Thr Thr Ala Cys Val Leu Thr Thr Ala Ala
             20                  25                  30

Val Gln Leu Glu Leu Ile Thr Pro Phe Gln Leu Tyr Phe Asn Pro
             35                  40                  45

Glu Leu Ile Phe Lys His Phe Gln Ile Trp Arg Leu Ile Thr Asn
             50                  55                  60

Phe Leu Phe Phe Gly Pro Val Gly Phe Asn Phe Leu Phe Asn Met
             65                  70                  75

Ile Phe Leu Tyr Arg Tyr Cys Arg Met Leu Glu Glu Gly Ser Phe
             80                  85                  90

Arg Gly Arg Thr Ala Asp Phe Val Phe Met Phe Leu Phe Gly Gly
             95                 100                 105

Phe Leu Met Thr Leu Phe Gly Leu Phe Val Ser Leu Val Phe Leu
            110                 115                 120

Gly Gln Ala Phe Thr Ile Met Leu Val Tyr Val Trp Ser Arg Arg
            125                 130                 135

Asn Pro Tyr Val Arg Met Asn Phe Phe Gly Leu Leu Asn Phe Gln
            140                 145                 150

Ala Pro Phe Leu Pro Trp Val Leu Met Gly Phe Ser Leu Leu Leu
            155                 160                 165

Gly Asn Ser Ile Ile Val Asp Leu Leu Gly Ile Ala Val Gly His
            170                 175                 180

Ile Tyr Phe Phe Leu Glu Asp Val Phe Pro Asn Gln Pro Gly Gly
            185                 190                 195

Ile Arg Ile Leu Lys Thr Pro Ser Ile Leu Lys Ala Ile Phe Asp
            200                 205                 210
```

```
Thr Pro Asp Glu Asp Pro Asn Tyr Asn Pro Leu Pro Glu Glu Arg
                215                 220                 225

Pro Gly Gly Phe Ala Trp Gly Glu Gly Gln Arg Leu Gly Gly
                230                 235
```

(2) INFORMATION FOR SEQ ID NO:     23:

(i) SEQUENCE CHARACTERISTICS:
        (A) LENGTH: 244 amino acids
        (B) TYPE: amino acid
        (C) STRANDEDNESS: single
        (D) TOPOLOGY: linear (vii) IMMEDIATE SOURCE:
        (A) LIBRARY: SPLNNOT04
        (B) CLONE: 1561587

(xi) SEQUENCE DESCRIPTION: SEQ ID NO: 23 :

```
Met Met Arg Thr Gln Cys Leu Leu Gly Leu Arg Thr Phe Val Ala
                  5                  10                  15

Phe Ala Ala Lys Leu Trp Ser Phe Phe Ile Tyr Leu Leu Arg Arg
                 20                  25                  30

Gln Ile Arg Thr Val Ile Gln Tyr Gln Thr Val Arg Tyr Asp Ile
                 35                  40                  45

Leu Pro Leu Ser Pro Val Ser Arg Asn Arg Leu Ala Gln Val Lys
                 50                  55                  60

Arg Lys Ile Leu Val Leu Asp Leu Asp Glu Thr Leu Ile His Ser
                 65                  70                  75

His His Asp Gly Val Leu Arg Pro Thr Val Arg Pro Gly Thr Pro
                 80                  85                  90

Pro Asp Phe Ile Leu Lys Val Val Ile Asp Lys His Pro Val Arg
                 95                 100                 105

Phe Phe Val His Lys Arg Pro His Val Asp Phe Phe Leu Glu Val
                110                 115                 120

Val Ser Gln Trp Tyr Glu Leu Val Val Phe Thr Ala Ser Met Glu
                125                 130                 135

Ile Tyr Gly Ser Ala Val Ala Asp Lys Leu Asp Asn Ser Arg Ser
                140                 145                 150

Ile Leu Lys Arg Arg Tyr Tyr Arg Gln His Cys Thr Leu Glu Leu
                155                 160                 165

Gly Ser Tyr Ile Lys Asp Leu Ser Val Val His Ser Asp Leu Ser
                170                 175                 180

Ser Ile Val Ile Leu Asp Asn Ser Pro Gly Ala Tyr Arg Ser His
                185                 190                 195

Pro Asp Asn Ala Ile Pro Ile Lys Ser Trp Phe Ser Asp Pro Ser
                200                 205                 210

Asp Thr Ala Leu Leu Asn Leu Leu Pro Met Leu Asp Ala Leu Arg
                215                 220                 225

Phe Thr Ala Asp Val Arg Ser Val Leu Ser Arg Asn Leu His Gln
                230                 235                 240

His Arg Leu Trp
```

(2) INFORMATION FOR SEQ ID NO:     24:

(i) SEQUENCE CHARACTERISTICS:
        (A) LENGTH: 431 amino acids
        (B) TYPE: amino acid
        (C) STRANDEDNESS: single
        (D) TOPOLOGY: linear (vii) IMMEDIATE SOURCE:
      (A) LIBRARY: UTRSNOT05
      (B) CLONE: 1568361

(xi) SEQUENCE DESCRIPTION: SEQ ID NO: 24 :

Met Ser Ser Val Glu Glu Asp Tyr Asp Thr Leu Thr Asp Ile
                  5                  10                  15

Asp Ser Asp Lys Asn Val Ile Arg Thr Lys Gln Tyr Leu Tyr Val
                 20                  25                  30

Ala Asp Leu Ala Arg Lys Asp Lys Arg Val Leu Arg Lys Lys Tyr
             35                  40                      45

Gln Ile Tyr Phe Trp Asn Ile Ala Thr Ile Ala Val Phe Tyr Ala
             50                  55                      60

Leu Pro Val Val Gln Leu Val Ile Thr Tyr Gln Thr Val Val Asn
             65                  70                      75

Val Thr Gly Asn Gln Asp Ile Cys Tyr Tyr Asn Phe Leu Cys Ala
             80                  85                      90

His Pro Leu Gly Asn Leu Ser Ala Phe Asn Asn Ile Leu Ser Asn
             95                 100                     105

Leu Gly Tyr Ile Leu Leu Gly Leu Leu Phe Leu Leu Ile Ile Leu
            110                 115                     120

Gln Arg Glu Ile Asn His Asn Arg Ala Leu Leu Arg Asn Asp Leu
            125                 130                     135

Cys Ala Leu Glu Cys Gly Ile Pro Lys His Phe Gly Leu Phe Tyr
            140                 145                     150

Ala Met Gly Thr Ala Leu Met Met Glu Gly Leu Leu Ser Ala Cys
            155                 160                     165

Tyr His Val Cys Pro Asn Tyr Thr Asn Phe Gln Phe Asp Thr Ser
            170                 175                     180

Phe Met Tyr Met Ile Ala Gly Leu Cys Met Leu Lys Leu Tyr Gln
            185                 190                     195

Lys Arg His Pro Asp Ile Asn Ala Ser Ala Tyr Ser Ala Tyr Ala
            200                 205                     210

Cys Leu Ala Ile Val Ile Phe Xaa Ser Val Leu Gly Val Val Phe
            215                 220                     225

Gly Lys Gly Asn Thr Ala Phe Trp Ile Val Phe Ser Ile Ile His
            230                 235                     240

Ile Ile Ala Thr Leu Leu Leu Ser Thr Gln Leu Tyr Tyr Met Gly
            245                 250                     255

Arg Trp Lys Leu Asp Ser Gly Ile Phe Arg Arg Ile Leu His Val
            260                 265                     270

Leu Tyr Thr Asp Cys Ile Arg Gln Cys Ser Gly Pro Leu Tyr Val
            275                 280                     285

Asp Arg Met Val Leu Leu Val Met Gly Asn Val Ile Asn Trp Ser
            290                 295                     300

Leu Ala Ala Tyr Gly Leu Ile Met Arg Pro Asn Asp Phe Ala Ser
            305                 310                     315

Tyr Leu Leu Ala Ile Gly Ile Cys Asn Leu Leu Leu Tyr Phe Ala
            320                 325                     330

Phe Tyr Ile Ile Met Lys Leu Arg Ser Gly Glu Arg Ile Lys Leu
            335                 340                     345

Ile Pro Leu Leu Cys Ile Val Cys Thr Ser Val Val Trp Gly Phe
            350                 355                     360

Ala Leu Phe Phe Phe Phe Gln Gly Leu Ser Thr Trp Gln Lys Thr
                365                 370                 375

Pro Ala Glu Ser Arg Glu His Asn Arg Asp Cys Ile Leu Leu Asp
                380                 385                 390

Phe Phe Asp Asp His Asp Ile Trp His Phe Leu Ser Ser Ile Ala
                395                 400                 405

Met Phe Gly Ser Phe Leu Val Leu Leu Thr Leu Asp Asp Asp Leu
                410                 415                 420

Asp Thr Val Gln Arg Asp Lys Ile Tyr Val Phe
                425                 430

(2) INFORMATION FOR SEQ ID NO:     25:

(i) SEQUENCE CHARACTERISTICS:
        (A) LENGTH: 376 amino acids
        (B) TYPE: amino acid
        (C) STRANDEDNESS: single
        (D) TOPOLOGY: linear (vii) IMMEDIATE SOURCE:
        (A) LIBRARY: LNODNOT03
        (B) CLONE: 1572888

(xi) SEQUENCE DESCRIPTION: SEQ ID NO: 25 :

Met Gly His Arg Phe Leu Arg Gly Leu Leu Thr Leu Leu Leu Pro
                  5                  10                  15

Pro Pro Pro Leu Tyr Thr Arg His Arg Met Leu Gly Pro Glu Ser
                 20                  25                  30

Val Pro Pro Pro Lys Arg Ser Arg Ser Lys Leu Met Ala Pro Pro
                 35                  40                  45

Arg Ile Gly Thr His Asn Gly Thr Phe His Cys Asp Glu Ala Leu
                 50                  55                  60

Ala Cys Ala Leu Leu Arg Leu Leu Pro Glu Tyr Arg Asp Ala Glu
                 65                  70                  75

Ile Val Arg Thr Arg Asp Pro Glu Lys Leu Ala Ser Cys Asp Ile
                 80                  85                  90

Val Val Asp Val Gly Gly Glu Tyr Asp Pro Arg Arg His Arg Tyr
                 95                 100                 105

Asp His His Gln Arg Ser Phe Thr Glu Thr Met Ser Ser Leu Ser
                110                 115                 120

Pro Gly Lys Pro Trp Gln Thr Lys Leu Ser Ser Ala Gly Leu Ile
                125                 130                 135

Tyr Leu His Phe Gly His Lys Leu Leu Ala Gln Leu Leu Gly Thr
                140                 145                 150

Ser Glu Glu Asp Ser Met Val Gly Thr Leu Tyr Asp Lys Met Tyr
                155                 160                 165

Glu Asn Phe Val Glu Glu Val Asp Ala Val Asp Asn Gly Ile Ser
                170                 175                 180

Gln Trp Ala Glu Gly Glu Pro Arg Tyr Ala Leu Thr Thr Thr Leu
                185                 190                 195

Ser Ala Arg Val Ala Arg Leu Asn Pro Thr Trp Asn His Pro Asp
                200                 205                 210

Gln Asp Thr Glu Ala Gly Phe Lys Arg Ala Met Asp Leu Val Gln
                215                 220                 225

Glu Glu Phe Leu Gln Arg Leu Asp Phe Tyr Gln His Ser Trp Leu
                230                 235                 240

Pro Ala Arg Ala Leu Val Glu Glu Ala Leu Ala Gln Arg Phe Gln

-continued

```
                245                 250                 255
Val Asp Pro Ser Gly Glu Ile Val Glu Leu Ala Lys Gly Ala Cys
                260                 265                 270

Pro Trp Lys Glu His Leu Tyr His Leu Glu Ser Gly Leu Ser Pro
                275                 280                 285

Pro Val Ala Ile Phe Phe Val Ile Tyr Thr Asp Gln Ala Gly Gln
                290                 295                 300

Trp Arg Ile Gln Cys Val Pro Lys Glu Pro His Ser Phe Gln Ser
                305                 310                 315

Arg Leu Pro Leu Pro Glu Pro Trp Arg Gly Leu Arg Asp Glu Ala
                320                 325                 330

Leu Asp Gln Val Ser Gly Ile Pro Gly Cys Ile Phe Val His Ala
                335                 340                 345

Ser Gly Phe Ile Gly Gly His Arg Thr Arg Glu Gly Ala Leu Ser
                350                 355                 360

Met Ala Arg Ala Thr Leu Ala Gln Arg Ser Tyr Leu Pro Gln Ile
                365                 370                 375

Ser
```

(2) INFORMATION FOR SEQ ID NO:  26:

(i) SEQUENCE CHARACTERISTICS:
        (A) LENGTH: 340 amino acids
        (B) TYPE: amino acid
        (C) STRANDEDNESS: single
        (D) TOPOLOGY: linear (vii) IMMEDIATE SOURCE:
        (A) LIBRARY: LNODNOT03
        (B) CLONE: 1573677

(xi) SEQUENCE DESCRIPTION: SEQ ID NO: 26 :

```
Met Arg Leu Arg Gly Leu Leu Gln Gly Thr Leu Arg Phe His Thr
                  5                  10                  15

Ser Pro Pro Thr Asp Ser Ser Val Thr Glu Thr Ile Ile Leu Cys
                 20                  25                  30

Thr Met Leu Phe Leu Gly Ser Leu Gly Ala Trp Gly Thr Thr Ser
                 35                  40                  45

Ile Ser Thr Gly Ser Ile Phe Ser Leu Lys Thr Leu Arg Ser Gln
                 50                  55                  60

His Gly Gly Gln Val Gly Leu Lys Val Ser Arg Pro Arg Ala Gln
                 65                  70                  75

Pro Leu Pro Ala Gln Pro Pro Ala Leu Ala Gln Pro Gln Tyr Gln
                 80                  85                  90

Ser Pro Gln Gln Pro Pro Gln Thr Arg Trp Val Ala Pro Arg Asn
                 95                 100                 105

Arg Asn Ala Ala Phe Gly Gln Ser Gly Gly Ala Gly Ser Asp Ser
                110                 115                 120

Asn Ser Pro Gly Asn Val Gln Pro Asn Ser Ala Pro Ser Val Glu
                125                 130                 135

Ser His Pro Val Leu Glu Lys Leu Lys Ala Ala His Ser Tyr Asn
                140                 145                 150

Pro Lys Glu Phe Glu Trp Asn Leu Lys Ser Gly Arg Val Phe Ile
                155                 160                 165

Ile Lys Ser Tyr Ser Glu Asp Asp Ile His Arg Ser Ile Lys Tyr
                170                 175                 180
```

-continued

```
Ser Ile Trp Cys Ser Thr Glu His Gly Asn Lys Arg Leu Asp Ser
                185                 190                 195

Ala Phe Arg Cys Met Ser Ser Lys Gly Pro Val Tyr Leu Leu Phe
                200                 205                 210

Ser Val Asn Gly Ser Gly His Phe Cys Gly Val Ala Glu Met Lys
                215                 220                 225

Ser Pro Val Asp Tyr Gly Thr Ser Ala Gly Val Trp Ser Gln Asp
                230                 235                 240

Lys Trp Lys Gly Lys Phe Asp Val Gln Trp Ile Phe Val Lys Asp
                245                 250                 255

Val Pro Asn Asn Gln Leu Arg His Ile Arg Leu Glu Asn Asn Asp
                260                 265                 270

Asn Lys Pro Val Thr Asn Ser Arg Asp Thr Gln Glu Val Pro Leu
                275                 280                 285

Glu Lys Ala Lys Gln Val Leu Lys Ile Ile Ser Ser Tyr Lys His
                290                 295                 300

Thr Thr Ser Ile Phe Asp Asp Phe Ala His Tyr Glu Lys Arg Gln
                305                 310                 315

Arg Arg Arg Arg Trp Cys Ala Arg Asn Gly Arg Val Glu Thr Asn
                320                 325                 330

Asn Glu Gly Glu Pro Val Ser Tyr Met Phe
                335                 340

(2) INFORMATION FOR SEQ ID NO:     27:

(i) SEQUENCE CHARACTERISTICS:
        (A) LENGTH: 174 amino acids
        (B) TYPE: amino acid
        (C) STRANDEDNESS: single
        (D) TOPOLOGY: linear (vii) IMMEDIATE SOURCE:
        (A) LIBRARY: LNODNOT03
        (B) CLONE: 1574624

(xi) SEQUENCE DESCRIPTION: SEQ ID NO: 27 :

Met Ala Asp Val Leu Asp Leu His Glu Ala Gly Gly Glu Asp Phe
                  5                  10                  15

Ala Met Asp Glu Asp Gly Asp Glu Ser Ile His Lys Leu Lys Glu
                 20                  25                  30

Lys Ala Lys Lys Arg Lys Gly Arg Gly Phe Gly Ser Glu Glu Gly
                 35                  40                  45

Ser Arg Ala Arg Met Arg Glu Asp Tyr Asp Ser Val Glu Gln Asp
                 50                  55                  60

Gly Asp Glu Pro Gly Pro Gln Arg Ser Val Glu Gly Trp Ile Leu
                 65                  70                  75

Phe Val Thr Gly Val His Glu Glu Ala Thr Glu Glu Asp Ile His
                 80                  85                  90

Asp Lys Phe Ala Glu Tyr Gly Glu Ile Lys Asn Ile His Leu Asn
                 95                 100                 105

Leu Asp Arg Arg Thr Gly Tyr Leu Lys Gly Tyr Thr Leu Val Glu
                110                 115                 120

Tyr Glu Thr Tyr Lys Glu Ala Gln Ala Ala Met Glu Gly Leu Asn
                125                 130                 135

Gly Gln Asp Leu Met Gly Gln Pro Ile Ser Val Asp Trp Cys Phe
                140                 145                 150

Val Arg Gly Pro Pro Lys Gly Lys Arg Arg Gly Gly Arg Arg Arg
```

```
                    155                 160                 165
Ser Arg Ser Pro Asp Arg Arg Arg Arg
                170
```

(2) INFORMATION FOR SEQ ID NO:   28:

(i) SEQUENCE CHARACTERISTICS:
      (A) LENGTH: 179 amino acids
      (B) TYPE: amino acid
      (C) STRANDEDNESS: single
      (D) TOPOLOGY: linear (vii) IMMEDIATE SOURCE:
      (A) LIBRARY: LNODNOT03
      (B) CLONE: 1577239

(xi) SEQUENCE DESCRIPTION: SEQ ID NO: 28 :

```
Met Val Gln Ala Trp Tyr Met Asp Asp Ala Pro Gly Asp Pro Arg
                  5                  10                  15

Gln Pro His Arg Pro Asp Pro Gly Arg Pro Val Gly Leu Glu Gln
                 20                  25                  30

Leu Arg Arg Leu Gly Val Leu Tyr Trp Lys Leu Asp Ala Asp Lys
                 35                  40                  45

Tyr Glu Asn Asp Pro Glu Leu Glu Lys Ile Arg Arg Glu Arg Asn
                 50                  55                  60

Tyr Ser Trp Met Asp Ile Ile Thr Ile Cys Lys Asp Lys Leu Pro
                 65                  70                  75

Asn Tyr Glu Glu Lys Ile Lys Met Phe Tyr Glu Glu His Leu His
                 80                  85                  90

Leu Asp Asp Glu Ile Arg Tyr Ile Leu Asp Gly Ser Gly Tyr Phe
                 95                 100                 105

Asp Val Arg Asp Lys Glu Asp Gln Trp Ile Arg Ile Phe Met Glu
                110                 115                 120

Lys Gly Asp Met Val Thr Leu Pro Ala Gly Ile Tyr His Arg Phe
                125                 130                 135

Thr Val Asp Glu Lys Asn Tyr Thr Lys Ala Met Arg Leu Phe Val
                140                 145                 150

Gly Glu Pro Val Trp Thr Ala Tyr Asn Arg Pro Ala Asp His Phe
                155                 160                 165

Glu Ala Arg Gly Gln Tyr Val Lys Phe Leu Ala Gln Thr Ala
                170                 175
```

(2) INFORMATION FOR SEQ ID NO:   29:

(i) SEQUENCE CHARACTERISTICS:
      (A) LENGTH: 205 amino acids
      (B) TYPE: amino acid
      (C) STRANDEDNESS: single
      (D) TOPOLOGY: linear (vii) IMMEDIATE SOURCE:
      (A) LIBRARY: BLADNOT03
      (B) CLONE: 1598203

(xi) SEQUENCE DESCRIPTION: SEQ ID NO: 29 :

```
Met Ala Ala Ala Arg Pro Ser Leu Gly Arg Val Leu Pro Gly Ser
                  5                  10                  15

Ser Val Leu Phe Leu Cys Asp Met Gln Glu Lys Phe Arg His Asn
                 20                  25                  30

Ile Ala Tyr Phe Pro Gln Ile Val Ser Val Ala Ala Arg Met Leu
                 35                  40                  45
```

```
Lys Val Ala Arg Leu Leu Glu Val Pro Val Met Leu Thr Glu Gln
                50                  55                  60

Tyr Pro Gln Gly Leu Gly Pro Thr Val Pro Glu Leu Gly Thr Glu
                65                  70                  75

Gly Leu Arg Pro Leu Ala Lys Thr Cys Phe Ser Met Val Pro Ala
                80                  85                  90

Leu Gln Gln Glu Leu Asp Ser Arg Pro Gln Leu Arg Ser Val Leu
                95                 100                 105

Leu Cys Gly Ile Glu Ala Gln Ala Cys Ile Leu Asn Thr Thr Leu
               110                 115                 120

Asp Leu Leu Asp Arg Gly Leu Gln Val His Val Val Asp Ala
               125                 130                 135

Cys Ser Ser Arg Ser Gln Val Asp Arg Leu Val Ala Leu Ala Arg
               140                 145                 150

Met Arg Gln Ser Gly Ala Phe Leu Ser Thr Ser Glu Gly Leu Ile
               155                 160                 165

Leu Gln Leu Val Gly Asp Ala Val His Pro Gln Phe Lys Glu Ile
               170                 175                 180

Gln Lys Leu Ile Lys Glu Pro Ala Pro Asp Ser Gly Leu Leu Gly
               185                 190                 195

Leu Phe Gln Gly Gln Asn Ser Leu Leu His
               200                 205
```

(2) INFORMATION FOR SEQ ID NO: 30:

(i) SEQUENCE CHARACTERISTICS:
        (A) LENGTH: 419 amino acids
        (B) TYPE: amino acid
        (C) STRANDEDNESS: single
        (D) TOPOLOGY: linear (vii) IMMEDIATE SOURCE:
        (A) LIBRARY: BLADNOT03
        (B) CLONE: 1600438

(xi) SEQUENCE DESCRIPTION: SEQ ID NO: 30 :

```
Met Asn Lys His Gln Lys Pro Val Leu Thr Gly Gln Arg Phe Lys
                 5                  10                  15

Thr Arg Lys Arg Asp Glu Lys Glu Lys Phe Glu Pro Thr Val Phe
                20                  25                  30

Arg Asp Thr Leu Val Gln Gly Leu Asn Glu Ala Gly Asp Asp Leu
                35                  40                  45

Glu Ala Val Ala Lys Phe Leu Asp Ser Thr Gly Ser Arg Leu Asp
                50                  55                  60

Tyr Arg Arg Tyr Ala Asp Thr Leu Phe Asp Ile Leu Val Ala Gly
                65                  70                  75

Ser Met Leu Ala Pro Gly Gly Thr Arg Ile Asp Asp Gly Asp Lys
                80                  85                  90

Thr Lys Met Thr Asn His Cys Val Phe Ser Ala Asn Glu Asp His
                95                 100                 105

Glu Thr Ile Arg Asn Tyr Ala Gln Val Phe Asn Lys Leu Ile Arg
               110                 115                 120

Arg Tyr Lys Tyr Leu Glu Lys Ala Phe Glu Asp Glu Met Lys Lys
               125                 130                 135

Leu Leu Leu Phe Leu Lys Ala Phe Ser Glu Thr Glu Gln Thr Lys
               140                 145                 150
```

```
Leu Ala Met Leu Ser Gly Ile Leu Leu Gly Asn Gly Thr Leu Pro
                155                 160                 165

Ala Thr Ile Leu Thr Ser Leu Phe Thr Asp Ser Leu Val Lys Glu
                170                 175                 180

Gly Ile Ala Ala Ser Phe Ala Val Lys Leu Phe Lys Ala Trp Met
                185                 190                 195

Ala Glu Lys Asp Ala Asn Ser Val Thr Ser Ser Leu Arg Lys Ala
                200                 205                 210

Asn Leu Asp Lys Arg Leu Leu Glu Leu Phe Pro Val Asn Arg Gln
                215                 220                 225

Ser Val Asp His Phe Ala Lys Tyr Phe Thr Asp Ala Gly Leu Lys
                230                 235                 240

Glu Leu Ser Asp Phe Leu Arg Val Gln Gln Ser Leu Gly Thr Arg
                245                 250                 255

Lys Glu Leu Gln Lys Glu Leu Gln Glu Arg Leu Ser Gln Glu Cys
                260                 265                 270

Pro Ile Lys Glu Val Val Leu Tyr Val Lys Glu Glu Met Lys Arg
                275                 280                 285

Asn Asp Leu Pro Glu Thr Ala Val Ile Gly Leu Leu Trp Thr Cys
                290                 295                 300

Ile Met Asn Ala Val Glu Trp Asn Lys Lys Glu Glu Leu Val Ala
                305                 310                 315

Glu Gln Ala Leu Lys His Leu Lys Gln Tyr Ala Pro Leu Leu Ala
                320                 325                 330

Val Phe Ser Ser Gln Gly Gln Ser Glu Leu Ile Leu Leu Gln Lys
                335                 340                 345

Val Gln Glu Tyr Cys Tyr Asp Asn Ile His Phe Met Lys Ala Phe
                350                 355                 360

Gln Lys Ile Val Val Leu Phe Tyr Lys Ala Asp Val Leu Ser Glu
                365                 370                 375

Glu Ala Ile Leu Lys Trp Tyr Lys Glu Ala His Val Ala Lys Gly
                380                 385                 390

Lys Ser Val Phe Leu Asp Gln Met Lys Lys Phe Val Glu Trp Leu
                395                 400                 405

Gln Asn Ala Glu Glu Glu Ser Glu Ser Glu Gly Glu Glu Asn
                410                 415
```

(2) INFORMATION FOR SEQ ID NO: 31:

(i) SEQUENCE CHARACTERISTICS:
        (A) LENGTH: 376 amino acids
        (B) TYPE: amino acid
        (C) STRANDEDNESS: single
        (D) TOPOLOGY: linear (vii) IMMEDIATE SOURCE:
        (A) LIBRARY: BLADNOT03
        (B) CLONE: 1600518

(xi) SEQUENCE DESCRIPTION: SEQ ID NO: 31 :

```
Met Lys Asp Val Pro Gly Phe Leu Gln Gln Ser Gln Ser Ser Gly
                5                  10                  15

Pro Gly Gln Pro Ala Val Trp His Arg Leu Glu Glu Leu Tyr Thr
                20                  25                  30

Lys Lys Leu Trp His Gln Leu Thr Leu Gln Val Leu Asp Phe Val
                35                  40                  45

Gln Asp Pro Cys Phe Ala Gln Gly Asp Gly Leu Ile Lys Leu Tyr
```

-continued

```
                     50                   55                    60
Glu Asn Phe Ile Ser Glu Phe Glu His Arg Val Asn Pro Leu Ser
                 65                   70                    75
Leu Val Glu Ile Ile Leu His Val Val Arg Gln Met Thr Asp Pro
                 80                   85                    90
Asn Val Ala Leu Thr Phe Leu Glu Lys Thr Arg Glu Lys Val Lys
                 95                  100                   105
Ser Ser Asp Glu Ala Val Ile Leu Cys Lys Thr Ala Ile Gly Ala
                110                  115                   120
Leu Lys Leu Asn Ile Gly Asp Leu Gln Val Thr Lys Glu Thr Ile
                125                  130                   135
Glu Asp Val Glu Glu Met Leu Asn Asn Leu Pro Gly Val Thr Ser
                140                  145                   150
Val His Ser Arg Phe Tyr Asp Leu Ser Ser Lys Tyr Tyr Gln Thr
                155                  160                   165
Ile Gly Asn His Ala Ser Tyr Tyr Lys Asp Ala Leu Arg Phe Leu
                170                  175                   180
Gly Cys Val Asp Ile Lys Asp Leu Pro Val Ser Glu Gln Gln Glu
                185                  190                   195
Arg Ala Phe Thr Leu Gly Leu Ala Gly Leu Leu Gly Glu Gly Val
                200                  205                   210
Phe Asn Phe Gly Glu Leu Leu Met His Pro Val Leu Glu Ser Leu
                215                  220                   225
Arg Asn Thr Asp Arg Gln Trp Leu Ile Asp Thr Leu Tyr Ala Phe
                230                  235                   240
Asn Ser Gly Asn Val Glu Arg Phe Gln Thr Leu Lys Thr Ala Trp
                245                  250                   255
Gly Gln Gln Pro Asp Leu Ala Ala Asn Glu Ala Gln Leu Leu Arg
                260                  265                   270
Lys Ile Gln Leu Leu Cys Leu Met Glu Met Thr Phe Thr Arg Pro
                275                  280                   285
Ala Asn His Arg Gln Leu Thr Phe Glu Glu Ile Ala Lys Ser Ala
                290                  295                   300
Lys Ile Thr Val Asn Glu Val Glu Leu Leu Val Met Lys Ala Leu
                305                  310                   315
Ser Val Gly Leu Val Lys Gly Ser Ile Asp Glu Val Asp Lys Arg
                320                  325                   330
Val His Met Thr Trp Val Gln Pro Arg Val Leu Asp Leu Gln Gln
                335                  340                   345
Ile Lys Gly Met Lys Asp Arg Leu Glu Phe Trp Cys Thr Asp Val
                350                  355                   360
Lys Ser Met Glu Met Leu Val Glu His Gln Ala His Asp Ile Leu
                365                  370                   375
Thr (2) INFORMATION FOR SEQ ID NO:    32:

(i) SEQUENCE CHARACTERISTICS:
        (A) LENGTH: 237 amino acids
        (B) TYPE: amino acid
        (C) STRANDEDNESS: single
        (D) TOPOLOGY: linear (vii) IMMEDIATE SOURCE:
        (A) LIBRARY: BLADNOT03
        (B) CLONE: 1602473
```

(xi) SEQUENCE DESCRIPTION: SEQ ID NO: 32 :

Met Leu Gly Gly Ser Leu Gly Ser Arg Leu Leu Arg Gly Val Gly
                 5                  10                  15

Gly Ser His Gly Arg Phe Gly Ala Arg Gly Val Arg Glu Gly Gly
                20                  25                  30

Ala Ala Met Ala Ala Gly Glu Ser Met Ala Gln Arg Met Val Trp
            35                  40                      45

Val Asp Leu Glu Met Thr Gly Leu Asp Ile Glu Lys Asp Gln Ile
            50                  55                      60

Ile Glu Met Ala Cys Leu Ile Thr Asp Ser Asp Leu Asn Ile Leu
            65                  70                      75

Ala Glu Gly Pro Asn Leu Ile Ile Lys Gln Pro Asp Glu Leu Leu
            80                  85                      90

Asp Ser Met Ser Asp Trp Cys Lys Glu His His Gly Lys Ser Gly
            95                 100                     105

Leu Thr Lys Ala Val Lys Glu Ser Thr Ile Thr Leu Gln Gln Ala
           110                 115                     120

Glu Tyr Glu Phe Leu Ser Phe Val Arg Gln Gln Thr Pro Pro Gly
           125                 130                     135

Leu Cys Pro Leu Ala Gly Asn Ser Val His Glu Asp Lys Lys Phe
           140                 145                     150

Leu Asp Lys Tyr Met Pro Gln Phe Met Lys His Leu His Tyr Arg
           155                 160                     165

Ile Ile Asp Val Ser Thr Val Lys Glu Leu Cys Arg Arg Trp Tyr
           170                 175                     180

Pro Glu Glu Tyr Glu Phe Ala Pro Lys Lys Ala Ala Ser His Arg
           185                 190                     195

Ala Leu Asp Asp Ile Ser Glu Ser Ile Lys Glu Leu Gln Phe Tyr
           200                 205                     210

Arg Asn Asn Ile Phe Lys Lys Lys Ile Asp Glu Lys Lys Arg Lys
           215                 220                     225

Ile Ile Glu Asn Gly Glu Asn Glu Lys Thr Val Ser
           230                 235

(2) INFORMATION FOR SEQ ID NO:     33:

(i) SEQUENCE CHARACTERISTICS:
        (A) LENGTH: 152 amino acids
        (B) TYPE: amino acid
        (C) STRANDEDNESS: single
        (D) TOPOLOGY: linear (vii) IMMEDIATE SOURCE:
         (A) LIBRARY: LUNGNOT15
         (B) CLONE: 1605720

(xi) SEQUENCE DESCRIPTION: SEQ ID NO: 33 :

Met Glu Ala Val Leu Asn Glu Leu Val Ser Val Glu Asp Leu Leu
                 5                  10                  15

Lys Phe Glu Lys Lys Phe Gln Ser Glu Lys Ala Ala Gly Ser Val
                20                  25                  30

Ser Lys Ser Thr Gln Phe Glu Tyr Ala Trp Cys Leu Val Arg Ser
            35                  40                      45

Lys Tyr Asn Asp Asp Ile Arg Lys Gly Ile Val Leu Glu Glu
            50                  55                      60

Leu Leu Pro Lys Gly Ser Lys Glu Glu Gln Arg Asp Tyr Val Phe

```
                    65                  70                  75
Tyr Leu Ala Val Gly Asn Tyr Arg Leu Lys Glu Tyr Glu Lys Ala
                80                  85                  90

Leu Lys Tyr Val Arg Gly Leu Leu Gln Thr Glu Pro Gln Asn Asn
                95                 100                 105

Gln Ala Lys Glu Leu Glu Arg Leu Ile Asp Lys Ala Met Lys Lys
               110                 115                 120

Asp Gly Leu Val Gly Met Ala Ile Val Gly Met Ala Leu Gly
               125                 130                 135

Val Ala Gly Leu Ala Gly Leu Ile Gly Leu Ala Val Ser Lys Ser
               140                 145                 150

Lys Phe (2) INFORMATION FOR SEQ ID NO:    34:

(i) SEQUENCE CHARACTERISTICS:
        (A) LENGTH: 179 amino acids
        (B) TYPE: amino acid
        (C) STRANDEDNESS: single
        (D) TOPOLOGY: linear (vii) IMMEDIATE SOURCE:
        (A) LIBRARY: COLNTUT06
        (B) CLONE: 1610501

(xi) SEQUENCE DESCRIPTION: SEQ ID NO: 34 :

Met Pro Ser Lys Ser Leu Val Met Glu Tyr Leu Ala His Pro Ser
                 5                  10                  15

Thr Leu Gly Leu Ala Val Gly Val Ala Cys Gly Met Cys Leu Gly
                20                  25                  30

Trp Ser Leu Arg Val Cys Phe Gly Met Leu Pro Lys Ser Lys Thr
                35                  40                  45

Ser Lys Thr His Thr Asp Thr Glu Ser Glu Ala Ser Ile Leu Gly
                50                  55                  60

Asp Ser Gly Glu Tyr Lys Met Ile Leu Val Val Arg Asn Asp Leu
                65                  70                  75

Lys Met Gly Lys Gly Lys Val Ala Ala Gln Cys Ser His Ala Ala
                80                  85                  90

Val Ser Ala Tyr Lys Gln Ile Gln Arg Arg Asn Pro Glu Met Leu
                95                 100                 105

Lys Gln Trp Glu Tyr Cys Gly Gln Pro Lys Val Val Lys Ala
               110                 115                 120

Pro Asp Glu Glu Thr Leu Ile Ala Leu Leu Ala His Ala Lys Met
               125                 130                 135

Leu Gly Leu Thr Val Ser Leu Ile Gln Asp Ala Gly Arg Thr Gln
               140                 145                 150

Ile Ala Pro Gly Ser Gln Thr Val Leu Gly Ile Gly Pro Gly Pro
               155                 160                 165

Ala Asp Leu Ile Asp Lys Val Thr Gly His Leu Lys Leu Tyr
               170                 175

(2) INFORMATION FOR SEQ ID NO:    35:

(i) SEQUENCE CHARACTERISTICS:
        (A) LENGTH: 196 amino acids
        (B) TYPE: amino acid
        (C) STRANDEDNESS: single
        (D) TOPOLOGY: linear
```

```
        (vii) IMMEDIATE SOURCE:
              (A) LIBRARY: BLADNOT06
              (B) CLONE: 1720770

(xi) SEQUENCE DESCRIPTION: SEQ ID NO: 35 :

Met Ser Glu Gly Asp Ser Val Gly Glu Ser Val His Gly Lys Pro
                 5                  10                  15

Ser Val Val Tyr Arg Phe Phe Thr Arg Leu Gly Gln Ile Tyr Gln
                20                  25                  30

Ser Trp Leu Asp Lys Ser Thr Pro Tyr Thr Ala Val Arg Trp Val
                35                  40                  45

Val Thr Leu Gly Leu Ser Phe Val Tyr Met Ile Arg Val Tyr Leu
                50                  55                  60

Leu Gln Gly Trp Tyr Ile Val Thr Tyr Ala Leu Gly Ile Tyr His
                65                  70                  75

Leu Asn Leu Phe Ile Ala Phe Leu Ser Pro Lys Val Asp Pro Ser
                80                  85                  90

Leu Met Glu Asp Ser Asp Asp Gly Pro Ser Leu Pro Thr Lys Gln
                95                 100                 105

Asn Glu Glu Phe Arg Pro Phe Ile Arg Arg Leu Pro Glu Phe Lys
               110                 115                 120

Phe Trp His Ala Ala Thr Lys Gly Ile Leu Val Ala Met Val Cys
               125                 130                 135

Thr Phe Phe Asp Ala Phe Asn Val Pro Val Phe Trp Pro Ile Leu
               140                 145                 150

Val Met Tyr Phe Ile Met Leu Phe Cys Ile Thr Met Lys Arg Gln
               155                 160                 165

Ile Lys His Met Ile Lys Tyr Arg Tyr Ile Pro Phe Thr His Gly
               170                 175                 180

Lys Arg Arg Tyr Arg Gly Lys Glu Asp Ala Gly Lys Ala Phe Ala
               185                 190                 195

Ser (2) INFORMATION FOR SEQ ID NO:     36:

(i) SEQUENCE CHARACTERISTICS:
              (A) LENGTH: 612 amino acids
              (B) TYPE: amino acid
              (C) STRANDEDNESS: single
              (D) TOPOLOGY: linear (vii) IMMEDIATE SOURCE:
              (A) LIBRARY: BRAINON01
              (B) CLONE: 1832295

(xi) SEQUENCE DESCRIPTION: SEQ ID NO: 36 :

Met Ala Ala Ala Gly Arg Leu Pro Ser Ser Trp Ala Leu Phe Ser
                 5                  10                  15

Pro Leu Leu Ala Gly Leu Ala Leu Leu Gly Val Gly Pro Val Pro
                20                  25                  30

Ala Arg Ala Leu His Asn Val Thr Ala Glu Leu Phe Gly Ala Glu
                35                  40                  45

Ala Trp Gly Thr Leu Ala Ala Phe Gly Asp Leu Asn Ser Asp Lys
                50                  55                  60

Gln Thr Asp Leu Phe Val Leu Arg Glu Arg Asn Asp Leu Ile Val
                65                  70                  75

Phe Leu Ala Asp Gln Asn Ala Pro Tyr Phe Lys Pro Lys Val Lys
                80                  85                  90
```

```
Val Ser Phe Lys Asn His Ser Ala Leu Ile Thr Ser Val Val Pro
             95                 100                 105

Gly Asp Tyr Asp Gly Asp Ser Gln Met Asp Val Leu Leu Thr Tyr
            110                 115                 120

Leu Pro Lys Asn Tyr Ala Lys Ser Glu Leu Gly Ala Val Ile Phe
            125                 130                 135

Trp Gly Gln Asn Gln Thr Leu Asp Pro Asn Asn Met Thr Ile Leu
            140                 145                 150

Asn Arg Thr Phe Gln Asp Glu Pro Leu Ile Met Asp Phe Asn Gly
            155                 160                 165

Asp Leu Ile Pro Asp Ile Phe Gly Ile Thr Asn Glu Ser Asn Gln
            170                 175                 180

Pro Gln Ile Leu Leu Gly Gly Asn Leu Ser Trp His Pro Ala Leu
            185                 190                 195

Thr Thr Thr Ser Lys Met Arg Ile Pro His Ser His Ala Phe Ile
            200                 205                 210

Asp Leu Thr Glu Asp Phe Thr Ala Asp Leu Phe Leu Thr Thr Leu
            215                 220                 225

Asn Ala Thr Thr Ser Thr Phe Gln Phe Glu Ile Trp Glu Asn Leu
            230                 235                 240

Asp Gly Asn Phe Ser Val Ser Thr Ile Leu Glu Lys Pro Gln Asn
            245                 250                 255

Met Met Val Val Gly Gln Ser Ala Phe Ala Asp Phe Asp Gly Asp
            260                 265                 270

Gly His Met Asp His Leu Leu Pro Gly Cys Glu Asp Lys Asn Cys
            275                 280                 285

Gln Lys Ser Thr Ile Tyr Leu Val Arg Ser Gly Met Lys Gln Trp
            290                 295                 300

Val Pro Val Leu Gln Asp Phe Ser Asn Lys Gly Thr Leu Trp Gly
            305                 310                 315

Phe Val Pro Phe Val Asp Glu Gln Gln Pro Thr Glu Ile Pro Ile
            320                 325                 330

Pro Ile Thr Leu His Ile Gly Asp Tyr Asn Met Asp Gly Tyr Pro
            335                 340                 345

Asp Ala Leu Val Ile Leu Lys Asn Thr Ser Gly Ser Asn Gln Gln
            350                 355                 360

Ala Phe Leu Leu Glu Asn Val Pro Cys Asn Asn Ala Ser Cys Glu
            365                 370                 375

Glu Ala Arg Arg Met Phe Lys Val Tyr Trp Glu Leu Thr Asp Leu
            380                 385                 390

Asn Gln Ile Lys Asp Ala Met Val Ala Thr Phe Phe Asp Ile Tyr
            395                 400                 405

Glu Asp Gly Ile Leu Asp Ile Val Val Leu Ser Lys Gly Tyr Thr
            410                 415                 420

Lys Asn Asp Phe Ala Ile His Thr Leu Lys Asn Asn Phe Glu Ala
            425                 430                 435

Asp Ala Tyr Phe Val Lys Val Ile Val Leu Ser Gly Leu Cys Ser
            440                 445                 450

Asn Asp Cys Pro Arg Lys Ile Thr Pro Phe Gly Val Asn Gln Pro
            455                 460                 465

Gly Pro Tyr Ile Met Tyr Thr Thr Leu Asp Ala Asn Gly Tyr Leu
            470                 475                 480
```

-continued

```
Lys Asn Gly Ser Ala Gly Gln Leu Ser Gln Ser Ala His Leu Ala
                485                 490                 495

Leu Gln Leu Pro Tyr Asn Val Leu Gly Leu Gly Arg Ser Ala Asn
                500                 505                 510

Phe Leu Asp His Leu Tyr Val Gly Ile Pro Arg Pro Ser Gly Glu
                515                 520                 525

Lys Ser Ile Arg Lys Gln Glu Trp Thr Ala Ile Ile Pro Asn Ser
                530                 535                 540

Gln Leu Ile Val Ile Pro Tyr Pro His Asn Val Pro Arg Ser Trp
                545                 550                 555

Ser Ala Lys Leu Tyr Leu Thr Pro Ser Asn Ile Val Leu Leu Thr
                560                 565                 570

Ala Ile Ala Leu Ile Gly Val Cys Val Phe Ile Leu Ala Ile Ile
                575                 580                 585

Gly Ile Leu His Trp Gln Glu Lys Lys Ala Asp Asp Arg Glu Lys
                590                 595                 600

Arg Gln Glu Ala His Arg Phe His Phe Asp Ala Met
                605                 610
```

(2) INFORMATION FOR SEQ ID NO:    37:

(i) SEQUENCE CHARACTERISTICS:
        (A) LENGTH: 101 amino acids
        (B) TYPE: amino acid
        (C) STRANDEDNESS: single
        (D) TOPOLOGY: linear (vii) IMMEDIATE SOURCE:
        (A) LIBRARY: CORPNOT02
        (B) CLONE: 1990522

(xi) SEQUENCE DESCRIPTION: SEQ ID NO: 37 :

```
Met Ala Ala Pro Leu Ser Val Glu Val Glu Phe Gly Gly Gly Ala
                  5                  10                  15

Glu Leu Leu Phe Asp Gly Ile Lys Lys His Arg Val Thr Leu Pro
                 20                  25                  30

Gly Gln Glu Glu Pro Trp Asp Ile Arg Asn Leu Leu Ile Trp Ile
                 35                  40                  45

Lys Lys Asn Leu Leu Lys Glu Arg Pro Glu Leu Phe Ile Gln Gly
                 50                  55                  60

Asp Ser Val Arg Pro Gly Ile Leu Val Leu Ile Asn Asp Ala Asp
                 65                  70                  75

Trp Glu Leu Leu Gly Glu Leu Asp Tyr Gln Leu Gln Asp Gln Asp
                 80                  85                  90

Ser Val Leu Phe Ile Ser Thr Leu His Gly Gly
                 95                 100
```

(2) INFORMATION FOR SEQ ID NO:    38:

(i) SEQUENCE CHARACTERISTICS:
        (A) LENGTH: 132 amino acids
        (B) TYPE: amino acid
        (C) STRANDEDNESS: single
        (D) TOPOLOGY: linear (vii) IMMEDIATE SOURCE:
        (A) LIBRARY: BRAITUT02
        (B) CLONE: 2098087

(xi) SEQUENCE DESCRIPTION: SEQ ID NO: 38 :

Met Ala Lys Asp Ile Leu Gly Glu Ala Gly Leu His Phe Asp Glu

```
                   5                    10                    15
Leu Asn Lys Leu Arg Val Leu Asp Pro Glu Val Thr Gln Gln Thr
                  20                    25                    30

Ile Glu Leu Lys Glu Cys Lys Asp Phe Val Asp Lys Ile Gly
                  35                    40                    45

Gln Phe Gln Lys Ile Val Gly Gly Leu Ile Glu Leu Val Asp Gln
                  50                    55                    60

Leu Ala Lys Glu Ala Glu Asn Glu Lys Met Lys Ala Ile Gly Ala
                  65                    70                    75

Arg Asn Leu Leu Lys Ser Ile Ala Lys Gln Arg Glu Ala Gln Gln
                  80                    85                    90

Gln Gln Leu Gln Ala Leu Ile Ala Glu Lys Lys Met Gln Leu Glu
                  95                   100                   105

Arg Tyr Arg Val Glu Tyr Glu Ala Leu Cys Lys Val Glu Ala Glu
                 110                   115                   120

Gln Asn Glu Phe Ile Asp Gln Phe Ile Phe Gln Lys
                 125                   130
```

(2) INFORMATION FOR SEQ ID NO:    39:

(i) SEQUENCE CHARACTERISTICS:
        (A) LENGTH: 188 amino acids
        (B) TYPE: amino acid
        (C) STRANDEDNESS: single
        (D) TOPOLOGY: linear (vii) IMMEDIATE SOURCE:
        (A) LIBRARY: BRAITUT03
        (B) CLONE: 2112230

(xi) SEQUENCE DESCRIPTION: SEQ ID NO: 39 :

```
Met Ala Asn Ser Gly Cys Lys Asp Val Thr Gly Pro Asp Glu Glu
                   5                    10                    15

Ser Phe Leu Tyr Phe Ala Tyr Gly Ser Asn Leu Leu Thr Glu Arg
                  20                    25                    30

Ile His Leu Arg Asn Pro Ser Ala Ala Phe Phe Cys Val Ala Arg
                  35                    40                    45

Leu Gln Asp Phe Lys Leu Asp Phe Gly Asn Ser Gln Gly Lys Thr
                  50                    55                    60

Ser Gln Thr Trp His Gly Gly Ile Ala Thr Ile Phe Gln Ser Pro
                  65                    70                    75

Gly Asp Glu Val Trp Gly Val Trp Lys Met Asn Lys Ser Asn
                  80                    85                    90

Leu Asn Ser Leu Asp Glu Gln Glu Gly Val Lys Ser Gly Met Tyr
                  95                   100                   105

Val Val Ile Glu Val Lys Val Ala Thr Gln Glu Gly Lys Glu Ile
                 110                   115                   120

Thr Cys Arg Ser Tyr Leu Met Thr Asn Tyr Glu Ser Ala Pro Pro
                 125                   130                   135

Ser Pro Gln Tyr Lys Lys Ile Ile Cys Met Gly Ala Lys Glu Asn
                 140                   145                   150

Gly Leu Pro Leu Glu Tyr Gln Glu Lys Leu Lys Ala Ile Glu Pro
                 155                   160                   165

Asn Asp Tyr Thr Gly Lys Val Ser Glu Glu Ile Glu Asp Ile Ile
                 170                   175                   180

Lys Lys Gly Glu Thr Gln Thr Leu
                 185
```

(2) INFORMATION FOR SEQ ID NO:    40:

(i) SEQUENCE CHARACTERISTICS:
       (A) LENGTH: 86 amino acids
       (B) TYPE: amino acid
       (C) STRANDEDNESS: single
       (D) TOPOLOGY: linear (vii) IMMEDIATE SOURCE:
       (A) LIBRARY: BRSTTUT02
       (B) CLONE: 2117050

(xi) SEQUENCE DESCRIPTION: SEQ ID NO: 40 :

Met Thr Asp Arg Tyr Thr Ile His Ser Gln Leu Glu His Leu Gln
                5                  10                  15

Ser Lys Tyr Ile Gly Thr Gly His Ala Asp Thr Thr Lys Trp Glu
                20                 25                  30

Trp Leu Val Asn Gln His Arg Asp Ser Tyr Cys Ser Tyr Met Gly
                35                 40                  45

His Phe Asp Leu Leu Asn Tyr Phe Ala Ile Ala Glu Asn Glu Ser
                50                 55                  60

Lys Ala Arg Val Arg Phe Asn Leu Met Glu Lys Met Leu Gln Pro
                65                 70                  75

Cys Gly Pro Pro Ala Asp Lys Pro Glu Glu Asn
                80                 85

(2) INFORMATION FOR SEQ ID NO:    41:

(i) SEQUENCE CHARACTERISTICS:
       (A) LENGTH: 222 amino acids
       (B) TYPE: amino acid
       (C) STRANDEDNESS: single
       (D) TOPOLOGY: linear (vii) IMMEDIATE SOURCE:
       (A) LIBRARY: SININOT01
       (B) CLONE: 2184712

(xi) SEQUENCE DESCRIPTION: SEQ ID NO: 41 :

Met Ser Gly Leu Gly Arg Leu Phe Gly Lys Gly Lys Lys Glu Lys
                5                  10                  15

Gly Pro Thr Pro Glu Glu Ala Ile Gln Lys Leu Lys Glu Thr Glu
                20                 25                  30

Lys Ile Leu Ile Lys Lys Gln Glu Phe Leu Glu Gln Lys Ile Gln
                35                 40                  45

Gln Glu Leu Gln Thr Ala Lys Lys Tyr Gly Thr Lys Asn Lys Arg
                50                 55                  60

Ala Ala Leu Gln Ala Leu Arg Arg Lys Lys Arg Phe Glu Gln Gln
                65                 70                  75

Leu Ala Gln Thr Asp Gly Thr Leu Ser Thr Leu Glu Phe Gln Arg
                80                 85                  90

Glu Ala Ile Glu Asn Ala Thr Thr Asn Ala Glu Val Leu Arg Thr
                95                 100                 105

Met Glu Leu Ala Ala Gln Ser Met Lys Lys Ala Tyr Gln Asp Met
                110                115                 120

Asp Ile Asp Lys Val Asp Glu Leu Met Thr Asp Ile Thr Glu Gln
                125                130                 135

Gln Glu Val Ala Gln Gln Ile Ser Asp Ala Ile Ser Arg Pro Met
                140                145                 150

```
Gly Phe Gly Asp Asp Val Asp Glu Asp Leu Leu Glu Glu Leu
                155                 160                 165

Glu Glu Leu Glu Gln Glu Leu Ala Gln Glu Leu Leu Asn Val
            170                 175                 180

Gly Asp Lys Glu Glu Pro Ser Val Lys Leu Pro Ser Val Pro
            185                 190                 195

Ser Thr His Leu Pro Ala Gly Pro Ala Pro Lys Val Asp Glu Asp
                200                 205                 210

Glu Glu Ala Leu Lys Gln Leu Ala Glu Trp Val Ser
            215                 220
```

(2) INFORMATION FOR SEQ ID NO:   42:

(i) SEQUENCE CHARACTERISTICS:
      (A) LENGTH: 300 amino acids
      (B) TYPE: amino acid
      (C) STRANDEDNESS: single
      (D) TOPOLOGY: linear (vii) IMMEDIATE SOURCE:
      (A) LIBRARY: BRAINON01
      (B) CLONE: 2290475

(xi) SEQUENCE DESCRIPTION: SEQ ID NO: 42 :

```
Met Ser Gly Ser Asn Gly Ser Lys Glu Asn Ser His Asn Lys Ala
                 5                  10                  15

Arg Thr Ser Pro Tyr Pro Gly Ser Lys Val Glu Arg Ser Gln Val
            20                  25                  30

Pro Asn Glu Lys Val Gly Trp Leu Val Glu Trp Gln Asp Tyr Lys
            35                  40                  45

Pro Val Glu Tyr Thr Ala Val Ser Val Leu Ala Gly Pro Arg Trp
            50                  55                  60

Ala Asp Pro Gln Ile Ser Glu Ser Asn Phe Ser Pro Lys Phe Asn
            65                  70                  75

Glu Lys Asp Gly His Val Glu Arg Lys Ser Lys Asn Gly Leu Tyr
            80                  85                  90

Glu Ile Glu Asn Gly Arg Pro Arg Asn Pro Ala Gly Arg Thr Gly
            95                  100                 105

Leu Val Gly Arg Gly Leu Leu Gly Arg Trp Gly Pro Asn His Ala
            110                 115                 120

Ala Asp Pro Ile Ile Thr Arg Trp Lys Arg Asp Ser Ser Gly Asn
            125                 130                 135

Lys Ile Met His Pro Val Ser Gly Lys His Ile Leu Gln Phe Val
            140                 145                 150

Ala Ile Lys Arg Lys Asp Cys Gly Glu Trp Ala Ile Pro Gly Gly
            155                 160                 165

Met Val Asp Pro Gly Glu Lys Ile Ser Ala Thr Leu Lys Arg Glu
            170                 175                 180

Phe Gly Glu Glu Ala Leu Asn Ser Leu Gln Lys Thr Ser Ala Glu
            185                 190                 195

Lys Arg Glu Ile Glu Glu Lys Leu His Lys Leu Phe Ser Gln Asp
            200                 205                 210

His Leu Val Ile Tyr Lys Gly Tyr Val Asp Asp Pro Arg Asn Thr
            215                 220                 225

Asp Asn Ala Trp Met Glu Thr Glu Ala Val Asn Tyr His Asp Glu
            230                 235                 240

Thr Gly Glu Ile Met Asp Asn Leu Met Leu Glu Ala Gly Asp Asp
```

```
                      245                 250                 255

Ala Gly Lys Val Lys Trp Val Asp Ile Asn Asp Lys Leu Lys Leu
                  260                 265                 270

Tyr Ala Ser His Ser Gln Phe Ile Lys Leu Val Ala Glu Lys Arg
                  275                 280                 285

Asp Ala His Trp Ser Glu Asp Ser Glu Ala Asp Cys His Ala Leu
                  290                 295                 300

(2) INFORMATION FOR SEQ ID NO:      43:

(i) SEQUENCE CHARACTERISTICS:
        (A) LENGTH: 112 amino acids
        (B) TYPE: amino acid
        (C) STRANDEDNESS: single
        (D) TOPOLOGY: linear (vii) IMMEDIATE SOURCE:
        (A) LIBRARY: LUNGNOT20
        (B) CLONE: 2353452

(xi) SEQUENCE DESCRIPTION: SEQ ID NO: 43 :

Met Glu Ala Tyr Glu Gln Val Gln Lys Gly Pro Leu Lys Leu Lys
                    5                  10                  15

Gly Val Ala Glu Leu Gly Val Thr Lys Arg Lys Lys Lys Lys Lys
                   20                  25                  30

Asp Lys Asp Lys Ala Lys Leu Leu Glu Ala Met Gly Thr Ser Lys
                   35                  40                  45

Lys Asn Glu Glu Glu Lys Arg Arg Gly Leu Asp Lys Arg Thr Pro
                   50                  55                  60

Ala Gln Ala Ala Phe Glu Lys Met Gln Glu Lys Arg Gln Met Glu
                   65                  70                  75

Arg Ile Leu Lys Lys Ala Ser Lys Thr His Lys Gln Arg Val Glu
                   80                  85                  90

Asp Phe Asn Arg His Leu Asp Thr Leu Thr Glu His Tyr Asp Ile
                   95                 100                 105

Pro Lys Val Ser Trp Thr Lys
                  110

(2) INFORMATION FOR SEQ ID NO:      44:

(i) SEQUENCE CHARACTERISTICS:
        (A) LENGTH: 251 amino acids
        (B) TYPE: amino acid
        (C) STRANDEDNESS: single
        (D) TOPOLOGY: linear (vii) IMMEDIATE SOURCE:
        (A) LIBRARY: THP1NOT03
        (B) CLONE: 2469611

(xi) SEQUENCE DESCRIPTION: SEQ ID NO: 44 :

Met Ser Asp Ile Gly Asp Trp Phe Arg Ser Ile Pro Ala Ile Thr
                    5                  10                  15

Arg Tyr Trp Phe Ala Ala Thr Val Ala Val Pro Leu Val Gly Lys
                   20                  25                  30

Leu Gly Leu Ile Ser Pro Ala Tyr Leu Phe Leu Trp Pro Glu Ala
                   35                  40                  45

Phe Leu Tyr Arg Phe Gln Ile Trp Arg Pro Ile Thr Ala Thr Phe
                   50                  55                  60

Tyr Phe Pro Val Gly Pro Gly Thr Gly Phe Leu Tyr Leu Val Asn
                   65                  70                  75
```

```
Leu Tyr Phe Leu Tyr Gln Tyr Ser Thr Arg Leu Glu Thr Gly Ala
                80                  85                  90

Phe Asp Gly Arg Pro Ala Asp Tyr Leu Phe Met Leu Leu Phe Asn
                95                 100                 105

Trp Ile Cys Ile Val Ile Thr Gly Leu Ala Met Asp Met Gln Leu
               110                 115                 120

Leu Met Ile Pro Leu Ile Met Ser Val Leu Tyr Val Trp Ala Gln
               125                 130                 135

Leu Asn Arg Asp Met Ile Val Ser Phe Trp Phe Gly Thr Arg Phe
               140                 145                 150

Lys Ala Cys Tyr Leu Pro Trp Val Ile Leu Gly Phe Asn Tyr Ile
               155                 160                 165

Ile Gly Gly Ser Val Ile Asn Glu Leu Ile Gly Asn Leu Val Gly
               170                 175                 180

His Leu Tyr Phe Phe Leu Met Phe Arg Tyr Pro Met Asp Leu Gly
               185                 190                 195

Gly Arg Asn Phe Leu Ser Thr Pro Gln Phe Leu Tyr Arg Trp Leu
               200                 205                 210

Pro Ser Arg Arg Gly Gly Val Ser Gly Phe Gly Val Pro Pro Ala
               215                 220                 225

Ser Met Arg Arg Ala Ala Asp Gln Asn Gly Gly Gly Arg His
               230                 235                 240

Asn Trp Gly Gln Gly Phe Arg Leu Gly Asp Gln
               245                 250

(2) INFORMATION FOR SEQ ID NO:   45:

(i) SEQUENCE CHARACTERISTICS:
         (A) LENGTH: 811 amino acids
         (B) TYPE: amino acid
         (C) STRANDEDNESS: single
         (D) TOPOLOGY: linear (vii) IMMEDIATE SOURCE:
         (A) LIBRARY: LIVRTUT04
         (B) CLONE: 2515476

(xi) SEQUENCE DESCRIPTION: SEQ ID NO: 45 :

Met Pro Leu Ser Ser Pro Asn Ala Ala Ala Thr Ala Ser Asp Met
                 5                  10                  15

Asp Lys Asn Ser Gly Ser Asn Ser Ser Ala Ser Ser Gly Ser
                20                  25                  30

Ser Lys Gly Gln Gln Pro Pro Arg Ser Ala Ser Ala Gly Pro Ala
                35                  40                  45

Gly Glu Ser Lys Pro Lys Ser Asp Gly Lys Asn Ser Ser Gly Ser
                50                  55                  60

Lys Arg Tyr Asn Arg Lys Arg Glu Leu Ser Tyr Pro Lys Asn Glu
                65                  70                  75

Ser Phe Asn Asn Gln Ser Arg Arg Ser Ser Gln Lys Ser Lys
                80                  85                  90

Thr Phe Asn Lys Met Pro Pro Gln Arg Gly Gly Ser Ser Lys
                95                 100                 105

Leu Phe Ser Ser Ser Phe Asn Gly Gly Arg Arg Asp Glu Val Ala
               110                 115                 120

Glu Ala Gln Arg Ala Glu Phe Ser Pro Ala Gln Phe Ser Gly Pro
               125                 130                 135
```

-continued

```
Lys Lys Ile Asn Leu Asn His Leu Leu Asn Phe Thr Phe Glu Pro
                140                 145                 150

Arg Gly Gln Thr Gly His Phe Glu Gly Ser Gly His Gly Ser Trp
                155                 160                 165

Gly Lys Arg Asn Lys Trp Gly His Lys Pro Phe Asn Lys Glu Leu
                170                 175                 180

Phe Leu Gln Ala Asn Cys Gln Phe Val Val Ser Glu Asp Gln Asp
                185                 190                 195

Tyr Thr Ala His Phe Ala Asp Pro Asp Thr Leu Val Asn Trp Asp
                200                 205                 210

Phe Val Glu Gln Val Arg Ile Cys Ser His Glu Val Pro Ser Cys
                215                 220                 225

Pro Ile Cys Leu Tyr Pro Pro Thr Ala Ala Lys Ile Thr Arg Cys
                230                 235                 240

Gly His Ile Phe Cys Trp Ala Cys Ile Leu His Tyr Leu Ser Leu
                245                 250                 255

Ser Glu Lys Thr Trp Ser Lys Cys Pro Ile Cys Tyr Ser Ser Val
                260                 265                 270

His Lys Lys Asp Leu Lys Ser Val Val Ala Thr Glu Ser His Gln
                275                 280                 285

Tyr Val Gly Asp Thr Ile Thr Met Gln Leu Met Lys Arg Glu
                290                 295                 300

Lys Gly Val Leu Val Ala Leu Pro Lys Ser Lys Trp Met Asn Val
                305                 310                 315

Asp His Pro Ile His Leu Gly Asp Glu Gln His Ser Gln Tyr Ser
                320                 325                 330

Lys Leu Leu Leu Ala Ser Lys Glu Gln Val Leu His Arg Val Val
                335                 340                 345

Leu Glu Glu Lys Val Ala Leu Glu Gln Leu Ala Glu Glu Lys
                350                 355                 360

His Thr Pro Glu Ser Cys Phe Ile Glu Ala Ala Ile Gln Glu Leu
                365                 370                 375

Lys Thr Arg Glu Glu Ala Leu Ser Gly Leu Ala Gly Ser Arg Arg
                380                 385                 390

Glu Val Thr Gly Val Val Ala Ala Leu Glu Gln Leu Val Leu Met
                395                 400                 405

Ala Pro Leu Ala Lys Glu Ser Val Phe Gln Pro Arg Lys Gly Val
                410                 415                 420

Leu Glu Tyr Leu Ser Ala Phe Asp Glu Glu Thr Thr Glu Val Cys
                425                 430                 435

Ser Leu Asp Thr Pro Ser Arg Pro Leu Ala Leu Pro Leu Val Glu
                440                 445                 450

Glu Glu Glu Ala Val Ser Glu Pro Glu Pro Glu Gly Leu Pro Glu
                455                 460                 465

Ala Cys Asp Asp Leu Glu Leu Ala Asp Asp Asn Leu Lys Glu Gly
                470                 475                 480

Thr Ile Cys Thr Glu Ser Ser Gln Glu Pro Ile Thr Lys Ser
                485                 490                 495

Gly Phe Thr Arg Leu Ser Ser Pro Cys Tyr Tyr Phe Tyr Gln
                500                 505                 510

Ala Glu Asp Gly Gln His Met Phe Leu His Pro Val Asn Val Arg
                515                 520                 525

Cys Leu Val Arg Glu Tyr Gly Ser Leu Glu Arg Ser Pro Glu Lys
```

```
                    530                 535                 540
Ile Ser Ala Thr Val Val Glu Ile Ala Gly Tyr Ser Met Ser Glu
                545                 550                 555
Asp Val Arg Gln Arg His Arg Tyr Leu Ser His Leu Pro Leu Thr
                560                 565                 570
Cys Glu Phe Ser Ile Cys Glu Leu Ala Leu Gln Pro Pro Val Val
                575                 580                 585
Ser Lys Glu Thr Leu Glu Met Phe Ser Asp Asp Ile Glu Lys Arg
                590                 595                 600
Lys Arg Gln Arg Gln Lys Lys Ala Arg Glu Glu Arg Arg Arg Glu
                605                 610                 615
Arg Arg Ile Glu Ile Glu Glu Asn Lys Lys Gln Gly Lys Tyr Pro
                620                 625                 630
Glu Val His Ile Pro Leu Glu Asn Leu Gln Gln Phe Pro Ala Phe
                635                 640                 645
Asn Ser Tyr Thr Cys Ser Ser Asp Ser Ala Leu Gly Pro Thr Ser
                650                 655                 660
Thr Glu Gly His Gly Ala Leu Ser Ile Ser Pro Leu Ser Arg Ser
                665                 670                 675
Pro Gly Ser His Ala Asp Phe Leu Leu Thr Pro Leu Ser Pro Thr
                680                 685                 690
Ala Ser Gln Gly Ser Pro Ser Phe Cys Val Gly Ser Leu Glu Glu
                695                 700                 705
Asp Ser Pro Phe Pro Ser Phe Ala Gln Met Leu Arg Val Gly Lys
                710                 715                 720
Ala Lys Ala Asp Val Trp Pro Lys Thr Ala Pro Lys Lys Asp Glu
                725                 730                 735
Asn Ser Leu Val Pro Pro Ala Pro Val Asp Ser Asp Gly Glu Ser
                740                 745                 750
Asp Asn Ser Asp Arg Val Pro Val Pro Ser Phe Gln Asn Ser Phe
                755                 760                 765
Ser Gln Ala Ile Glu Ala Ala Phe Met Lys Leu Asp Thr Pro Ala
                770                 775                 780
Thr Ser Asp Pro Leu Ser Glu Glu Lys Gly Gly Lys Lys Arg Lys
                785                 790                 795
Lys Gln Lys Gln Lys Leu Leu Phe Ser Thr Ser Val Val His Thr
                800                 805                 810
Lys (2) INFORMATION FOR SEQ ID NO:     46:

(i) SEQUENCE CHARACTERISTICS:
        (A) LENGTH: 352 amino acids
        (B) TYPE: amino acid
        (C) STRANDEDNESS: single
        (D) TOPOLOGY: linear (vii) IMMEDIATE SOURCE:
        (A) LIBRARY: THP1AZS08
        (B) CLONE: 2754573

(xi) SEQUENCE DESCRIPTION: SEQ ID NO: 46 :

Met His Val Val Ala Pro Ala Ser Leu Arg Leu Gly Thr Gly Thr
                  5                  10                  15
Asn Leu Pro Pro Ser Pro Thr Cys Leu Thr Lys Leu Ala Leu Pro
                 20                  25                  30
```

-continued

```
Pro Ala Ala Glu Pro Ser Leu Leu Ala Met Ser Gln Ser Arg His
                 35                  40                  45

Arg Ala Glu Ala Pro Pro Leu Glu Arg Glu Asp Ser Gly Thr Phe
             50                  55                  60

Ser Leu Gly Lys Met Ile Thr Ala Lys Pro Gly Lys Thr Pro Ile
             65                  70                  75

Gln Val Leu His Glu Tyr Gly Met Lys Thr Lys Asn Ile Pro Val
             80                  85                  90

Tyr Glu Cys Glu Arg Ser Asp Val Gln Ile His Val Pro Thr Phe
             95                 100                 105

Thr Phe Arg Val Thr Val Gly Asp Ile Thr Cys Thr Gly Glu Gly
            110                 115                 120

Thr Ser Lys Lys Leu Ala Lys His Arg Ala Ala Glu Ala Ala Ile
            125                 130                 135

Asn Ile Leu Lys Ala Asn Ala Ser Ile Cys Phe Ala Val Pro Asp
            140                 145                 150

Pro Leu Met Pro Asp Pro Ser Lys Gln Pro Lys Asn Gln Leu Asn
            155                 160                 165

Pro Ile Gly Ser Leu Gln Glu Leu Ala Ile His His Gly Trp Arg
            170                 175                 180

Leu Pro Glu Tyr Thr Leu Ser Gln Glu Gly Gly Pro Ala His Lys
            185                 190                 195

Arg Glu Tyr Thr Thr Ile Cys Arg Leu Glu Ser Phe Met Glu Thr
            200                 205                 210

Gly Lys Gly Ala Ser Lys Lys Gln Ala Lys Arg Asn Ala Ala Glu
            215                 220                 225

Lys Phe Leu Ala Lys Phe Ser Asn Ile Ser Pro Glu Asn His Ile
            230                 235                 240

Ser Leu Thr Asn Val Val Gly His Ser Leu Gly Cys Thr Trp His
            245                 250                 255

Ser Leu Arg Asn Ser Pro Gly Glu Lys Ile Asn Leu Leu Lys Arg
            260                 265                 270

Ser Leu Leu Ser Ile Pro Asn Thr Asp Tyr Ile Gln Leu Leu Ser
            275                 280                 285

Glu Ile Ala Lys Glu Gln Gly Phe Asn Ile Thr Tyr Leu Asp Ile
            290                 295                 300

Asp Glu Leu Ser Ala Asn Gly Gln Tyr Gln Cys Leu Ala Glu Leu
            305                 310                 315

Ser Thr Ser Pro Ile Thr Val Cys His Gly Ser Gly Ile Ser Cys
            320                 325                 330

Gly Asn Ala Gln Ser Asp Ala Ala His Asn Ala Leu Gln Tyr Leu
            335                 340                 345

Lys Ile Ile Ala Glu Arg Lys
            350
```

(2) INFORMATION FOR SEQ ID NO:      47:

(i) SEQUENCE CHARACTERISTICS:
        (A) LENGTH: 432 amino acids
        (B) TYPE: amino acid
        (C) STRANDEDNESS: single
        (D) TOPOLOGY: linear (vii) IMMEDIATE SOURCE:
        (A) LIBRARY: TLYMNOT04
        (B) CLONE: 2926777

(xi) SEQUENCE DESCRIPTION: SEQ ID NO: 47 :

```
Met Ile Ser Ala Ala Gln Leu Leu Asp Glu Leu Met Gly Arg Asp
                  5                  10                  15
Arg Asn Leu Ala Pro Asp Glu Lys Arg Thr Asn Val Arg Trp Asp
                 20                  25                  30
His Glu Ser Val Cys Lys Tyr Tyr Leu Cys Gly Phe Cys Pro Ala
                 35                  40                  45
Glu Leu Phe Thr Asn Thr Arg Ser Asp Leu Gly Pro Cys Glu Lys
                 50                  55                  60
Ile His Asp Glu Asn Leu Arg Lys Gln Tyr Glu Lys Ser Ser Arg
                 65                  70                  75
Phe Met Lys Val Gly Tyr Glu Arg Asp Phe Leu Arg Tyr Leu Gln
                 80                  85                  90
Ser Leu Leu Ala Glu Val Glu Arg Arg Ile Arg Arg Gly His Ala
                 95                 100                 105
Arg Leu Ala Leu Ser Gln Asn Gln Gln Ser Ser Gly Ala Ala Gly
                110                 115                 120
Pro Thr Gly Lys Asn Glu Glu Lys Ile Gln Val Leu Thr Asp Lys
                125                 130                 135
Ile Asp Val Leu Leu Gln Gln Ile Glu Glu Leu Gly Ser Glu Gly
                140                 145                 150
Lys Val Glu Glu Ala Gln Gly Met Met Lys Leu Val Glu Gln Leu
                155                 160                 165
Lys Glu Glu Arg Glu Leu Leu Arg Ser Thr Thr Ser Thr Ile Glu
                170                 175                 180
Ser Phe Ala Ala Gln Glu Lys Gln Met Glu Val Cys Glu Val Cys
                185                 190                 195
Gly Ala Phe Leu Ile Val Gly Asp Ala Gln Ser Arg Val Asp Asp
                200                 205                 210
His Leu Met Gly Lys Gln His Met Gly Tyr Ala Lys Ile Lys Ala
                215                 220                 225
Thr Val Glu Glu Leu Lys Glu Lys Leu Arg Lys Arg Thr Glu Glu
                230                 235                 240
Pro Asp Arg Asp Glu Arg Leu Lys Lys Glu Lys Gln Glu Arg Glu
                245                 250                 255
Glu Arg Glu Lys Glu Arg Glu Arg Glu Glu Arg Glu Arg
                260                 265                 270
Lys Arg Arg Arg Glu Glu Glu Arg Glu Lys Glu Arg Ala Arg
                275                 280                 285
Asp Arg Glu Arg Arg Lys Arg Ser Arg Ser Arg Ser His Ser
                290                 295                 300
Ser Arg Thr Ser Asp Arg Arg Cys Ser Arg Ser Arg Asp His Lys
                305                 310                 315
Arg Ser Arg Ser Arg Glu Arg Arg Thr Arg Ser Arg Asp Arg
                320                 325                 330
Arg Arg Ser Arg Ser His Asp Arg Ser Glu Arg Lys His Arg Ser
                335                 340                 345
Arg Ser Arg Asp Arg Arg Ser Lys Ser Arg Asp Arg Lys Ser
                350                 355                 360
Tyr Lys His Arg Ser Lys Ser Arg Asp Arg Glu Gln Asp Arg Lys
                365                 370                 375
Ser Lys Glu Lys Glu Lys Arg Gly Ser Asp Asp Lys Lys Ser Ser
                380                 385                 390
```

```
Val Lys Ser Gly Ser Arg Glu Lys Gln Ser Glu Asp Thr Asn Thr
            395                 400                 405

Glu Ser Lys Glu Ser Asp Thr Lys Asn Glu Val Asn Gly Thr Ser
            410                 415                 420

Glu Asp Ile Lys Ser Glu Gly Asp Thr Gln Ser Asn
            425                 430
```

(2) INFORMATION FOR SEQ ID NO:    48:

(i) SEQUENCE CHARACTERISTICS:
        (A) LENGTH: 180 amino acids
        (B) TYPE: amino acid
        (C) STRANDEDNESS: single
        (D) TOPOLOGY: linear (vii) IMMEDIATE SOURCE:
        (A) LIBRARY: TESTNOT07
        (B) CLONE: 3217567

(xi) SEQUENCE DESCRIPTION: SEQ ID NO: 48 :

```
Met Ala Ala Ala Glu Glu Asp Gly Gly Pro Glu Gly Pro Asn
            5                   10                  15

Arg Glu Arg Gly Gly Ala Gly Ala Thr Phe Glu Cys Asn Ile Cys
            20                  25                  30

Leu Glu Thr Ala Arg Glu Ala Val Val Ser Val Cys Gly His Leu
            35                  40                  45

Tyr Cys Trp Pro Cys Leu His Gln Trp Leu Glu Thr Arg Pro Glu
            50                  55                  60

Arg Gln Glu Cys Pro Val Cys Lys Ala Gly Ile Ser Arg Glu Lys
            65                  70                  75

Val Val Pro Leu Tyr Gly Arg Gly Ser Gln Lys Pro Gln Asp Pro
            80                  85                  90

Arg Leu Lys Thr Pro Pro Arg Pro Gln Gly Gln Arg Pro Ala Pro
            95                  100                 105

Glu Ser Arg Gly Gly Phe Gln Pro Phe Gly Asp Thr Gly Gly Phe
            110                 115                 120

His Phe Ser Phe Gly Val Gly Ala Phe Pro Phe Gly Phe Phe Thr
            125                 130                 135

Thr Val Phe Asn Ala His Glu Pro Phe Arg Arg Gly Thr Gly Val
            140                 145                 150

Asp Leu Gly Gln Gly His Pro Ala Ser Ser Trp Gln Asp Ser Leu
            155                 160                 165

Phe Leu Phe Leu Ala Ile Phe Phe Phe Phe Trp Leu Leu Ser Ile
            170                 175                 180
```

(2) INFORMATION FOR SEQ ID NO:    49:

(i) SEQUENCE CHARACTERISTICS:
        (A) LENGTH: 137 amino acids
        (B) TYPE: amino acid
        (C) STRANDEDNESS: single
        (D) TOPOLOGY: linear (vii) IMMEDIATE SOURCE:
        (A) LIBRARY: SPLNNOT10
        (B) CLONE: 3339274

(xi) SEQUENCE DESCRIPTION: SEQ ID NO: 49 :

```
Met Ser Ser Leu Ile Arg Arg Val Ile Ser Thr Ala Lys Ala Pro
            5                   10                  15
```

```
Gly Ala Ile Gly Pro Tyr Ser Gln Ala Val Leu Val Asp Arg Thr
             20                  25                  30

Ile Tyr Ile Ser Gly Gln Ile Gly Met Asp Pro Ser Ser Gly Gln
             35                  40                  45

Leu Val Ser Gly Gly Val Ala Glu Glu Ala Lys Gln Ala Leu Lys
             50                  55                  60

Asn Met Gly Glu Ile Leu Lys Ala Ala Gly Cys Asp Phe Thr Asn
             65                  70                  75

Val Val Lys Thr Thr Val Leu Leu Ala Asp Ile Asn Asp Phe Asn
             80                  85                  90

Thr Val Asn Glu Ile Tyr Lys Gln Tyr Phe Lys Ser Asn Phe Pro
             95                 100                 105

Ala Arg Ala Ala Tyr Gln Val Ala Ala Leu Pro Lys Gly Ser Arg
            110                 115                 120

Ile Glu Ile Glu Ala Val Ala Ile Gln Gly Pro Leu Thr Thr Ala
            125                 130                 135

Ser Leu
```

(2) INFORMATION FOR SEQ ID NO: 50:

(i) SEQUENCE CHARACTERISTICS:
      (A) LENGTH: 1600 base pairs
      (B) TYPE: nucleic acid
      (C) STRANDEDNESS: single
      (D) TOPOLOGY: linear (vii) IMMEDIATE SOURCE:
      (A) LIBRARY: U937NOT01
      (B) CLONE: 133

(xi) SEQUENCE DESCRIPTION: SEQ ID NO: 50 :

```
CCCGGGGGCC CGGGCGGCAG GGCAAGCAGC GCGGCCTCGG CCTATGCGAC CGGTGGCGCC    60
GGCGCGGCTT CTGCCTGGAG AGGATTCAAG ATGACCAACG AAGAACCTCT TCCCAAGAAG   120
GTTCGATTGA GTGAAACAGA CTTCAAAGTT ATGGCAAGAG ATGAGTTAAT TCTAAGATGG   180
AAACAATATG AAGCATATGT ACAAGCTTTG GAGGGCAAGT ACACAGATCT TAACTCTAAT   240
GATGTAACTG GCCTAAGAGA GTCTGAAGAA AAACTAAAGC AACAACAGCA GGAGTCTGCA   300
CGCAGGGAAA ACATCCTTGT AATGCGACTA GCAACCAAGG AACAAGAGAT GCAAGAGTGT   360
ACTACTCAAA TCCAGTACCT CAAGCAAGTC CAGCAGCCGA GCGTTGCCCA ACTGAGATCA   420
ACAATGGTAG ACCCAGCGAT CAACTTGTTT TTCCTAAAAA TGAAAGGTGA ACTGGAACAG   480
ACTAAAGACA AACTGGAACA AGCCCAAAAT GAACTGAGTG CCTGGAAGTT TACGCCTGAT   540
AGGTAAACAA ATCATACTCC CCAGTCAAGA CTTCCCTGAC AGTCCCACTA CGAGAAAGCT   600
GTGGTGGGAC AGCCAAGTAC TCGTTTCCAC ACCAAGACTC AGACTTTTTG AGCCAAAAAA   660
AAGCCACATT CTTACACTGT CCAGCTTGTA ATGGTTAATG TAAAACTTAC CAGATGAACC   720
TTGTGTTTCA GCTTTTTTCT TTTCCCCTTC CCCTTGCTTC AGAGGCCTGA TGGCGTCGGA   780
CTATTCCGAA GAAGTGGCCA CCTCCGAAAA ATTCCCCTTC TAGAACATGT AGACACTTGA   840
GAAATGTTTC TGTTTGAAGA AAATAGAGGG AGAAACAGAA GTCTTAAGTC TGTGGCACAC   900
TGTGTCTTCA GACAGTTTGA AGGAATGAAA ACCTAGAGAT TTTAAATCAT GAATTGAACA   960
TGTAAAATTC CAGTAAAATG TAAAAACGGA ATATGCATCG CTCTTAACCT TGAGCATAGT  1020
GACTTAGAGA CACTGTGTAT CAGTTTTGCC AATAAGACTG TGGACTTCAT GATTGTTGTT  1080
GAACTTCTGG GTCAAAACTC AAATGAGGTG AATTTTGCCT TTAAAGGGTT TATTTGCTGA  1140
```

```
GAACCAACTT TCAATAGTCA TGAGAGAATC AAATAATAGA TGTCCGTACA AGTAGCGCAT    1200

ATATTTAACC ATTTAGTTTG GGGCTCTATA TTACTTGCTT GAGCCTTAAT CAATGTGGTT    1260

TTATTCAATG GTTTGTTCTT TGAATGGTTG CAAAAACTGT AGATAATCTT ACTGAGGACT    1320

GTACAAACAT GAAGGTGTGG TATCAAACTT CAGGTTGAAA CTGTTTGAAG CATTATAAAC    1380

ATTCATTTCA CAACTAGATT GTATAAGGAT ATTAGCTGTG ATGAGACTCA CTGCATTATT    1440

TTTTTTAGTG AATTTTATGA AATCCCCGTT CCATTCAACA GGCACATGTT TAAAAGAGCT    1500

TTGTCGTTGG TGTTAATGGG GGAATGTGTT CCTTCATTGT ATTTGGGCCT TTTGTATTGC    1560

ACTCTTGATA TTAAATTAAA TGTGCCTTGA AAAAAAAAA                           1600
```

(2) INFORMATION FOR SEQ ID NO:   51:

(i) SEQUENCE CHARACTERISTICS:
        (A) LENGTH: 1033 base pairs
        (B) TYPE: nucleic acid
        (C) STRANDEDNESS: single
        (D) TOPOLOGY: linear (vii) IMMEDIATE SOURCE:
        (A) LIBRARY: U937NOT01
        (B) CLONE: 1762

(xi) SEQUENCE DESCRIPTION: SEQ ID NO: 51 :

```
GCCGCCGGGA GCCGGTGCGG CTGTGAGGGG CCGCGTCTCG CAGCAGCCGC CCGGACCGGC      60

ATGGTGTTGG GCGCCGGGCC CGCCTCGCCT GTCTCGGGGA GCCCAGGGTA AAGGCAGCAG     120

TAATGCTAAC GCTAGCAAGT AAACTGAAGC GTGACGATGG TCTCAAAGGG TCCCGGACGG     180

CAGCCACAGC GTCCGACTCG ACTCGGAGGG TTTCTGTGAG AGACAAATTG CTTGTTAAAG     240

AGGTTGCAGA ACTTGAAGCT AATTTACCTT GTACATGTAA AGTGCATTTT CCTGATCCAA     300

ACAAGCTTCA TTGTTTTCAG CTAACAGTAA CCCCAGATGA GGGTTACTAC CAGGGTGGAA     360

AATTTCAGTT TGAAACTGAA GTTCCCGATG CGTACAACAT GGTGCCTCCC AAAGTGAAAT     420

GCCTGACCAA GATCTGGCAC CCCAACATCA CAGAGACAGG GGAAATATGT CTGAGTTTAT     480

TGAGAGAACA TTCAATTGAT GGCACTGGCT GGGCTCCCAC AAGAACATTA AAGGATGTCG     540

TTTGGGGATT AAACTCTTTG TTTACTGATC TTTTGAATTT TGATGATCCA CTGAATATTG     600

AAGCTGCAGA ACATCATTTG CGGGACAAGG AGGACTTCCG GAATAAAGTG GATGACTACA     660

TCAAACGTTA TGCCAGATGA TAAAAGGGGA CGATTGCAGG CCCATGGACT GTGTTACAGT     720

TTGTCTCTAA CATGAAACAG CAAGAGGTAG CCCCCTCTCC CGTCCTCATG CTCCCTCTCA     780

GTCCCCTGGA TTGCCCCAGT CCTGTGACCA TGTTGCCCTG AAGAAGACCA TCTTCATGAC     840

TGCTCATTGT AGATGGAGAA TTCAACATAA ATACAGCAAG AAAATGTGTT TGGGCTTCTG     900

AAGAGTTGTC TGCTTACCTT AACATGTTTA CTTTTTTGAA CTTGTACTGT ATAGGCTGTT     960

GGTGAAATTC TTAAGAAGTT GTAATGAACT CAAAATTGAG GCCAGAGCTT GCTTTCCCTT    1020

TTCCCAAACA AAA                                                      1033
```

(2) INFORMATION FOR SEQ ID NO:   52:

(i) SEQUENCE CHARACTERISTICS:
        (A) LENGTH: 1837 base pairs
        (B) TYPE: nucleic acid
        (C) STRANDEDNESS: single
        (D) TOPOLOGY: linear (vii) IMMEDIATE SOURCE:
        (A) LIBRARY: U937NOT01
        (B) CLONE: 1847

(xi) SEQUENCE DESCRIPTION: SEQ ID NO: 52 :

```
TCGGAGAGGC ATCTGGGTTC GGACTGGGGC CGCCATGGGG AAAGTGAATG TGGCCAAGTT      60
GCGTTACATG AGCCGAGATG ACTTCAGGGT CTTGACCGCG GTTGAAATGG GCATGAAGAA     120
CCATGAAATT GTTCCCGGCA GTTTGATTGC TTCTATAGCC AGCCTTAAAC ATGGTGGCTG     180
TAATAAAGTT TTAAGAGAAT TAGTGAAACA TAAACTCATA GCTTGGGAGC GTACCAAAAC     240
TGTCCAGGGC TATCGGTTGA CAAATGCAGG ATATGATTAC CTAGCTTTGA AAACACTTTC     300
TTCTAGGCAA GTAGTTGAGT CTGTTGGAAA CCAGATGGGT GTTGGCAAAG AATCAGATAT     360
TTACATTGTT GCAAATGAAG AAGGACAACA ATTTGCATTA AAGCTTCACA GACTAGGAAG     420
AACCTCGTTT CGAAATTTGA AAAACAAACG CGATTATCAT AAACATAGGC ACAATGTGTC     480
TTGGCTTTAT TTATCTCGTC TCTCTGCCAT GAAGGAATTT GCCTATATGA AGGCATTGTA     540
TGAGAGGAAA TTTCCAGTTC AAAGCCAAT TGATTACAAT CGTCATGCAG TGGTCATGGA      600
ACTCATAAAT GGTTATCCAC TATGTCAGAT ACACCATGTT GAAGATCCTG CATCAGTATA     660
TGATGAAGCT ATGGAACTAA TTGTCAAACT TGCAAATCAT GGGCTGATTC ATGGAGATTT     720
TAATGAATTT AATCTCATTT TGGATGAAAG TGACCATATC ACCATGATTG ATTTTCCACA     780
GATGGTTTCA ACTTCTCATC CCAATGCTGA GTGGTATTTT GACAGAGATG TTAAATGCAT     840
TAAAGATTTC TTTATGAAAC GTTTCAGCTA CGAAAGTGAG CTTTTTCCAA CTTTTAAGGA     900
TATCAGGAGA GAAGACACTC TTGATGTGGA GGTTTCTGCC AGTGGCTACA CAAAGGAAAT     960
GCAGGCAGAT GATGAACTGC TTCATCCATT AGGTCCAGAT GATAAAAATA TTGAAACAAA    1020
AGAGGGATCT GAATTCTCAT TTTCAGATGG AGAAGTGGCA GAAAAAGCAG AGGTTTACGG    1080
GTCAGAAAAT GAAAGTGAAC GGAACTGTCT AGAAGAATCA GAGGGCTGCT ATTGCAGATC    1140
ATCTGGAGAC CCTGAACAAA TAAAGGAAGA CAGTTTATCA GAAGAGAGTG CTGATGCACG    1200
GAGTTTTGAA ATGACTGAAT TCAATCAAGC TTTAGAAGAA ATAAAAGGGC AGGTTGTTGA    1260
AAACAACTCT GTAACTGAAT TTTCTGAGGA GAAAAACAGA ACTGAAAATT ACAACAGGCA    1320
AGATGGTCAG AGAGTTCAAG GAGGAGTCCC TGCTGGCTCT GACGAGTATG AAGATGAATG    1380
CCCTCATCTA ATTGCCTTGT CGTCATTAAA TAGAGAATTC AGGCCTTTCA GAGATGAAGA    1440
AAATGTGGGA GCTATGAATC AGTATAGAAC AAGAACTCTG AGTATCACTT CTTCAGGCAG    1500
TGCTGTAAGC TGTTCAACAA TTCCTCCAGA ACTGGTGAAA CAGAAGGTGA AACGTCAGTT    1560
GACAAAACAG CAAAAATCAG CTGTCAGACG TCGATTGCAG AAAGGAGAAG CAAATATATT    1620
TACCAAGCAA CGTAGGGAAA ACATGCAAAA TATCAAATCA AGTTTGGAAG CAGCTAGCTT    1680
TTGGGGAGAA TAATATATTT AGGATCTTGG ATATGTTTAA TATATTTTTT AAAGTTACTG    1740
TAATTCCTTT TTGAGCCCTC ATTTGTCTTT TTTGAGCCAA GGCTATCATA TATTAATAAA    1800
TAAACCCTCC TTTCATCTAT AAAAAAAAAA AAAAAAA                             1837
```

(2) INFORMATION FOR SEQ ID NO: 53:

(i) SEQUENCE CHARACTERISTICS:
        (A) LENGTH: 2031 base pairs
        (B) TYPE: nucleic acid
        (C) STRANDEDNESS: single
        (D) TOPOLOGY: linear (vii) IMMEDIATE SOURCE:
        (A) LIBRARY: HMC1NOT01
        (B) CLONE: 9337

(xi) SEQUENCE DESCRIPTION: SEQ ID NO: 53 :

```
CGCGCCGGGA CTCTGCCCAC TTCCACCAGA GACACATTGA GAAGGAGGAA ACTATGGCCT      60

CCAGGCTTCC GACGGCCTGG TCCTGTGAAC CAGTGACCTT TGAAGATGTA ACACTGGGTT     120

TTACCCCGGA AGAGTGGGGA CTGCTGGACC TCAAACAGAA GTCCCTGTAC AGGGAAGTGA     180

TGCTGGAGAA CTACAGGAAC CTGGTCTCAG TGGAACATCA GCTTTCCAAA CCAGATGTGG     240

TATCTCAGTT AGAGGAGGCA GAAGATTTCT GGCCAGTGGA GAGAGGAATT CCTCAAGACA     300

CCATTCCAGA GTATCCTGAG CTCCAGCTGG ACCCTAAATT GGATCCTCTT CCTGCTGAGA     360

GTCCCCTAAT GAACATTGAG GTTGTTGAGG TCCTCACACT GAACCAGGAG GTGGCTGGTC     420

CCCGGAATGC CCAGATCCAG GCCCTATATG CTGAAGATGG AAGCCTGAGT GCAGATGCCC     480

CCAGTGAGCA GGTCCAACAG CAGGGCAAGC ATCCAGGTGA CCCTGAGGCC GCGCGCCAGA     540

GGTTCCGGCA GTTCCGTTAT AAGGACATGA CAGGTCCCCG GGAGGCCCTG GACCAGCTCC     600

GAGAGCTGTG TCACCAGTGG CTACAGCCTA AGGCACGCTC CAAGGAGCAG ATCCTGGAGC     660

TGCTGGTGCT GGAGCAGTTC CTAGGTGCAC TGCCTGTGAA GCTCCGGACA TGGGTGGAAT     720

CGCAGCACCC AGAGAACTGC CAAGAGGTGG TGGCCCTGGT AGAGGGTGTG ACCTGGATGT     780

CTGAGGAGGA AGTACTTCCT GGCAGGACAA CCTGCCGAGG GCACCACCTG CTGCCTCGAG     840

GTCACTGCCC AGCAGGAGGA GAAGCAGGAG GATGCAGCCA TCTGCCCAGT GACAGTGCTC     900

CCTGAGGAGC CAGTGACCTT CCAGGATGTG GCTGTGGACT TCAGCCGGGA GGAGTGGGGG     960

CTGCTGGGCC CGACACAGAG GACCGAGTAC CGCGATGTGA TGCTGGAGAC CTTTGGGCAC    1020

CTGGTCTCTG TGGGGTGGGA GACTACACTG GAAAATAAAG AGTTAGCTCC AAATTCTGAC    1080

ATTCCTGAGG AAGAACCAGC CCCCAGCCTG AAAGTACAAG AATCCTCAAG GGATTGTGCC    1140

TTGTCCTCTA CATTAGAAGA TACCTTGCAG GGTGGGGTCC AGGAAGTCCA AGACACAGTG    1200

TTGAAGCAGA TGGAGTCTGC TCAGGAAAAA GACCTTCCTC AGAAGAAGCA CTTTGACAAC    1260

CGTGAGTCCC AGGCAAACAG TGGTGCTCTT GACACAAACC AAGTTTCGCT CCAGAAAATT    1320

GACAACCCTG AGTCCCAGGC AAACAGTGGC GCTCTTGACA CAAACCAAGT TTTGCTCCAC    1380

AAAATTCCTC CTAGAAAACG ATTGCGCAAA CGTGACTCAC AAGTTAAAAG TATGAAACAT    1440

AATTCACGTG TAAAAATTCA TCAGAAGAGC TGTGAAAGGC AAAAGGCCAA GGAAGGCAAT    1500

GGTTGTAGGA AAACCTTCAG TCGGAGTACT AAACAGATTA CGTTTATAAG AATTCACAAG    1560

GGGAGCCAAG TTTGCCGATG CAGTGAATGT GGTAAAATAT TCCGGAACCC AAGATACTTT    1620

TCTGTGCATA AGAAAATCCA TACCGGAGAG AGGCCCTATG TGTGTCAAGA CTGTGGGAAA    1680

GGATTTGTTC AGAGCTCTTC CCTCACACAG CATCAGAGAG TTCATTCTGG AGAGAGACCA    1740

TTTGAATGTC AGGAGTGTGG GAGGACCTTC AATGATCGCT CAGCCATCTC CCAGCACCTG    1800

AGGACTCACA CTGGCGCTAA GCCCTACAAG TGTCAGGACT GTGGAAAAGC CTTCCGCCAG    1860

AGCTCCCACC TCATCAGACA TCAGAGGACT CACACCGGGG AGCGCCCATA TGCATGCAAC    1920

AAATGTGGAA AGGCCTTCAC CCAGAGCTCA CACCTTATTG GGCACCAGAG AACCCACAAT    1980

AGGACAAAGC GAAAGAAGAA ACAGCCTACC TCATAGCTCT CAAGCCAGTT G             2031
```

(2) INFORMATION FOR SEQ ID NO: 54:

(i) SEQUENCE CHARACTERISTICS:
        (A) LENGTH: 1750 base pairs
        (B) TYPE: nucleic acid
        (C) STRANDEDNESS: single
        (D) TOPOLOGY: linear (vii) IMMEDIATE SOURCE:

(A) LIBRARY: HMC1NOT01
        (B) CLONE: 9476

(xi) SEQUENCE DESCRIPTION: SEQ ID NO: 54 :

GCCGCATGGT AACTCAGGCG CCGGGCGCAC TGTCCTAGCT GCTGGTTTTC CACGCTGGTT      60

TTAGCTCCCG GCGTCTGCAA AATGAAGATT GAGGAGGTGA AGAGCACTAC GAAGACGCAG     120

CGCATCGCCT CCCACAGCCA CGTGAAAGGG CTGGGGCTGG ACGAGAGCGG CTTGGCCAAG     180

CAGGCGGCCT CAGGGCTTGT GGGCCAGGAG AACGCGCGAG AGGCATGTGG CGTCATAGTA     240

GAATTAATCG AAAGCAAGAA AATGGCTGGA AGAGCTGTCT TGTTGGCAGG ACCTCCTGGA     300

ACTGGCAAGA CAGCTCTGGC TCTGGCTATT GCTCAGGAGC TGGGTAGTAA GGTCCCCTTC     360

TGCCCAATGG TGGGGAGTGA AGTTTACTCA ACTGAGATCA AGAAGACAGA GGTGCTGATG     420

GAGAACTTCC GCAGGGCCAT TGGGCTGCGA ATAAAGGAGA CCAAGGAAGT TTATGAAGGT     480

GAAGTCACAG AGCTAACTCC GTGTGAGACA GAGAATCCCA TGGAGGATA TGGCAAAACC     540

ATTAGCCATG TGATCATAGG ACTCAAAACA GCCAAAGGAA CCAAACAGTT GAAACTGGAC     600

CCCAGCATTT TTGAAAGTTT GCAGAAAGAG CGAGTAGAAG CTGGAGATGT GATTTACATT     660

GAAGCCAACA GTGGGGCCGT GAAGAGGCAG GGCAGGTGTG ATACCTATGC CACAGAATTC     720

GACCTTGAAG CTGAAGAGTA TGTCCCCTTG CCAAAAGGGG ATGTGCACAA AAAGAAAGAA     780

ATCATCCAAG ATGTGACCTT GCATGACTTG GATGTGGCTA ATGCGCGGCC CCAGGGGGGA     840

CAAGATATCC TGTCCATGAT GGGCCAGCTA ATGAAGCCAA AGAAGACAGA AATCACAGAC     900

AAACTTCGAG GGGAGATTAA TAAGGTGGTG AACAAGTACA TCGACCAGGG CATTGCTGAG     960

CTGGTCCCGG GTGTGCTGTT TGTTGATGAG GTCCACATGC TGGACATTGA GTGCTTCACC    1020

TACCTGCACC GCGCCCTGGA GTCTTCTATC GCTCCCATCG TCATCTTTGC ATCCAACCGA    1080

GGCAACTGTG TCATCAGAGG CACTGAGGAC ATCACATCCC CTCACGGCAT CCCTCTTGAC    1140

CTTCTGGACC GAGTGATGAT AATCCGGACC ATGCTGTATA CTCCACAGGA AATGAAACAG    1200

ATCATTAAAA TCCGTGCCCA GACGGAAGGA ATCAACATCA GTGAGGAGGC ACTGAACCAC    1260

CTGGGGGAGA TTGGCACCAA GACCACACTG AGGTACTCAG TGCAGCTGCT GACCCCGGCC    1320

AACTTGCTTG CTAAAATCAA CGGGAAGGAC AGCATTGAGA AAGAGCATGT CGAAGAGATC    1380

AGTGAACTTT TCTATGATGC CAAGTCCTCC GCCAAAATCC TGGCTGACCA GCAGGATAAG    1440

TACATGAAGT GAGATGGCTG AGGTTTTCAG CAGTAAGAGA CTCCCCAGGT GTGCCTGGCC    1500

TGGGTCCAGC CTGTGGGCGC TTGCCCCTGG GCTTGGGGCT GCCGTCCCCA CTCAGGCGTG    1560

GTCTGCAGCG CTGTCAGTTC AGTGTGGAAA GCATTTCTTT TTAAGTTATC GTAACTGTTC    1620

CTGTGGTTGC TTTGAAAGAA CCCTTCCTTA CCTGGTGTGT TTTCTATAAA TCTTCATAGG    1680

TTATTTTGAT TCTCTCTCTC TCTCTCTCTA AGTTTTTTAA AATAAACTT TTCAGAACAG    1740

AAAAAAAAAA                                                          1750

(2) INFORMATION FOR SEQ ID NO:   55:

(i) SEQUENCE CHARACTERISTICS:
        (A) LENGTH: 1234 base pairs
        (B) TYPE: nucleic acid
        (C) STRANDEDNESS: single
        (D) TOPOLOGY: linear (vii) IMMEDIATE SOURCE:
        (A) LIBRARY: THP1PLB01
        (B) CLONE: 10370

(xi) SEQUENCE DESCRIPTION: SEQ ID NO: 55 :

```
GGGCGGGGCC GGTCGGTGAG TCAGCGGCTC TCTGATCCAG CCCGGGAGAG GACCGAGCTG      60

GAGGAGCTGG GTGTGGGGTG CGTTGGGCTG GTGGGAGGC CTAGTTTGGG TGCAAGTAGG      120

TCTGATTGAG CTTGTGTTGT GCTGAAGGGA CAGCCCTGGG TCTAGGGGAG AGAGTCCCTG     180

AGTGTGAGAC CCGCCTTCCC CGGTCCCAGC CCCTCCCAGT TCCCCCAGGG ACGGCCACTT    240

CCTGGTCCCC GACGCAACCA TGGCTGAAGA ACAACCGCAG GTCGAATTGT TCGTGAAGGC    300

TGGCAGTGAT GGGGCCAAGA TTGGGAACTG CCCATTCTCC CAGAGACTGT TCATGGTACT   360

GTGGCTCAAG GGAGTCACCT TCAATGTTAC CACCGTTGAC ACCAAAAGGC GGACCGAGAC   420

AGTGCAGAAG CTGTGCCCAG GGGGGCAGCT CCCATTCCTG CTGTATGGCA CTGAAGTGCA   480

CACAGACACC AACAAGATTG AGGAATTTCT GGAGGCAGTG CTGTGCCCTC CCAGGTACCC   540

CAAGCTGGCA GCTCTGAACC CTGAGTCCAA CACAGCTGGG CTGGACATAT TTGCCAAATT   600

TTCTGCCTAC ATCAAGAATT CAAACCCAGC ACTCAATGAC AATCTGGAGA AGGGACTCCT   660

GAAAGCCCTG AAGGTTTTAG ACAATTACTT AACATCCCCC CTCCCAGAAG AAGTGGATGA   720

AACCAGTGCT GAAGATGAAG GTGTCTCTCA GAGGAAGTTT TTGGATGGCA ACGAGCTCAC   780

CCTGGCTGAC TGCAACCTGT TGCCAAAGTT ACACATAGTA CAGGTGGTGT GTAAGAAGTA   840

CCGGGGATTC ACCATCCCCG AGGCCTTCCG GGGAGTGCAT CGGTACTTGA GCAATGCCTA   900

CGCCCGGGAA GAATTCGCTT CCACCTGTCC AGATGATGAG GAGATCGAGC TCGCCTATGA   960

GCAAGTGGCA AAGGCCCTCA ATAAGCCCC TCCTGGGACT CCCTCAACCC CCTCCATTTT   1020

CTCCACAAAG GCCCTGGTGG TTTCCACATT GCTACCCAAT GGACACACTC CAAAATGGCC   1080

AGTGGGCAGG GAATCCTGGA GCACTTGTTC CGGGATGGTG TGGTGGAAGA GGGGATGAGG   1140

GAAAGAAATG GGGGGCCTGG GTCAGATTTT TATTGTGGGG TGGGATGAGT AGGACAACAT   1200

ATTTCAGTAA TAAATACAG AATAAAAAAA AAAA                                1234

(2) INFORMATION FOR SEQ ID NO:   56:

(i) SEQUENCE CHARACTERISTICS:
        (A) LENGTH: 872 base pairs
        (B) TYPE: nucleic acid
        (C) STRANDEDNESS: single
        (D) TOPOLOGY: linear (vii) IMMEDIATE SOURCE:
        (A) LIBRARY: THP1NOB01
        (B) CLONE: 30137

(xi) SEQUENCE DESCRIPTION: SEQ ID NO: 56 :

CACGCGTGCT GTCGGGGAG GGATGCTGGG ACAGCTGCTC CCGCACACGG CTCGCGGTCT      60

CGGCGCCGCG GAGATGCCCG CCAGGGTCC GGGGTCCGAC TGGACGGAGC GTAGCTCTTC     120

TGCAGAGCCG CCCGCTGTGG CCGGGACCGA GGGTGGCGGC GGCGGATCAG CTGGATACTC    180

TTGTTACCAG AATTCCAAAG GTTCTGATAG AATCAAAGAT GGATACAAAG TGAACTCACA   240

CATAGCTAAG CTGCAAGAGT TATGGAAAAC TCCCCAAAAT CAAACAATCC ACCTCTCTAA   300

ATCAATGATG GAGGCGTCCT TTTTCAAGCA TCCAGACCTC ACCACAGGCC AGAAGCGTTA   360

CCTGTGCAGC ATTGCTAAAA TCTATAATGC AAACTATCTG AAGATGTTAA TGAAGAGGCA   420

GTACATGCAC GTACTTCAGC ACAGCTCACA AAAGCCAGGT GTCCTCACTC ATCACAGAAG   480

CCGCCTTAGC TCCCGTTACT CACAGAAACA GCATTACCCT TGCACTACAT GGCGACATCA   540

ACTGGAGAGA GAGGACTCGG GGTCTTCTGA TATCGCAGCT GCATCTGCAC CTGAAATGCT   600

CATACAGCAT TCCCTTTGGC GGCCAGTGAG AAACAAAGAA GGGATAAAAA CTGGATATGC   660
```

```
ATCTAAAACA AGATGTAAGT CACTGAAGAT TTTTAGAAGA CCAAGGAAAC TGTTCATGCA      720

AACAGTTTCT TCAGATGATT CTGAATCACA CATGAGTGGA GAAAAAAAGG GAAGAGGATT      780

TACTACATAA TTTTATGCAA TCCATGTCAA TTGAGGACAA GGGGGACATC TGATGTTNAC      840

TTGACAGTCT TGTCTCGTGT ATTGAATTCG TG                                    872

(2) INFORMATION FOR SEQ ID NO:    57:

(i) SEQUENCE CHARACTERISTICS:
         (A) LENGTH: 691 base pairs
         (B) TYPE: nucleic acid
         (C) STRANDEDNESS: single
         (D) TOPOLOGY: linear (vii) IMMEDIATE SOURCE:
         (A) LIBRARY: SYNORAB01
         (B) CLONE: 77180

(xi) SEQUENCE DESCRIPTION: SEQ ID NO: 57 :

GGGAAAATGG CGCTGGCCAT GCTGGTCTTG GTGGTTTCGC CGTGGTCTGC GGCCCGGGGA       60

GTGCTTCGAA ACTACTGGGA GCGACTGCTA CGGAAGCTTC CGCAGAGCCG GCCGGGCTTT      120

CCCAGTCCTC CGTGGGGACC AGCATTAGCA GTACAGGGCC CAGCCATGTT TACAGAGCCA      180

GCAAATGATA CCAGTGGAAG TAAAGAGAAT TCCAGCCTTT TGGACAGTAT CTTTTGGATG      240

GCAGCTCCCA AAAATAGACG CACCATTGAA GTTAACCGGT GTAGGAGAAG AAATCCGCAG      300

AAGCTTATTA AAGTTAAGAA CAACATAGAC GTTTGTCCTG AATGTGGTCA CCTGAAACAG      360

AAACATGTCC TTTGTGCCTA CTGCTATGAA AAGGTGTGCA AGGAGACTGC AGAAATCAGA      420

CGACAGATAG GGAAGCAAGA AGGGGGCCCT TTTAAGGCTC CCACCATAGA GACTGTGGTG      480

CTGTACACAG GAGAGACACC GTCTGAACAA GATCAGGGCA AGAGGATCAT TGAACGAGAC      540

AGAAAGCGAC CATCCTGGTT CACCCAGAAT TGACACCAAA GATGTTAAAA GGATAACTTC      600

ACAGTAAATC ATTTCTCCTG AAATAGAGGA AGATTCTTTA CGTTGTTGTG CTTGTTTTTA      660

AATCATCAGT ATAGTTTAAC ACATTCTTTC T                                    691

(2) INFORMATION FOR SEQ ID NO:    58:

(i) SEQUENCE CHARACTERISTICS:
         (A) LENGTH: 1994 base pairs
         (B) TYPE: nucleic acid
         (C) STRANDEDNESS: single
         (D) TOPOLOGY: linear (vii) IMMEDIATE SOURCE:
         (A) LIBRARY: PITUNOR01
         (B) CLONE: 98974

(xi) SEQUENCE DESCRIPTION: SEQ ID NO: 58 :

CGGCTCGAGG CGTCTTGGCG GCAGTTGGTG GAACCGGAGC TTCGAGTCCG TCCCCGGTGC       60

TGCCTGCGCG TTCACCTGAG TCTCGCTGGA GCTCTTCTCG CCCGCCCACC TCATCTCAAC      120

CCACTTTCCG CGGGGAGCGG CGCCAAGCTG GGCCTTCCTC GGATCAGGCG TCCCCTGAAG      180

TCGGCACGCC CCTCTGCGTC CCCCTTCGGT CCCGCTAGGA CCCCGTCCGG GCTGCCGTCG      240

CCTCGTCGCT ATGGCGCCCA CCATCCAGAC CCAGGCCCAG CGGGAGGATG GCACAGGCC       300

CAATTCCCAC CGGACTCTGC CTGAGAGGTC TGGAGTGGTC TGCCGAGTCA AGTACTGCAA      360

TAGCCTCCCT GATATCCCCT TCGACCCCAA GTTCATCACC TACCCCTTCG ACCAGAACAG      420

GTTCGTCCAG TACAAAGCCA CTTCCTTGGA GAAACAGCAC AAACATGACC TCCTGACTGA      480
```

```
GCCAGACCTG GGGGTCACCA TCGATCTCAT CAATCCTGAC ACCTACCGCA TCGACCCCAA      540

TGTTCTTCTA GATCCAGCTG ATGAGAAACT TTTGGAAGAG GAGATTCAGG CCCCCACCAG      600

CTCCAAGAGA TCCCAGCAGC ATGCGAAGGT GGTGCCATGG ATGCGAAAGA CAGAGTACAT      660

CTCCACTGAG TTCAACCGTT ATGGCATCTC CAATGAGAAG CCTGAGGTCA AGATTGGGGT      720

TTCTGTGAAG CAGCAGTTTA CCGAGGAAGA AATATACAAA GACAGGGATA GCCAGATCAC      780

AGCCATTGAG AAGACTTTTG AGGATGCCCA GAAATCAATC TCACAGCATT ACAGCAAACC      840

CCGAGTCACA CCGGTGGAGG TCATGCCTGT CTTCCCAGAC TTTAAGATGT GGATCAATCC      900

ATGTGCTCAG GTGATCTTTG ACTCAGACCC AGCCCCCAAG GACACGAGTG GTGCAGCTGC      960

GTTGGAGATG ATGTCTCAGG CCATGATTAG GGGCATGATG GATGAGGAAG GAACCAGTT     1020

TGTGGCCTAT TTCCTGCCTG TAGAAGAGAC GTTGAAGAAA CGAAAGCGGG ACCAGGAGGA     1080

GGAGATGGAC TATGCACCAG ATGATGTGTA TGACTACAAA ATTGCTCGGG AGTACAACTG     1140

GAACGTGAAG AACAAAGCTA GCAAGGGCTA TGAGGAAAAC TACTTCTTCA TCTTCCGAGA     1200

GGGTGACGGG GTTTACTACA ATGAGTTGGA ACCAGGGTC CGCCTTAGTA AGCGCCGGGC     1260

CAAGGCTGGG GTTCAGTCAG GCACCAACGC CCTGCTTGTG GTCAAACATC GGGACATGAA     1320

TGAGAAGGAA CTGGAAGCTC AGGAGGCACG GAAGGCCCAG CTAGAAAACC ACGAACCGGA     1380

GGAGGAAGAG GAAGAGGAGA TGGAGACAGA AGAGAAAGAA GCTGGGGGCT CAGATGAGGA     1440

GCAGGAGAAG GGCAGCAGCA GTGAGAAGGA GGGCAGTGAA GATGAGCACT CGGGCAGCGA     1500

GAGTGAACGG GAGGAAGGTG ACAGGGACGA GGCCAGTGAC AAGAGTGGCA GTGGTGAGGA     1560

CGAGAGCAGC GAGGATGAGG CCCGGGCTGC CCGTGACAAA GAGGAGATCT TTGGCAGTGA     1620

TGCTGATTCT GAGGACGATG CCGACTCTGA TGATGAGGAC AGAGGACAGG CCCAAGGTGG     1680

CAGTGACAAT GATTCAGACA GCGGCAGCAA TGGGGGTGGC CAGCGGAGCC GGAGCCACAG     1740

CCGCAGCGCC AGTCCCTTCC CCAGTGGCAG CGAGCACTCG GCCCAGGAGG ATGGCAGTGA     1800

AGCTGCAGCT TCTGATTCCA GTGAAGCTGA TAGTGACAGT GACTGAGTCC CAGGGCATTC     1860

AGGGCTGGTT CAGACACCAT TATTGTGAGC AGCAAAGCAC TTTTCTAGTG GTCTGTTTGT     1920

GAGCCTTTCA CTTGTTTGTT CCCCACCCCC AAACCTTTGC TGTTAATAAA GTCAACTTCT     1980

CTTTAAAAAA AAAA                                                      1994

(2) INFORMATION FOR SEQ ID NO:   59:

(i) SEQUENCE CHARACTERISTICS:
        (A) LENGTH: 1594 base pairs
        (B) TYPE: nucleic acid
        (C) STRANDEDNESS: single
        (D) TOPOLOGY: linear (vii) IMMEDIATE SOURCE:
         (A) LIBRARY: MUSCNOT01
         (B) CLONE: 118160

(xi) SEQUENCE DESCRIPTION: SEQ ID NO: 59 :

CCGCCCCCGC CGGGCGTGTG TGTCGTGTGT GTTTGGGGCC CGCGCGGGTT GCGCGCCCTC       60

CGCCTTCGCG CCTCCTGCCC CCGAGGCCCT ACTGCTGCCC CTGTGCCCCT CGCCCCGCCG      120

GGCGTCGCGG GCCAACATGG GCCAGGAAGA GGAGCTGCTG AGGATCGCCA AAAAGCTGGA      180

GAAGATGGTG GCCAGGAAGA ACACGGAAGG GGCCCTGGAC CTTCTGAAGA AGCTGCACAG      240

CTGCCAGATG TCCATCCAGC TACTACGAC AACCAGGATT GGAGTTGCTG TTAATGGGGT      300

CCGCAAGCAC TGCTCAGACA AGGAGGTGGT GTCCTTGGCC AAAGTCCTTA TCAAAAACTG      360
```

```
GAAGCGGCTG CTAGACTCCC CTGGACCCCC AAAAGGAGAA AAAGGAGAGG AAAGAGAAAA      420

GGCAAAGAAG AAGGAAAAAG GGCTTGAGTG TTCAGACTGG AAGCCAGAAG CAGGCCTTTC      480

TCCACCAAGG AAAAAACGAG AAGACCCCAA AACCAGGAGA GACTCTGTGG ACTCCAAGTC      540

TTCTGCCTCC TCCTCTCCAA AAAGACCATC GGTGGAAAGA TCAAACAGCA GCAAATCAAA      600

AGCGGAGAGC CCCAAAACAC CTAGCAGCCC CTTGACCCCC ACGTTTGCCT CTTCCATGTG      660

TCTCCTGGCC CCCTGCTATC TCACAGGGGA CTCTGTCCGG GACAAGTGTG TGGAGATGCT      720

GTCAGCAGCC CTGAAGGCGG ACGATGATTA CAAGGACTAT GGAGTCAACT GTGACAAGAT      780

GGCATCAGAA ATCGAAGATC ATATCTACCA AGAGCTCAAG AGCACGGACA TGAAGTACCG      840

GAACCGCGTG CGCAGCCGCA TAAGCAACCT CAAGGACCCC AGGAACCCCG GCCTGCGGCG      900

GAACGTGCTC AGTGGGGCCA TCTCCGCAGG GCTTATAGCC AAGATGACGG CAGAGGAAAT      960

GGCCAGTGAT GAACTGAGGG AGTTGAGGAA TGCCATGACC CAGGAGGCCA TCCGTGAGCA     1020

CCAGATGGCC AAGACTGGCG GCACCACCAC TGACCTCTTC CAGTGCAGCA AATGCAAGAA     1080

GAAGAACTGC ACCTATAACC AGGTGCAGAC ACGCAGTGCT GATGAGCCCA TGACTACCTT     1140

TGTCTTATGC AATGAATGTG GCAATCGCTG GAAGTTCTGC TGATGGAACA GCCAGCCATG     1200

AACAAGGTGA GGAAGAAGAA AGAGGAAGCG CTGAATTATC TGAACTGGAG AAGCAATAAA     1260

AATTAAAGTG AAGGAAAATA CTGAACTCTG TCTGAGTGGG ATGGTATGAG TTAGAGGAAG     1320

AATTCTCTTG CAAATTAATA ATCGGTCATT AGAAACAATT GGTTAATGGG GGAGCCTAAT     1380

TGGAGAATGA TGCTGAGAAT TTGTATTGAT GAACCTCTTT TAGAAACTGC AGAGGGCTGG     1440

GCACGGTGGC TTATGGCTGT AATCTGCAAA CTCTGGGAGG CTGAGGTGGG AGAATCGCTT     1500

AACCCCAGAA GTTTGAGTCC AGCCCAGGCA ACACAGCAAG ACCCCATCTC TATAAAAGA     1560

AAAAATAAAG AAATTGTAGA CGCCTCGGGG ACAT                                 1594
```

(2) INFORMATION FOR SEQ ID NO:    60:

(i) SEQUENCE CHARACTERISTICS:
        (A) LENGTH: 1460 base pairs
        (B) TYPE: nucleic acid
        (C) STRANDEDNESS: single
        (D) TOPOLOGY: linear (vii) IMMEDIATE SOURCE:
        (A) LIBRARY: TLYMNOR01
        (B) CLONE: 140516

(xi) SEQUENCE DESCRIPTION: SEQ ID NO: 60 :

```
GGCCGTCCGG CCTCCCTGAC ATGCAGATTT CCACCCAGAA GACAGAGAAG GAGCCAGTGG       60

TCATGGAATG GGCTGGGGTC AAAGACTGGG TGCCTGGGAG CTGAGGTAGC CACCGTTTCA      120

GCCTGGCCAG CCCTCTGGAC CCCGAGGTTG GACCCTACTG TGACACACCT ACCATGCGGA      180

CACTCTTCAA CCTCCTCTGG CTTGCCCTGG CCTGCAGCCC TGTTCACACT ACCCTGTCAA      240

AGTCAGATGC CAAAAAAGCC GCCTCAAAGA CGCTGCTGGA GAAGAGTCAG TTTTCAGATA      300

AGCCGGTGCA AGACCGGGGT TTGGTGGTGA CGGACCTCAA AGCTGAGAGT GTGGTTCTTG      360

AGCATCGCAG CTACTGCTCG GCAAAGGCCC GGGACAGACA CTTTGCTGGG GATGTACTGG      420

GCTATGTCAC TCCATGGAAC AGCCATGGCT ACGATGTCAC CAAGGTCTTT GGGAGCAAGT      480

TCACACAGAT CTCACCCGTC TGGCTGCAGC TGAAGAGACG TGGCCGTGAG ATGTTTGAGG      540

TCACGGGCCT CCACGACGTG GACCAAGGGT GGATGCGAGC TGTCAGGAAG CATGCCAAGG      600

GCCTGCACAT AGTGCCTCGG CTCCTGTTTG AGGACTGGAC TTACGATGAT TTCCGGAACG      660
```

```
TCTTAGACAG TGAGGATGAG ATAGAGGAGC TGAGCAAGAC CGTGGTCCAG GTGGCAAAGA      720

ACCAGCATTT CGATGGCTTC GTGGTGGAGG TCTGGAACCA GCTGCTAAGC CAGAAGCGCG      780

TGGGCCTCAT CCACATGCTC ACCCACTTGG CCGAGGCTCT GCACCAGGCC CGGCTGCTGG      840

CCCTCCTGGT CATCCCGCCT GCCATCACCC CCGGGACCGA CCAGCTGGGC ATGTTCACGC      900

ACAAGGAGTT TGAGCAGCTG GCCCCCGTGC TGGATGGTTT CAGCCTCATG ACCTACGACT      960

ACTCTACAGC GCATCAGCCT GGCCCTAATG CACCCCTGTC CTGGGTTCGA GCCTGCGTCC     1020

AGGTCCTGGA CCCGAAGTCC AAGTGGCGAA GCAAAATCCT CCTGGGGCTC AACTTCTATG     1080

GTATGGACTA CGCGACCTCC AAGGATGCCC GTGAGCCTGT TGTCGGGGCC AGGTACATCC     1140

AGACACTGAA GGACCACAGG CCCCGGATGG TGTGGGACAG CCAGGCCTCA GAGCACTTCT     1200

TCGAGTACAA GAAGAGCCGC AGTGGGAGGC ACGTCGTCTT CTACCCAACC CTGAAGTCCC     1260

TGCAGGTGCG GCTGGAGCTG GCCCGGGAGC TGGGCGTTGG GGTCTCTATC TGGGAGCTGG     1320

GCCAGGGCCT GGACTACTTC TACGACCTGC TCTAGGTGGG CATTGCGGCC TCCGCGGTGG     1380

ACGTGTTCTT TTCTAAGCCA TGGAGTGAGT GAGCAGGTGT GAAATACAGG CCTCCACTCC     1440

GTTTGCTGTG AAAAAAAAAA                                                 1460

(2) INFORMATION FOR SEQ ID NO:   61:

(i) SEQUENCE CHARACTERISTICS:
        (A) LENGTH: 1594 base pairs
        (B) TYPE: nucleic acid
        (C) STRANDEDNESS: single
        (D) TOPOLOGY: linear (vii) IMMEDIATE SOURCE:
        (A) LIBRARY: SPLNNOT02
        (B) CLONE: 207452

(xi) SEQUENCE DESCRIPTION: SEQ ID NO: 61 :

CGGCTCGAGC GGCTCGAGCG GCTCGAGGCG GAGAGCGCGG AGCCGGGCCG CACCCGCCGA       60

GCCGTGAAAA AAGTACATCT CCTGGAAGGG ATGCTTTTTA GCTGAGCTCT GGTGGATGAG      120

AGGAGCTAGC CTTGAAAAAC TTGATACTGA TGGACATTGT GTGGGCCAGA GGCAGGGATG      180

GTTGGCTATG ACCCCAAACC AGATGGCAGG AATAACACCA AGTTCCAGGT GGCAGTGGCT      240

GGGTCTGTGT CTGGACTTGT TACTCGGGCG CTGATCAGTC CCTTCGACGT CATCAAGATC      300

CGTTTCCAGC TTCAGCATGA GCGCCTGTCT CGCAGTGACC CCAGCGCAAA GTACCATGGC      360

ATCCTCCAGG CCTCTAGGCA GATTCTGCAG GAGGAGGGTC CGACAGCTTT CTGGAAAGGA      420

CACGTCCCAG CTCAGATTCT CTCCATAGGC TATGGAGCTG TCCAATTCTT GTCATTTGAA      480

ATGCTGACGG AGCTGGTCCA CAGAGGCAGC GTGTACGACG CCCGGGAATT CTCAGTGCAC      540

TTTGTATGTG GTGGCCTGGC TGCCTGTATG GCCACCCTCA CTGTGCACCC CGTGGATGTT      600

CTGCGCACCC GCTTTGCAGC TCAGGGTGAG CCCAAGGTCT ATAATACGCT GCGCCACGCC      660

GTGGGGACCA TGTATAGGAG CGAAGGCCCC CAGGTTTTCT ACAAAGGCTT GGCTCCCACC      720

TTGATCGCCA TCTTCCCCTA CGCCGGGCTG CAGTTCTCTT GCTACAGCTC CTTGAAGCAC      780

CTGTACAAGT GGGCCATACC AGCCGAAGGA AAGAAAAATG AGAACCTCCA AAACCTGCTT      840

TGTGGCAGTG GAGCTGGTGT CATCAGCAAG ACCCTGACAT ATCCGCTGGA CCTCTTCAAG      900

AAGCGGCTAC AGGTTGGAGG GTTTGAGCAT GCCAGAGCTG CCTTTGGCCA GGTACGGAGA      960

TACAAGGGCC TCATGGACTG TGCCAAGCAG GTGCTGCAAA AGGAAGGCGC CCTGGGCTTC     1020

TTCAAGGGCC TGTCCCCCAG CTTGCTGAAG GCTGCCCTCT CCACAGGCTT CATGTTCTTC     1080
```

```
TCGTATGAAT TCTTCTGTAA TGTCTTCCAC TGCATGAACA GGACAGCCAG CCAGCGCTGA    1140

GCGCAGGAAG GACCCCAGGT CTTCCCTGGA GGCAGCCTCC TGAAGGAAGG AAGATTCAGT    1200

CTCCACTGAG AGGTGCCGTC TGGCCCTTCC CTGCAGGCCA GCTGCCCCAA GCGGGGTAGC    1260

AGCCTTGAAC CCACCCAGCT GGGACACCAC CAGAAGGTCC AGGGCTCTCC CCATGAGAGA    1320

ATCAGAGGGA TGCAGGACGT GGTCTATGGT GAGCCAACGA CACAGTGAGA AGGAGCAGGA    1380

AGTTGCTGTT TCTCCTCTGA CCAGCCCACA CTGCAAAGGA AACAGACGCC ATCCTACACC    1440

TATCAGCCCT GCCTGCCAGG AGAACAGAGC ACACTCCTGG TCTGGATGGG GCTGCTGCTT    1500

GAGTGCAGAG GGCTGCGGTA GGCCCTTTGC AGGAGTCAGG TCCCTACACT TGGCCTGTTT    1560

GTGCAACCTA TTTAATAGAC GATTAAAGCC TAGA                              1594

(2) INFORMATION FOR SEQ ID NO:    62:

(i) SEQUENCE CHARACTERISTICS:
        (A) LENGTH: 1249 base pairs
        (B) TYPE: nucleic acid
        (C) STRANDEDNESS: single
        (D) TOPOLOGY: linear (vii) IMMEDIATE SOURCE:
        (A) LIBRARY: SPLNNOT02
        (B) CLONE: 208836

(xi) SEQUENCE DESCRIPTION: SEQ ID NO: 62 :

TCTGCTAGGG CACAAGAGAG ACGGGCGCTC GCGCTCTCGC AGTCCTCTTC CGTCAGTGTC      60

TTTTGCTTCG ACTCCCGGCG GAGCGCGCAA CGTGGAGTGA CGTGCAGGGG CCAAGTGCAA    120

CCCAGGCAGC CACGGCTGTT TCGGAGCTCA GGACTCTAAA ATGGCAGAGC AGCTTTCTCC    180

AGGAAAGGCG GTGGATCAGG TGTGCACCTT CCTTTTCAAA AAGCCTGGGC GGAAAGGGGC    240

TGCTGGACGC AGAAAGCGCC CGGCCTGCGA CCCAGAGCCC GGAGAAAGCG GCAGCAGTAG    300

CGACGAAGGC TGCACTGTGG TTCGACCGGA AAAGAAGCGG GTGACCCACA ATCCAATGAT    360

GCAGAAGACC CGTGACAGTG GTAAACAGAA GGCGGCTTAC GGCGACTTGA GCAGCGAAGA    420

GGAAGAGGAA AATGAGCCCG AGAGTCTCGG CGTGGTTTAT AAATCCACCC GTTCGGCGAA    480

ACCCGTGGGA CCAGAGGATA TGGGAGCGAC AGCCGTCTAT GAGCTGGACA CAGAGAAAGA    540

GCGCGATGCA CAAGCCATCT TTGAGCGCAG CCAGAAGATC CAGGAGGAGC TGAGGGGCAA    600

GGAGGATGAC AAGATCTATC GGGGAATCAA CAATTATCAG AAATACATGA AGCCCAAGGA    660

TACGTCTATG GGCAATGCCT CTTCCGGGAT GGTGAGGAAG GGCCCCATCC GAGCGCCCGA    720

GCATCTACGT GCCACCGTGC GCTGGGATTA CCAGCCCGAC ATCTGTAAGG ACTACAAAGA    780

GACTGGCTTC TGCGGCTTCG GAGACAGCTG CAAATTCCTC CATGACCGTT CAGATTACAA    840

GCATGGGTGG CAGATCGAAC GTGAGCTTGA TGAGGGTCGC TATGGTGTCT ATGAGGATGA    900

AAACTATGAA GTGGGAAGCG ATGATGAGGA AATACCATTC AAGTGTTTCA TCTGTCGCCA    960

GAGCTTCCAA AACCCAGTTG TCACCAAGTG CAGGCATTAT TTCTGCGAGA GCTGTGCACT    1020

GCAGCATTTC CGCACCACCC CGCGCTGCTA TGTCTGTGAC CAGCAGACCA ATGGCGTCTT    1080

CAATCCAGCG AAAGAATTGA TTGCTAAACT AGAGAAGCAT CGAGCTACAG GAGAGGGTGG    1140

TGCTTCCGAC TTGCCAGAAG ACCCCGATGA GGATGCAATT CCCATTACTT AGGTTTCCCA    1200

TAATTCTTAA ATTTAAAAAA TAAACGTTTT GTTCTTTTGG AAAAAAAA                1249

(2) INFORMATION FOR SEQ ID NO:    63:

(i) SEQUENCE CHARACTERISTICS:
```

(A) LENGTH: 1309 base pairs
        (B) TYPE: nucleic acid
        (C) STRANDEDNESS: single
        (D) TOPOLOGY: linear (vii) IMMEDIATE SOURCE:
        (A) LIBRARY: MMLR3DT01
        (B) CLONE: 569710

(xi) SEQUENCE DESCRIPTION: SEQ ID NO: 63 :

| | | | |
|---|---|---|---|
| CAGGCCCGCA | GACCGGAAGC | AGCCCGCGCC | GGGGGCTTCT GGGAAAAGGC TTGTGAACGG | 60 |
| CGTTTCTGCG | TCTGCCGTGG | ACAGCGAANT | GCTTGCGGTT CCTGAGCCGG AGGAGTGCCT | 120 |
| GTGAAGAAAA | CGGGGTATTG | CCCTGAGGCT | TATATTCTGC CTCAGTTGTC TTTTCTTGAA | 180 |
| ATATTATAAA | TCAGAATGTC | TGCACAGTCA | GTGGAAGAAG ATTCAATACT TATCATCCCA | 240 |
| ACTCCAGATG | AAGAGGAAAA | AATTCTGAGA | GTGAAGTTGG AGGAGGATCC TGATGGCGAA | 300 |
| GAGGGATCAA | GTATCCCCTG | GAACCATCTC | CCAGACCCAG AGATTTTCCG ACAGCGATTC | 360 |
| AGGCAGTTTG | GATACCAGGA | TTCACCTGGG | CCCCGTGAGG CTGTGAGCCA GCTCCGAGAA | 420 |
| CTTTGCCGTC | TGTGGCTCAG | GCCAGAGACG | CACACAAAAG AACAAATCTT GGAGCTGGTA | 480 |
| GTGCTGGAGC | AGTTTGTTGC | CATCCTACCC | AAAGAGCTAC AGACTTGGGT TCGAGATCAT | 540 |
| CATCCAGAGA | ATGAGAGGA  | GGCAGTGACA | GTGCTGGAGG ATTTGGAGAG TGAACTTGAT | 600 |
| GACCCTGGAC | AACCGGTTTC | TCTCCGTCGA | CGAAAACGGG AAGTACTAGT AGAAGACATG | 660 |
| GTATCTCAAG | AAGAAGCTCA | GGGATTACCA | AGTTCTGAGC TTGATGCTGT GGAGAACCAG | 720 |
| CTCAAGTGGG | CATCCTGGGA | GCTCCATTCC | CTAAGGCACT GTGATGATGA TGGTAGGACT | 780 |
| GAAAATGGAG | CACTAGCTCC | AAAGCAGGAG | CTTCCTTCAG CATTAGAATC CCATGAAGTT | 840 |
| CCTGGCACTC | TCAGTATGGG | TGTTCCTCAA | ATTTTTAAAT ATGGAGAAAC CTGTTTCCCC | 900 |
| AAGGGCAGGT | TTGAAAGAAA | GAGAAATCCC | TCTCGAAAGA AACAACATAT ATGTGATGAA | 960 |
| TGTGGAAAAC | ACTTCAGTCA | GGGCTCAGCC | CTTATTCTTC ATCAAAGAAT TCACAGTGGG | 1020 |
| GAGAAACCTT | ATGGATGTGT | TGAGTGTGGG | AAAGCATTCA GCCGAAGTTC CATTCTTGTG | 1080 |
| CAACACCAGA | GAGTCCACAC | TGGAGAAAAA | CCTTACAAAT GTCTTGAATG TGGGAAAGCC | 1140 |
| TTTAGCCAGA | ATTCGGGGCT | TATTAATCAT | CAGAGAATCC ATACTGGGGA GAAACCTTAT | 1200 |
| GAATGCGTTC | AGTGTGGGAA | ATCGTATAGT | CAAAGCTCAA ATCTTTTTAG ACATCAGAGA | 1260 |
| AGACACAATG | CAGAAAAACT | TCTGAATGTT | GTGAAAGTTT AAGAAATTG | 1309 |

(2) INFORMATION FOR SEQ ID NO:   64:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (vii) IMMEDIATE SOURCE:
        (A) LIBRARY: BRSTTUT01
        (B) CLONE: 606742

(xi) SEQUENCE DESCRIPTION: SEQ ID NO: 64 :

TTTTTTTTTT TTTTTTGTTG GAAAGGAGAT GTTTATTTTC TTCTTCCCAT GCTATGGAAG    60

GACATTGTAT TCCGCA    76

(2) INFORMATION FOR SEQ ID NO:   65:

(i) SEQUENCE CHARACTERISTICS:
        (A) LENGTH: 1327 base pairs (B) TYPE: nucleic acid
        (C) STRANDEDNESS: single
        (D) TOPOLOGY: linear (vii) IMMEDIATE SOURCE:
        (A) LIBRARY: COLNNOT01
        (B) CLONE: 611135

(xi) SEQUENCE DESCRIPTION: SEQ ID NO: 65 :

| | | | | | |
|---|---|---|---|---|---|
| CCTACCCTCT | TCTGTTGCTT | TCTCCCTGTG | GCTCGCGCCG | TCCCCCGCCG | CCCGTCGACC | 60 |
| CCGCTTCCAT | GTCCCTGGCG | GACACAGCTC | CCAGGAACCT | CCACGCCCAT | GGCCACTAGG | 120 |
| CAGAGGGAAT | CCTCTATCAC | CTCCTGCTGT | TCCACCTCGA | GCTGCGACGC | AGACGACGAG | 180 |
| GGCGTGCGCG | GCACCTGCGA | AGATGCTTCC | CTGTGCAAGA | GGTTTGCAGT | AAGCATTGGC | 240 |
| TACTGGCATG | ACCCTTACAT | ACAGCACTTT | GTGAGACTGT | CTAAAGAGAG | GAAAGCCCCT | 300 |
| GAAATCAACA | GAGGATATTT | TGCTCGAGTC | CATGGTGTCA | GTCAGCTTAT | AAAGGCATTT | 360 |
| CTACGGAAGA | CAGAATGTCA | TTGTCAAATT | GTCAACCTTG | GGGCAGGCAT | GGATACCACC | 420 |
| TTCTGGAGAT | TAAAGGATGA | AGATCTTCTC | CCAAGTAAAT | ATTTTGAGGT | TGACTTTCCA | 480 |
| ATGATTGTCA | CGAGAAAGCT | GCACAGTATC | AAATGCAAGC | CTCCCCTATC | CAGCCCCATT | 540 |
| CTAGAACTGC | ATTCAGAGGA | CACACTTCAG | ATGGATGGAC | ACATACTGGA | TTCAAAGAGA | 600 |
| TATGCCGTTA | TTGGAGCAGA | TCTCCGAGAC | CTGTCTGAAC | TGGAAGAGAA | GCTAAAGAAA | 660 |
| TGTAACATGA | ATACACAATT | GCCAACACTC | CTGATAGCTG | AATGTGTGCT | GGTTTACATG | 720 |
| ACTCCAGAGC | AGTCCGCAAA | CCTCCTGAAG | TGGGCAGCCA | ACAGTTTTGA | GAGAGCCATG | 780 |
| TTCATAAACT | ACGAACAGGT | GAACATGGGT | GATCGGTTTG | GGCAGATCAT | GATTGAAAAC | 840 |
| CTGCGGAGAC | GCCAGTGTGA | CCTGGCGGGA | GTGGAGACCT | GCAAGTCATT | AGAGTCACAG | 900 |
| AAAGAACGGC | TCCTGTCGAA | TGGGTGGGAA | ACAGCATCGG | CCGTCGACAT | GATGGAGTTG | 960 |
| TACAACAGGT | TACCTCGAGC | TGAAGTGAGC | AGGATAGAAT | CACTTGAATT | CCTGGATGAA | 1020 |
| ATGGAGCTGC | TGGAGCAGCT | CATGCGGCAT | TACTGCCTTT | GCTGGGCAAC | CAAAGGAGGA | 1080 |
| AATGAGCTTG | GGCTGAAGGA | GATAACTTAT | TAATCTGTCG | AAGGCTTATG | CCGAGCCAGA | 1140 |
| AGCCGAAGCC | ACTTGCCCTC | CTGGAGGAGA | CCTGCAAGCT | CCCTGAGCGG | TGGGCGGGCC | 1200 |
| TCGTCCGCAG | GTCTCATCCC | ACACTCTTGA | GAAGCCTTGG | TCACTACAGT | GGTCGCACAT | 1260 |
| GTTCCTCTTC | CTGTTCCTGT | TGACATGTCG | TTGTTTAAAT | AAATCTCACT | TGCCACCAAA | 1320 |
| AAAAAAA | | | | | | 1327 |

(2) INFORMATION FOR SEQ ID NO:   66:

(i) SEQUENCE CHARACTERISTICS:
        (A) LENGTH: 1892 base pairs
        (B) TYPE: nucleic acid
        (C) STRANDEDNESS: single
        (D) TOPOLOGY: linear (vii) IMMEDIATE SOURCE:
        (A) LIBRARY: BRSTNOT03
        (B) CLONE: 641127

(xi) SEQUENCE DESCRIPTION: SEQ ID NO: 66 :

| | | | | | |
|---|---|---|---|---|---|
| AGGCGTGGGG | TTCCACGTGG | GAGGTGAGAC | TGGCCGGGCT | TCCCCAGCCG | CTGGCAGAGG | 60 |
| CGTTCAGGGG | TCAGGAAATG | GGTGTGCCGC | GGGAGACTTG | AATGAAAATT | CTGTGGAGAA | 120 |
| TCTTCAACAG | AAAACACTTC | AGGATCTGTT | ACATGAGCTT | TCCTCCTGGC | TAGTTTTGGA | 180 |
| AGGCATGGCC | AGTACAATTA | CTGGAAGTCA | GGATTGTATT | GTGAATCATC | GAGGGAAGT | 240 |

-continued

```
GGATGGGGAG CCTGAACTAG ATATTTCCCC TTGTCAACAG TGGGGAGAAG CATCTTCTCC        300

TATTTCCAGA AACAGGGACA GTGTGATGAC TCTTCAAAGT GGTTGTTTCG AAAACATTGA        360

AAGTGAAACA TATTTGCCTT TGAAAGTCTC AAGCCAAATA GACACACAAG ACTCTTCAGT        420

GAAGTTCTGT AAGAATGAGC CTCAGGATCA TCAGGAAAGC AGACGTCTCT TTGTAATGGA        480

AGAAAGCACT GAGAGAAAAG TGATAAAGGG GGAAAGTTGT TCAGAGAACC TTCAAGTTAA        540

ACTGGTGTCT GATGGACAAG AACTGGCCTC GCCATTGTTA AATGGTGAGG CAACTTGCCA        600

GAATGGCCAG TTAAAAGAAT CTTTGGATCC CATTGACTGT AACTGCAAAG ACATTCATGG        660

ATGGAAATCA CAGGTGGTCA GTTGTAGTCA GCAGAGAGGT CATACAGAGG AGAAACCCTG        720

TGACCATAAT AACTGTGGGA AAATACTTAA CACCAGCCCA GATGGTCATC CATATGAGAA        780

AATCCACACT GCAGAGAAAC AATACGAAGG TAGTCAGTGT GGTAAGAACT TCAGTCAAAG        840

CTCAGAGCTA CTACTTCATC AGAGAGACCA CACAGAAGAA AAACCCTACA AATGTGAGCA        900

ATGTGGGAAG GGCTTCACAA GGAGCTCGAG TCTGCTTATC CATCAGGCAG TCCACACAGA        960

TGAGAAGCCT TATAAGTGTG ACAAGTGTGG GAAGGGCTTC ACCAGGAGCT CAAGTCTGCT       1020

CATCCATCAT GCCGTCCATA CAGGCGAAAA ACCTTATAAA TGTGACAAGT GTGGGAAGGG       1080

CTTTAGTCAG AGCTCCAAAC TGCACATCCA CCAGCGAGTC CACACTGGAG AGAAGCCCTA       1140

TGAGTGTGAG GAGTGTGGTA TGAGCTTCAG TCAGCGCTCA AACCTGCACA TCCACCAGCG       1200

AGTACACACA GGAGAGAGGC CCTACAAGTG TGGTGAGTGT GGGAAGGGCT TCAGTCAGAG       1260

CTCGAACCTT CACATTCACC GGTGCATCCA CACAGGAGAG AAGCCTTACC AATGCTATGA       1320

GTGTGGGAAG GGTTTCAGCC AGAGCTCGGA TCTTCGCATC CATCTCAGAG TCCACACTGG       1380

AGAGAAGCCC TATCACTGTG GCAAGTGTGG GAAGGGATTT AGCCAGAGTT CCAAACTCCT       1440

CATCCACCAG AGAGTACATA CTGGAGAGAA GCCCTATGAG TGCAGCAAGT GTGGGAAGGG       1500

CTTCAGCCAG AGCTCCAACC TTCACATCCA CCAGCGGGTT CACAAGAGAG ATCCTCGAGC       1560

CCATCCAGGT CTTCACAGCG CTCATACTGT AAACACTGTT AAATATTTAG TATCACTCTT       1620

ACTTTATATT CTACAAAGGA GAGAGATGTA AGGGTTATTT AGATATGTTC CCTCACTGAA       1680

AAATCACTCA TTCAACATAT TTAAGTATCA AGCACTTTGT TATGCTGTAC AATGAATGGA       1740

TTGCTCTTGT TTCTCAGATG GGTAGAGTAA AAGTGTCTGT ACTTTACCGT TCAACTACAT       1800

GTTCTACCCA GCATTTTAAC GGCAAGAACT TTATATTTAT TCTCATAGCA GGGCATGTTT       1860

CCCTTTGATC ACAGGCTCTG AGAATGCTTT AT                                    1892
```

(2) INFORMATION FOR SEQ ID NO: 67:

(i) SEQUENCE CHARACTERISTICS:
        (A) LENGTH: 843 base pairs
        (B) TYPE: nucleic acid
        (C) STRANDEDNESS: single
        (D) TOPOLOGY: linear (vii) IMMEDIATE SOURCE:
        (A) LIBRARY: LUNGTUT02
        (B) CLONE: 691768

(xi) SEQUENCE DESCRIPTION: SEQ ID NO: 67 :

```
GGAAGTGTCT TCAGGGAGAG GAAGCCGGCG GCCTCACTGC TATGGGCCGC AACAAGAAGA         60

AGAAGCGAGA TGGTGACGAC CGGCGGCCGA GGCTCGTTCT TAGCTTCGAC GAGGAGAAGA        120

GGCGGGAGTA CCTGACAGGC TTCCACAAGC GGAAGGTCGA GCGAAAGAAG GCAGCCATTG        180

AGGAGATTAA GCAGCGGCTG AAAGAGGAGC AGAGGAAGCT TCGGGAGGAG CGCCACCAGG        240
```

| | |
|---|---|
| AATACTTGAA GATGCTGGCA GAGAGAGAAG AGGCTCTGGA GGAGGCAGAT GAGCTGGACC | 300 |
| GGTTGGTGAC AGCAAAGACG GAGTCGGTGC AGTATGACCA CCCCAACCAC ACAGTCACCG | 360 |
| TGACCACCAT CAGTGACCTG GACCTCTCGG GGGCCCGGCT GCTCGGGCTG ACCCCACCTG | 420 |
| AGGGAGGGGC TGGAGACAGG TCTGAGGAGG AGGCGTCATC CACGGAGAAA CCAACCAAAG | 480 |
| CCTTGCCCAG GAAGTCCAGA GACCCCCTGC TCTCTCAGCG GATCTCCTCC CTCACAGCAT | 540 |
| CACTACATGC ACACAGCCGC AAAAAGGTCA AGAGGAAACA TTCCCGACGG GCCCAGGACT | 600 |
| CCAAAAAGCC CCCAAAGGGC CCTTCGTACC AGCAAAGGCC CAGCGGCGCC GTCTTCACAG | 660 |
| GCAAAGCACC GGCACAGCGG GGGAATTNAA GANCCGAGAA CGAAGCCGGT TGCCCCCATT | 720 |
| CTAAGGCTTN CCGGGGANCT TGTTCCCTTG GTTCAGCTTT GGCTGTTCCC CTGTTAGNCC | 780 |
| CAGCCTTGNA ACTTAAGGTG TTGCCTTAAC CGGCATTGTT TGCCCGCTTG GCTGGTTTTC | 840 |
| TTG | 843 |

(2) INFORMATION FOR SEQ ID NO: 68:

(i) SEQUENCE CHARACTERISTICS:
        (A) LENGTH: 1643 base pairs
        (B) TYPE: nucleic acid
        (C) STRANDEDNESS: single
        (D) TOPOLOGY: linear (vii) IMMEDIATE SOURCE:
        (A) LIBRARY: SYNOOAT01
        (B) CLONE: 724157

(xi) SEQUENCE DESCRIPTION: SEQ ID NO: 68 :

| | |
|---|---|
| GGGAGGCTGA AGCAAGAGAA CCGCTTGAAC GGGGGTGGAT GTTGCAGTGA GCCAAGATGG | 60 |
| TGCCACTGCA CTCCAGCCTG GCAACAGTGC GCAGAGCGAG ACGCCGTCTC AAAACAAAAG | 120 |
| TCTCACAGTG GCCCAGCCTC CTTTCCTGCC ATCCCTGGAG TTGTGGTCTG TTTGAGGTTT | 180 |
| GGTTTTCAGG ACTGAAGCTT CAAGATGGCT GACCAGGACC CTGCGGGCAT CAGCCCCCTC | 240 |
| CAGCAAATGG TGGCCTCAGG CACCGGGGCT GTGGTTACCT CTCTCTTCAT GACACCCCTG | 300 |
| GACGTGGTGA AGGTTCGCCT GCAGTCTCAG CGGCCCTCCA TGGCCAGCGA GCTGATGCCT | 360 |
| TCCTCCAGAC TGTGGAGCCT CTCCTATACC AAATGGAAGT GCCTCCTGTA TTGCAATGGT | 420 |
| GTCCTGGAGC CTCTGTACCT GTGCCCAAAT GGTGCCCGCT GTGCCACCTG GTTTCAAGAC | 480 |
| CCTACCCGCT TCACTGGCAC CATGGATGCC TTCGTGAAGA TCGTGAGGCA CGAGGGCACC | 540 |
| AGGACCCTCT GGAGCGGCCT CCCCGCCACC CTGGTGATGA CTGTGCCAGC TACCGCCATC | 600 |
| TACTTCACTG CCTATGACCA ACTGAAGGCC TTCCTGTGTG GTCGAGCCCT GACCTCTGAC | 660 |
| CTCTACGCAC CCATGGTGGC TGGCGCGCTG GCCCGCTTGG GCACCGTGAC TGTGATCAGC | 720 |
| CCCCTGGAGC TTATGCGGAC AAAGCTGCAG GCTCAGCATG TGTCGTACCG GGAGCTGGGT | 780 |
| GCCTGTGTTC GAACTGCAGT GGCTCAGGGT GGCTGGCGCT CACTGTGGCT GGGCTGGGGC | 840 |
| CCCACTGCCC TTCGAGATGT GCCCTTCTCA GCCCTGTACT GGTTCAACTA TGAGCTGGTG | 900 |
| AAGAGCTGGC TCAATGGGCT CAGGCCGAAG GACCAGACTT CTGTGGGCAT GAGCTTTGTG | 960 |
| GCTGGTGGCA TCTCAGGGAC GGTGGCTGCA GTGCTGACTC TACCCTTTGA CGTGGTAAAG | 1020 |
| ACCCAACGCC AGGTCGCTCT GGGAGCGATG GAGGCTGTGA GAGTGAACCC CCTGCATGTG | 1080 |
| GACTCCACCT GGCTGCTGCT GCGGAGGATC CGGGCCGAGT CGGGCACCAA GGGACTCTTT | 1140 |
| GCAGGCTTCC TTCCTCGGAT CATCAAGGCT GCCCCTCCT GTGCCATCAT GATCAGCACC | 1200 |
| TATGAGTTCG GCAAAAGCTT CTTCCAGAGG CTGAACCAGG ACCGGCTTCT GGGCGGCTGA | 1260 |

-continued

| | |
|---|---|
| AAGGGGCAAG GAGGCAAGGA CCCCGTCTCT CCCACGGATG GGGAGAGGGC AGGAGGAGAC | 1320 |
| CCAGCCAAGT GCCTTTTCCT CAGCACTGAG GGAGGGGGCT TGTTTCCCTT CCCTCCCGGC | 1380 |
| GACAAGCTCC AGGGCAGGGC TGTCCCTCTG GGCGGCCCAG CACTTCCTCA GACACAACTT | 1440 |
| CTTCCTGCTG CTCCAGTCGT GGGGATCATC ACTTACCCAC CCCCCAAGTT CAAGACCAAA | 1500 |
| TCTTCCAGCT GCCCCCTTCG TGTTTCCCTG TGTTTGCTGT AGCTGGGCAT GTCTCCAGGA | 1560 |
| ACCAAGAAGC CCTCAGCCTG GTGTAGTCTC CCTGACCCTT GTTAATTCCT TAAGTCTAAA | 1620 |
| GATGATGAAC TTCAAAAAAA AAA | 1643 |

(2) INFORMATION FOR SEQ ID NO:   69:

(i) SEQUENCE CHARACTERISTICS:
        (A) LENGTH: 2029 base pairs
        (B) TYPE: nucleic acid
        (C) STRANDEDNESS: single
        (D) TOPOLOGY: linear (vii) IMMEDIATE SOURCE:
        (A) LIBRARY: BRAITUT03
        (B) CLONE: 864683

(xi) SEQUENCE DESCRIPTION: SEQ ID NO: 69 :

| | |
|---|---|
| GCAGCTGTGA GGGAGTCGCT GTGATCCGGG GCCCCGGAAC CCGAGCTGGA GCTGAAGCGC | 60 |
| AGGCTGCGGG GCGCGGAGTC GGGAGTGCAG GCCTGAGTGT TCCTTCCAGC ATGTCGGAGG | 120 |
| GGGAGTCCCA GACAGTACTT AGCAGTGGCT CAGACCCAAA GGTAGAATCC TCATCTTCAG | 180 |
| CTCCTGGCCT GACATCAGTG TCACCTCCTG TGACCTCCAC AACCTCAGCT GCTTCCCCAG | 240 |
| AGGAAGAAGA AGAAAGTGAA GATGAGTCTG AGATTTTGGA AGAGTCGCCC TGTGGGCGCT | 300 |
| GGCAGAAGAG GCGAGAAGAG GTGAATCAAC GGAATGTACC AGGTATTGAC AGTGCATACC | 360 |
| TGGCCATGGA TACAGAGGAA GGTGTAGAGG TTGTGTGGAA TGAGGTACAG TTCTCTGAAC | 420 |
| GCAAGAACTA CAAGCTGCAG GAGGAAAAGG TTCGTGCTGT GTTTGATAAT CTGATTCAAT | 480 |
| TGGAGCATCT TAACATTGTT AAGTTTCACA AATATTGGGC TGACATTAAA GAGAACAAGG | 540 |
| CCAGGGTCAT TTTTATCACA GAATACATGT CATCTGGGAG TCTGAAGCAA TTTCTGAAGA | 600 |
| AGACCAAAAA GAACCACAAG ACGATGAATG AAAAGGCATG GAAGCGTTGG TGCACACAAA | 660 |
| TCCTCTCTGC CCTAAGCTAC CTGCACTCCT GTGACCCCCC CATCATCCAT GGGAACCTGA | 720 |
| CCTGTGACAC CATCTTCATC CAGCACAACG GACTCATCAA GATTGGCTCT GTGGCTCCTG | 780 |
| ACACTATCAA CAATCATGTG AAGACTTGTC GAGAAGAGCA GAAGAATCTA CACTTCTTTG | 840 |
| CACCAGAGTA TGGAGAAGTC ACTAATGTGA CAACAGCAGT GGACATCTAC TCCTTTGGCA | 900 |
| TGTGTGCACT GGAGATGGCA GTGCTGGAGA TTCAGGGCAA TGGAGAGTCC TCATATGTGC | 960 |
| CACAGGAAGC CATCAGCAGT GCCATCCAGC TTCTAGAAGA CCCATTACAG AGGGAGTTCA | 1020 |
| TTCAAAAGTG CCTGCAGTCT GAGCCTGCTC GCAGACCAAC AGCCAGAGAA CTTCTGTTCC | 1080 |
| ACCCAGCATT GTTTGAAGTG CCCTCGCTCA AACTCCTTGC GGCCCACTGC ATTGTGGGAC | 1140 |
| ACCAACACAT GATCCCAGAG AACGCTCTAG AGGAGATCAC CAAAAACATG GATACTAGTG | 1200 |
| CCGTACTGGC TGAAATCCCT GCAGGACCAG GAAGAGAACC AGTTCAGACT TTGTACTCTC | 1260 |
| AGTCACCAGC TCTGGAATTA GATAAATTCC TTGAAGATGT CAGGAATGGG ATCTATCCTC | 1320 |
| TGACAGCCTT TGGGCTGCCT CGGCCCCAGC AGCCACAGCA GGAGGAGGTG ACATCACCTG | 1380 |
| TCGTGCCCCC CTCTGTCAAG ACTCCGACAC CTGAACCAGC TGAGGTGGAG ACTCGCAAGG | 1440 |
| TGGTGCTGAT GCAGTGCAAC ATTGAGTCGG TGGAGGAGGG AGTCAAACAC CACCTGACAC | 1500 |

-continued

| TTCTGCTGAA GTTGGAGGAC AAACTGAACC GGCACCTGAG CTGTGACCTG ATGCCAAATG | 1560 |
| AGAATATCCC CGAGTTGGCG GCTGAGCTGG TGCAGCTGGG CTTCATTAGT GAGGCTGACC | 1620 |
| AGAGCCGGTT GACTTCTCTG CTAGAAGAGA CCTTGAACAA GTTCAATTTT GCCAGGAACA | 1680 |
| GTACCCTCAA CTCAGCCGCT GTCACCGTCT CCTCTTAGAG CTCACTCGGG CCAGGCCCTG | 1740 |
| ATCTGCGCTC TGGCTGTCCC TGGACGTGCT GCAGCCCTCC TGTCCCTTCC CCCCAGTCAG | 1800 |
| TATTACCCTG TGAAGCCCCT TCCCTCCTTT ATTATTCAGG AGGGCTGGGG GGGCTCCCTG | 1860 |
| GTTCTGAGCA TCATCCTTTC CCCTCCCCTC TCTTCCTCCC CTCTGCACTT TGTTTACTTG | 1920 |
| TTTTGCACAG ACGTGGGCCT GGGCCTTCTC AGCAGCCGCC TTCTAGTTGG GGGCTAGTCG | 1980 |
| CTGATCTGCC GGCTCCCGCC CAGCCTGTGT GGAAAGGAGG CCCACGGGC | 2029 |

(2) INFORMATION FOR SEQ ID NO:    70:

(i) SEQUENCE CHARACTERISTICS:
        (A) LENGTH: 821 base pairs
        (B) TYPE: nucleic acid
        (C) STRANDEDNESS: single
        (D) TOPOLOGY: linear (vii) IMMEDIATE SOURCE:
        (A) LIBRARY: CERVNOT01
        (B) CLONE: 933353

(xi) SEQUENCE DESCRIPTION: SEQ ID NO: 70 :

| CGGGTCGCCG CTGCGCCGGG CCGGGATGGC GGCCACCGCG CTGCTGGAGG CCGGCCTGGC | 60 |
| GCGGGTGCTC TTCTACCCGA CGCTGCTCTA CACCCTGTTC CGCGGGAAGG TGCCGGGTCG | 120 |
| GGCGCACCGG GACTGGTACC ACCGCATCGA CCCCACCGTG CTGCTGGGCG CGCTGCCGTT | 180 |
| GCGGAGCTTG ACGCGCCAGC TGGTACAGGA CGAGAACGTG CGCGGGGTGA TCACCATGAA | 240 |
| CGAGGAGTAC GAGACGAGGT TCCTGTGCAA CTCTTCACAG GAGTGGAAGA GACTAGGAGT | 300 |
| TGAGCAGCTG CGGCTCAGCA CAGTAGACAT GACTGGGATC CCCACCTTGG ACAACCTCCA | 360 |
| GAAGGGAGTC CAATTTGCTC TCAAGTACCA GTCGCTGGGC CAGTGTGTTT ACGTGCATTG | 420 |
| TAAGGCTGGG CGCTCCAGGA GTGCCACTAT GGTGGCAGCA TACCTGATTC AGGTGCACAA | 480 |
| ATGGAGTCCA GAGGAGGCTG TAAGAGCCAT CGCCAAGATC CGGTCATACA TCCACATCAG | 540 |
| GCCTGGCCAG CTGGATGTTC TTAAAGAGTT CCACAAGCAG ATTACTGCAC GGGCAACAAA | 600 |
| GGATGGGACT TTTGTCATTT CAAAGACATG ATGTATGGGG ATTAGAAAGA ACTCAAGACA | 660 |
| CTCCTGCTTG ATACAGAACA AAAAGAGCTT AACAGGACCA ACAGGGCTTA AGCCCAGACT | 720 |
| TGACGTAACA GAAATGTGCC AATAGGTAAT AGGTAATTTT TCTTTCTCTG ACTTGTTTTG | 780 |
| TTTTCTTGAA ATAACACTGT TGTGTGGCTA GAAAAAAAA A | 821 |

(2) INFORMATION FOR SEQ ID NO:    71:

(i) SEQUENCE CHARACTERISTICS:
        (A) LENGTH: 1139 base pairs
        (B) TYPE: nucleic acid
        (C) STRANDEDNESS: single
        (D) TOPOLOGY: linear (vii) IMMEDIATE SOURCE:
        (A) LIBRARY: LATRTUT02
        (B) CLONE: 1404643

(xi) SEQUENCE DESCRIPTION: SEQ ID NO: 71 :

| CGGCGACGGT GGGGAAGATG GCGTACCAGA GCTTGCGGCT GGAGTACCTG CAGATCCCAC | 60 |
| CGGTCAGCCG CGCCTACACC ACTGCCTGCG TCCTCACCAC CGCCGCCGTG CAGTTGGAAT | 120 |

```
TGATCACACC TTTTCAGTTG TACTTCAATC CTGAATTAAT CTTTAAACAC TTTCAAATAT    180

GGAGATTAAT CACCAACTTC TTATTTTTTG GGCCAGTTGG ATTCAATTTT TTATTTAACA    240

TGATTTTTCT ATATCGTTAC TGTCGAATGC TAGAAGAAGG CTCTTTCCGA GGTCGGACAG    300

CAGACTTTGT ATTTATGTTC CTTTTTGGTG GATTCTTAAT GACCCTTTTT GGTCTGTTTG    360

TGAGCTTAGT TTTCTTGGGC CAGGCCTTTA CAATAATGCT CGTCTATGTG TGGAGCCGAA    420

GGAACCCCTA TGTCCGCATG AACTTCTTCG GCCTTCTCAA CTTCCAGGCC CCCTTTCTGC    480

CCTGGGTGCT CATGGGATTT TCCTTGTTGT TGGGGAACTC AATCATTGTG GACCTTTTGG    540

GTATTGCAGT TGGACACATA TATTTTTTCT TGGAAGATGT ATTTCCCAAT CAACCTGGTG    600

GAATAAGAAT TCTGAAAACA CCATCTATTT TGAAAGCTAT TTTTGATACA CCAGATGAGG    660

ATCCAAATTA CAATCCACTA CCTGAGGAAC GGCCAGGAGG CTTCGCCTGG GGTGAGGGCC    720

AGCGGCTTGG AGGTTAAAGC AGCAGTGCCA ATAATGAGAC CCAGCTGGGA AGGACTCGGT    780

GATACCCACT GGGATCTTTT ATCCTTTGTT GCAAAAGTGT GGACACTTTT GACAGCTTGG    840

CAGATTTTAA CTCCAGAAGC ACTTTATGAA ATGGTACACT GACTAATCCA GAAGACATTT    900

CCAACAGTTT GCCAGTGGTT CCTCACTACA CTGGTACTGA AAGTGTAATT TCTTAGAGCC    960

AAAAAACTGG AGAAACAAAT ATCCTGCCAC CTCTAACAAG TACATGAGTA CTTGATTTTT   1020

ATGGTATAAG GCAGAGCCTT TTCTTCCTCT TCTTGATAGA TGAGGCCATG GTGTAAATGG   1080

AAGTTTCAGA GAGGACAAAA TAAAACGGAA TTCCATTTTT CTCTCACTGT AAAAAAAAA   1139

(2) INFORMATION FOR SEQ ID NO:   72:

(i) SEQUENCE CHARACTERISTICS:
         (A) LENGTH: 1406 base pairs
         (B) TYPE: nucleic acid
         (C) STRANDEDNESS: single
         (D) TOPOLOGY: linear (vii) IMMEDIATE SOURCE:
         (A) LIBRARY: SPLNNOT04
         (B) CLONE: 1561587

(xi) SEQUENCE DESCRIPTION: SEQ ID NO: 72 :

GGGCTGCCCC CGGGGGGCTG GCGGACTGGG CCGCGGGGGC CCCGGGGCCG GCGGTGCCGG     60

GGTCATCGGG ATGATGCGGA CGCAGTGTCT GCTGGGGCTG CGCACGTTCG TGGCCTTCGC    120

CGCCAAGCTC TGGAGCTTCT TCATTTACCT TTTGCGGAGG CAGATCCGCA CGGTAATTCA    180

GTACCAAACT GTTCGATATG ATATCCTCCC CTTATCTCCT GTGTCCCGGA ATCGGCTAGC    240

CCAGGTGAAG AGGAAGATCC TGGTGCTGGA TCTGGATGAG ACACTTATTC ACTCCCACCA    300

TGATGGGGTC CTGAGGCCCA CAGTCCGGCC TGGTACGCCT CCTGACTTCA TCCTCAAGGT    360

GGTAATAGAC AAACATCCTG TCCGGTTTTT TGTACATAAG AGGCCCCATG TGGATTTCTT    420

CCTGGAAGTG GTGAGCCAGT GGTACGAGCT GGTGGTGTTT ACAGCAAGCA TGGAGATCTA    480

TGGCTCTGCT GTGGCAGATA AACTGGACAA TAGCAGAAGC ATTCTTAAGA GGAGATATTA    540

CAGACAGCAC TGCACTTTGG AGTTGGGCAG CTACATCAAG GACCTCTCTG TGGTCCACAG    600

TGACCTCTCC AGCATTGTGA TCCTGGATAA CTCCCCAGGG GCTTACAGGA GCCATCCAGA    660

CAATGCCATC CCCATCAAAT CCTGGTTCAG TGACCCCAGC GACACAGCCC TTCTCAACCT    720

GCTCCCAATG CTGGATGCCC TCAGGTTCAC CGCTGATGTT CGTTCCGTGC TGAGCCGAAA    780

CCTTCACCAA CATCGGCTCT GGTGACAGCT GCTCCCCCTC CACCTGAGTT GGGGTGGGGG    840

GGAAAGGGAG GGCGAGCCCT TGGGATGCCG TCTGATGCCC TGTCCAATGT GAGGACTGCC    900
```

| | |
|---|---:|
| TGGGCAGGGT CTGCCCCTCC CACCCCTCTC TGCCCTGGGA GCCCTACACT CCACTTGGAG | 960 |
| TCTGGATGGA CACATGGGCC AGGGGCTCTG AAGCAGCCTC ACTCTTAACT TCGTGTTCAC | 1020 |
| ACTCCATGGA AACCCCAGAC TGGGACACAG GCGGAAGCCT AGGAGAGCCG AATCAGTGTT | 1080 |
| TGTGAAGAGG CAGGACTGGC CAGAGTGACA GACATACGGT GATCCAGGAG GCTCAAAGAG | 1140 |
| AAGCCAAGTC AGCTTTGTTG TGATTTGATT TTTTTTAAAA AACTCTTGTA CAAAACTGAT | 1200 |
| CTAATTCTTC ACTCCTGCTC CAAGGGCTGG GCTGTGGGTG GGATACTGGG ATTTTGGGCC | 1260 |
| ACTGGATTTT CCCTAAATTT GTCCCCCCTT TACTCTCCCT CTATTTTTCT CTCCTTAGAC | 1320 |
| TCCCTCAGAC CTGTAACCAG CTTTGTGTCT TTTTTCCTTT TCTCTCTTTT AAACCATGCA | 1380 |
| TTATAACTTT GAAACCAAAA AAAAAA | 1406 |

(2) INFORMATION FOR SEQ ID NO: 73:

(i) SEQUENCE CHARACTERISTICS:
        (A) LENGTH: 2028 base pairs
        (B) TYPE: nucleic acid
        (C) STRANDEDNESS: single
        (D) TOPOLOGY: linear (vii) IMMEDIATE SOURCE:
        (A) LIBRARY: UTRSNOT05
        (B) CLONE: 1568361

(xi) SEQUENCE DESCRIPTION: SEQ ID NO: 73 :

| | |
|---|---:|
| GNANANNACC CTGCNGGNNG CCATTCACCG ACCCTGCCCA NACAGCCGTC ACCCTCGANT | 60 |
| CCTGGCTGAN TCTNTTCCTG GCAGTTCCCC TTATNANGGT TACAACTATG GCTCCTTTNA | 120 |
| CAATGTNTCT NTATCTACCG ATGGTCTGGT TNACAGCNCT GGCACTGGGG ACCTCTCTTA | 180 |
| CGGTTACCAG GGCCGCTCCT TTGAACCTGT AGGTACTCGG CCCCGAGTGG ACTCCATGAG | 240 |
| CTCTGTGGAG GAGGATGACT ACGACACATT GACCGACATC GATTCCGACA AGAATGTCAT | 300 |
| TCGCACCAAG CAATACCTCT ATGTGGCTGA CCTGGCACGG AAGGACAAGC GTGTTCTGCG | 360 |
| GAAAAAGTAC CAGATCTACT TCTGGAACAT TGCCACCATT GCTGTCTTCT ATGCCCTTCC | 420 |
| TGTGGTGCAG CTGGTGATCA CCTACCAGAC GGTGGTGAAT GTCACAGGGA ATCAGGACAT | 480 |
| CTGCTACTAC AACTTCCTCT GCGCCCACCC ACTGGGCAAT CTCAGCGCCT TCAACAACAT | 540 |
| CCTCAGCAAC CTGGGGTACA TCCTGCTGGG GCTGCTTTTC CTGCTCATCA TCCTGCAACG | 600 |
| GGAGATCAAC CACAACCGGG CCCTGCTGCG CAATGACCTC TGTGCCCTGG AATGTGGGAT | 660 |
| CCCCAAACAC TTTGGGCTTT TCTACGCCAT GGGCACAGCC CTGATGATGG AGGGGCTGCT | 720 |
| CAGTGCTTGC TATCATGTGT GCCCCAACTA TACCAATTTC CAGTTTGACA CATCGTTCAT | 780 |
| GTACATGATC GCCGGACTCT GCATGCTGAA GCTCTACCAG AAGCGGCACC CGGACATCAA | 840 |
| CGCCAGCGCC TACAGTGCCT ACGCCTGCCT GGCCATTGTC ATCTTCTTNT CTGTGCTGGG | 900 |
| CGTGGTCTTT GGCAAAGGGA ACACGGCGTT CTGGATCGTC TTCTCCATCA TTCACATCAT | 960 |
| CGCCACCCTG CTCCTCAGCA CGCAGCTCTA TTACATGGGC CGGTGGAAAC TGGACTCGGG | 1020 |
| GATCTTCCGC CGCATCCTCC ACGTGCTCTA CACAGACTGC ATCCGGCAGT GCAGCGGGCC | 1080 |
| GCTCTACGTG GACCGCATGG TGCTGCTGGT CATGGGCAAC GTCATCAACT GGTCGCTGGC | 1140 |
| TGCCTATGGG CTTATCATGC GCCCCAATGA TTTCGCTTCC TACTTGTTGG CCATTGGCAT | 1200 |
| CTGCAACCTG CTCCTTTACT TCGCCTTCTA CATCATCATG AAGCTCCGGA GTGGGGAGAG | 1260 |
| GATCAAGCTC ATCCCCCTGC TCTGCATCGT TTGCACCTCC GTGGTCTGGG GCTTCGCGCT | 1320 |
| CTTCTTCTTC TTCCAGGGAC TCAGCACCTG GCAGAAAACC CCTGCAGAGT CGAGGGAGCA | 1380 |

-continued

```
CAACCGGGAC TGCATCCTCC TCGACTTCTT TGACGACCAC GACATCTGGC ACTTCCTCTC    1440

CTCCATCGCC ATGTTCGGGT CCTTCCTGGT GTTGCTGACA CTGGATGACG ACCTGGATAC    1500

TGTGCAGCGG GACAAGATCT ATGTCTTCTA GCAGGAGCTG GGCCCTTCGC TTCACCTCAA    1560

GGGGCCCTGA GCTCCTTTGT GTCATAGACC GGTCACTCTG TCGTGCTGTG GGGATGAGTC    1620

CCAGCACCGC TGCCCAGCAC TGGATGGCAG CAGGACAGCC AGGTCTAGCT TAGGCTTGGC    1680

CTGGGACAGC CATGGGGTGG CATGGAACCT TGCAGCTGCC CTCTGCCGAG GAGCAGGCCT    1740

GCTCCCCTGG AACCCCCAGA TGTTGGCCAA ATTGCTGCTT TCTTCTCAGT GTTGGGGCCT    1800

TCCATGGGCC CCTGTCCTTT GGCTCTCCAT TTGTCCCTTT GCAAGAGGAA GGATGGAAGG    1860

GACACCCTCC CCATTTCATG CCTTGCATTT TGCCCGTCCT CCTCCCCACA ATGCCCCAGC    1920

CTGGGACCTA AGGCCTCTTT TTCCTCCCAT ACTCCCACTC CAGGGCCTAG TCTGGGGCCT    1980

GAATCTCTGT CCTGTATCAG GGCCCCAGTT CTCTTTGGGC TGTCCCTG                2028
```

(2) INFORMATION FOR SEQ ID NO: 74:

(i) SEQUENCE CHARACTERISTICS:
        (A) LENGTH: 1380 base pairs
        (B) TYPE: nucleic acid
        (C) STRANDEDNESS: single
        (D) TOPOLOGY: linear (vii) IMMEDIATE SOURCE:
        (A) LIBRARY: LNODNOT03
        (B) CLONE: 1572888

(xi) SEQUENCE DESCRIPTION: SEQ ID NO: 74 :

```
CTCGAGCCGA ATTCGGCTCG AGCGGCGCTC CTGCCTCCCT GCAGGGAGCT GCTTATGGGA      60

CACCGCTTCC TGCGCGGCCT CTTAACGCTG CTGCTGCCGC CGCCACCCCT GTATACCCGG     120

CACCGCATGC TCGGTCCAGA GTCCGTCCCG CCCCCAAAAC GATCCCGCAG CAAACTCATG     180

GCACCGCCCC GAATCGGGAC GCACAATGGC ACCTTCCACT GCGACGAGGC ACTGGCATGC     240

GCACTGCTTC GCCTCCTGCC GGAGTACCGG GATGCAGAGA TTGTGCGGAC CCGGGATCCC     300

GAAAAACTCG CTTCCTGTGA CATCGTGGTG GACGTGGGGG GCGAGTACGA CCCTCGGAGA     360

CACCGATATG ACCATCACCA GAGGTCTTTC ACAGAGACCA TGAGCTCCCT GTCCCCTGGG     420

AAGCCGTGGC AGACCAAGCT GAGCAGTGCG GGACTCATCT ATCTGCACTT CGGGCACAAG     480

CTGCTGGCCC AGTTGCTGGG CACTAGTGAA GAGGACAGCA TGGTGGGCAC CCTCTATGAC     540

AAGATGTATG AGAACTTTGT GGAGGAGGTG GATGCTGTGG ACAATGGGAT CTCCCAGTGG     600

GCAGAGGGGG AGCCTCGATA TGCACTGACC ACTACCCTGA GTGCACGAGT TGCTCGACTT     660

AATCCTACCT GGAACCACCC CGACCAAGAC ACTGAGGCAG GGTTCAAGCG TGCAATGGAT     720

CTGGTTCAAG AGGAGTTTCT GCAGAGATTA GATTTCTACC AACACAGCTG GCTGCCAGCC     780

CGGGCCTTGG TGGAAGAGGC CCTTGCCCAG CGATTCCAGG TGGACCCAAG TGGAGAGATT     840

GTGGAACTGG CGAAAGGTGC ATGTCCCTGG AAGGAGCATC TCTACCACCT GGAATCTGGG     900

CTGTCCCCTC CAGTGGCCAT CTTCTTTGTT ATCTACACTG ACCAGGCTGG ACAGTGGCGA     960

ATACAGTGTG TGCCCAAGGA GCCCCACTCA TTCCAAAGCC GGCTGCCCCT GCCAGAGCCA    1020

TGGCGGGGTC TTCGGGACGA GGCCCTGGAC CAGGTCAGTG GGATCCCTGG CTGCATCTTC    1080

GTCCATGCAA GCGGCTTCAT TGGCGGTCAC CGCACCCGAG AGGGTGCCTT GAGCATGGCC    1140

CGTGCCACCT TGGCCCAGCG CTCATACCTC CCACAAATCT CCTAGTCTAA TAAAACCTTC    1200

CATCTCATAC TGACAAAAAA AAAATGGTAG CTCGGGGGGC GTTAGGATAG ATCTTTAGAC    1260
```

```
CCGGTGGGGT TTCTAAGCTG GAGAAGTGTT AGAAAAAAAG GGCGGCCGCC CATCAAATTA    1320

GTTCTCTGCC CCGGGATTTT TTTTCGGGCC GGTACCCTTG GGGGGACCAA ATTTCCCCTT    1380
```

(2) INFORMATION FOR SEQ ID NO: 75:

(i) SEQUENCE CHARACTERISTICS:
        (A) LENGTH: 2028 base pairs
        (B) TYPE: nucleic acid
        (C) STRANDEDNESS: single
        (D) TOPOLOGY: linear (vii) IMMEDIATE SOURCE:
        (A) LIBRARY: LNODNOT03
        (B) CLONE: 1573677

(xi) SEQUENCE DESCRIPTION: SEQ ID NO: 75 :

```
CAAAAGGACA AGATAATAAA GTACAAAATG GTTCGTTACA TCAGAAGGAT ACAGTTCATG      60

ACAATGACTT TGAGCCCTAC CTTACTGGAC AGTCAAATCA GAGTAACAGT TACCCCTCAA     120

TGAGCGACCC CTACCTGTCC AGCTATTACC CGCCGTCCAT GGATTTCCT TACTCCCTCA      180

ATGAGGCTCC GTGGTCTACT GCAGGGGACC CTCCGATTCC ATACCTCACC ACCTACGGAC     240

AGCTCAGTAA CGGAGACCAT CATTTTATGC ACGATGCTGT TTTTGGGCAG CCTGGGGGCC     300

TGGGAACAA CATCTATCAG CACAGGTTCA ATTTTTTCCC TGAAAACCCT GCGTTCTCAG      360

CATGGGGGAC AAGTGGGTCT CAAGGTCAGC AGACCCAGAG CTCAGCCTCT CCCAGCACAG     420

CCCCCAGCTT TGGCTCAACC GCAGTATCAG AGCCCTCAGC AGCCACCCCA GACCCGCTGG     480

GTTGCCCCAC GCAACAGAAA CGCGGCGTTT GGGCAGAGCG GAGGGGCTGG CAGCGATAGC     540

AACTCTCCTG GAAACGTCCA GCCTAATTCT GCCCCCAGCG TCGAATCCCA CCCCGTCCTT     600

GAAAAACTGA AGGCTGCTCA CAGCTACAAC CCGAAAGAGT TTGAGTGGAA TCTGAAAAGC     660

GGGCGTGTGT TCATCATCAA GAGCTACTCT GAGGACGACA TCCACCGCTC CATTAAGTAC     720

TCCATCTGGT GTAGCACAGA GCACGGCAAC AAGCGCCTGG ACAGCGCCTT CCGCTGCATG     780

AGCAGCAAGG GGCCCGTCTA CCTGCTCTTC AGCGTCAATG GGAGTGGGCA TTTTTGTGGG     840

GTGGCCGAGA TGAAGTCCCC CGTGGACTAC GGCACCAGTG CCGGGGTCTG GTCTCAGGAC     900

AAGTGGAAGG GGAAGTTTGA TGTCCAGTGG ATTTTTGTTA AGGATGTACC CAATAACCAG     960

CTCCGGCACA TCAGGCTGGA GAATAACGAC AACAAACCGG TCACAAACTC CCGGGACACC    1020

CAGGAGGTGC CCTTAGAAAA AGCCAAGCAA GTGCTGAAAA TTATCAGTTC CTACAAGCAC    1080

ACAACCTCCA TCTTCGACGA CTTTGCTCAC TACGAGAAGC GCCAGAGGAG GAGGAGGTGG    1140

TGCGCAAGGA ACGGCAGAGT CGAAACAAAC AATGAGGGCG AACCAGTTTC TTACATGTTC    1200

TAACGTTTGA CTTTGAAAAC AGTTTAAAAC ACGTGTGCTT GGTCAGCTCC AGTGTGTCGT    1260

CCCGTGCGGG GGTTGAGTGT TGCATCTTTG CCTTTCTTGT CGTTGATTTT TGCCCAGATG    1320

GATCTGCATT TATTTGTACT TTTTCTATGT ATTATAATCC TGTAGAAGTC ACTAATAAAG    1380

GAGTATTTTT TTTTGTCAGC TTATCAATCA GACTGATCTA ATGTGAAATG TAAGTATCCT    1440

TAAAAACAAA GCATCTATTT TGGCAGAAAT TGTGTTCTTA AATTCAGTCA TTTGATATTC    1500

TGTGAGACTT CATATTTCTC ATCCCTTTAT TGCTTTTTAG CAAACATAAG AAACCATGAG    1560

TCATTTTGTC ATTTAGAGTA TTCTGATAAA ATCTCTTGAA AATACTGAAA TCAAAAGGTT    1620

AATGATTTTT TGTTCATTCT GATTTGTCAT TTTATTATCT GTTATCGGTC TAAAGTGCTA    1680

ATTTACCCAT TTGATTTTTC TGCTAGACAG ATAACTTTTA ATTTTTCAAA TTTGGCAGAC    1740

ACTTTTTTTT TTTTTTTGAA AATCTTTCCT TCCAGATCTG TTGCCCACTG AACAGCCACC    1800
```

```
CGTCCCTCAC TGTCCTGGTG TCCGATTGGG CTGGATGGTG TTGGGGCATG ATGTGTGGAG      1860

GAACTGGAAG GTGCTTTAGG TCTGGTTCAG GGTCGGGCAT TCTTTGTTGT TTGCACATCT      1920

TTTTAAATTT TACACCTTTT CTTAAGAATT CTAATGCCGT CTTAAGTTTT TATACCAATA      1980

ATGCTGAGCT TTAAGTGTAG GATCTGGTAG TACAGACAGT GTGATGGA                   2028
```

(2) INFORMATION FOR SEQ ID NO: 76:

(i) SEQUENCE CHARACTERISTICS:
        (A) LENGTH: 1170 base pairs
        (B) TYPE: nucleic acid
        (C) STRANDEDNESS: single
        (D) TOPOLOGY: linear (vii) IMMEDIATE SOURCE:
        (A) LIBRARY: LNODNOT03
        (B) CLONE: 1574624

(xi) SEQUENCE DESCRIPTION: SEQ ID NO: 76 :

```
TCCGCACTAG GCCCGCCCCA ATTTGCGTGT TTTTACCGTG CAGAGGGAGG GATTTAGAGT        60

TAGCCTTTGA TTGGTCAGCT TGACTGGCGA CCTTTCCCCT CTGCGACAGT TTCCCGAGGT       120

ACCTAGTGTC TGAGCGGCAC AGACGAGATC TCGATCGAAG GCGAGATGGC GGACGTGCTA       180

GATCTTCACG AGGCTGGGGG CGAAGATTTC GCCATGGATG AGGATGGGGA CGAGAGCATT       240

CACAAACTGA AGAAAAAGC GAAGAAACGG AAGGGTCGCG GCTTTGGCTC CGAAGAGGGG        300

TCCCGAGCGC GGATGCGTGA GGATTATGAC AGCGTGGAGC AGGATGGCGA TGAACCCGGA       360

CCACAACGCT CTGTTGAAGG CTGGATTCTC TTTGTAACTG GAGTCCATGA GGAAGCCACC       420

GAAGAAGACA TACACGACAA ATTCGCAGAA TATGGGAAA TTAAAAACAT TCATCTCAAC        480

CTCGACAGGC GAACAGGATA TCTGAAGGGG TATACTCTAG TTGAATATGA AACATACAAG       540

GAAGCCCAGG CTGCTATGGA GGGACTCAAT GGCCAGGATT TGATGGGACA GCCCATCAGC       600

GTTGACTGGT GTTTTGTTCG GGGTCCACCA AAAGGCAAGA GGAGAGGTGG CCGAAGACGC       660

AGCAGAAGTC CAGACCGGAG ACGTCGCTGA CAGGTCCTCT GTTGTCCAGG TGTTCTCTTC       720

AAGATTCCAT TTGACCATGC AGCCTTGGAC AAATAGGACT GGGGTGGAAC TTGCTGTGTT       780

TATATTTAAT CTCTTACCGT ATATGCGTAG TATTTGAGTT GCGAATAAAT GTTCCATTTT       840

TGTTTTCTAC ATTTAATGTT ACTTTCCTGT TCCCAAAATT GAAAGTTCTA AAGCATAGCA       900

AGGCTGTATG GATCATTTGG AAAGATACCT TCTAGGGACT GAACCCCAAG TANTTCCTTT       960

TNTTCCCTTT TCCGAAAATA ATCCCTGCTG TGTTTACCCG GGTGTGATTG CCCCTGATTA      1020

TATCCCACTG CCGTCTCCAA ACTTTTGGGC TTCATCCTTC TTTCTGCCTC CTTGTCTCTA      1080

ATTTTTTGGG ATAATAGGCC CTTCTCCCCT CCCCATCAAA TATTTTATTA TTTTTTTCAA      1140

AAAAGGTTTT TCCGTTTTTC ACGGGCCCT                                         1170
```

(2) INFORMATION FOR SEQ ID NO: 77:

(i) SEQUENCE CHARACTERISTICS:
        (A) LENGTH: 1107 base pairs
        (B) TYPE: nucleic acid
        (C) STRANDEDNESS: single
        (D) TOPOLOGY: linear (vii) IMMEDIATE SOURCE:
        (A) LIBRARY: LNODNOT03
        (B) CLONE: 1577239

(xi) SEQUENCE DESCRIPTION: SEQ ID NO: 77 :

| | |
|---|---|
| CCGAGCGCGG CCCCTGGGTT CGAACACGGC ACCCGCACTG CGCGTCATGG TGCAGGCCTG | 60 |
| GTATATGGAC GACGCCCCGG GCGACCCGCG GCAACCCCAC CGCCCCGACC CCGGCCGCCC | 120 |
| AGTGGGCCTG GAGCAGCTGC GGCGGCTCGG GGTGCTCTAC TGGAAGCTGG ATGCTGACAA | 180 |
| ATATGAGAAT GATCCAGAAT TAGAAAAGAT CCGAAGAGAG AGGAACTACT CCTGGATGGA | 240 |
| CATCATAACC ATATGCAAAG ATAAACTACC AAATTATGAA GAAAGATTA AGATGTTCTA | 300 |
| CGAGGAGCAT TTGCACTTGG ACGATGAGAT CCGCTACATC CTGGATGGCA GTGGGTACTT | 360 |
| CGACGTGAGG GACAAGGAGG ACCAGTGGAT CCGGATCTTC ATGGAGAAGG GAGACATGGT | 420 |
| GACGCTCCCC GCGGGGATCT ATCACCGCTT CACGGTGGAC GAGAAGAACT ACACGAAGGC | 480 |
| CATGCGGCTG TTTGTGGGAG AACCGGTGTG GACAGCGTAC AACCGGCCCG CTGACCATTT | 540 |
| TGAAGCCCGC GGGCAGTACG TGAAATTTCT GGCACAGACC GCCTAGCAGT GCTGCCTGGG | 600 |
| AACTAACACG CGCCTCGTAA AGGTCCCCAA TGTAATGACT GAGCAGAAAA TCAATCACTT | 660 |
| TCTCTTTGCT TTTAGAGGAT AGCCTTGAGG CTAGATTATC TTTCCTTTGT AAGATTATTT | 720 |
| GATCAGAATA TTTTGTAATG AAAGGATCTA GAAAGCAACT TGGAAGTGTA AAGAGTCACC | 780 |
| TTCATTTTCT GTAACTCAAT CAAGACTGGT GGGTCCATGG CCCTGTGTTA GTTCATGCAT | 840 |
| TCAGTTGAGT CCCAAATGAA AGTTTCATCT CCCGAAATGC AGTTCCTTAG ATGCCCATCT | 900 |
| GGACGTGATG CCGCGCCTGC CGTGTAAGAA GGTGCAATCC TAGATAACAC AGCTAGCCAG | 960 |
| ATAGAAGACA CTTTTTTCTC CAAAATGATG CCTTGGGGTG GGGAGTGGTA GGGGGAAGAG | 1020 |
| CTCCCACCCT AAGGGGCACA CACTGAGTTG CTTATGCCAC TTCCTTGTTC AAAATAAAGT | 1080 |
| AACTGCCTTA ATCTTATACT CATGGCT | 1107 |

(2) INFORMATION FOR SEQ ID NO: 78:

(i) SEQUENCE CHARACTERISTICS:
        (A) LENGTH: 1075 base pairs
        (B) TYPE: nucleic acid
        (C) STRANDEDNESS: single
        (D) TOPOLOGY: linear (vii) IMMEDIATE SOURCE:
        (A) LIBRARY: BLADNOT03
        (B) CLONE: 1598203

(xi) SEQUENCE DESCRIPTION: SEQ ID NO: 78 :

| | |
|---|---|
| CGGTAACCAG CCCTGGGAAG CCCGCAAGAG GCCTCAGCGG TGGCCGTCCG AGAGCCGAGA | 60 |
| GGTGAGGGTG CCCCCGCCTC ACCTGCAGAG GGGCCGTTCC GGGCTCGAAC CCGGCACCTT | 120 |
| CCGGAAAATG GCGGCTGCCA GGCCCAGCCT GGGCCGAGTC CTCCCAGGAT CCTCTGTCCT | 180 |
| GTTCCTGTGT GACATGCAGG AGAAGTTCCG CCACAACATC GCCTACTTCC CACAGATCGT | 240 |
| CTCAGTGGCT GCCCGCATGC TCAAGGTGGC CCGGCTGCTT GAGGTGCCAG TCATGCTGAC | 300 |
| GGAGCAGTAC CCACAAGGCC TGGGCCCCAC GGTGCCCGAG CTGGGGACTG AGGGCCTTCG | 360 |
| GCCGCTGGCC AAGACCTGCT TCAGCATGGT GCCTGCCCTG CAGCAGGAGC TGGACAGTCG | 420 |
| GCCCCAGCTG CGCTCTGTGC TGCTCTGTGG CATTGAGGCA CAGGCCTGCA TCTTGAACAC | 480 |
| GACCCTGGAC CTCCTAGACC GGGGGCTGCA GGTCCATGTG GTGGTGGACG CCTGCTCCTC | 540 |
| ACGCAGCCAG GTGGACCGGC TGGTGGCTCT GGCCCGCATG AGACAGAGTG GTGCCTTCCT | 600 |
| CTCCACCAGC GAAGGGCTCA TTCTGCAGCT TGTGGGCGAT GCCGTCCACC CCAGTTCAA | 660 |
| GGAGATCCAG AAACTCATCA AGGAGCCCGC CCCAGACAGC GGACTGCTGG GCCTCTTCCA | 720 |
| AGGCCAGAAC TCCCTCCTCC ACTGAACTCC AACCCTGCCT TGAGGGAAGA CCACCCTCCT | 780 |

```
GTCACCCGGA CCTCAGTGGA AGCCCGTTCC CCCCATCCCT GGATCCCAAG AGTGGTGCGA      840

TCCACCAGGA GTGCCGCCCC CTTGTGGGGG GGGGCAGGGT GCTGCCTTCC CATTGGACAG      900

CTGCTCCCGG AAATGCAAAT GAGACTCCTG GAAACTGGGT GGGAATTGGC TGAGCCAAGA      960

TGGAGGCGGG GCTCGGCCCC GGGCCACTTC ACGGGGCGGG AAGGGGAGGG GAAGAAGAGT     1020

CTCAGACTGT GGGACACGGA CTCGCAGAAT AAACATATAT GTGGCAAAAA AAAAA          1075

(2) INFORMATION FOR SEQ ID NO:    79:

(i) SEQUENCE CHARACTERISTICS:
        (A) LENGTH: 1830 base pairs
        (B) TYPE: nucleic acid
        (C) STRANDEDNESS: single
        (D) TOPOLOGY: linear (vii) IMMEDIATE SOURCE:
        (A) LIBRARY: BLADNOT03
        (B) CLONE: 1600438

(xi) SEQUENCE DESCRIPTION: SEQ ID NO: 79 :

GTCAATGTGT CTGTCCTTCA CTCCTCCATT GTCTGCCGCC ACTGCTGCTG CTGCTGCTGC       60

TGCCGCTGCT GCTGCACGAA TCGTCGCAGC CCCCAGCCTT GCGCGTCGTC GCTACCTCCT      120

CGGACAGAAA TTTTATGAAT AAGCATCAGA AGCCAGTGCT AACAGGCCAG CGGTTCAAAA      180

CTCGGAAAAG GGATGAAAAA GAGAAATTCG AACCCACAGT CTTCAGGGAT ACACTTGTCC      240

AGGGGCTTAA TGAGGCTGGT GATGACCTTG AAGCTGTAGC CAAATTTCTG GACTCTACAG      300

GCTCAAGATT AGATTATCGT CGCTATGCAG ACACACTCTT CGATATCCTG GTGGCTGGCA      360

GTATGCTTGC CCCTGGAGGA ACGCGCATAG ATGATGGTGA CAAGACCAAG ATGACCAACC      420

ACTGTGTGTT TTCAGCAAAT GAAGATCATG AAACCATCCG AAACTATGCT CAGGTCTTCA      480

ATAAACTCAT CAGGAGATAT AAGTATTTGG AGAAGGCATT TGAAGATGAA ATGAAAAAGC      540

TTCTCCTCTT CCTTAAAGCC TTTTCCGAAA CAGAGCAGAC AAAGTTGGCG ATGCTGTCGG      600

GGATTCTGCT GGGCAATGGC ACCCTGCCCG CCACCATCCT CACCAGTCTC TTCACCGACA      660

GCTTAGTCAA AGAAGGCATT GCGGCCTCAT TTGCTGTCAA GCTTTTCAAA GCATGGATGG      720

CAGAAAAGA TGCCAACTCT GTTACCTCGT CTTTGAGAAA AGCCAACTTA GACAAGAGGC      780

TGCTTGAACT CTTTCCAGTT AACAGACAGA GTGTGGATCA TTTTGCTAAA TACTTCACTG      840

ACGCAGGTCT TAAGGAGCTT TCCGACTTCC TCCGAGTCCA GCAGTCCCTG GGCACCAGGA      900

AGGAACTGCA GAAGGAGCTC CAGGAGCGTC TTTCTCAGGA ATGCCCGATC AAGGAGGTGG      960

TGCTTTATGT CAAAGAAGAA ATGAAGAGGA ATGATCTTCC AGAAACAGCA GTGATTGGTC     1020

TTCTGTGGAC ATGTATAATG AACGCTGTTG AGTGGAACAA GAAGGAAGAA CTTGTTGCAG     1080

AGCAGGCTCT GAAGCACCTG AAGCAATATG CTCCCCTGCT GGCCGTGTTC AGCTCCCAAG     1140

GCCAGTCAGA GCTGATCCTC CTCCAGAAGG TTCAGGAATA CTGCTACGAC AACATCCATT     1200

TCATGAAAGC CTTTCAGAAG ATTGTGGTTC TCTTTTATAA AGCTGATGTT CTGAGCGAAG     1260

AAGCAATACT GAAATGGTAT AAGGAAGCAC ATGTTGCTAA AGGCAAAAGT GTTTTCTTG      1320

ACCAGATGAA GAAATTTGTT GAGTGGTTAC AAAATGCAGA AGAAGAATCC GAATCGGAAG     1380

GTGAGGAAAA TTAAATGGCT CAACAAGCAC AATACCTAGG TTACCACACA CCACTTTTTG     1440

ATTGGGAATG CTGAACCATT TGAGAAGAGA AACTTGGCTT CTGTTTTCGC AAAGGAAAAA     1500

AAAAATAGGA TAGGCTTCCC TTGTGCAGAG GGAGAAATGG TTTTGTTTTT GTTTTGTTTT     1560

TAAATGGAGC CCTGAGGCAT CAGCTATTAT ACTTGGGACT CTACCTCTCA CTCACTATAT     1620
```

```
GCTAACTTAA AGCCATTCAA CAAGGAGTCA AGTAGATCTG AAATTAAATA CTCAACAGAC    1680

TCCTCCTTTT TTAGCTGTAT TTTTCAGGTA CTGTGTGGTG ACCGCCCCAC TGGTGTCTAT    1740

TACAGGCCAC TTTGGTAGTT GTGTATCTGC TCATGTATGT GATTTGACAA ACCAGTTTTT    1800

TAAAATAAAT GGCTTTTTAA GAAAAAAAAA                                     1830
```

(2) INFORMATION FOR SEQ ID NO: 80:

(i) SEQUENCE CHARACTERISTICS:
        (A) LENGTH: 1330 base pairs
        (B) TYPE: nucleic acid
        (C) STRANDEDNESS: single
        (D) TOPOLOGY: linear (vii) IMMEDIATE SOURCE:
        (A) LIBRARY: BLADNOT03
        (B) CLONE: 1600518

(xi) SEQUENCE DESCRIPTION: SEQ ID NO: 80 :

```
CCGGCAGCCA TCCCCGCGGT GCTGACATCC CGGTTGTTCT TCTGTGCCGG GGGTCTTCCT      60

GCTGTCATGA AGGACGTACC GGGCTTCCTA CAGCAGAGCC AGAGCTCCGG GCCCGGGCAG     120

CCCGCTGTGT GGCACCGTCT GGAGGAGCTC TACACGAAGA AGTTGTGGCA TCAGCTGACA     180

CTTCAGGTGC TTGATTTTGT GCAGGATCCG TGCTTTGCCC AAGGAGATGG TCTCATTAAG     240

CTTTATGAAA ACTTTATCAG TGAATTTGAA CACAGGGTGA ATCCTTTGTC CCTCGTGGAA     300

ATCATTCTTC ATGTAGTTAG ACAGATGACT GATCCTAATG TGGCTCTTAC TTTTCTGGAA     360

AAGACTCGTG AGAAGGTGAA AAGTAGTGAT GAGGCAGTGA TCCTGTGTAA AACAGCAATT     420

GGAGCTCTAA AATTAAACAT CGGGGACCTA CAGGTTACAA AGGAAACAAT TGAAGATGTT     480

GAAGAAATGC TCAACAACCT TCCTGGTGTG ACATCGGTTC ACAGTCGTTT CTATGATCTC     540

TCCAGTAAAT ACTATCAAAC AATCGGAAAC CACGCGTCCT ACTACAAAGA TGCTCTGCGG     600

TTTTTGGGCT GTGTTGACAT CAAGGATCTA CCAGTGTCTG AGCAGCAGGA GAGAGCCTTC     660

ACGCTGGGGC TAGCAGGACT TCTCGGCGAG GGAGTTTTTA ACTTTGGAGA ACTCCTCATG     720

CACCCTGTGC TGGAGTCCCT GAGGAATACT GACCGGCAGT GGCTGATTGA CACCCTCTAT     780

GCCTTCAACA GTGGCAACGT AGAGCGGTTC CAGACTCTGA AGACTGCCTG GGGCCAGCAG     840

CCTGATTTAG CAGCTAATGA AGCCCAGCTT CTGAGGAAAA TTCAGTTGTT GTGCCTCATG     900

GAGATGACTT TCACACGACC TGCCAATCAC AGACAACTCA CTTTTGAAGA AATTGCCAAA     960

AGTGCTAAAA TCACAGTGAA TGAGGTGGAG CTTCTGGTGA TGAAGGCCCT TTCGGTGGGG    1020

CTGGTGAAAG GCAGTATAGA CGAGGTGGAC AAACGAGTCC ACATGACCTG GGTGCAGCCC    1080

CGAGTGTTGG ATTTGCAACA GATCAAGGGA ATGAAGGACC GCCTGGAGTT CTGGTGCACG    1140

GATGTGAAGA GCATGGAGAT GCTGGTGGAG CACCAGGCCC ATGACATCCT CACCTAGGGC    1200

CCCCTGGTTC CCCGTCGTGT CTCCTTTGAC TCACCTGAGA GAGGCGTTTG CAGCCAATGA    1260

AGCTGGCTGC TCAGACGGTC GACATTGAAT TTGGGTGGGG GTTGGGATCC TGTCTGAAGT    1320

ACAGAATGTT                                                           1330
```

(2) INFORMATION FOR SEQ ID NO: 81:

(i) SEQUENCE CHARACTERISTICS:
        (A) LENGTH: 1152 base pairs
        (B) TYPE: nucleic acid
        (C) STRANDEDNESS: single
        (D) TOPOLOGY: linear (vii) IMMEDIATE SOURCE:

```
        (A) LIBRARY: BLADNOT03
        (B) CLONE: 1602473

(xi) SEQUENCE DESCRIPTION: SEQ ID NO: 81 :

CGAGCCGGCG CACCGTACGC TGGGACGTGT GGTTTCAGCT CGTGCGCCTC CCCGTGGGTT      60

TGCGACGTTT AGCGACTATT GCGCCTGCGC CAGCGCCGGC TGCGAGACTG GGGCCGTGGC     120

TGCTGGTCCC GGGTGATGCT AGGCGGCTCC CTGGGCTCCA GGCTGTTGCG GGGTGTAGGT     180

GGGAGTCACG GACGGTTCGG GGCCCGAGGT GTCCGCGAAG GTGGCGCAGC CATGGCGGCA     240

GGGGAGAGCA TGGCTCAGCG GATGGTCTGG GTGGACCTGG AGATGACAGG ATTGGACATT     300

GAGAAGGACC AGATTATTGA GATGGCCTGT CTGATAACTG ACTCTGATCT CAACATTTTG     360

GCTGAAGGTC CTAACCTGAT TATAAAACAA CCAGATGAGT TGCTGGACAG CATGTCAGAT     420

TGGTGTAAGG AGCATCACGG GAAGTCTGGC CTTACCAAGG CAGTGAAGGA GAGTACAATT     480

ACATTGCAGC AGGCAGAGTA TGAATTTCTG TCCTTTGTAC GACAGCAGAC TCCTCCAGGG     540

CTCTGTCCAC TTGCAGGAAA TTCAGTTCAT GAAGATAAGA AGTTTCTTGA CAAATACATG     600

CCCCAGTTCA TGAAACATCT TCATTATAGA ATAATTGATG TGAGCACTGT TAAAGAACTG     660

TGCAGACGCT GGTATCCAGA AGAATATGAA TTTGCACCAA AGAAGGCTGC TTCTCATAGG     720

GCACTTGATG ACATTAGTGA AAGCATCAAA GAGCTTCAGT TTTACCGAAA TAACATCTTC     780

AAGAAAAAAA TAGATGAAAA GAAGAGGAAA ATTATAGAAA ATGGGAAAA TGAGAAGACC      840

GTGAGTTGAT GCCAGTTATC ATGCTGCCAC TACATCGTTA TCTGGAGGCA ACTTCTGGTG     900

GTTTTTTTTT CTCACGCTGA TGGCTTGGCA GAGCACCTTC GGTTAACTTG CATCTCCAGA     960

TTGATTACTC AAGCAGACAG CACACGAAAT ACTATTTTTC TCCTAATATG CTGTTTCCAT    1020

TATGACACAG CAGCTCCTTT GTAAGTACCA GGTCATGTCC ATCCCTTGGT ACATATATGC    1080

ATTTGCTTTT AAACCATTTC TTTTGTTTAA ATAAATAAAT AAGTAAATAA AGCTAGTTCT    1140

ATTGAAATGC AA                                                        1152

(2) INFORMATION FOR SEQ ID NO:    82:

(i) SEQUENCE CHARACTERISTICS:
         (A) LENGTH: 566 base pairs
         (B) TYPE: nucleic acid
         (C) STRANDEDNESS: single
         (D) TOPOLOGY: linear (vii) IMMEDIATE SOURCE:
         (A) LIBRARY: LUNGNOT15
         (B) CLONE: 1605720

(xi) SEQUENCE DESCRIPTION: SEQ ID NO: 82 :

GTTCTCCGCC CCTGCCACTG GGCCATGGAG ACTGTGGCAC AGTAGACTGT AGTGTGAGGC      60

TCGCGGGGGC AGTGGCCATG GAGGCCGTGC TGAACGAGCT GGTGTCTGTG GAGGACCTGC     120

TGAAGTTTGA AAAGAAATTT CAGTCTGAGA AGGCAGCAGG CTCGGTGTCC AAGAGCACGC     180

AGTTTGAGTA CGCCTGGTGC CTGGTGCGGA GCAAGTACAA TGATGACATC CGTAAAGGCA     240

TCGTGCTGCT CGAGGAGCTG CTGCCCAAAG GGAGCAAGGA GGAACAGCGG GATTACGTCT     300

TCTACCTGGC CGTGGGGAAC TACCGGCTCA AGGAATACGA GAAGGCCTTA AAGTACGTCC     360

GCGGGTTGCT GCAGACAGAG CCCCAGAACA ACCAGGCCAA GGAACTGGAG CGGCTCATTG     420

ACAAGGCCAT GAAGAAAGAT GGACTCGTGG GCATGGCCAT CGTGGGAGGC ATGGCCCTGG     480

GTGTGGCGGG ACTTGCCGGA CTCATCGGAC TTGCTGTGTC CAAGTCCAAA TTCTGAAGGA     540

GACGCGGGAG CCCACGGAGA ACGCTC                                          566
```

(2) INFORMATION FOR SEQ ID NO: 83:

(i) SEQUENCE CHARACTERISTICS:
        (A) LENGTH: 745 base pairs
        (B) TYPE: nucleic acid
        (C) STRANDEDNESS: single
        (D) TOPOLOGY: linear (vii) IMMEDIATE SOURCE:
        (A) LIBRARY: COLNTUT06
        (B) CLONE: 1610501

(xi) SEQUENCE DESCRIPTION: SEQ ID NO: 83 :

```
CGGAAGAGGT AGCTCACGCG ATAGAAACGT GTTCGCTGCC CAGAAGAAGG GAAGGCGCGA    60
GTGAGGAAAG GAGGTACTGT AGATGCCCTC CAAATCCTTG GTTATGGAAT ATTTGGCTCA   120
TCCCAGTACA CTCGGCTTGG CTGTTGGAGT TGCTTGTGGC ATGTGCCTGG GCTGGAGCCT   180
TCGAGTATGC TTTGGGATGC TCCCCAAAAG CAAGACGAGC AAGACACACA CAGATACTGA   240
AAGTGAAGCA AGCATCTTGG GAGACAGCGG GGAGTACAAG ATGATTCTTG TGGTTCGAAA   300
TGACTTAAAG ATGGGAAAAG GGAAAGTGGC TGCCCAGTGC TCTCATGCTG CTGTTTCAGC   360
CTACAAGCAG ATTCAAAGAA GAAATCCTGA AATGCTCAAA CAATGGGAAT ACTGTGGCCA   420
GCCCAAGGTG GTGGTCAAAG CTCCTGATGA AGAAACCCTG ATTGCATTAT TGGCCCATGC   480
AAAAATGCTG GGACTGACTG TAAGTTTAAT TCAAGATGCT GGACGTACTC AGATTGCACC   540
AGGCTCTCAA ACTGTCCTAG GGATTGGGCC AGGACCAGCA GACCTAATTG ACAAAGTCAC   600
TGGTCACCTA AAACTTTACT AGGTGGACTT TGATATGACA CAACCCCTC CATCACAAGT   660
GTTTGAAGCC TGTCAGATTC TAACAACAAA AGCTGAATTT CTTCACCCAA CTTAAATGTT   720
CTTGAGATGA AATAAAACC TATTA                                          745
```

(2) INFORMATION FOR SEQ ID NO: 84:

(i) SEQUENCE CHARACTERISTICS:
        (A) LENGTH: 909 base pairs
        (B) TYPE: nucleic acid
        (C) STRANDEDNESS: single
        (D) TOPOLOGY: linear (vii) IMMEDIATE SOURCE:
        (A) LIBRARY: BLADNOT06
        (B) CLONE: 1720770

(xi) SEQUENCE DESCRIPTION: SEQ ID NO: 84 :

```
TGAGGGAGAC CGCGGCTCGG CCGTAGCGGA GCTGCGAGGT GGCAGGGCCC AGCCCCGAAC    60
CAGACAAGGG ACCCCTCAAG GAGCTTCATT CTAGCAGGAG AAAATTGAGA AGTAAACCAG   120
AAAGTTACAG AATGTCTGAA GGGGACAGTG TGGGAGAATC CGTCCATGGG AAACCTTCGG   180
TGGTGTACAG ATTTTTCACA AGACTTGGAC AGATTTATCA GTCCTGGCTA GACAAGTCCA   240
CACCCTACAC GGCTGTGCGA TGGGTCGTGA CACTGGGCCT GAGCTTTGTC TACATGATTC   300
GAGTTTACCT GCTGCAGGGT TGGTACATTG TGACCTATGC CTTGGGGATC TACCATCTAA   360
ATCTTTTCAT AGCTTTTCTT TCTCCCAAAG TGGATCCTTC CTTAATGGAA GACTCAGATG   420
ACGGTCCTTC GCTACCCACC AAACAGAACG AGGAATTCCG CCCCTTCATT CGAAGGCTCC   480
CAGAGTTTAA ATTTTGGCAT GCGGCTACCA AGGGCATCCT TGTGGCTATG GTCTGTACTT   540
TCTTCGACGC TTTCAACGTC CCGGTGTTCT GGCCGATTCT GGTGATGTAC TTCATCATGC   600
TCTTCTGTAT CACGATGAAG AGGCAAATCA AGCACATGAT TAAGTACCGG TACATCCCGT   660
```

```
TCACACATGG GAAGAGAAGG TACAGAGGCA AGGAGGATGC CGGCAAGGCC TTCGCCAGCT      720

AGAAGCGGGA CTGAGGCTGC CTCACGTGTT GCAAGAACAG TTTTGAGCCA TTGTTAACAA      780

TGCCTTTTTT CTTCACATAA AGTAGTTGAT TACGAGGGAG TCAAATTTTC TTTTTAAAAA      840

GGAGCTTCAA TGATTTGTAA CTGAAATATC AGGTTCTAGA AGAAACTGGC GCTTAAACCA     900

AAAAAAAAA                                                              909

(2) INFORMATION FOR SEQ ID NO:     85:

(i) SEQUENCE CHARACTERISTICS:
        (A) LENGTH: 2028 base pairs
        (B) TYPE: nucleic acid
        (C) STRANDEDNESS: single
        (D) TOPOLOGY: linear (vii) IMMEDIATE SOURCE:
        (A) LIBRARY: BRAINON01
        (B) CLONE: 1832295

(xi) SEQUENCE DESCRIPTION: SEQ ID NO: 85 :

CCGGCGGGCG GGGGCTGAGG GGCTGCCATG GCGGCGGCGG GCCGGCTCCC GAGCTCCTGG       60

GCCCTCTTCT CGCCGCTCCT CGCAGGGCTT GCACTACTGG GAGTCGGGCC GGTCCCAGCG      120

CGGGCGCTGC ACAACGTCAC GGCCGAGCTC TTTGGGGCCG AGGCCTGGGG CACCCTTGCG      180

GCTTTCGGGG ACCTCAACTC CGACAAGCAG ACGGATCTCT TCGTGCTGCG GGAAAGAAAT      240

GACTTAATCG TCTTTTTGGC AGACCAGAAT GCACCCTATT TTAAACCCAA AGTAAAGGTA      300

TCTTTCAAGA ATCACAGTGC ATTGATAACA AGTGTAGTCC CTGGGGATTA TGATGGAGAT      360

TCTCAAATGG ATGTCCTTCT GACATATCTT CCCAAAAATT ATGCCAAGAG TGAATTAGGA      420

GCTGTTATCT TCTGGGACA AAATCAAACA TTAGATCCTA ACAATATGAC CATACTCAAT       480

AGGACTTTTC AAGATGAGCC ACTAATTATG GATTTCAATG GTGATCTAAT TCCTGATATT      540

TTTGGTATCA CAAATGAATC CAACCAGCCA CAGATACTAT TAGGAGGGAA TTTATCATGG      600

CATCCAGCAT TGACCACTAC AAGTAAAATG CGAATTCCAC ATTCTCATGC ATTTATTGAT      660

CTGACTGAAG ATTTTACAGC AGATTTATTC CTGACGACAT TGAATGCCAC CACTAGTACC      720

TTCCAGTTTG AAATATGGGA AAATTTGGAT GGAAACTTCT CTGTCAGTAC TATATTGGAA      780

AAACCTCAAA ATATGATGGT GGTTGGACAG TCAGCATTTG CAGACTTTGA TGGAGATGGA      840

CACATGGATC ATTTACTGCC AGGCTGTGAA GATAAAAATT GCCAAAAGAG TACCATCTAC      900

TTAGTGAGAT CTGGGATGAA GCAGTGGGTT CCAGTCCTAC AAGATTTCAG CAATAAGGGC      960

ACACTCTGGG GCTTTGTGCC ATTTGTGGAT GAACAGCAAC CAACTGAAAT ACCAATTCCA     1020

ATTACCCTTC ATATTGGAGA CTACAATATG GATGGCTATC CAGACGCTCT GGTCATACTA     1080

AAGAACACAT CTGGAAGCAA CCAGCAGGCC TTTTTACTGG AGAACGTCCC TTGTAATAAT     1140

GCAAGCTGTG AAGAGGCGCG TCGAATGTTT AAAGTCTACT GGGAGCTGAC AGACCTAAAT     1200

CAAATTAAGG ATGCCATGGT TGCCACCTTC TTTGACATTT ACGAAGATGG AATCTTGGAC     1260

ATTGTAGTGC TAAGTAAAGG ATATACAAAG AATGATTTTG CCATTCATAC ACTAAAAAAT     1320

AACTTTGAAG CAGATGCTTA TTTTGTTAAA GTTATTGTTC TTAGTGGTCT GTGTTCTAAT     1380

GACTGTCCTC GTAAGATAAC GCCCTTTGGA GTGAATCAAC CTGGACCTTA TATCATGTAT     1440

ACAACTTTAG ATGCAAATGG GTATCTGAAA AATGGATCAG CTGGCCAACT CAGCCAATCC     1500

GCACATTTAG CTCTCCAACT ACCATACAAC GTGCTTGGTT TAGGTCGGAG CGCAAATTTT     1560

CTTGACCATC TCTACGTTGG TATTCCCCGT CCATCTGGAG AAAAATCTAT ACGAAAACAA     1620
```

```
GAGTGGACTG CAATCATTCC AAATTCCCAG CTAATTGTCA TTCCATACCC TCACAATGTC    1680

CCTCGAAGTT GGAGTGCCAA ACTGTATCTT ACACCAAGTA ATATTGTTCT GCTTACTGCT    1740

ATAGCTCTCA TCGGTGTCTG TGTTTTCATC TTGGCAATAA TTGGCATTTT ACATTGGCAG    1800

GAAAAGAAAG CAGATGATAG AGAAAAACGA CAAGAAGCCC ACCGGTTTCA TTTTGATGCT    1860

ATGTGACTTG CCTTTAATAT TACATAATGG AATGGCTGTT CACTTGATTA GTTGAAACAC    1920

AAATTCTGGC TTGAAAAAAT AGGGGAGATT AAATATTATT TATAAATGAT GTATCCCATG    1980

GTAATTATTG GAAAGTATTC AAATAAATAT GGTTTGAATA TGTCACAA                2028

(2) INFORMATION FOR SEQ ID NO:    86:

(i) SEQUENCE CHARACTERISTICS:
         (A) LENGTH: 372 base pairs
         (B) TYPE: nucleic acid
         (C) STRANDEDNESS: single
         (D) TOPOLOGY: linear (vii) IMMEDIATE SOURCE:
         (A) LIBRARY: CORPNOT02
         (B) CLONE: 1990522

(xi) SEQUENCE DESCRIPTION: SEQ ID NO: 86 :

GCGAGCTCGG CTTCCTCAAC ATGGCTGCGC CCTTGTCAGT GGAGGTGGAG TTCGGAGGTG      60

GTGCGGAGCT CCTGTTTGAC GGTATTAAGA ACATCGAGT CACTTTGCCT GGACAGGAGG     120

AACCCTGGGA CATCCGGAAC CTGCTCATCT GGATCAAGAA GAATTTGCTA AAAGAGCGGC     180

CAGAGTTGTT CATCCAGGGA GACAGCGTGC GGCCAGGAAT TCTGGTGCTG ATTAACGATG     240

CCGACTGGGA GCTACTGGGT GAGCTGGACT ACCAGCTTCA GGACCAGGAC AGCGTCCTCT     300

TCATCTCCAC TCTGCACGGC GGCTGAGGGC CCTTCTCTGG GGCTGGGCAA CCTTAGAGGG     360

GAGAACGAAA AA                                                         372

(2) INFORMATION FOR SEQ ID NO:    87:

(i) SEQUENCE CHARACTERISTICS:
         (A) LENGTH: 829 base pairs
         (B) TYPE: nucleic acid
         (C) STRANDEDNESS: single
         (D) TOPOLOGY: linear (vii) IMMEDIATE SOURCE:
         (A) LIBRARY: BRAITUT02
         (B) CLONE: 2098087

(xi) SEQUENCE DESCRIPTION: SEQ ID NO: 87 :

CAGGCTCTGT ATCCGTGGCA GCGGCCGTGG CAGGCTGGCT GGGTACCGGC TGTCGCTGAC      60

CCAGGAGAAG CTGCCTGTCT ACATCAGCCT GGGCTGCAGC GCGCTGCCGC CGCGGGGCCG     120

GCAGCCATGG CCAAGGACAT CCTGGGTGAA GCAGGGCTAC ACTTTGATGA ACTGAACAAG     180

CTGAGGGTGT TGGACCCAGA GGTTACCCAG CAGACCATAG AGCTGAAGGA AGAGTGCAAA     240

GACTTTGTGG ACAAAATTGG CCAGTTTCAG AAAATAGTTG GTGGTTTAAT TGAGCTTGTT     300

GATCAACTTG CAAAAGAAGC AGAAAATGAA AAGATGAAGG CCATCGGTGC TCGGAACTTG     360

CTCAAATCTA TAGCAAAGCA GAGAGAAGCT CAACAGCAGC AACTTCAAGC CCTAATAGCA     420

GAAAAGAAAA TGCAGCTAGA AAGGTATCGG GTTGAATATG AAGCTTTGTG TAAAGTAGAA     480

GCAGAACAAA ATGAATTTAT TGACCAATTT ATTTTTCAGA AATGAACTGA AAATTTCGCT     540

TTTATAGTAG GAAGGCAAAA CAAAAAAAAG CCTCTCAAAA CCAAAAAAAC CTCTGTAGCA     600

TTCCAGCGGC TTGACCAATG ACCTATGTCA CAAGAGGTGC GTGTAAGGAA TGCAGCCCCA     660
```

```
TGGAACGTGC TATTCACGTC TGTGGGAGCC AGTTTTAACA TCAGTGCACA GCTGCTGCTG      720

GTGGCCCTGC AGTGTACGTT CTCACCTCTT ATGCTTAGTT GGAACCCGAA CAAAAATAAA      780

CTTTCATCCT TTTGTGTGTA ACTTCTCCAG AATACTAAAT AAAAAGTTC                  829
```

(2) INFORMATION FOR SEQ ID NO: 88:

(i) SEQUENCE CHARACTERISTICS:
        (A) LENGTH: 1178 base pairs
        (B) TYPE: nucleic acid
        (C) STRANDEDNESS: single
        (D) TOPOLOGY: linear (vii) IMMEDIATE SOURCE:
        (A) LIBRARY: BRAITUT03
        (B) CLONE: 2112230

(xi) SEQUENCE DESCRIPTION: SEQ ID NO: 88 :

```
CTTCCCGCCA GTCCCCTAAC CCTGAGGCTG CCGCGCGGCG GTCACTGCGC CGGGGTAGTG       60

GGCCCCAGTG TTGCGCTCTC TGGCCGTTCC TTACACTTTG CTTCAGGCTC CAGTGCAGGG      120

GCGTAGTGGG ATATGGCCAA CTCGGGCTGC AAGGACGTCA CGGGTCCAGA TGAGGAGAGT      180

TTTCTGTACT TTGCCTACGG CAGCAACCTG CTGACAGAGA GGATCCACCT CCGAAACCCC      240

TCGGCGGCGT TCTTCTGTGT GGCCCGCCTG CAGGATTTTA AGCTTGACTT TGGCAATTCC      300

CAAGGCAAAA CAAGTCAAAC TTGGCATGGA GGGATAGCCA CCATTTTTCA GAGTCCTGGC      360

GATGAAGTGT GGGGAGTAGT ATGGAAAATG AACAAAAGCA ATTTAAATTC TCTGGATGAG      420

CAAGAAGGGG TTAAAAGTGG AATGTATGTT GTAATAGAAG TTAAAGTTGC AACTCAAGAA      480

GGAAAAGAAA TAACCTGTCG AAGTTATCTG ATGACAAATT ACGAAAGTGC TCCCCCATCC      540

CCACAGTATA AAAAGATTAT TTGCATGGGT GCAAAAGAAA ATGGTTTGCC GCTGGAGTAT      600

CAAGAGAAGT TAAAAGCAAT AGAACCAAAT GACTATACAG GAAGGTCTC AGAAGAAATT       660

GAAGACATCA TCAAAAAGGG GGAAACACAA ACTCTTTAGA ACATAACAGA ATATATCTAA      720

GGGTATTCTA TGTGCTAATA TAAAATATTT TTAACACTTG AGAACAGGGA TCTGGGGGAT      780

CTCCACGTTT GATCCATTTT CAGCAGTGCT CTGAAGGAGT ATCTTACTTG GGTGATTCCT      840

TGTTTTTAGA CTATAAAAAG AAACTGGGAT AGGAGTTAGA CAATTTAAAA GGGGTGTATG      900

AGGGCCTGAA ATATGTGACA AATGAATGTG AGTACCCCTT CTGTGAACAC TGAAAGCTAT      960

TCTCTTGAAT TGATCTTAAG TGTCTCCTTG CTCTGGTAAA AGATAGATTT GTAGCTCACT     1020

TGATGATGGT GCTGGTGAAT TGCTCTGCTC TGTCTGAGAT TTTTAAAAAT CAGCTTAATG     1080

AGAGTAATCT GCAGACAATT GATAATAACA TTTTGAAAAT TGGAAAGATG GTATACTGTT     1140

TTTAGAGGAA TAAACGTATT TGTGGTTTAA AAAAAAA                              1178
```

(2) INFORMATION FOR SEQ ID NO: 89:

(i) SEQUENCE CHARACTERISTICS:
        (A) LENGTH: 748 base pairs
        (B) TYPE: nucleic acid
        (C) STRANDEDNESS: single
        (D) TOPOLOGY: linear (vii) IMMEDIATE SOURCE:
        (A) LIBRARY: BRSTTUT02
        (B) CLONE: 2117050

(xi) SEQUENCE DESCRIPTION: SEQ ID NO: 89 :

```
CCCACGCGTC CGGCGACGGC GCGGACCTGG AGCTTCCGCG CGGTGGCTTC ACTCTCCTGT       60
```

```
AAAACGCTAG AGCGGCGAGT TGTTACCTGC GTCCTCTGAC CTGAGAGCGA AGGGGAAAGC      120

GGCGAGATGA CTGACCGCTA CACCATCCAT AGCCAGCTGG AGCACCTGCA GTCCAAGTAC      180

ATCGGCACGG GCCACGCCGA CACCACCAAG TGGGAGTGGC TGGTGAACCA ACACCGCGAC      240

TCGTACTGCT CCTACATGGG CCACTTCGAC CTTCTCAACT ACTTCGCCAT TGCGGAGAAT      300

GAGAGCAAAG CGCGAGTCCG CTTCAACTTG ATGGAAAAGA TGCTTCAGCC TTGTGGACCG      360

CCAGCCGACA AGCCCGAGGA GAACTGAGAC TCTGCCTTAC CACCGCAGTG CGGGGGCACC      420

TCTCCCAGCG TTTCTCCGGT TTGCCAATCC TCTTAAGTAT TCCTGTCTCC AAAGGACCGG      480

CTCTCCATGG CTCCTGCGCC TCGTGCTTTC CGCGTACAGA AGTGCTTGCC CGGGGAGTCC      540

CGCCTGACCT GCCTTCATGT GGACCCTTAG AACAGCACTG GGAGACCAGC AGGACTCCTG      600

AGAACTGTGC TGGTGGAGAG GTCCTAGAGC CGGCGAGCGT TTGAGAAGAG GGCATGGCGC      660

TGGAGTGAGA TGGGATTTGG CGTCTCGTTT TTGGCTAATT GATTGTCATT GGCTTTTTCC      720

ATAAAGTTTA GAAATCGTAA AAAAAAAA                                        748
```

(2) INFORMATION FOR SEQ ID NO: 90:

(i) SEQUENCE CHARACTERISTICS:
        (A) LENGTH: 1078 base pairs
        (B) TYPE: nucleic acid
        (C) STRANDEDNESS: single
        (D) TOPOLOGY: linear (vii) IMMEDIATE SOURCE:
        (A) LIBRARY: SININOT01
        (B) CLONE: 2184712

(xi) SEQUENCE DESCRIPTION: SEQ ID NO: 90 :

```
GCAGGACGGA TTGGGCAAGG CTGGTCCCTG TGTGATGAGA CATCACCCTC CCAGGAGCAA       60

GGCGGAAGTC TGGAGGACGC TGAGGGGCGG AGGCGGGAGA GGCGAGCTCG CGATGAGTGG      120

TCTCGGCAGG CTCTTCGGGA AGGGGAAGAA GGAGAAAGGG CCAACCCCTG AAGAAGCAAT      180

ACAGAAACTG AAGGAGACAG AGAAGATACT GATCAAGAAA CAGGAATTTT TGGAGCAGAA      240

GATTCAACAG GAGCTACAAA CAGCCAAGAA GTATGGGACC AAGAATAAGA GAGCTGCCCT      300

ACAGGCTTTG CGGAGGAAGA AAAGATTCGA ACAGCAGCTG GCACAAACTG ACGGGACATT      360

ATCCACCCTG GAGTTTCAGC GTGAGGCCAT TGAGAATGCC ACTACCAATG CAGAAGTCCT      420

TCGTACCATG GAGCTTGCTG CCCAAAGCAT GAAGAAGGCC TACCAGGACA TGGACATTGA      480

CAAGGTAGAT GAACTGATGA CTGACATCAC GGAACAACAG GAGGTGGCCC AGCAGATCTC      540

AGATGCCATT TCTCGGCCTA TGGGCTTTGG AGATGATGTG GATGAGGATG AACTGCTGGA      600

GGAGCTAGAG GAGCTGGAGC AGGAGGAATT GGCCCAGGAG TTGTTAAATG TGGGCGACAA      660

GGAAGAAGAA CCCTCAGTCA AATTGCCTAG TGTACCTTCT ACTCATCTGC CGGCAGGGCC      720

AGCTCCCAAA GTGGATGAAG ATGAAGAAGC ACTAAAGCAG TTGGCTGAGT GGGTATCCTG      780

ATAAATCTGG GCTTGTCTTC CTAATGCTAC CTTTGTTGGT CCTTTCTTCC TTAAGTGCCA      840

AGTGCTGAGC TAAAGGAGGA TAACTTTTTG GGGAAGTCAT GCTGAGGGTG GTAGTGTGAC      900

CCTGCCTGAA AAAAGGGTCT CTTACCCTCC CAGCCCTGGC TCAACTCTGA AGAAGGATCT      960

TGCTACAGAA GGAGCCCTTG GGCTCCCTTC TCTTTGATAG CAGTTATAAT GCCCTTGTTC     1020

CCAATAAAAC TGGGCAGATG GAATCCTAGT GTCTATACTG CCTTGTCTAC CCCTGAAG      1078
```

(2) INFORMATION FOR SEQ ID NO: 91:

(i) SEQUENCE CHARACTERISTICS:

(A) LENGTH: 1446 base pairs
        (B) TYPE: nucleic acid
        (C) STRANDEDNESS: single
        (D) TOPOLOGY: linear (vii) IMMEDIATE SOURCE:
        (A) LIBRARY: BRAINON01
        (B) CLONE: 2290475

(xi) SEQUENCE DESCRIPTION: SEQ ID NO: 91 :

| | | | | | |
|---|---|---|---|---|---|
| TGGGAGGCGG | AGGCACAACT | AAGAGCGACC | TAGCATCGCA | AAGCCGCCCT | CGGGGCGCTC | 60 |
| ATGGCGGGAC | GCTCCTGGGA | AAGGCTTTAG | CGCGGTGTCT | CTCTCTCTGG | CCTTGGCCTC | 120 |
| TGTGACTATC | AGGTCCTCGC | GCTGCCGCGG | CATCCAGGCG | TTCAGAAACT | CGTTTTCATC | 180 |
| TTCTTGGTTT | CATCTTAATA | CCAACGTCAT | GTCTGGTTCT | AATGGTTCCA | AAGAAAATTC | 240 |
| TCACAATAAG | GCTCGGACGT | CTCCTTACCC | AGGTTCAAAA | GTTGAACGAA | GCCAGGTTCC | 300 |
| TAATGAGAAA | GTGGGCTGGC | TTGTTGAGTG | GCAAGACTAT | AAGCCTGTGG | AATACACTGC | 360 |
| AGTCTCTGTC | TTGGCTGGAC | CCAGGTGGGC | AGATCCTCAG | ATCAGTGAAA | GTAATTTTTC | 420 |
| TCCCAAGTTT | AACGAAAAGG | ATGGGCATGT | TGAGAGAAAG | AGCAAGAATG | CCTGTATGA  | 480 |
| GATTGAAAAT | GGAAGACCGA | GAAATCCTGC | AGGACGGACT | GGACTGGTGG | GCCGGGGGCT | 540 |
| TTTGGGGCGA | TGGGGCCCAA | ATCACGCTGC | AGATCCCATT | ATAACCAGAT | GGAAAAGGGA | 600 |
| TAGCAGTGGA | AATAAAATCA | TGCATCCTGT | TTCTGGGAAG | CATATCTTAC | AATTTGTTGC | 660 |
| AATAAAAAGG | AAAGACTGTG | GAGAATGGGC | AATCCCAGGG | GGGATGGTGG | ATCCAGGAGA | 720 |
| GAAGATTAGT | GCCACACTGA | AAAGAGAATT | TGGTGAGGAA | GCTCTCAACT | CCTTACAGAA | 780 |
| AACCAGTGCT | GAGAAGAGAG | AAATAGAGGA | AAAGTTGCAC | AAACTCTTCA | GCCAAGACCA | 840 |
| CCTAGTGATA | TATAAGGGAT | ATGTTGATGA | TCCTCGAAAC | ACTGATAATG | CATGGATGGA | 900 |
| GACAGAAGCT | GTGAACTACC | ATGACGAAAC | AGGTGAGATA | ATGGATAATC | TTATGCTAGA | 960 |
| AGCTGGAGAT | GATGCTGGAA | AAGTGAAATG | GGTGGACATC | AATGATAAAC | TGAAGCTTTA | 1020 |
| TGCCAGTCAC | TCTCAATTCA | TCAAACTTGT | GGCTGAGAAA | CGAGATGCAC | ACTGGAGCGA | 1080 |
| GGACTCTGAA | GCTGACTGCC | ATGCGTTGTA | GCTGATGGTC | TCCGTGTAAG | CCAAAGGCCC | 1140 |
| ACAGAGGAGC | ATATACTGAA | AGAAGGCAG | TATCACAGAA | TTTATACTAT | AAAAAGGGCA | 1200 |
| GGGTAGGCCA | CTTGGCCTAT | TTACTTTCAA | AACAATTTGC | ATTTAGAGTG | TTTCGCATCA | 1260 |
| GAATAACATG | AGTAAGATGA | ACTGGAACAC | AAAATTTTCA | GCTCTTTGGT | CAAAAGGAAT | 1320 |
| ATAAGTAATC | ATATTTTGTA | TGTATTCGAT | TTAAGCATGG | CTTAAATTAA | ATTTAAACAA | 1380 |
| CTAATGCTCT | TTGAAGAATC | ATAATCAGAA | TAAAGATAAA | TTCTTGATCA | GCTATAAAAA | 1440 |
| AAAAAA | | | | | | 1446 |

(2) INFORMATION FOR SEQ ID NO:    92:

(i) SEQUENCE CHARACTERISTICS:
        (A) LENGTH: 659 base pairs
        (B) TYPE: nucleic acid
        (C) STRANDEDNESS: single
        (D) TOPOLOGY: linear (vii) IMMEDIATE SOURCE:
        (A) LIBRARY: LUNGNOT20
        (B) CLONE: 2353452

(xi) SEQUENCE DESCRIPTION: SEQ ID NO: 92 :

| | | | | | |
|---|---|---|---|---|---|
| CCAGCTACCG | AAGCACTGGA | GAGTGTCATG | GAGGCCTACG | AGCAGGTCCA | AAAGGGACCC | 60 |
| CTGAAGCTGA | AAGGCGTCGC | AGAGCTGGGA | GTGACCAAGC | GGAAGAAGAA | AAAGAAGGAC | 120 |

```
AAAGACAAAG CGAAACTCCT GGAAGCAATG GGAACGAGCA AAAAGAACGA GGAGGAGAAG    180

CGGCGCGGCC TGGACAAGCG GACCCCGGCC CAGGCGGCCT TCGAGAAAAT GCAGGAGAAG    240

CGGCAAATGG AAAGGATCCT AAAGAAGGCA TCCAAAACCC ACAAGCAGAG AGTGGAGGAC    300

TTCAACAGAC ACCTGGACAC ACTCACGGAG CATTACGACA TTCCCAAAGT CAGCTGGACG    360

AAGTAGCCGC CTGCCCCCAG TATGGAGCAG CATCGAGGGT TCGCAAAAGG CCACACTGGG    420

GTTGTGTGTG TTTCCTTTGG TATATTCTGG AAACATGGCT ACACACACCC TTGCATCTTC    480

TGCTACAGAC TGCTTTTCGA AGCTGTGTAC CCTCATTCTG GAACTTGATT AAAGTAAGAT    540

CGTCCTTGTA CTCAGTTTAG GCTTCTTGGC AACATACAGA AGATACACCC TTTTCGTTTG    600

GATGGAAAGT TTCTAAGTTT ATCCAGAGGT AAAGCCCATT GTGTGTCTGT GTCATGTAA     659

(2) INFORMATION FOR SEQ ID NO:   93:

(i) SEQUENCE CHARACTERISTICS:
        (A) LENGTH: 1572 base pairs
        (B) TYPE: nucleic acid
        (C) STRANDEDNESS: single
        (D) TOPOLOGY: linear (vii) IMMEDIATE SOURCE:
        (A) LIBRARY: THP1NOT03
        (B) CLONE: 2469611

(xi) SEQUENCE DESCRIPTION: SEQ ID NO: 93 :

GGAAGGGGAA GTTTCGCCTC AGAAGGCTGC CTCGCTGGTC CGAATTCGGT GGCGCCACGT     60

CCGCCCGTCT CCGCCTTCTG CATCGCGGCT TCGGCGGCTT CCACCTAGAC ACCTAACAGT    120

CGCGGAGCCG GCCGCGTCGT GAGGGGGTCG GCACGGGGAG TCGGGCGGTC TTGTGCATCT    180

TGGCTACCTG TGGGTCGAAG ATGTCGGACA TCGGAGACTG GTTCAGGAGC ATCCCGGCGA    240

TCACGCGCTA TTGGTTCGCC GCCACCGTCG CCGTGCCCTT GGTCGGCAAA CTCGGCCTCA    300

TCAGCCCGGC CTACCTCTTC CTCTGGCCCG AAGCCTTCCT TTATCGCTTT CAGATTTGGA    360

GGCCAATCAC TGCCACCTTT TATTTCCCTG TGGGTCCAGG AACTGGATTT CTTTATTTGG    420

TCAATTTATA TTTCTTATAT CAGTATTCTA CGCGACTTGA ACAGGAGCT TTTGATGGGA     480

GGCCAGCAGA CTATTTATTC ATGCTCCTCT TTAACTGGAT TTGCATCGTG ATTACTGGCT    540

TAGCAATGGA TATGCAGTTG CTGATGATTC CTCTGATCAT GTCAGTACTT TATGTCTGGG    600

CCCAGCTGAA CAGAGACATG ATTGTATCAT TTTGGTTTGG AACACGATTT AAGGCCTGCT    660

ATTTACCCTG GGTTATCCTT GGATTCAACT ATATCATCGG AGGCTCGGTA ATCAATGAGC    720

TTATTGGAAA TCTGGTTGGA CATCTTTATT TTTTCCTAAT GTTCAGATAC CCAATGGACT    780

TGGGAGGAAG AAATTTTCTA TCCACACCTC AGTTTTTGTA CCGCTGGCTG CCCAGTAGGA    840

GAGGAGGAGT ATCAGGATTT GGTGTGCCCC CTGCTAGCAT GAGGCGAGCT GCTGATCAGA    900

ATGGCGGAGG CGGGAGACAC AACTGGGGCC AGGGCTTTCG ACTTGGAGAC CAGTGAAGGG    960

GCGGCCTCGG GCAGCCGCTC CTCTCAAGCC ACATTTCCTC CCAGTGCTGG GTGCGCTTAA   1020

CAACTGCGTT CTGGCTAACA CTGTTGGACC TGACCCACAC TGAATGTAGT CTTTCAGTAC   1080

GAGACAAAGT TTCTTAAATC CCGAAGAAAA ATATAAGTGT TCCACAAGTT TCACGATTCT   1140

CATTCAAGTC CTTACTGCTG TGAAGAACAA ATACCAACTG TGCAAATTGC AAAACTGACT   1200

ACATTTTTTG GTGTCTTCTC TTCTCCCCTT TCCGTCTGAA TAATGGGTTT TAGCGGGTCC   1260

TAGTCTGCTG GCATTGAGCT GGGGCTGGGT CACCAAACCC TTCCCAAAAG GACCCTTATC   1320

TCTTCTCTTG CACACATGCC TCTCTCCCAC TTTTCCCAAC CCCCACATTT GCAACTAGAA   1380
```

-continued

```
GAGGTTTGCC ATAAAATTGC TCTGCCCTTG ACAAGTTCTG TTAATTTATT GACTTTTGCC    1440

AAGGCCTGGT CACAACAATC ATATTTCACG TATTTTCCCC CTTTGGTGGC ANGACTGTAN    1500

GCAATAGGGG GAGAAGACAA GCAGCGGATG GAAGCGTTTT TCTCAAGTTT TGGGAATTGC    1560

TTCGANCTGA CA                                                        1572
```

(2) INFORMATION FOR SEQ ID NO: 94:

(i) SEQUENCE CHARACTERISTICS:
        (A) LENGTH: 3520 base pairs
        (B) TYPE: nucleic acid
        (C) STRANDEDNESS: single
        (D) TOPOLOGY: linear (vii) IMMEDIATE SOURCE:
        (A) LIBRARY: LIVRTUT04
        (B) CLONE: 2515476

(xi) SEQUENCE DESCRIPTION: SEQ ID NO: 94 :

```
GAGAAGCCAA GGAAGGAAAC AGGGAAAAAT GTCGCCATGA AGGCCGAGAA CCGCTGCCGC      60

CGCCGACCCC CGCCGGCCCT GAACGCCATG AGCCTGGGTC CCCGCCGCGC CCGCTCCGCT     120

TCGACTGCCG TCGCCGCCGA GGCCCCCGTT GATGCCGCTG AGCTCCCCCA ACGCCGCCGC     180

CACCGCCTCC GACATGGACA AGAACAGCGG CTCCAACAGC TCCTCCGCCT CTTCGGGCAG     240

CAGCAAAGGG CAACAGCCGC CCCGCTCCGC CTCGGCGGGG CCAGCCGGCG AGTCTAAACC     300

CAAGAGCGAT GGAAAGAACT CCAGTGGATC CAAGCGTTAT AATCGCAAAC GTGAACTTTC     360

CTACCCCAAA AATGAAAGTT TTAACAACCA GTCCCGTCGC TCCAGTTCAC AGAAAAGCAA     420

GACTTTTAAC AAGATGCCTC CTCAAAGGGG CGGCGGCAGC AGCAAACTCT TTAGCTCTTC     480

TTTTAATGGT GGAAGACGAG ATGAGGTAGC AGAGGCTCAA CGGGCAGAGT TTAGCCCTGC     540

CCAGTTCTCT GGTCCTAAGA AGATCAACCT GAACCACTTG TTGAATTTCA CTTTTGAACC     600

CCGTGGCCAG ACGGGTCACT TTGAAGGCAG TGGACATGGT AGCTGGGGAA AGAGGAACAA     660

GTGGGACAT AAGCCTTTTA ACAAGGAACT CTTTTTACAG GCCAACTGCC AATTTGTGGT      720

GTCTGAAGAC CAAGACTACA CAGCTCATTT TGCTGATCCT GATACATTAG TTAACTGGGA     780

CTTTGTGGAA CAAGTGCGCA TTTGTAGCCA TGAAGTGCCA TCTTGCCCAA TATGCCTCTA     840

TCCACCTACT GCAGCCAAGA TAACCCGTTG TGGACACATC TTCTGCTGGG CATGCATCCT     900

GCACTATCTT TCACTGAGTG AGAAGACGTG GAGTAAATGT CCCATCTGTT ACAGTTCTGT     960

GCATAAGAAG GATCTCAAGA GTGTTGTTGC CACAGAGTCA CATCAGTATG TTGTTGGTGA    1020

TACCATTACG ATGCAGCTGA TGAAGAGGGA GAAAGGGGTG TTGGTGGCTT TGCCCAAATC    1080

CAAATGGATG AATGTAGACC ATCCCATTCA TCTAGGAGAT GAACAGCACA GCCAGTACTC    1140

CAAGTTGCTG CTGGCCTCTA AGGAGCAGGT GCTCACCGG GTAGTTCTGG AGGAGAAAGT     1200

AGCACTAGAG CAGCAGCTGG CAGAGGAGAA GCACACTCCC GAGTCCTGCT TTATTGAGGC    1260

AGCTATCCAG GAGCTCAAGA CTCGGGAAGA GGCTCTGTCG GGATTGGCCG GAAGCAGAAG    1320

GGAGGTCACT GGTGTTGTGG CTGCTCTGGA ACAACTGGTG CTGATGGCTC CCTTGGCGAA    1380

GGAGTCTGTT TTTCAACCCA GGAAGGGTGT GCTGGAGTAT CTGTCTGCCT TCGATGAAGA    1440

AACCACGGAA GTTTGTTCTC TGGACACTCC TTCTAGACCT CTTGCTCTCC CTCTGGTAGA    1500

AGAGGAGGAA GCAGTGTCTG AACCAGAGCC TGAGGGGTTG CCAGAGGCCT GTGATGACTT    1560

GGAGTTAGCA GATGACAATC TTAAAGAGGG GACCATTTGC ACTGAGTCCA GCCAGCAGGA    1620

ACCCATCACC AAGTCAGGCT TCACACGCCT CAGCAGCTCT CCTTGTTACT ACTTTTACCA    1680
```

```
AGCGGAAGAT GGACAGCATA TGTTCCTGCA CCCTGTGAAT GTGCGCTGCC TCGTGCGGGA    1740

GTACGGCAGC CTGGAGAGGA GCCCCGAGAA GATCTCAGCA ACTGTGGTGG AGATTGCTGG    1800

CTACTCCATG TCTGAGGATG TTCGACAGCG TCACAGATAT CTCTCTCACT TGCCACTCAC    1860

CTGTGAGTTC AGCATCTGTG AACTGGCTTT GCAACCTCCT GTGGTCTCTA AGGAAACCCT    1920

AGAGATGTTC TCAGATGACA TTGAGAAGAG GAAACGTCAG CGCCAAAAGA AGGCTCGGGA    1980

GGAACGCCGC CGAGAGCGCA GGATTGAGAT AGAGGAGAAC AAGAAACAGG GCAAGTACCC    2040

AGAAGTCCAC ATTCCCCTCG AGAATCTACA GCAGTTTCCT GCCTTCAATT CTTATACCTG    2100

CTCCTCTGAT TCTGCTTTGG GTCCCACCAG CACCGAGGGC CATGGGGCCC TCTCCATTTC    2160

TCCTCTCAGC AGAAGTCCAG GTTCCCATGC AGACTTTCTG CTGACCCCTC TGTCACCCAC    2220

TGCCAGTCAG GGCAGTCCCT CATTCTGCGT TGGGAGTCTG GAAGAAGACT CTCCCTTCCC    2280

TTCCTTTGCC CAGATGCTGA GGGTTGGAAA AGCAAAAGCA GATGTGTGGC CCAAAACTGC    2340

TCCAAAGAAA GATGAGAACA GCTTAGTTCC TCCTGCCCCT GTGGACAGCG ACGGGGAGAG    2400

TGATAATTCA GACCGTGTTC CTGTGCCCAG TTTTCAAAAT TCCTTCAGCC AAGCTATTGA    2460

AGCAGCCTTC ATGAAACTGG ACACACCAGC TACTTCAGAT CCCCTCTCTG AAGAGAAAGG    2520

AGGAAAGAAA AGAAAAAAAC AGAAACAGAA GCTCCTGTTC AGCACCTCAG TCGTCCACAC    2580

CAAGTGACAC TACTGGCCCA GGCTACCTTC TCCATCTGGT TTTTGTTTTT GTTTTTTTTT    2640

CCCCCATGCT TTTGTTTGGC TGCTGTAATT TTTAAGTATT TGAGTTTGAA CAGATTAGCT    2700

CTGGGGGGAG GGGGTTTCCA CAATGTGAGG GGGAACCAAG AAAATTTTAA ATACAGTGTA    2760

TTTTCCAGCT TCCTGTCTTT ACACCAAAAT AAAGTATTGA CACAAGAGAT CTCTTCCTGC    2820

CAAGGTTTTT AGTTCATTGC CAGTTTAGTC TTTTTGACCC ATGTGTAATT AATTTTTCTC    2880

AACCCAAAGT AAGATTGAGT CCCCTTTGAG ATGCATTAGA GCAGTCCAAC CCAGAATGGC    2940

ACACACTGCT CTGCTGTACC ATCATGTCAG GGCTTCCTGG ACTCAGTACA CCTCTCAGTT    3000

TGTCTTTTAA AAAACAGCTG AATCTTTACT ACCTATTTAG TTCTCCTTGT TAAAGAAACA    3060

GGGGTGGGAA TAAAATGGAT TTAGGACACC CAGTTTGAAT TGCAGTTTTT TTTTTTCTGA    3120

CACATGGCCA GGCTGTGGTG CCAGCTTAAT GGAGTAGGCT GTCCTTGGCA CTTGCATGTG    3180

TGAAAGGAGG GTTTTGCCTC TTCTTGAGCA TGGCTTGAGT TGGTAAGGAA AGCTGTAACT    3240

CACGAAGCCC TGAGACCTGC TACCCCTAAG ATCGAGCTTG TTTTCAGTGA CTGGCTTGAG    3300

TCATAGGAGG AGGAGTCTGG TACAGCTGCA GGAGAGCAGG GCCATCTGAA GCGGTAGCAT    3360

TGCCACCATC TCCCTCTCAT CTAGAGCAGT TTTCTTATGC CTTGGTTTGA GCTGAATTTG    3420

ATGTGAATTC TTTTGCTGCT TAATAAAGTG ACCTCTAGGT GCATTAGAAT GCGAAGGCAA    3480

ATAGTTGCAA TAAATCACCT GCACAAGCAA AAAAAAAAA                          3520
```

(2) INFORMATION FOR SEQ ID NO: 95:

(i) SEQUENCE CHARACTERISTICS:
        (A) LENGTH: 1904 base pairs
        (B) TYPE: nucleic acid
        (C) STRANDEDNESS: single
        (D) TOPOLOGY: linear (vii) IMMEDIATE SOURCE:
        (A) LIBRARY: THP1AZS08
        (B) CLONE: 2754573

(xi) SEQUENCE DESCRIPTION: SEQ ID NO: 95 :

```
CGGGGGAGTC GGAGGAGGTG GCGGCGCTGG ANNTCCTCCC GGGGACCAGC GACCCGGGAG      60
```

```
CATGCACGTC GTCGCACCAG CTTCACTGAG GCTTGGAACA GGAACTAATC TCCCTCCATC     120

TCCAACTTGC TTGACAAAGC TCGCTCTTCC TCCAGCCGCT GAGCCGTCCC TTCTCGCCAT     180

GTCCCAGAGC AGGCACCGCG CCGAGGCCCC GCCGCTGGAG CGCGAGGACA GTGGGACCTT     240

CAGTTTGGGG AAGATGATAA CAGCTAAGCC AGGGAAAACA CCGATTCAGG TATTACACGA     300

ATACGGCATG AAGACCAAGA ACATCCCAGT TTATGAATGT GAAAGATCTG ATGTGCAAAT     360

ACACGTGCCC ACTTTCACCT TCAGAGTAAC CGTTGGTGAC ATAACCTGCA CAGGTGAAGG     420

TACAAGTAAG AAGCTGGCGA ACATAGAGC TGCAGAGGCT GCCATAAACA TTTTGAAAGC      480

CAATGCAAGT ATTTGCTTTG CAGTTCCTGA CCCCTTAATG CCTGACCCTT CCAAGCAACC     540

AAAGAACCAG CTTAATCCTA TTGGTTCATT ACAGGAATTG GCTATTCATC ATGGCTGGAG     600

ACTTCCTGAA TATACCCTTT CCCAGGAGGG AGGACCTGCT CATAAGAGAG AATATACTAC     660

AATTTGCAGG CTAGAGTCAT TTATGGAAAC TGGAAAGGGG GCATCAAAAA AGCAAGCCAA     720

AAGGAATGCT GCTGAGAAAT TCTTGCCAA ATTTAGTAAT ATTTCTCCAG AGAACCACAT      780

TTCTTTAACA AATGTAGTAG GACATTCTTT AGGATGTACT TGGCATTCCT TGAGGAATTC     840

TCCTGGTGAA AAGATCAACT TACTGAAAAG AAGCCTCCTT AGTATTCCAA ATACAGATTA    900

CATCCAGCTG CTTAGTGAAA TTGCCAAGGA ACAAGGTTTT AATATAACAT ATTTGGATAT     960

AGATGAACTG AGCGCCAATG GACAATATCA ATGTCTTGCT GAACTGTCCA CCAGCCCCAT    1020

CACAGTCTGT CATGGCTCCG GTATCTCCTG TGGCAATGCA CAAAGTGATG CAGCTCACAA    1080

TGCTTTGCAG TATTTAAAGA TAATAGCAGA AGAAAGTAA ATCGGAGCA ACTTAAAAAA      1140

TCTTTCAGTA GCACATAAAA AGTTCCCCTC TGGCCCCTTC CCAAGTAAAA CTTTTACCGT    1200

AGTGTTTATG TCTTGTTTCT AAATCTCTTC ATAGATTCCA TCAACACTCC AGATTTAATT    1260

ATCTCCTCAT AGTTGTTATT AAGCTCTTTT TAATGGCTTC AACTTTGTAT CAGTATACTG    1320

TATTTATAAA CTTTGTACCA CAAGAGAGAG TGTAGCACCC ATTTTACAGT GCCATGCACA    1380

TCAGAGAAAG AAACTGCATG TTTGTTGTTG ATGATGAAAT AAAAATGCTA GCGACAGTCT    1440

TTCTTACTGG TGCTTAAGCT CTTCTTTGCA CAAAGCTTTA TAAAGGGAAT TCAAAGGAAG    1500

CCCTTTAGAA TTAGAGTCTT GAGGGACAGC ACTAACAGGC CTTTATTAAG TATGATTGAT    1560

TGTTAAATTT CAGGGAACAT GATTGGTCTG CTGTGTATTT GAATTCATGT AACAAAGAAC    1620

TGTTACGATG GGATTCTGCT CATTTTATTA AAAGCTACT GACTTGACTG TCATCCTGTT     1680

CTTGTTAGCC ATTGTGAATA AGATTTTAAT GTTGATAATT CTGTTATTTA CATATCTCTA    1740

ATTTACTTTG AAATTCAAAG GTGAAAATAA AAAATGATGG CCTAAGTAAA ATTTACAAAC    1800

ATACATGTAA TGGGTTACTT CCTTACTTTC TCTAAGCGTA TGCAACCTTG TATTTTTCTT    1860

TGACATAACC ATACACAGGT GAATTACTAG TTTAAAAAGC ATTT                     1904
```

(2) INFORMATION FOR SEQ ID NO:    96:

(i) SEQUENCE CHARACTERISTICS:
        (A) LENGTH: 1621 base pairs
        (B) TYPE: nucleic acid
        (C) STRANDEDNESS: single
        (D) TOPOLOGY: linear (vii) IMMEDIATE SOURCE:
        (A) LIBRARY: TLYMNOT04
        (B) CLONE: 2926777

(xi) SEQUENCE DESCRIPTION: SEQ ID NO: 96 :

```
ATTTGGGTTT TTAAAGGGAA GGCGTCCGCG CGGCGGCCAT TTTGTCTTGT CGGCTCCTGT      60
```

```
GTGTAGGAGG GATTTCGGCC TGAGAGCGGG CCGAGGAGAT TGGCGACGGT GTCGCCCGTG      120

CTTTTCGTTG GCGGGTGCCT GGGCTGGTGG AACAGCCGC  CCGAAGGAAG CACCATGATT      180

TCGGCCGCGC AGTTGTTGGA TGAGTTAATG GGCCGGGACC GAAACCTAGC CCCGGACGAG      240

AAGCGCACAA ACGTGCGGTG GGACCACGAG AGCGTTTGTA AATATTATCT CTGTGGTTTT      300

TGTCCTGCGG AATTGTTCAC AAATACACGT TCTGATCTTG GTCCGTGTGA AAAAATTCAT      360

GATGAAAATC TACGAAAACA GTATGAGAAG AGCTCTCGTT TCATGAAAGT TGGCTATGAG      420

AGAGATTTTT TGCGATACTT ACAGAGCTTA CTTGCAGAAG TAGAACGTAG GATCAGACGA      480

GGCCATGCTC GTTTGGCATT ATCTCAAAAC CAGCAGTCTT CTGGGCCGC  TGGCCCAACA      540

GGCAAAAATG AAGAAAAAAT TCAGGTTCTA ACAGACAAAA TTGATGTACT TCTGCAACAG      600

ATTGAAGAAT TAGGGTCTGA AGGAAAAGTA GAAGAAGCCC AGGGGATGAT GAAATTAGTT      660

GAGCAATTAA AGAAGAGAG  AGAACTGCTA AGGTCCACAA CGTCGACAAT TGAAAGCTTT      720

GCTGCACAAG AAAACAAAT  GGAAGTTTGT GAAGTATGTG GAGCCTTTTT AATAGTAGGA      780

GATGCCCAGT CCCGGGTAGA TGACCATTTG ATGGGAAAAC AACACATGGG CTATGCCAAA      840

ATTAAAGCTA CTGTAGAAGA ATTAAAAGAA AAGTTAAGGA AAAGAACCGA AGAACCTGAT      900

CGTGATGAGC GTCTAAAAAA GGAGAAGCAA GAAAGAGAAG AAAGAGAAAA AGAACGGGAG      960

AGAGAAAGGG AAGAAAGAGA AAGGAAAAGA CGAAGGGAAG AGGAAGAAAG AGAAAAAGAA     1020

AGGGCTCGTG ACAGAGAAAG AAGAAAGAGA AGTCGTTCAC GAAGTAGACA CTCAAGCCGA     1080

ACATCAGACA GAAGATGCAG CAGGTCTCGG GACCACAAAA GGTCACGAAG TAGAGAAAGA     1140

AGGCGGACCA GAAGTAGAGA TCGACGAAGA AGCAGAAGCC ATGATCGATC AGAAAGAAAA     1200

CACAGATCTC GAAGTCGGGA TCGAAGAAGA TCAAAAAGCC GGGATCGAAA GTCATATAAG     1260

CACAGGAGCA AAAGTCGGGA CAGAGAACAA GATAGAAAAT CCAAGGAGAA AGAAAAGAGG     1320

GGATCTGATG ATAAAAAAAG TAGTGTGAAG TCCGGTAGTC GAGAAAAGCA GAGTGAAGAC     1380

ACAAACACTG AATCGAAGGA AAGTGATACT AAGAATGAGG TCAATGGGAC CAGTGAAGAC     1440

ATTAAATCTG AAGGTGACAC TCAGTCCAAT TAAAACTGAT CTGATAAGAC CTCAGATCAG     1500

ACAGAGGACT ACTGTTCGAA GATTTTTGGA AGAATACTGA GAACGGCATA AAGTGAAGAT     1560

CGACATTTAA AAAATGAGGT GAAAGAAAGC TATAGTGGCA TAGAAAAAGT ATAAAGCTCA     1620

G                                                                    1621

(2) INFORMATION FOR SEQ ID NO:    97:

(i) SEQUENCE CHARACTERISTICS:
        (A) LENGTH: 1112 base pairs
        (B) TYPE: nucleic acid
        (C) STRANDEDNESS: single
        (D) TOPOLOGY: linear (vii) IMMEDIATE SOURCE:
        (A) LIBRARY: TESTNOT07
        (B) CLONE: 3217567

(xi) SEQUENCE DESCRIPTION: SEQ ID NO: 97 :

CAACGATCGT GGGNCAGGTA GGTGGTTTCT GGTTTGTTGG GGCGTGTGTA TGTGTATTTA       60

GGGGGACTGA AGGGTACGTG GGGCGAAACA AAACCGGCCA TGGCAGCAGC GGAGGAGGAG      120

GACGGGGGCC CCGAAGGGCC AAATCGCGAG CGGGGCGGGG CGGGCGCGAC CTTCGAATGT      180

AATATATGTT TGGAGACTGC TCGGGAAGCT GTGGTCAGTG TGTGTGGCCA CCTGTACTGT      240

TGGCCATGTC TTCATCAGTG GCTGGAGACA CGGCCAGAAC GGCAAGAGTG TCCAGTATGT      300
```

```
AAAGCTGGGA TCAGCAGAGA GAAGGTTGTC CCGCTTTATG GGCGAGGGAG CCAGAAGCCC      360

CAGGATCCCA GATTAAAAAC TCCACCCCGC CCCCAGGGCC AGAGACCAGC TCCGGAGAGC      420

AGAGGGGGAT TCCAGCCATT TGGTGATACC GGGGGCTTCC ACTTCTCATT TGGTGTTGGT      480

GCTTTTCCCT TTGGCTTTTT CACCACCGTC TTCAATGCCC ATGAGCCTTT CCGCCGGGGT      540

ACAGGTGTGG ATCTGGGACA GGGTCACCCA GCCTCCAGCT GGCAGGATTC CCTCTTCCTG      600

TTTCTCGCCA TCTTCTTCTT TTTTTGGCTG CTCAGTATTT GAGCTATGTC TGCTTCCTGC      660

CCACCTCCAG CCAGAGAAGA ATCAGTATTG AGGGTCCCTG CTGACCCTTC CGTACTCCTG      720

GACCCCCTTG ACCCCTCTAT TTCTGTTGGC TAAGGCCAGC CCTGGACATT GTCCAGGAAG      780

GCCTGGGGAG GAGGAGTGAA GTCTGTGCAT AGATGGGAGA GCCTTCTGCT CAGAGGCTCA      840

CTCAGTAACG TTGTTTAATT CTCTGCCCTG GGGAAGGAGG ATGGATTGAG AGAATGTCTT      900

TCTCCTCTCC TAAGTCTTTG CTTTCCCTGA TTTCTTGATT TGATCTTCAA AGGTGGGCAA      960

AGTTCCCTCT GACTCTTCCC CCACTCCCCA TCTTACTGAT TTAATTTAAT TTTTCACTCC     1020

CCAGAGTCTA ATATGGATTC TGACTCTTAA GTGCTTCCGC CCCCTCACTA CCTCCTTTAA     1080

TACAAATTCA ATAAAAAAGG TGAAATATAA AA                                   1112

(2) INFORMATION FOR SEQ ID NO:   98:

(i) SEQUENCE CHARACTERISTICS:
           (A) LENGTH: 1040 base pairs
           (B) TYPE: nucleic acid
           (C) STRANDEDNESS: single
           (D) TOPOLOGY: linear (vii) IMMEDIATE SOURCE:
           (A) LIBRARY: SPLNNOT10
           (B) CLONE: 3339274

(xi) SEQUENCE DESCRIPTION: SEQ ID NO: 98 :

CGAGCCCNCC CCCAGCGGGA GCTGTGGGGC AGAGGCGCTG CTGTGGTTGG TCAGTCCAGT       60

AAGAAGCCAG CAGGGCTGGG TGCTGGGGCT TCTTCTCCTG AAGGGGCTGC AAGAGGGAAG      120

GCTTAGCCAT GTCGTCCTTG ATCAGAAGGG TGATCAGCAC CGCGAAAGCC CCAGGGGCCA      180

TTGGACCCTA CAGTCAAGCT GTATTAGTCG ACAGGACCAT TTACATTTCA GGACAGATAG      240

GCATGGACCC TTCAAGTGGA CAGCTTGTGT CAGGAGGGGT AGCAGAAGAA GCTAAACAAG      300

CTCTTAAAAA CATGGGTGAA ATTCTGAAAG CTGCAGGCTG TGACTTCACT AACGTGGTGA      360

AAACAACTGT TCTTCTGGCT GACATAAATG ACTTCAATAC TGTCAATGAA ATCTACAAAC      420

AGTATTTCAA GAGTAATTTT CCTGCTAGAG CTGCTTACCA AGTTGCTGCT TTACCCAAAG      480

GCAGCCGAAT TGAAATTGAA GCAGTAGCTA TCCAAGGACC ACTGACAACG GCATCACTAT      540

AAGTGGGCCC AGTGCTGTGT AGTCTGGAAT TGTTAACATT TTAATTTTTA CAATTGATGT      600

AACATCTTAA TTAACCTTTT AATTTTCACA ATTGATGACA GTGTGAGTTT GATGAAAATA      660

TCTGAAGCTA TTATGGAAAT ACCATGTAAT AGGGAGAGTT GAACATGAAT ATTAGAGAAG      720

GAATCCAGTT ACTTTTTTAA ATTACACCTG TGTGCACCTG TATTACTGAA TATAGGAAAG      780
```

-continued

```
AGATACCCAT TACATAGTTA CTCAGTAAAC AAAAGAGAAA TACCAGGTAG GAAAGAAGAG      840

TTACTATTCC TGAGAAATAA TCAAGAACAT ATTTAATTTA AACTAATGAT GTGAACTATT      900

TAGTTTTGAT GTCCGTTATG TGATTCTGCT TTTACTTGAG TAAAATTAAA GTGTTTAAAT      960

TTGAGATCAA GGAGAAGATA GTGGAACAAA ATGTTATATA GATAATATTT TTCTAATGGA     1020

AATAAAATAG GCAGATTTCC                                                 1040
```

HUMAN REGULATORY MOLECULES

This application is a divisional application of U.S. application Ser. No. 08/933,750, filed on Sep. 23, 1997 now U.S. Pat. No. 5,932,442.

FIELD OF THE INVENTION

This invention relates to nucleic acid and amino acid sequences of human regulatory molecules which are important in disease and to the use of these sequences in the diagnosis, prevention, and treatment of diseases associated with cell proliferation.

BACKGROUND OF THE INVENTION

Cells grow and differentiate, carry out their structural or metabolic roles, participate in organismal development, and respond to their environment by altering their gene expression. Cellular functions are controlled by the timing and amount of expression attributable to thousands of individual genes. The regulation of expression is metabolically vital in that it conserves energy and prevents the synthesis and accumulation of intermediates such as RNA and incomplete or inactive proteins when the gene product is not needed.

Regulatory protein molecules are absolutely essential in the control of gene expression. These molecules turn individual or groups of genes on and off in response to various inductive mechanisms of the cell or organism; act as transcription factors by determining whether or not transcription is initiated, enhanced, or repressed; and splice transcripts as dictated in a particular cell or tissue. Although regulatory molecules interact with short stretches of DNA scattered throughout the entire genome, most gene expression is regulated near the site at which transcription starts or within the open reading frame of the gene being expressed. The regulated stretches of the DNA can be simple and interact with only a single protein, or they can require several proteins acting as part of a complex in order to regulate gene expression.

The double helix structure and repeated sequences of DNA create external features which can be recognized by the regulatory molecules. These external features are hydrogen bond donor and acceptor groups, hydrophobic patches, major and minor grooves, and regular, repeated stretches of sequence which cause distinct bends in the helix. Such features provide recognition sites for the binding of regulatory proteins. Typically, these recognition sites are less than 20 nucleotides in length although multiple sites may be adjacent to each other and each may exert control over a single gene. Hundreds of these DNA sequences have been identified, and each is recognized by a different protein or complex of proteins which carry out gene regulation.

The regulatory protein molecules or complexes recognize and bind to specific nucleotide sequences of upstream (5') nontranslated regions, which precede the first translated exon of the open reading frame (ORF); of intron junctions, which occur between the many exons of the OR; and of downstream (3') untranslated regions, which follow the ORF. The regulatory molecule surface features are extensively complementary to the surface features of the double helix. Even though each individual contact between the protein(s) and helix may be relatively weak (hydrogen bonds, ionic bonds, and/or hydrophobic interactions) and the 20 or more contacts occurring between the protein and DNA result in a highly specific and very strong interaction.

Families of Regulatory Molecules

Many of the regulatory molecules incorporate one of a set of DNA-binding structural motifs, each of which contains either α helices or β sheets and binds to the major groove of DNA. Seven of the structural motifs common to regulatory molecules are helix-turn-helix, homeodomains, zinc finger, steroid receptor, β sheets, leucine zipper, and helix-loop-helix.

The helix-turn-helix motif is constructed from two α helices connected by a short chain of amino acids, which constitutes the "turn". The two helices interact with each other to form a fixed angle. The more carboxy-terminal helix is called the recognition helix because it fits into the major groove of the DNA. The amino acid side chains of the helix recognize the specific DNA sequence to which the protein binds. The remaining structure varies a great deal among the regulatory proteins incorporating this motif. The helix-turn-helix configuration is not stable without the rest of the protein and will not bind to DNA without other peptide regions providing stability. Other peptide regions also interact with the DNA, increasing the number of unique sequences a helix-turn-helix can recognize.

Many sequence-specific DNA binding proteins actually bind as symmetric dimers to DNA sequences that are composed of two very similar half-sites, also arranged symmetrically. This configuration allows each protein monomer to interact in the same way with the DNA recognition site and doubles the number of contacts with the DNA. This doubling of contacts greatly increases the binding affinity while only doubling the free energy of the interaction. Helix-turn-helix motifs always bind to DNA that is in the B-DNA form.

The homeodomain motif is found in a special group of helix-turn-helix proteins that are encoded by homeotic selector genes, so called because the proteins encoded by these genes control developmental switches. For example, mutations in these genes cause one body part to be converted into another in the fruit fly, Drosophila. These genes have been found in every eukaryotic organism studied. The helix-turn-helix region of different homeodomains is always surrounded by the same structure, but not necessarily the same sequence, and the motif is always presented to DNA the same way. This helix-turn-helix configuration is stable by itself and, when isolated, can still bind to DNA. It may be significant that the helices in homeodomains are generally longer than the helices in most HLH regulatory proteins. Portions of the motif which interact most directly with DNA differ among these two families. Detailed examples of DNA-protein binding are described in Pabo, C. O. and R. T. Sauer (1992; Ann. Rev. Biochem. 61:1053–95).

A third motif incorporates zinc molecules into the crucial portion of the protein. These proteins are most often referred to as having zinc fingers, although their structure can be one of several types. Proteins in this family often contain tandem repeats of the 30-residue zinc finger motif, including the sequence patterns Cys-X2 or 4-Cys-X12-His-X3-5-His. Each of these regulatory proteins has an α helix and an antiparallel β sheet. Two histidines in the α helix and 2 cysteines near the turn in the β sheet interact with the zinc ion which holds the α helix and the β sheet together. Contact with the DNA is made by the arginine preceding the α helix, and by the second, third, and sixth residues of the α helix. When this arrangement is repeated as a cluster of several fingers, the α helix of each finger can contact and interact with the major groove of the DNA. By changing the number of zinc fingers, the specificity and strength of the binding interaction can be altered.

The steroid receptors are a family of intracellular proteins that include receptors for steroids, retinoids, vitamin D, thyroid hormones, and other important compounds. The DNA binding domain of these proteins contains about 70 residues, eight of which are conserved cysteines. The steroid receptor motif forms a structure in which two α helices are packed perpendicularly to each other, forming more of a globular shape than a finger. Each helix has a zinc ion which holds a peptide loop against the N-terminal end of the helix. The first helix fits into the major groove of DNA, and side chains make contacts with edges of the DNA base pairs. The steroid receptor proteins, like the helix-turn-helix proteins, form dimers that bind the DNA. The second helix of each monomer contacts the phosphate groups of the DNA backbone and also provides the dimerization interface. In some cases, multiple choices can exist for heterodimerization which produces another mechanism for fine-tuning the regulation of numerous genes.

Another family of regulatory protein molecules uses a motif consisting of a two-stranded antiparallel β sheet to recognize the major groove of DNA. The exact DNA sequence recognized by the motif depends on the amino acid sequence in the β sheet from which the amino acid side chains extend and contact the DNA. In two prokaryotic examples of the β sheet, the regulatory proteins form tetramers when binding. DNA.

The leucine zipper motif commonly forms dimers and has a 30–40 residue motif in which two α helices (one from each monomer) are joined to form a short coiled-coil. The helices are held together by interactions among hydrophobic amino acid side chains (often on heptad-repeated leucines) that extend from one side of each helix. Beyond this, the helices separate, and each basic region contacts the major groove of DNA. Proteins with the leucine zipper motif can also form either homodimers or heterodimers, thus extending the specific combinations available to activate or repress expression.

Yet another important motif is the helix-loop-helix, which consists of a short α helix connected by a loop to a longer α helix. The loop is flexible and allows the two helices to fold back against each other. The α helices bind both to DNA and to the HLH structure of another protein. The second protein can be the same (producing homodimers) or different (producing heterodimers). Some HLH monomers lack sufficient α helix to bind DNA, but they can still form heterodimers which can serve to inactivate specific regulatory proteins.

Hundreds of regulatory proteins have been identified to date, and more are being characterized in a wide variety of organisms. Most regulatory proteins have at least one of the common structural motifs for making contact with DNA, but several important regulatory proteins, such as the p53 tumor suppressor gene, do not share their structure with other known regulatory proteins. Variations on the known motifs and new motifs have been and are currently being characterized (Faisst, S. and S. Meyer (1992) Nucl. Acids Res. 20: 3–26).

Although binding of DNA to a regulatory protein is very specific, there is no way to predict the exact DNA sequence to which a particular regulatory protein will bind or the primary structure of a regulatory protein for a specific DNA sequence. Thus, interactions of DNA and regulatory proteins are not limited to the motifs described above. Other domains of the proteins often form crucial contacts with the DNA, and accessory proteins can provide important interactions which may convert a particular protein complex to an activator or a repressor, or may prevent binding (Alberts, B. et al. (1994) *Molecular Biology of the Cell*, Garland Publishing Co, New York, N.Y. pp.401–74).

Diseases and Disorders Related to Gene Regulation

Many neoplastic growths in humans can be traced to problems of gene regulation. Malignant growth of cells may be the result of excess transcriptional activator or loss of an inhibitor or suppressor (Cleary M L (1992) Cancer Surv. 15:89–104). Alternatively, gene fusion may produce chimeric loci with switched domains, such that the level of activation is no longer correct for the gene specificity of that factor.

The cellular response to infection or trauma is beneficial when gene expression is appropriate. However, when hyperresponsivity or another imbalance occurs for any reason, improper or insufficient regulation of gene expression may cause considerable tissue or organ damage. This damage is well documented in immunological responses to allergens, heart attack, stroke, and infections (*Harrison's Principles of Internal Medicine*, 13/e°, (1994) McGraw Hill, Inc. and Teton Data Systems Software). In addition, the accumulation of somatic mutations and the increasing inability to regulate cellular responses is seen in the prevalence of osteoarthritis and onset of other disorders associated with aging.

The discovery of new human regulatory protein molecules which are important in disease development and the polynucleotides encoding them satisfies a need in the art by providing new compositions which are useful in the diagnosis, prevention and treatment of diseases associated with cell proliferation, particularly immune responses and cancers.

SUMMARY OF THE INVENTION

The invention features substantially purified polypeptides, human regulatory molecules, collectively referred to as HRM and individually referred to as HRM-1 through HRM-49, HRM-1, HRM-2, HRM-3, HRM-4, HRM-5, HRM-6, HRM-7, HRM-8, HRM-9, HRM-10, HRM-11, HRM-12, HRM-13, HRM-14, HRM-15, HRM-16, HRM-17, HRM-18, HRM-19, HRM-20, HRM-21, HRM-22, HRM-23, HRM-24, HRM-25, HRM-26, HRM-27, HRM-28, HRM-29, HRM-30, HRM-31, HRM-32, HRM-33, HRM-34, HRM-35, HRM-36, HRM-37, HRM-38, HRM-39, HRM-40, HRM-41, HRM-42, HRM-43, HRM-44, HRM-45, HRM-46, HRM-47, HRM-48, and HRM-49, having at least one of the amino acid sequences selected from the group consisting of SEQ ID NOs:1–49.

The invention further provides isolated and substantially purified polynucleotide sequences encoding HRM. In a particular aspect, the polynucleotide is at least one of the nucleotide sequences selected from the group consisting of SEQ ID NOs:50–98.

In addition, the invention provides a polynucleotide sequence, or fragment thereof, which hybridizes under stringent conditions to any of the polynucleotide sequences of SEQ ID NOs:50–98. In another aspect the invention provides compositions comprising isolated and purified polynucleotide sequences of SEQ ID NOs:50–98.

The invention further provides a polynucleotide sequence comprising the complement or fragments thereof of any one of the polynucleotide sequences encoding HRM. In another aspect the invention provides compositions comprising isolated and purified polynucleotide sequences comprising the complements of SEQ ID NOs:50–98.

The present invention further provides an expression vector containing at least a fragment of any one of the polynucleotide sequences of SEQ ID NOs:50–98. In yet another aspect, the expression vector containing the polynucleotide sequence is contained within a host cell.

The invention also provides a method for producing a polypeptide or a fragment thereof, the method comprising the steps of: a) culturing the host cell containing an expression vector containing at least a fragment of the polynucleotide sequence encoding an HRM under conditions suitable for the expression of the polypeptide; and b) recovering the polypeptide from the host cell culture.

The invention also provides a pharmaceutical composition comprising a substantially purified HRM in conjunction with a suitable pharmaceutical carrier.

The invention also provides a purified antagonist of HRM. In one aspect the invention provides a purified antibody which binds to an HRM.

Still further, the invention provides a purified agonist of HRM.

The invention also provides a method for treating or preventing a cancer comprising administering to a subject in need of such treatment an effective amount of a pharmaceutical composition containing HRM.

The invention also provides a method for treating or preventing a cancer comprising administering to a subject in need of such treatment an effective amount of an antagonist of HRM.

The invention also provides a method for treating or preventing an immune response associated with the increased expression or activity of HRM comprising administering to a subject in need of such treatment an effective amount of an antagonist of HRM.

The invention also provides a method for stimulating cell proliferation comprising administering to a cell an effective amount of purified HRM.

The invention also provides a method for detecting a polynucleotide which encodes a human regulatory molecule in a biological sample comprising the steps of: a) hybridizing a polynucleotide sequence complementary to a polynucleotide encoding HRM to nucleic acid material of a biological sample, thereby forming a hybridization complex; and b) detecting the hybridization complex, wherein the presence of the complex correlates with the presence of a polynucleotide encoding the human regulatory molecule in the biological sample.

The invention also provides a microarray which contains at least a fragment of at least one of the polynucleotide sequences encoding HRM. In a particular aspect, the microarray contains at least a fragment of at least one of the sequences selected from the group consisting of SEQ ID NOs:50–98.

The invention also provides a method for the simultaneous detection of the levels of expression of polynucleotides which encode human regulatory molecules in a biological sample comprising the steps of: a) hybridizing said microarray to labeled complementary nucleotides of a biological sample, comprising at least a fragment of at least one of the polynucleotides encoding HRM, thereby forming hybridization complexes; and b) quantifying expression, wherein the signal produced by the hybridization complexes correlates with expression of particular polynucleotides encoding human regulatory molecules in the biological sample. In a preferred embodiment, prior to hybridization, the nucleic acid material of the biological sample is amplified and labeled by the polymerase chain reaction.

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, arrays and methodologies which are reported in the publications which might be used in connection with the invention. Nothing herein is to be construed as an admission that the invention is not entitled to antedate such disclosure by virtue of prior invention.

DEFINITIONS

HRM, as used herein, refers to the amino acid sequences of substantially purified HRM obtained from any species, particularly mammalian, including bovine, ovine, porcine, murine, equine, and preferably human, from any source whether natural, synthetic, semi-synthetic, or recombinant.

The term "agonist", as used herein, refers to a molecule which, when bound to HRM, increases or prolongs the duration of the effect of HRM. Agonists may include proteins, nucleic acids, carbohydrates, or any other molecules which bind to and modulate the effect of HRM.

An "allele" or "allelic sequence", as used herein, is an alternative form of the gene encoding HRM. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding HRM, as used herein, include those with deletions, insertions, or substitutions of different nucleotides resulting in a polynucleotide that encodes the same or a functionally equivalent HRM. Included within this definition are polymorphisms which may or may not be readily detectable using a particular oligonucleotide probe of the polynucleotide encoding HRM, and improper or unexpected hybridization to alleles, with a locus other than the normal chromosomal locus for the polynucleotide sequence encoding HRM. The encoded protein may also be "altered" and contain deletions, insertions, or substitutions of amino acid residues which produce a silent change and result in a functionally equivalent HRM. Deliberate amino acid substitutions may be made on the basis of similarity in polarity, charge, solubility, hydrophobicity, hydrophilicity, and/or the amphipathic nature of the residues as long as the biological or immunological activity of HRM is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence", as used herein, refers to an oligopeptide, peptide, polypeptide, or protein sequence, and fragment thereof, and to naturally occurring or synthetic molecules. Fragments of HRM are preferably about 5 to about 15 amino acids in length and retain the biological activity or the immunological activity of HRM. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification", as used herein, refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "antagonist", as used herein, refers to a molecule which, when bound to HRM, decreases the amount or the duration of the effect of the biological or immunological activity of HRM. Antagonists may include proteins, nucleic acids, carbohydrates, or any other molecules which decrease the effect of HRM.

As used herein, the term "antibody" refers to intact molecules as well as fragments thereof, such as Fa, F(ab')$_2$, and Fv, which are capable of binding the epitopic determinant. Antibodies that bind HRM polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active", as used herein, refers to a protein having structural, regulatory, or biochemical functions of a naturally occurring molecule. Likewise, "immunologically active" refers to the capability of the natural, recombinant, or synthetic HRM, or any oligopeptide thereof, to induce a specific immune response in appropriate animals or cells and to bind with specific antibodies.

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence", as used herein, refers broadly to any composition containing the given polynucleotide sequence. The composition may comprise a dry formulation or an aqueous solution. Compositions comprising polynucleotide sequences encoding HRM SEQ ID NOs:50–98 or fragments thereof may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

"Consensus", as used herein, refers to a nucleic acid sequence which has been resequenced to resolve uncalled bases, has been extended using XL-PCR kit (Perkin Elmer, Norwalk, Conn.) in the 5' and/or the 3' direction and resequenced, or has been assembled from the overlapping sequences of more than one Incyte Clone using a computer program for fragment assembly (e.g., GELVIEW Fragment Assembly system, GCG, Madison, Wis.). Some sequences have been both extended and assembled to produce the consensus sequence.

The term "correlates with expression of a polynucleotide", as used herein, indicates that the detection of the presence of a ribonucleic acid that is similar to a polynucleotide encoding an HRM by northern analysis is indicative of the presence of mRNA encoding HRM in a sample and thereby correlates with expression of the transcript from the polynucleotide encoding the protein.

The term "HRM" refers to any or all of the human polypeptides, HRM-1 through HRM-49.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to HRM or the encoded HRM. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Human artificial chromosomes (HACs) are linear microchromosomes which may contain DNA sequences of 10K to 10M in size and contain all of the elements required for stable mitotic chromosome segregation and maintenance (Harrington, J. J. et al. (1997) Nat Genet. 15:345–355).

The term "humanized antibody", as used herein, refers to antibody molecules in which amino acids have been replaced in the non-antigen binding regions in order to more closely resemble a human antibody, while still retaining the original binding ability.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule.

"Microarray" refers to an array (or arrangement) of distinct oligonucleotides synthesized on a substrate, such as paper, nylon or other type of membrane, filter, gel, polymer, chip, glass slide, or any other suitable support.

The term "modulate", as used herein, refers to a change in the activity of HRM. For example, modulation may cause an increase or a decrease in protein activity, binding characteristics, or any other biological, functional or immunological properties of HRM.

"Nucleic acid sequence", as used herein, refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides in length, and most preferably includes fragments that are at least 100 nucleotides or at least 1000 nucleotides, and at least 10,000 nucleotides in length.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or hybridization assays. As used herein, oligonucleotide is substantially equivalent to the terms "amplimers","primers", "oligomers", and "probes", as commonly defined in the art.

"Peptide nucleic acid", PNA as used herein, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and stop transcript elongation (Nielsen, P. E. et al. (1993) Anticancer Drug Des. 8:53–63).

The term "portion", as used herein, with regard to a protein (as in "a portion of a given protein") refers to fragments of that protein. The fragments may range in size from five amino acid residues to the entire amino acid sequence minus one amino acid. Thus, a protein "comprising at least a portion of the amino acid sequence of an HRM encompasses the full-length HRM and fragments thereof.

The term "sample", as used herein, is used in its broadest sense. A biological sample suspected of containing nucleic acid encoding HRM, or fragments thereof, or HRM itself may comprise a bodily fluid, extract from a cell, chromosome, organelle, or membrane isolated from a cell, a cell, genomic DNA, RNA, or cDNA (in solution or bound to a solid support, a tissue, a tissue print, and the like).

The terms "specific binding" or "specifically binding", as used herein, refer to that interaction between a protein or peptide and an agonist, an antibody and an antagonist. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

The terms "stringent conditions" or "stringency", as used herein, refer to the conditions for hybridization as defined by the nucleic acid, salt, and temperature. These conditions are well known in the art and may be altered in order to identify or detect identical or related polynucleotide sequences. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° C. below the melting temperature of the probe to about 20° C. to 25° C. below the melting temperature). One or more factors be may be varied to generate conditions of either low or high stringency different from, but equivalent to, the above listed conditions.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of HRM, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE software (DNASTAR Inc., Madison Wis.).

THE INVENTION

The invention is based on the discovery of human regulatory molecules (HRM) and the polynucleotides encoding HRM and or, and the use of these compositions for the diagnosis, prevention, or treatment of diseases associated with cell proliferation. Table 1 shows the protein and nucleotide sequence identification numbers, protein abbreviation, Incyte Clone number, cDNA library, NCBI homolog and NCBI sequence identifier for each of the human regulatory molecules disclosed herein.

TABLE 1

| Protein | Nucleotide | Abbreviation | Clone ID | Library | NCBI | Homolog |
|---|---|---|---|---|---|---|
| SEQ ID NO: 1 | SEQ ID NO: 50 | HRM-1 | 133 | U937NOT01 | g285947 | KIAA0105 |
| SEQ ID NO: 2 | SEQ ID NO: 51 | HRM-2 | 1762 | U937NOT01 | g1518121 | *Ascaris suum* |
| SEQ ID NO: 3 | SEQ ID NO: 52 | HRM-3 | 1847 | U937NOT01 | g1302211 | *Saccharomyces cerevisiae* |
| SEQ ID NO: 4 | SEQ ID NO: 53 | HRM-4 | 9337 | HMC1NOT01 | g1613852 | Human zinc finger protein (z12) |
| SEQ ID NO: 5 | SEQ ID NO: 54 | HRM-5 | 9476 | HMC1NOT01 | g755784 | *S. cerevisiae* |
| SEQ ID NO: 6 | SEQ ID NO: 55 | HRM-6 | 10370 | THP1PLB01 | g895845 | Human putative p64 CLCP protein |
| SEQ ID NO: 7 | SEQ ID NO: 56 | HRM-7 | 30137 | THP1NOB01 | g1710241 | Human clone 23733 mRNA |
| SEQ ID NO: 8 | SEQ ID NO: 57 | HRM-8 | 77180 | SYNORAB01 | g5372 | *S. cerevisiae* |
| SEQ ID NO: 9 | SEQ ID NO: 58 | HRM-9 | 98974 | PITUNOR01 | g1627704 | *Caenorhabditis elegans* |
| SEQ ID NO: 10 | SEQ ID NO: 59 | HRM-10 | 118160 | MUSCNOT01 | g220594 | *Mus musculus* |
| SEQ ID NO: 11 | SEQ ID NO: 60 | HRM-11 | 140516 | TLYMNOR01 | g1086723 | *C. elegans* |
| SEQ ID NO: 12 | SEQ ID NO: 61 | HRM-12 | 207452 | SPLNNOT02 | g1314086 | *S. cerevisiae* |
| SEQ ID NO: 13 | SEQ ID NO: 62 | HRM-13 | 208836 | SPLNNOT02 | g662126 | *S. cerevisiae* |
| SEQ ID NO: 14 | SEQ ID NO: 63 | HRM-14 | 569710 | MMLR3DT01 | g1698719 | Human zinc finger protein |
| SEQ ID NO: 15 | SEQ ID NO: 64 | HRM-15 | 606742 | BRSTTUT01 | g1710201 | Human clone 23679 mRNA |
| SEQ ID NO: 16 | SEQ ID NO: 65 | HRM-16 | 611135 | COLNNOT01 | g506882 | *C elegans* |
| SEQ ID NO: 17 | SEQ ID NO: 66 | HRM-17 | 641127 | BRSTNOT03 | g1310668 | Human Hok-2 gene product |
| SEQ ID NO: 18 | SEQ ID NO: 67 | HRM-18 | 691768 | LUNGTUT02 | g309183 | *Mus musculus* |
| SEQ ID NO: 19 | SEQ ID NO: 68 | HRM-19 | 724157 | SYNOOAT01 | g577542 | *C. elegans* C16C10 |
| SEQ ID NO: 20 | SEQ ID NO: 69 | HRM-20 | 864683 | BRAITUT03 | g1418563 | *C. elegans* |
| SEQ ID NO: 21 | SEQ ID NO: 70 | HRM-21 | 933353 | CERVNOT01 | g1657672 | *C. elegans* |
| SEQ ID NO: 22 | SEQ ID NO: 71 | HRM-22 | 1404643 | LATRTUT02 | g459002 | *C. elegans* |
| SEQ ID NO: 23 | SEQ ID NO: 72 | HRM-23 | 1561587 | SPLNNOT04 | g868266 | *C. elegans* |
| SEQ ID NO: 24 | SEQ ID NO: 73 | HRM-24 | 1568361 | UTRSNOT05 | g1834503 | Human mucin |
| SEQ ID NO: 25 | SEQ ID NO: 74 | HRM-25 | 1572888 | LNODNOT03 | g603396 | *S. cerevisiae* YER156c |
| SEQ ID NO: 26 | SEQ ID NO: 75 | HRM-26 | 1573677 | LNODNOT03 | g849195 | *S. cerevisiae* D9481.16 |
| SEQ ID NO: 27 | SEQ ID NO: 76 | HRM-27 | 1574624 | LNODNOT03 | g1067025 | *C. elegans* R07E5.14 |
| SEQ ID NO: 28 | SEQ ID NO: 77 | HRM-28 | 1577239 | LNODNOT03 | g728657 | *S. cerevisiae* |
| SEQ ID NO: 29 | SEQ ID NO: 78 | HRM-29 | 1598203 | BLADNOT03 | g1200033 | *C. elegans* F35G2 |
| SEQ ID NO: 30 | SEQ ID NO: 79 | HRM-30 | 1600438 | BLADNOT03 | g286001 | KIAA0005 |
| SEQ ID NO: 31 | SEQ ID NO: 80 | HRM-31 | 1600518 | BLADNOT03 | g790405 | *C. elegans* |
| SEQ ID NO: 32 | SEQ ID NO: 81 | HRM-32 | 1602473 | BLADNOT03 | g1574570 | *Haemophilus influenzae* |
| SEQ ID NO: 33 | SEQ ID NO: 82 | HRM-33 | 1605720 | LUNGNOT15 | g1055080 | *C. elegans* |
| SEQ ID NO: 34 | SEQ ID NO: 83 | HRM-34 | 1610501 | COLNTUT06 | g313741 | *S. cerevisiae* YBL0514 |
| SEQ ID NO: 35 | SEQ ID NO: 84 | HRM-35 | 1720770 | BLADNOT06 | g1006641 | *C. elegans* F46C5 |
| SEQ ID NO: 36 | SEQ ID NO: 85 | HRM-36 | 1832295 | BRAINON01 | g561637 | Human enigma protein |
| SEQ ID NO: 37 | SEQ ID NO: 86 | HRM-37 | 1990522 | CORPNOT02 | g558396 | *S. cerevisiae* |
| SEQ ID NO: 38 | SEQ ID NO: 87 | HRM-38 | 2098087 | BRAITUT02 | g1066284 | *Mus musculus* uterine mRNA |
| SEQ ID NO: 39 | SEQ ID NO: 88 | HRM-39 | 2112230 | BRAITUT03 | g861306 | *C. elegans* |
| SEQ ID NO: 40 | SEQ ID NO: 89 | HRM-40 | 2117050 | BRSTTUT02 | g687821 | *C. elegans* |
| SEQ ID NO: 41 | SEQ ID NO: 90 | HRM-41 | 2184712 | SININOT01 | g868241 | *C. elegans* C56C10 |
| SEQ ID NO: 42 | SEQ ID NO: 91 | HRM-42 | 2290475 | BRAINON01 | g733605 | *C. elegans* |
| SEQ ID NO: 43 | SEQ ID NO: 92 | HRM-43 | 2353452 | LUNGNOT20 | g1507666 | *Schizosaccharomyces pombe* |
| SEQ ID NO: 44 | SEQ ID NO: 93 | HRM-44 | 2469611 | THP1NOT03 | g1495332 | *C. elegans* |
| SEQ ID NO: 45 | SEQ ID NO: 94 | HRM-45 | 2515476 | LIVRTUT04 | g1665790 | KIAA0262 |
| SEQ ID NO: 46 | SEQ ID NO: 95 | HRM-46 | 2754573 | THP1AZS08 | g478990 | Human RNA binding protein |

TABLE 1-continued

| Protein | Nucleotide | Abbreviation | Clone ID | Library | NCBI | Homolog |
|---|---|---|---|---|---|---|
| SEQ ID NO: 47 | SEQ ID NO: 96 | HRM-47 | 2926777 | TLYMNOT04 | g687823 | *C. elegans* |
| SEQ ID NO: 48 | SEQ ID NO: 97 | HRM-48 | 3217567 | TESTNOT07 | g1841547 | Human HLA class III region |
| SEQ ID NO: 49 | SEQ ID NO: 98 | HRM-49 | 3339274 | SPLNNOT10 | g1177434 | Human mRNA |

HRM-1 (SEQ ID NO:1) was identified in Incyte Clone 133 from the U937NOT01 cDNA library using a computer search for amino acid sequence alignments. A consensus sequence, SEQ ID NO:50, was derived from the extended and overlapping nucleic acid sequences: Incyte Clones 133 (U937NOT01) 013508 (THP1PLB01), 210174 (SPLNNOT02), 1655863 (PROSTUT08), 1725724 (PROSNOT14), 1858205 (PROSNOT18), and 2646014 (OVARTUT05).

In one embodiment, the invention encompasses a polypeptide comprising the amino acid sequence of SEQ ID NO:1. HRM-1 is 151 amino acids in length and has four potential phosphorylation sites at T2, S14, S69, and T111. HRM-1 has sequence homology with human KIAA0105 (g285947) and is found in cDNA libraries which have proliferating cells and are associated with cancer or immune response.

HRM-2 (SEQ ID NO:2) was identified in Incyte Clone 1762 from the U937NOT01 cDNA library using a computer search for amino acid sequence alignments. A consensus sequence, SEQ ID NO:51, was derived from the extended and overlapping nucleic acid sequences: Incyte Clones 1762 (U937NOT01), 1254927 (LUNGFET03), and 2070865 (ISLTNOT01).

In one embodiment, the invention encompasses a polypeptide comprising the amino acid sequence of SEQ ID NO:2. HRM-2 is 185 amino acids in length and has a potential N glycosylation site at N 108; eight potential phosphorylation sites at T22,S26 T27, S31, T51, T70, and T135; a leucine zipper motif at $L_{136}$KDVVWGLNSLFTDLLNFDDPL; and a ubiquitin conjugation motif at $W_{105}$HPNITETGEICLSL. HRM-2 has sequence homology with a gene from *Ascaris suum* (g1518121) and is found in cDNA libraries which have secretory or proliferating cells and are associated with development.

HRM-3 (SEQ ID NO:3) was identified in Incyte Clone 1847 from the U937NOT01 cDNA library using a computer search for amino acid sequence alignments. A consensus sequence, SEQ ID NO:52, was derived from the extended and overlapping nucleic acid sequences: Incyte Clones 274 (U937NOT01), 1847 (U937NOT01), 262233 (HNT2AGT01), 972977 (MUSCNOT02), and 1859611 (PROSNOT18).

In one embodiment, the invention encompasses a polypeptide comprising the amino acid sequence of SEQ ID NO:3. HRM-3 is 59 amino acids in length and has four potential N glycosylation sites at N147, N352, N410, and N421, and 17 potential phosphorylation sites at S13, T21, S43. S89, S131, S207, T243, S278, T286, S335, S337, S350, S354, S369, S380, S412, and S542. HRM-3 has sequence homology with a *Saccharomyces cerevisiae* protein (g1302211) and is found in cDNA libraries which have proliferating or immortalized cells.

HRM-4 (SEQ ID NO:4) was identified in Incyte Clone 9337 from the HMC1NOT01 cDNA library using a computer search for amino acid sequence alignments. A consensus sequence, SEQ ID NO:53, was derived from the extended and overlapping nucleic acid sequences: Incyte Clones 9337 (HMC1NOT01), 670279 (CRBLNOT01), 717305 (PROSTUT01), 968249 (BRSTNOT05), and 1546506 (PROSTUT04).

In one embodiment, the invention encompasses a polypeptide comprising the amino acid sequence of SEQ ID NO:4. HRM-4 is 338 amino acids in length and has a potential N glycosylation site at N327, 11 potential phosphorylation sites at T15, S36, S42, S50, T51, S73, S144, S176, T256, S140, and T329; and five zinc finger motifs at $C_{192}RC_{194}$SECGKI FRNPRYFSVHKKIH, $C_{222}$QDCGKGFVQSSSLTQHQRVH, $C_{250}$QECGRTFNDRSAISQHLRTH, $C_{278}$QDCGKAFRQSSHLIRHQRTH, and $C_{306}$NKCGKAFTQSSHLIGHQRTH. HRM-4 has sequence homology with a human zinc finger protein (g1613852) and is found in cDNA libraries which have proliferating, cancerous, or secretory cells.

HRM-5 (SEQ ID NO:5) was identified in Incyte Clone 9476 from the HMC1NOT01 cDNA library using a computer search for amino acid sequence alignments. A consensus sequence, SEQ ID NO:54, was derived from the extended and overlapping nucleic acid sequences: Incyte Clones 9476 (HMC1NOT01), 010403 (THP1PLB01), 495099 (HNT2NOT01), 1670783 (BMARNOT03), 1997203 (BRSTTUT03), and 2190637 (THYRTUT03).

In one embodiment, the invention encompasses a polypeptide comprising the amino acid sequence of SEQ ID NO:5. HRM-5 is 456 amino acids in length and has a potential N glycosylation site at N385; 14 potential phosphorylation sites at T9, T12, S58, T74, T163, T139, S175, T211, T239, T272, S331, T367, T402, and S443; and an ATP/GTP binding motif at $G_{70}$PPGTGKT77. HRM-5 has sequence homology with a *S. cerevisiae* protein (g755784) and is found in cDNA libraries which have dividing, cancerous or immortalized cells and are associated with immune response.

HRM-6 (SEQ ID NO:6) was identified in Incyte Clone 10370 from the THP1PLB01 cDNA library using a computer search for amino acid sequence alignments. A consensus sequence. SEQ ID NO:55, was derived from the extended and overlapping nucleic acid sequences: Incyte Clones 010370 (THP1PLB01), 109018 (AMLBNOT01), 259388 (HNT2RAT01), and 1518624 (BLADTUT04).

In one embodiment, the invention encompasses a polypeptide comprising the amino acid sequence of SEQ ID NO:6. HRM-6 is 210 amino acids in length and has one potential N-glycosylation site at N11 and nine potential phosphorylation sites at T13, T21, T46, T124, S125, S132, T143, T167, and T191. HRM-6 has sequence homology with a putative p64 CLCP human protein (g895845) and is found in cDNA libraries which have dividing, cancerous or immortalized cells and are associated with immune response.

HRM-7 (SEQ ID NO:7) was identified in Incyte Clone 30137 from the THP1PLB01 cDNA library using a computer search for amino acid sequence alignments. A consensus sequence, SEQ ID NO:56, was derived from the extended and overlapping nucleic acid sequences: Incyte Clones 30137 (THP1NOB01), 531638 (BRAINOT03), 1653122 (PROSTUT08), and 1682227 (PROSNOT15).

In one embodiment, the invention encompasses a polypeptide comprising the amino acid sequence of SEQ ID NO:7. HRM-7 is 255 amino acids in length and has one potential N glycosylation site at N86 and 12 potential phosphorylation sites at T9, T28, S32, S61, S94, S142, S156, S160, T169, S188, S220, and S236. HRM-7 has sequence homology with human clone 23733 (g1710241) and is found in cDNA libraries which have dividing, cancerous or immortalized cells and are associated with immune response.

HRM-8 (SEQ ID NO:8) was identified in Incyte Clone 77180 from the SYNORAB01 cDNA library using a computer search for amino acid sequence alignments. A consensus sequence, SEQ ID NO:57, was derived from the extended and overlapping nucleic acid sequences: Incyte Clones 077180 (SYNORAB01), 604706 (BRSTTUT01), 977901 (BRSTNOT02), 1870373 (SKINBIT01), and 2169441 (ENDCNOT03).

In one embodiment, the invention encompasses a polypeptide comprising the amino acid sequence of SEQ ID NO:8. HRM-8 is 188 amino acids in length and has one potential amidation site, Q170GKR; two potential N glycosylation sites at N60 and N68; and four potential phosphorylation sites at S70, T164, T166, and S183. HRM-8 has sequence homology with a *S. cerevisiae* protein (g5372) and is found in cDNA libraries which have dividing, cancerous or immortalized cells and are associated with immune response.

HRM-9 (SEQ ID NO:9) was identified in Incyte Clone 98974 from the PITUNOR01 cDNA library using a computer search for amino acid sequence alignments. A consensus sequence, SEQ ID NO:58, was derived from the extended and overlapping nucleic acid sequences: Incyte Clones 98974 (PITUNOR01), 443924 (MPHGNOT03), 1401540 (BRAITUT08), 1507305 (BRAITUT07), 1700814 (BLADTUT05), and 1809947 (PROSTUT12).

In one embodiment, the invention encompasses a polypeptide comprising the amino acid sequence of SEQ ID NO:9. HRM-9 is 531 amino acids in length and has one potential N glycosylation site at N480; 37 potential phosphorylation sites at S19, T22, S38, T64, T76, T91, S117, S118, S158, T164, T177, T182, T200, T267, Y281, Y311, Y322, S333, S394, S402, S404, S409, S414, S416, S418, S429, S434, S439, S440, S456, S460, S466, S478, S505, S510, S524, S528, and one potential glycosaminoglycan motif at S434GSG. HRM-9 has sequence homology with a *Caenorhabditis elegans* protein (g1627704) and is found in cDNA libraries which have secretory, proliferating or immune cells.

HRM-10 (SEQ ID NO:10) was identified in Incyte Clone 118160 from the MUSCNOT01 cDNA library using a computer search for amino acid sequence alignments. A consensus sequence, SEQ ID NO:59, was derived from the extended and overlapping nucleic acid sequences: Incyte Clones 118160 (MUSCNOT01), 323015 (EOSIHET02), and 1856519 (PROSNOT18).

In one embodiment, the invention encompasses a polypeptide comprising the amino acid sequence of SEQ ID NO:10. HRM-10 is 348 amino acids in length and has two potential N glycosylation sites at N150 and N317; 17 potential phosphorylation sites at T23, T45, S60, T126, S130, S140, S145, S151, S154, S158, S186, Y208, Y234, S217, T271, T303, and S327, and a transcription factor signature at $C_{310}$SKCKKKNCTYNQVQTRSA DEPMT-TFVLCNEC. HRM-10 has sequence homology with a *Mus musculus* protein (g220594) and is found in cDNA libraries which have secretory or immune associations.

HRM-11 (SEQ ID NO:11) was identified in Incyte Clone 140516 from the TLYMNOR01 cDNA library using a computer search for amino acid sequence alignments. A consensus sequence, SEQ ID NO:60, was derived from the extended and overlapping nucleic acid sequences: Incyte Clones 140516 (TLYMNOR01), 143729 (TLYMNOR01), 1346014 (PROSNOT11), and 2074866 (ISLTNOT01).

In one embodiment, the invention encompasses a polypeptide comprising the amino acid sequence of SEQ ID NO:11. HRM-11 is 393 amino acids in length and has 14 potential phosphorylation sites at S22, T33, S41, S69, T156, Y157, S166, S199, T242, T308, T324, S350, T359, S378. HRM-11 has sequence homology with a *C. elegans* protein (g1086723) and is found in cDNA libraries which have proliferating, secretory, or immune cells.

HRM-12 (SEQ ID NO:12) was identified in Incyte Clone 207452 from the SPLNNOT02 cDNA library using a computer search for amino acid sequence alignments. A consensus sequence, SEQ ID NO:61, was derived from the extended and overlapping nucleic acid sequences: Incyte Clones 207452 (SPLNNOT02), 238306 (SINTNOT02), 1559492 (SPLNNOT04), and 1852567 (LUNGFET03).

In one embodiment, the invention encompasses a polypeptide comprising the amino acid sequence of SEQ ID NO:12. HRM-12 is 320 amino acids in length and one potential amidation site at $E_{210}$GKK; two potential N glycosylation sites at N12 and N314; seven potential phosphorylation sites at S34, S51, S56, S111, T157, S198, and S318; one potential glycosaminoglycan motif, S224GAG; one immunoglobulin major histocompatibility motif, $F_{305}$FCNVFH; and two mitochondrial carrier protein signatures, $P_{35}$FDVIKIRF and $P_{138}$VDVLRTRF. HRM-12 has sequence homology with a *S. cerevisiae* protein (g1314086) and is found in cDNA libraries which have secretory and proliferating cells.

HRM-13 (SEQ ID NO:13) was identified in Incyte Clone 208836 from the SPLNNOT02 cDNA library using a computer search for amino acid sequence alignments. A consensus sequence, SEQ ID NO:62, was derived from the extended and overlapping nucleic acid sequences: Incyte Clones 26879 (SPLNFET01), 208836 (SPLNNOT02), and 1916142 (PROSTUT04).

In one embodiment, the invention encompasses a polypeptide comprising the amino acid sequence of SEQ ID NO: 13. HRM-13 is 343 amino acids in length and has one potential N glycosylation site at N172; 17 potential phosphorylation sites at S45, S46, T62, S73, S84, S85, S102, S105, T124, S137, Y153, T192, S216, Y226, Y241, S253 and T293; and a zinc finger motif at $C_{277}$RHYFCESCA. HRM-13 has sequence homology with a *S. cerevisiae* protein (g662126) and is found in cDNA libraries which have proliferating cells and are associated with immune response.

HRM-14 (SEQ ID NO:14) was identified in Incyte Clone 569710 from the MMLR3DT01 cDNA library using a computer search for amino acid sequence alignments. A consensus sequence, SEQ ID NO:63, was derived from the extended and overlapping nucleic acid sequences: Incyte Clones 145344 (TLYMNORO01) and 569710 (MMLR3DT01).

In one embodiment, the invention encompasses a polypeptide comprising the amino acid sequence of SEQ ID NO:14. HRM-14 is 368 amino acids in length and has 10 potential phosphorylation sites at S5, T16, T125, S132, S142, S157, S167, S185, S208, and S246; and four zinc finger motifs at $C_{253}$DECGKHFSQGSALILHQRIH, $C_{281}$VECGKAFSRSSILVQH QRVH, $C_{309}$LECGKAFSQNSGLINHQRIH, and $C_{337}$VQCGKSYSQSSNLFRHQRRH. HRM-14 has sequence homology with a human zinc finger protein (g1698719) and is found in cDNA libraries which are associated with immune response.

HRM-15 (SEQ ID NO:15) was identified in Incyte Clone 606742 from the BRSTTUT01 cDNA library using a computer search for amino acid sequence alignments. A consensus sequence, SEQ ID NO:64, was derived from the extended and overlapping nucleic acid sequences: Incyte Clones 606742 (BRSTTUT01) and 1559478 (SPLNNOT04).

In one embodiment, the invention encompasses a polypeptide comprising the amino acid sequence of SEQ ID NO:15. HRM-15 is 158 amino acids in length and has two potential myristylation sites, G92GFHGQ and G96QMHSR, and one potential PKC phosphorylation site, S40. HRM-15 has sequence homology with human clone 23679 (g1710201) and is found in cDNA libraries with proliferating, secretory and/or cancerous cells.

HRM-16 (SEQ ID NO:16) was identified in Incyte Clone 611135 from the COLNNOT01 cDNA library using a computer search for amino acid sequence alignments. A consensus sequence, SEQ ID NO:65, was derived from the extended and overlapping nucleic acid sequences: Incyte Clones 611135 (COLNNOT01), 659029 (BRAINOT03), and 1861691 (PROSNOT19).

In one embodiment, the invention encompasses a polypeptide comprising the amino acid sequence of SEQ ID NO:16. HRM-16 is 334 amino acids in length and has 11 potential phosphosphorylation sites at S17, T29, T128, S133, S162, S176, S263, T257, S263, S277, and S294. HRM-16 has sequence homology with a C. elegans protein (g506882) and is found in cDNA libraries with secretory cells.

HRM-17 (SEQ ID NO:17) was identified in Incyte Clone 641127 from the BRSTNOT03 cDNA library using a computer search for amino acid sequence alignments. A consensus sequence, SEQ ID NO:66, was derived from the extended and overlapping nucleic acid sequences: Incyte Clones 641127 (BRSTNOT03) and 673153 (CRBLNOT01).

In one embodiment, the invention encompasses a polypeptide comprising the amino acid sequence of SEQ ID NO:17. HRM-17 is 488 amino acids in length and has one N glycosylation site at N215; 11 potential phosphorylation sites at S70, S78, S92, T102, S111, T190, Y235, S303, S329, S415, and T471; and eight zinc finger motifs at $C_{237}$EQCGKGFTRSSSLLIHQAVH, $C_{265}$DKCGKGFTRSSSLLIHHAVH, $C_{293}$DKCGKGFSQSSKLHIHQRVH, $C_{321}$EECGMSFSQRSNLHIHQRVH, $C_{349}$GECGKGFSQSSNLHIHRCIH, $C_{377}$YECGKGFSQSSDLRIHLRVH, $C_{405}$GKCGKGFSQSSKLLIHQRVH, and $C_{433}$SKCGKGFSQSSNLHIHQRVH. HRM-17 has sequence homology with a human HOK-2 gene product (g1310668) and is found in cDNA libraries associated with sensory and secretory functions.

HRM-18 (SEQ ID NO:18) was identified in Incyte Clone 691768 from the LUNGTUT02 cDNA library using a computer search for amino acid sequence alignments. A consensus sequence, SEQ ID NO:67, was derived from the extended and overlapping nucleic acid sequences: Incyte Clones 691768 (LUNGTUT02), 1417161 (BRAINOT12) and 1931861 (COLNNOT16).

In one embodiment, the invention encompasses a polypeptide comprising the amino acid sequence of SEQ ID NO:18. HRM-18 is 255 amino acids in length and has one potential N glycosylation site at N102 and 13 potential phosphorylation sites at S21, T90, T109, S111, T124, S134, S139, T141, S158, S172, S181, S187, and T206. HRM-18 has sequence homology with a M. musculus protein (g309183) and is found in cDNA libraries with proliferating or cancerous cells.

HRM-19 (SEQ ID NO:19) was identified in Incyte Clone 724157 from the SYNOOAT01 cDNA library using a computer search for amino acid sequence alignments. A consensus sequence, SEQ ID NO:68, was derived from the extended and overlapping nucleic acid sequences: Incyte Clones 724157 (SYNOOAT01), 1516153 (PANCTUT01), and 1610152 (COLNTUT06).

In one embodiment, the invention encompasses a polypeptide comprising the amino acid sequence of SEQ ID NO:19. HRM-19 is 351 amino acids in length and has eight potential phosphorylation sites at T30, S41, S53, T135, S172, S187, T273, and S331; one potential glycosaminoglycan site, $S_{18}$GTG; and one potential mitochondrial carrier motif, $P_{31}$LDVVKVRL. HRM-19 has sequence homology with C. elegans C16C10 (g577542) and is found in cDNA libraries associated with cell proliferation, cancer and immune response.

HRM-20 (SEQ ID NO:20) was identified in Incyte Clone 864683 from the BRAITUT03 cDNA library using a computer search for amino acid sequence alignments. A consensus sequence, SEQ ID NO:69, was derived from the extended and overlapping nucleic acid sequences: Incyte Clones 486297 (HNT2RAT01), 864683 (BRAITUT03), 1314465 (BLADTUT02), 1610776 (COLNTUT06), 1856771 (PROSNOT18), 1866081 (PROSNOT19), 1932221 (COLNNOT16), and 2125225 (BRSTNOT07).

In one embodiment, the invention encompasses a polypeptide comprising the amino acid sequence of SEQ ID NO:20. HRM-20 is 535 amino acids in length and has three potential N glycosylation sites at N202, N252, and N523; and 17 potential phosphorylation sites at S2, S12, S42, S49, S102, S157, T165, T171, T232, T255, T317, S332, S428, T441, S453, S500, and S509. HRM-20 has sequence homology with a C. elegans protein (g1418563) and is found in cDNA libraries associated with cell proliferation, cancer and immune response.

HRM-21 (SEQ ID NO:21) was identified in Incyte Clone 933353 from the CERVNOT01 cDNA library using a computer search for amino acid sequence alignments. A consensus sequence, SEQ ID NO:70, was derived from the extended and overlapping nucleic acid sequences: Incyte Clones 928904 (BRAINOT04), 933353 (CERVNOT01), and 2452674 (ENDANOT01).

In one embodiment, the invention encompasses a polypeptide comprising the amino acid sequence of SEQ ID NO:21. HRM-21 is 201 amino acids in length and has one potential N glycosylation site at N82; five potential phosphorylation sites at T70, S83, S98, S154, and T187; and one tyrosine phosphatase motif at $V_{130}$HCKAGRSRSATM. HRM-21 has sequence homology with a C. elegans protein (g1657672) and is found in cDNA libraries associated with immune response.

HRM-22 (SEQ ID NO:22) was identified in Incyte Clone 1404643 from the LATRTUT02 cDNA library using a computer search for amino acid sequence alignments. A consensus sequence, SEQ ID NO:71, was derived from the extended and overlapping nucleic acid sequences: Incyte Clones 878243 (LUNGAST01), 1404643 (LATRTUT02), 1508343 (LUNGNOT14) and 2585156 (BRAITUT22).

In one embodiment, the invention encompasses a polypeptide comprising the amino amino-acid sequence of SEQ ID NO:22. HRM-22 is 239 amino acids in length and has four potential phosphorylation sites at S5, S89, S133, and T211. HRM-22 has sequence homology with a *C. elegans* protein (g459002) and is found in cDNA libraries associated with cell proliferation, cancer and immune response.

HRM-23 (SEQ ID NO:23) was identified in Incyte Clone 1561587 from the SPLNNOT04 cDNA library using a computer search for amino acid sequence alignments. A consensus sequence, SEQ ID NO:72, was derived from the extended and overlapping nucleic acid sequences: Incyte Clones 522573 (MMLR2DT01), 773822 (COLNNOT05), 1304839 (PLACNOT02), 1381253 (BRAITUT08), 1452511 (PENITUT01), 1539060 (SINTTUT01), 1561587 (SPLNNOT04), and 2416572 (HNT3AZT01).

In one embodiment, the invention encompasses a polypeptide comprising the amino acid sequence of SEQ ID NO:23. HRM-23 is 244 amino acids in length and has five potential phosphorylation sites at T40, S75, T84, T89, and S194. HRM-23 has sequence homology with a *C. elegans* protein (g868266) and is found in cDNA libraries associated with cell proliferation, cancer and immune response.

HRM-24 (SEQ ID NO:24) was identified in Incyte Clone 1568361 from the UTRSNOT05 cDNA library using a computer search for amino acid sequence alignments. A consensus sequence, SEQ ID NO:73, was derived from the extended and overlapping nucleic acid sequences: Incyte Clones 927874 (BRAINOT04), 1255220 (MENITUT03), 1242340 (LUNGNOT03), 1349495 (LATRTUT02), 1381263 (BRAITUT08), 1500028 (SINTBST01). 1568361 (UTRSNOT05), 1653237 (PROSTUT08), 1975340 (PANCTUT02), and 3274608 (PROSBPT06).

In one embodiment, the invention encompasses a polypeptide comprising the amino acid sequence of SEQ ID NO:24. HRM-24 is 431 amino acids in length and has five potential N glycosylation sites at N75, N95, N171, N202, and N298; eight potential phosphorylation sites at S2, S3, T11, T13, S17, Y316, T375, and T415; and a leucine zipper motif, $L_{96}$SAFNNILSNLGYILLGLLFLL. HRM-24 has sequence homology with human mucin (g1834503) and is found in cDNA libraries with proliferating, cancerous or inflammed cells.

HRM-25 (SEQ ID NO:25) was identified in Incyte Clone 1572888 from the LNODNOT03 cDNA library using a computer search for amino acid sequence alignments. A consensus sequence, SEQ ID NO:74, was derived from the extended and overlapping nucleic acid sequences: Incyte Clones 1438142 (PANCNOT08), 1572888 (LNODNOT03), and 1665075 (BRSTNOT09).

In one embodiment, the invention encompasses a polypeptide comprising the amino acid sequence of SEQ ID NO:25. HRM-25 is 376 amino acids in length and has one N glycosylation site at N51 and five potential phosphorylation sites at S111, T150, S151, T159, and S196. HRM-25 has sequence homology with *S. cerevisiae* YER156c (g603396) and is found in cDNA libraries with secretory cells.

HRM-26 (SEQ ID NO:26) was identified in Incyte Clone 1573677 from the LNODNOT03 cDNA library using a computer search for amino acid sequence alignments. A consensus sequence, SEQ ID NO:75, was derived from the extended and overlapping nucleic acid sequences: Incyte Clones 040360 (TBLYNOT01), 065573 (PLACNOB01), 228382 (PANCNOT01), 1456688 (COLNFET02), 1573677 (LNODNOT03), andl 854560 (HNT3AZT01).

In one embodiment, the invention encompasses a polypeptide comprising the amino acid sequence of SEQ ID NO:26. HRM-26 is 340 amino acids in length and has one potential N glycosylation site at N213 and 13 potential phosphorylation sites at T10, S22, T53, T56, S160, S168, S170, S177, S201, S226, S297, S303, and T329. HRM-26 has sequence homology with *S. cerevisiae* D9481.16 (g849195) and is found in cDNA libraries associated with secretion, immune response, and cancer.

HRM-27 (SEQ ID NO:27) was identified in lncyte Clone 1574624 from the LNODNOT03 cDNA library using a computer search for amino acid sequence alignments. A consensus sequence, SEQ ID NO:76, was derived from the extended and overlapping nucleic acid sequences: Incyte Clones 90012 (HYPONOB01), 888491 (STOMTUT01), and 1574624 (LNODNOT03).

In one embodiment, the invention encompasses a polypeptide comprising the amino acid sequence of SEQ ID NO:27. HRM-27 is 174 amino acids in length and has one N glycosylation site at N51 and five potential phosphorylation sites at S111, T150, S151, T159, and S196. HRM-27 has sequence homology with a *C. elegans* protein (g1067025) and is found in cDNA libraries associated with secretion, immune response, and cancer.

HRM-28 (SEQ ID NO:28) was identified in Incyte Clone 1577239 from the LNODNOT03 cDNA library using a computer search for amino acid sequence alignments. A consensus sequence, SEQ ID NO:77, was derived from the extended and overlapping nucleic acid sequences: Incyte Clones 100565 (ADRENOT01), 1336693 (COLNNOT13), and 1577239 (LNODNOT03).

In one embodiment, the invention encompasses a polypeptide comprising the amino acid sequence of SEQ ID NO:28. HRM-28 is 179 amino acids in length and has one potential N glycosylation site at N60 and five potential phosphorylation sites at Y61, S62, Y104, T136, and Y142. HRM-28 has sequence homology with a *S. cerevisiae* protein (g728657) and is found in cDNA libraries associated with secretion and immune response.

HRM-29 (SEQ ID NO:29) was identified in Incyte Clone 1598203 from the BLADNOT03 cDNA library using a computer search for amino acid sequence alignments. A consensus sequence, SEQ ID NO:78, was derived from the extended and overlapping nucleic acid sequences: Incyte Clones 1598203 (BLADNOT03), 1697035 (COLNNOT23), and 1932332 (COLNNOT16).

In one embodiment, the invention encompasses a polypeptide comprising the amino acid sequence of SEQ ID NO:29. HRM-29 is 205 amino acids in length and has one potential N glycosylation site at N117 and five potential phosphorylation sites at T68, T118, S137, S140, and S159. HRM-29 has sequence homology with a *C. elegans* protein (g1200033) and is found in cDNA libraries associated with secretion.

HRM-30 (SEQ ID NO:30) was identified in Incyte Clone 1600438 from the BLADNOT03 cDNA library using a computer search for amino acid sequence alignments. A consensus sequence, SEQ ID NO:79, was derived from the extended and overlapping nucleic acid sequences: Incyte Clones 835283 (PROSNOT07), 1600044 (BLADNOT03), 1600438 (BLADNOT03), and 1922072 (BRSTTUT01).

In one embodiment, the invention encompasses a polypeptide comprising the amino acid sequence of SEQ ID NO:30. HRM-30 is 419 amino acids in length and has one potential N glycosylation site at N161; twelve potential phosphorylation sites at T16, S57, T67, T83, S100, T107, S144, S206, T254, Y351, S412, and S414; a leucine zipper motif, $L_{38}$NEAGDDLEAVAKFLDSTGSRL; and an ATP/GTP binding motif, $A_{385}$HVAKGKS. HRM-30 has sequence homology with human KIAA0005 (g286001) and is found in cDNA libraries associated with secretion and cancer.

HRM-31 (SEQ ID NO:31) was identified in Incyte Clone 1600518 from the BLADNOT03 cDNA library using a computer search for amino acid sequence alignments. A consensus sequence, SEQ ID NO:80, was derived from the extended and overlapping nucleic acid sequences: Incyte Clones 389679 (THYMNOT02), 1600518 (BLADNOT03), 2055734 (BEPINOT01), 2102793 (BRAITUT02), and 2509270 (CONUTUT01).

In one embodiment, the invention encompasses a polypeptide comprising the amino acid sequence of SEQ ID NO:31. HRM-31 is 376 amino acids in length and has one potential N glycosylation site at N161 and 14 potential phosphorylation sites at T30, S65, S75, S95, S106, T134, S159, S224, T228, T250, T292, S299, T303, and S323 and a glycosaminoglycan motif, S14GPG. HRM-31 has sequence homology with a C. elegans protein (g790405) and is found in cDNA libraries associated with immune response, secretion, and cancer.

HRM-32 (SEQ ID NO:32) was identified in Incyte Clone 1602473 from the BLADNOT03 cDNA library using a computer search for amino acid sequence alignments. A consensus sequence, SEQ ID NO:81, was derived from the extended and overlapping nucleic acid sequences: Incyte Clones 1351857 (LATRTUT02), 1602473 (BLADNOT03), and 2478778 (SMCANOT01).

In one embodiment, the invention encompasses a polypeptide comprising the amino acid sequence of SEQ ID NO:32. HRM-32 is 237 amino acids in length and has seven potential phosphorylation sites at T51, T68, S92, S143, T171, S193, and S203. HRM-32 has sequence homology with a Haemophilus influenzae protein (g1574570) and is found in cDNA libraries associated with immune response, secretion, and cancer.

HRM-33 (SEQ ID NO:33) was identified in Incyte Clone 1605720 from the LUNGNOT15 cDNA library using a computer search for amino acid sequence alignments. A consensus sequence, SEQ ID NO:82, was derived from the extended and overlapping nucleic acid sequences: Incyte Clones 660915 (BRAINOT03), 1347135 (PROSNOT11), and 1605720 (LUNGNOT15).

In one embodiment, the invention encompasses a polypeptide comprising the amino acid sequence of SEQ ID NO:33. HRM-33 is 152 amino acids in length and has four potential phosphorylation sites at S10, S23, T34, and S66; and a leucine zipper motif, $L_{77}$AVGNYRLKEYEKALKYVRGLL. HRM-33 has sequence homology with C. elegans (g1055080) and is found in cDNA libraries associated with secretion and immune response.

HRM-34 (SEQ ID NO:34) was identified in Incyte Clone 1610501 from the COLNTUT06 cDNA library using a computer search for amino acid sequence alignments. A consensus sequence, SEQ ID NO:83, was derived from the extended and overlapping nucleic acid sequences: Incyte Clones 1610501 (COLNTUT06) and 2477716 (SMCANOT01).

In one embodiment, the invention encompasses a polypeptide comprising the amino acid sequence of SEQ ID NO:34. HRM-34 is 179 amino acids in length and has five potential phosphorylation sites at S32, S48, T45, T50, and T52. HRM-34 has sequence homology with a S. cerevisiae protein (g313741) and is found in cDNA libraries associated with cancer and immune response.

HRM-35 (SEQ ID NO:35) was identified in Incyte Clone 1720770 from the BLADNOT06 cDNA library using a computer search for amino acid sequence alignments. A consensus sequence, SEQ ID NO:84, was derived from the extended and overlapping nucleic acid sequences: Incyte Clones 681455 (UTRSNOT02), 813292 (LUNGNOT04), 1223029 (COLNTUT02), 1444186 (THYRNOT03), 1522592 (BLADTUT04), 1720770 (BLADNOT06), and 1798409 (COLNNOT27).

In one embodiment, the invention encompasses a polypeptide comprising the amino acid sequence of SEQ ID NO:35. HRM-35 is 196 amino acids in length and has an amidation motif, $H_{17}9$GKR. and seven potential phosphorylation sites at S2, S6, S31, S84, S90, T136, and T161. HRM-35 has sequence homology with a C. elegans protein (g1006641) and is found in cDNA libraries associated with secretion, immune response, and cancer.

HRM-36 (SEQ ID NO:36) was identified in Incyte Clone 1832295 from the BRAINON01 cDNA library using a computer search for amino acid sequence alignments. A consensus sequence, SEQ ID NO:85, was derived from the extended and overlapping nucleic acid sequences: Incyte Clones 060275 (LUNGNOT01), 1823989 (GBLATUT01), and 1832295 (BRAINON01).

In one embodiment, the invention encompasses a polypeptide comprising the amino acid sequence of SEQ ID NO:36. HRM-36 is 612 amino acids in length and has 12 potential N glycosylation sites at N36, N95, N139, N146, N151, N176, N188, N226, N243, N353, N371, and N482; and 16 potential phosphorylation sites at S58, S92, S112, T153, T198, T248, S308, S373, T400, T420, T428, Y438, T458, T472, S527, and S556. HRM-36 has sequence homology with human enigma protein (g561637) and is found in cDNA libraries associated with secretion and immune response.

HRM-37 (SEQ ID NO:37) was identified in Incyte Clone 1990522 from the CORPNOT02 cDNA library using a computer search for amino acid sequence alignments. A consensus sequence, SEQ ID NO:86, was derived from the extended and overlapping nucleic acid sequences: Incyte Clones 264363 (HNT2AGT01), 1990522 (CORPNOT02), and 2451448 (ENDANOT01).

In one embodiment, the invention encompasses a polypeptide comprising the amino acid sequence of SEQ ID NO:37. HRM-37 is 101 amino acids in length and has a PKC phosphorylation site at S62. HRM-37 has sequence homology with a S. cerevisiae protein (g558396) and is found in cDNA libraries associated with immune response.

HRM-38 (SEQ ID NO:38) was identified in Incyte Clone 2098087 from the BRAITUT02 cDNA library using a computer search for amino acid sequence alignments. A consensus sequence, SEQ ID NO:87, was derived from the extended and overlapping nucleic acid sequences: Incyte Clones 690359 (LUNGTUT02), 1429907 (SINTBST01), and 2098087 (BRAITUT02).

In one embodiment, the invention encompasses a polypeptide comprising the amino acid sequence of SEQ ID NO:38. HRM-38 is 132 amino acids in length and has a potential ATP/GTP binding motif at $G_{74}$ARNLLKS. HRM-38 has sequence homology with M. musculus uterine protein (g1066284) and is found in cDNA libraries associated with immune response.

HRM-39 (SEQ ID NO:39) was identified in Incyte Clone 2112230 from the BRAITUT03 cDNA library using a computer search for amino acid sequence alignments. A consensus sequence, SEQ ID NO:88, was derived from the extended and overlapping nucleic acid sequences: Incyte Clones 1383278 (BRAITUT08), 1646103 (PROSTUT09), 2112230 (BRAITUT03), and 2510591 (CONUTUT01).

In one embodiment, the invention encompasses a polypeptide comprising the amino acid sequence of SEQ ID NO:39. HRM-39 is 188 amino acids in length and has a potential N glycosylation site at N87 and eight potential phosphorylation sites at T10, T28, S74, S93, T121, T128, Y168, and T169. HRM-39 has sequence homology with a *C. elegans* protein (g861306) and is found in cDNA libraries from cancerous tissues.

HRM-40 (SEQ ID NO:40) was identified in Incyte Clone 2117050 from the BRAITUT02 cDNA library using a computer search for amino acid sequence alignments. A consensus sequence, SEQ ID NO:89, was derived from the extended and overlapping nucleic acid sequences: Incyte Clones 941515 (ADRENOT03), 1549443 (PROSNOT06), 2113261 (BRAITUT03), 2117050 (BRSTTUT02), and 2530536 (GBLANOT02).

In one embodiment, the invention encompasses a polypeptide comprising the amino acid sequence of SEQ ID NO:40. HRM-40 is 86 amino acids in length and has a potential N glycosylation site at N58 and four potential phosphorylation sites at T2, S9, T26, and T27. HRM-40 has sequence homology with a *C. elegans* protein (g687821) and is found in cDNA libraries involved in cell proliferation, secretion, cancer, and immune response.

HRM-41 (SEQ ID NO:41) was identified in Incyte Clone 2184712 from the SININOT01 cDNA library using a computer search for amino acid sequence alignments. A consensus sequence, SEQ ID NO:90, was derived from the extended and overlapping nucleic acid sequences: Incyte Clones 922736 (RATRNOT02), 1976003 (PANCTUT02), and 2184712 (SININOT01).

In one embodiment, the invention encompasses a polypeptide comprising the amino acid sequence of SEQ ID NO:41. HRM-41 is 222 amino acids in length and has a potential amidation site, $K_{10}GKK$; a potential glycosaminoglycan site, $S_2GLG$; a potential N glycosylation site, N95; and seven potential phosphorylation sites at T18, T29, T50, S84, T98, S112, and S188. HRM-41 has sequence homology with a *C. elegans* protein (g868241) and is found in cDNA libraries involved in cell proliferation, secretion, cancer, and immune response.

HRM-42 (SEQ ID NO:42) was identified in Incyte Clone 2290475 from the BRAINON01 cDNA library using a computer search for amino acid sequence alignments. A consensus sequence, SEQ ID NO:91, was derived from the extended and overlapping nucleic acid sequences: Incyte Clones 238339 (SINTNOT02), 1657945 (URETTUT01), 1848691 (LUNGFET03), 2044604 (THP1T7T01), 2290475 (BRAINON01), and 2514944 (LIVRTUT04).

In one embodiment, the invention encompasses a polypeptide comprising the amino acid sequence of SEQ ID NO:42. HRM-42 is 300 amino acids in length and has a potential N glycosylation site, N5; seven potential phosphorylation sites at S23, S71, S132, S142, T176, T192, and S293; and a Mutt signature, $G_{165}MVDPGEKISATLKREFGEE$. HRM-42 has sequence homology with a *C. elegans* protein (g733605) and is found in cDNA libraries involved in cell proliferation, secretion, cancer, and immune response.

HRM-43 (SEQ ID NO:43) was identified in Incyte Clone 2353452 from the LUNGNOT20 cDNA library using a computer search for amino acid sequence alignments. A consensus sequence, SEQ ID NO:92, was derived from the extended and overlapping nucleic acid sequences: Incyte Clones 1000164 (BRSTNOT03), 1308080 (COLNFET02), 1900151 (BLADTUT06), and 2353452 (LUNGNOT20).

In one embodiment, the invention encompasses a polypeptide comprising the amino acid sequence of SEQ ID NO:43. HRM-43 is 112 amino acids in length and has six potential phosphorylation sites at T23, T43, S44, T79, T84, and T98. HRM-43 has sequence homology with a *Schizosaccharomvces pombe* protein (g1507666) and is found in cDNA libraries involved in cell proliferation, secretion, cancer, and immune response.

HRM-44 (SEQ ID NO:44) was identified in Incyte Clone 2469611 from the THP1NOT03 cDNA library using a computer search for amino acid sequence alignments. A consensus sequence, SEQ ID NO:93, was derived from the extended and overlapping nucleic acid sequences: Incyte clones 003088 (HMC1NOT01), 1448981 (PLACNOT02), 1453563 (PENITUT01), 1824146 (GBLATUT01), 2369282 (ADRENOT07), 2469611 (THP1NOT03), and 2622587 (KERANOT02).

In one embodiment, the invention encompasses a polypeptide comprising the amino acid sequence of SEQ ID NO:44. HRM-44 is 251 amino acids in length and has a potential glycosaminoglycan site, S218GFG, and four potential phosphorylation sites at T8, S83, S212, and S226. HRM-44 has sequence homology with a *C. elegans* protein (g1495332) and is found in cDNA libraries involved in cell proliferation, secretion, cancer, and immune response.

HRM-45 (SEQ ID NO:45) was identified in Incyte Clone 2515476 from the LIVRTUT04 cDNA library using a computer search for amino acid sequence alignments. A consensus sequence, SEQ ID NO:94, was derived from the extended and overlapping nucleic acid sequences: Incyte clones 18414 (HUVELPB01), 78341 (SYNORAB01), 143277 (TLYMNOR01), 181574 (PLACNOB01), 832996 (PROSTUT04), 962753 (BRSTTUT03), 1413604 (BRAINOT12), and 2515476 (LIVRTUT04).

In one embodiment, the invention encompasses a polypeptide comprising the amino acid sequence of SEQ ID NO:45. HRM-45 is 811 amino acids in length and has three potential amidation sites at $G_{113}GRR$, $W_{165}GKR$, and $G_{790}GKK$; four potential N glycosylation sites at N22, N56, N79, and N145; 24 potential phosphorylation sites at T11, S13, S30, S60, Y71, S81, S85, S86, S103, S254, S256, T377, S388, S425, S456, S487, T544, S552, S574, T659, S678, S702, S746, and S753; a potential glycosaminoglycan site, $S_{160}GHG$; and a potential zinc finger motif at $C_{240}GHIFCWACI$. HRM-45 has sequence homology with human KIAA0262 (g1665790) and is found in cDNA libraries involved in cell proliferation, secretion, cancer, and immune response.

HRM-46 (SEQ ID NO:46) was identified in Incyte Clone 2754573 from the THP1AZS08 cDNA library using a computer search for amino acid sequence alignments. A consensus sequence, SEQ ID NO:95, was derived from the extended and overlapping nucleic acid sequences: Incyte Clones 263630 (HNT2AGT01), 412307 (BRSTNOT01), 491644 (HNT2AGT01), 1253094 (LUNGFET03), 2270603 (PROSNON01) 2280508 (PROSNON01), 2375670 (ISLTNOT01), 2754573 (THP1AZSO8), and 3151587 (ADRENON04).

In one embodiment, the invention encompasses a polypeptide comprising the amino acid sequence of SEQ ID NO:46. HRM-46 is 352 amino acids in length and has two potential N glycosylation sites at N141 and N294, and thirteen potential phosphorylation sites at S8, T67, T106, T110, T121, S122, S169, S206, T210, S215, S256, S260, and T296. HRM-46 has sequence homology with human RNA binding protein (g478990) and is found in cDNA libraries involved in cell proliferation, secretion, and immune response.

HRM-47 (SEQ ID NO:47) was identified in Incyte Clone 2926777 from the TLYMNOT04 cDNA library using a computer search for amino acid sequence alignments. A consensus sequence, SEQ ID NO:96, was derived from the extended and overlapping nucleic acid sequences: Incyte Clones 040208 (TBLYNOT01), 900242 (BRSTTUT03), 963500 (BRSTTUT03), 1996474 (BRSTTUT03), and 2926777 (TLYMNOT04).

In one embodiment, the invention encompasses a polypeptide comprising the amino acid sequence of SEQ ID NO:47. HRM-47 is 432 amino acids in length and has a potential N glycosylation site at N417 and 24 potential phosphorylation sites at T51, S73, T122, T133, S177, S206, T226, T238, S293, S300, S304, S309, T325, S333, S339, S353, S360, Y361, S384, S390, T403, T412, T419, and S425. HRM-47 has sequence homology with a *C. elegans* protein (g687823) and is found in cDNA libraries involved in cell proliferation, secretion, cancer, and immune response.

HRM-48 (SEQ ID NO:48) was identified in Incyte Clone 3217567 from the TESTNOT07 cDNA library using a computer search for amino acid sequence alignments. A consensus sequence, SEQ ID NO:97, was derived from the extended and overlapping nucleic acid sequences: Incyte Clones 905037 (COLNNOT07), 1287503 (BRAINOT11), and 3217567 (TESTNOT07).

In one embodiment, the invention encompasses a polypeptide comprising the amino acid sequence of SEQ ID NO:48. HRM-48 is 180 amino acids in length and has a potential zinc finger motif, C42GHLYCWPCL, and five potential phosphorylation sites at T33, T57, S84, T148, and S160. HRM-48 has sequence homology with human HLA class III region (g1841547) and is found in cDNA libraries involved in secretion and immune response.

HRM-49 (SEQ ID NO:49) was identified in Incyte Clone 3339274 from the SPLNNOT10 cDNA library using a computer search for amino acid sequence alignments. A consensus sequence, SEQ ID NO:98, was derived from the extended and overlapping nucleic acid sequences: Incyte Clones 532254 (BRAINOT03), 941336 (ADRENOT03), 2447649 (THP1NOT03), and 3339274 (SPLNNOT10).

In one embodiment, the invention encompasses a polypeptide comprising the amino acid sequence of SEQ ID NO:49. HRM-49 is 137 amino acids in length and has three potential phosphorylation sites at T11, T91, and S119. HRM-49 has sequence homology with a deduced human translational inhibitor (g1177434) and is found in cDNA libraries. involved in secretion and immune response.

The invention also encompasses HRM variants which retain the biological or functional activity of HRM. A preferred HRM variant is one having at least 80%, and more preferably 90%, amino acid sequence identity to the HRM amino acid sequence. A most preferred HRM variant is one having at least 95% amino acid sequence identity to an HRM disclosed herein SEQ ID NOs:1–49.

The invention also encompasses polynucleotides which encode HRM. Accordingly, any nucleic acid sequence which encodes the amino acid sequence of HRM can be used to produce recombinant molecules which express HRM. In a particular embodiment, the invention encompasses a polynucleotide consisting of a nucleic acid sequence selected from the group consisting of SEQ ID NOs:50–98.

It will be appreciated by those skilled in the art that as a result of the degeneracy of the genetic code, a multitude of nucleotide sequences encoding HRM, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring HRM, and all such variations are to be considered as being specifically disclosed.

Although nucleotide sequences which encode HRM and its variants are preferably capable of hybridizing to the nucleotide sequence of the naturally occurring HRM under appropriately selected conditions of stringency, it may be advantageous to produce nucleotide sequences encoding HRM or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding HRM and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode HRM and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding HRM or any fragment thereof.

Also encompassed by the invention are polynucleotide sequences that are capable of hybridizing to the claimed nucleotide sequences, and in particular, those shown in SEQ ID NOs:50–98, under various conditions of stringency as taught in Wahl, G. M. and S. L. Berger (1987; Methods Enzymol. 152:399–407) and Kimmel, A. R. (1987; Methods Enzymol. 152:507–511).

Methods for DNA sequencing which are well known and generally available in the art and may be used to practice any of the embodiments of the invention. The methods may employ such enzymes as the Klenow fragment of DNA polymerase I, SEQUENASE (US Biochemical Corp, Cleveland, Ohio), Taq polymerase (Perkin Elmer), thermostable T7 polymerase (Amessham Pharmacia Biotech Piscataway, N.J.), or combinations of polymerases and proofreading exonucleases such as those found in the ELONGASE Amplification System marketed by Life Technologies (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI Catalyst and 373 and 377 DNA Sequencers (Perkin Elmer).

The nucleic acid sequences encoding HRM may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using commercially available software such as OLIGO 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown fragment of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTERFINDER libraries DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER and SEQUENCE NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode HRM may be used in recombinant DNA molecules to direct expression of HRM, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express HRM.

As will be understood by those of skill in the art, it may be advantageous to produce HRM-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter HRM encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants. introduce mutations and so forth.

In another embodiment of the invention, natural, modified. or recombinant nucleic acid sequences encoding HRM may be ligated to a heterologous sequence to encode a fusion protein. For example, to screen peptide libraries for inhibitors of HRM activity, it may be useful to encode a chimeric HRM protein that can be recognized by a commercially available antibody. A fusion protein may also be engineered to contain a cleavage site located between the HRM encoding sequence and the heterologous protein sequence, so that HRM may be cleaved and purified away from the heterologous moiety.

In another embodiment, sequences encoding HRM may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of HRM, or a fragment thereof. For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) Proteins, Structures and Molecular Principles, WH Freeman and Co., New York, N.Y.). The composition of the synthetic peptides may be confirmed by amino acid analysis or sequencing (e.g., the Edman degradation procedure; Creighton, supra). Additionally, the amino acid sequence of HRM, or any part thereof, may be altered during direct synthesis and/or combined using chemical methods with sequences from other proteins, or any part thereof, to produce a variant polypeptide.

In order to express a biologically active HRM, the nucleotide sequences encoding HRM or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding HRM and appropriate transcriptional and translational control elements. These methods include in vitro recombinant DNA techniques, synthetic techniques. and in vivo genetic recombination. Such techniques are described in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y.

A variety of expression vector/host systems may be utilized to contain and express sequences encoding HRM. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CAMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT1 plasmid (Life Technologies) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding HRM, vectors based on SV40 or EBV may be used with an appropriate selectable marker.

In bacterial systems, a number of expression vectors may be selected depending upon the use intended for HRM. For example, when large quantities of HRM are needed for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding HRM may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding HRM may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196).

An insect system may also be used to express HRM. For example, in one such system, *Autographa californica* nuclear polyhedrosis virus (AcNPV) is used as a vector to express foreign genes in *Spodoptera frugiperda* cells or in Trichoplusia larvae. The sequences encoding HRM may be cloned into a non-essential region of the virus, such as the polyhedrin gene, and placed under control of the polyhedrin promoter. Successful insertion of HRM will render the polyhedrin gene inactive and produce recombinant virus lacking coat protein. The recombinant viruses may then be used to infect, for example, *S. frugiperda* cells or Trichoplusia larvae in which HRM may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding HRM may be ligated into an adenovirus transcription/translation complex consisting of the late promoter and tripartite leader sequence. Insertion in a non-essential E1 or E3 region of the viral genome may be used to obtain a viable virus which is capable of expressing HRM in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation of sequences encoding HRM. Such signals include the ATG initiation codon and adjacent sequences. In cases where sequences encoding HRM, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines which stably express HRM may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk$^-$ or aprt$^-$ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides, neomycin and G-418 (Colbere-Garapin, F. et al (1981) J. Mol. Biol. 150:1–14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding HRM is inserted within a marker gene sequence, transformed cells containing sequences encoding HRM can be identified by the absence of marker gene function. Alternatively, a marker gene can be placed in tandem with a sequence encoding HRM under the control of a single promoter. Expression of the marker gene in response to induction or selection usually indicates expression of the tandem gene as well.

Alternatively, host cells which contain the nucleic acid sequence encoding HRM and express HRM may be identified by a variety of procedures known to those of skill in the art.

These procedures include, but are not limited to, DNA—DNA or DNA-RNA hybridizations and protein bioassay or immunoassay techniques which include membrane, solution, or chip based technologies for the detection and/or quantification of nucleic acid or protein.

The presence of polynucleotide sequences encoding HRM can be detected by DNA—DNA or DNA-RNA hybridization or amplification using probes or fragments or fragments of polynucleotides encoding HRM. Nucleic acid amplification based assays involve the use of oligonucleotides or oligomers based on the sequences encoding HRM to detect transformants containing DNA or RNA encoding HRM.

A variety of protocols for detecting and measuring the expression of HRM, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on HRM is preferred, but a competitive binding assay may be employed. These and other assays are described, among other places, in Hampton, R. et al. (1990; *Serological Methods, a Laboratory Manual*, APS Press, St Paul. Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HRM include oligolabeling, nick translation, end-labeling or PCR amplification using a labeled nucleotide. Alternatively, the sequences encoding HRM, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Amersham Pharmacia Biotech, Promega, and U.S. Biochemical). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding HRM may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode HRM may be designed to contain signal sequences which direct secretion of HRM through a prokaryotic or eukaryotic cell membrane. Other constructions may be used to join sequences encoding HRM to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and HRM may be used to facilitate purification. One such expression vector provides for expression of a fusion protein containing HRM and a nucleic acid encoding 6 histidine residues preceding a thioredoxin or an enterokinase cleavage site. The histidine residues facilitate purification on IMAC (immobilized metal ion affinity chromatography) as described in Porath, J. et al. (1992, Prot.

Exp. Purif. 3: 263–281) while the enterokinase cleavage site provides a means for purifying HRM from the fusion protein. A discussion of vectors which contain fusion proteins is provided in Kroll, D. J. et al. (1993; DNA Cell Biol. 12:441–453).

In addition to recombinant production, fragments of HRM may be produced by direct peptide synthesis using solid-phase techniques (Merrifield J. (1963) J. Am. Chem. Soc. 85:2149–2154). Protein synthesis may be performed using manual techniques or by automation. Automated synthesis may be achieved, for example, using Applied Biosystems 431A Peptide Synthesizer (Perkin Elmer). Various fragments of HRM may be chemically synthesized separately and combined using chemical methods to produce the full length molecule.

THERAPEUTICS

Chemical and structural homology exits among the human regulatory proteins of the invention. The expression of HRM is closely associated with cell proliferation. Therefore, in cancers or immune disorders where HRM is an activator, transcription factor, or enhancer, and is promoting cell proliferation; it is desirable to decrease the expression of HRM. In cancers where HRM is an inhibitor or suppressor and is controlling or decreasing cell proliferation, it is desirable to provide the protein or to increase the expression of HRM.

In one embodiment, where HRM is an inhibitor, HRM or a fragment or derivative thereof may be administered to a subject to prevent or treat a cancer such as adenocarcinoma, leukemia, lymphoma, melanoma, myeloma, sarcoma, and teratocarcinoma. Such cancers include, but are not limited to, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus.

In another embodiment, an agonist which is specific for HRM may be administered to a subject to prevent or treat a cancer including, but not limited to, those cancers listed above.

In another further embodiment. a vector capable of expressing HRM, or a fragment or a derivative thereof, may be administered to a subject to prevent or treat a cancer including, but not limited to, those cancers listed above.

In a further embodiment where HRM is promoting cell proliferation, antagonists which decrease the expression or activity of HRM may be administered to a subject to prevent or treat a cancer such as adenocarcinoma, leukemia, lymphoma, melanoma, myeloma, sarcoma, and teratocarcinoma. Such cancers include, but are not limited to, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, antibodies which specifically bind HRM may be used directly as an antagonist or indirectly as a targeting or delivery mechanism for bringing a pharmaceutical agent to cells or tissue which express HRM.

In another embodiment, a vector expressing the complement of the polynucleotide encoding HRM may be administered to a subject to treat or prevent a cancer including, but not limited to, those cancers listed above.

In yet another embodiment where HRM is promoting leukocyte activity or proliferation, antagonists which decrease the activity of HRM may be administered to a subject to prevent or treat an immune response. Such responses may be associated with AIDS, Addison's disease, adult respiratory distress syndrome, allergies, anemia, asthma, atherosclerosis, bronchitis, cholecystitus, Crohn's disease, ulcerative colitis, atopic dermatitis, dermatomyositis, diabetes mellitus, emphysema, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections; and trauma. In one aspect, antibodies which specifically bind HRM may be used directly as an antagonist or indirectly as a targeting or delivery mechanism for bringing a pharmaceutical agent to cells or tissue which express HRM.

In another embodiment, a vector expressing the complement of the polynucleotide encoding HRM may be administered to a subject to treat or prevent an immune response including, but not limited to, those listed above.

In one further embodiment, HRM or a fragment or derivative thereof may be added to cells to stimulate cell proliferation. In particular, HRM may be added to a cell in culture or cells in vivo using delivery mechanisms such as liposomes, viral based vectors, or electroinjection for the purpose of promoting cell proliferation and tissue or organ regeneration. Specifically, HRM may be added to a cell, cell line, tissue or organ culture in vitro or ex vivo to stimulate cell proliferation for use in heterologous or autologous transplantation. In some cases, the cell will have been preselected for its ability to fight an infection or a cancer or to correct a genetic defect in a disease such as sickle cell anemia, β thalassemia, cystic fibrosis, or Huntington's chorea.

In another embodiment, an agonist which is specific for HRM may be administered to a cell to stimulate cell proliferation, as described above.

In another embodiment, a vector capable of expressing HRM, or a fragment or a derivative thereof, may be administered to a cell to stimulate cell proliferation, as described above.

In other embodiments, any of the therapeutic proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above.

Using this approach, one may be able to achieve therapeutic efficacy with lower dosages of each agent, thus reducing the potential for adverse side effects.

Antagonists or inhibitors of HRM may be produced using methods which are generally known in the art. In particular, purified HRM may be used to produce antibodies or to screen libraries of pharmaceutical agents to identify those which specifically bind HRM.

Antibodies to HRM may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with HRM or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to HRM have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of HRM amino acids may be fused with those of another protein such as keyhole limpet hemocyanin and antibody produced against the chimeric molecule.

Monoclonal antibodies to HRM may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce HRM-specific single chain antibodies. Antibodies with related specificity, but of distinct idiotypic composition, may be generated by chain shuffling from random combinatorial immunoglobulin libraries (Burton D. R. (1991) Proc. Natl. Acad. Sci. 88:11120–3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349:293–299).

Antibody fragments which contain specific binding sites for HRM may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HRM and its specific antibody. A two-site, monoclonal-based immunoassay utilizing monoclonal antibodies reactive to two non-interfering HRM epitopes is preferred, but a competitive binding assay may also be employed (Maddox, supra).

In another embodiment of the invention, the polynucleotides encoding HRM, or any fragment or complement thereof, may be used for therapeutic purposes. In one aspect, the complement of the polynucleotide encoding HRM may be used in situations in which it would be desirable to block the transcription of the mRNA. In particular, cells may be transformed with sequences complementary to polynucleotides encoding HRM. Thus, complementary molecules or fragments may be used to modulate HRM activity, or to achieve regulation of gene function. Such technology is now well known in the art, and sense or antisense oligonucleotides or larger fragments, can be designed from various locations along the coding or control regions of sequences encoding HRM.

Expression vectors derived from retroviruses, adenovirus, herpes or vaccinia viruses, or from various bacterial plasmids may be used for delivery of nucleotide sequences to the targeted organ, tissue or cell population. Methods which are well known to those skilled in the art can be used to construct vectors which will express nucleic acid sequence which is complementary to the polynucleotides of the gene encoding HRM. These techniques are described both in Sambrook et al. (supra) and in Ausubel et al. (supra).

Genes encoding HRM can be turned off by transforming a cell or tissue with expression vectors which express high levels of a polynucleotide or fragment thereof which encodes HRM. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing complementary sequences or antisense molecules (DNA, RNA, or PNA) to the control, 5' or regulatory regions of the gene encoding HRM (signal sequence, promoters, enhancers, and introns). Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding HRM.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HRM. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et al. (1997) Nature Biotechnology 15:462–66; incorporated herein by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of HRM, antibodies to HRM, mimetics, agonists, antagonists, or inhibitors of HRM. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars. including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of HRM, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example HRM or fragments thereof, antibodies of HRM, agonists, antagonists or inhibitors of HRM, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, ED50/LD50.

Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind HRM may be used for the diagnosis of conditions or diseases characterized by expression of HRM, or in assays to monitor patients being treated with HRM, agonists, antagonists or inhibitors. The antibodies useful for diagnostic purposes may be prepared in the same manner as those described above for therapeutics. Diagnostic assays for HRM include methods which utilize the antibody and a label to detect HRM in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring HRM are known in the art and provide a basis for diagnosing altered or abnormal levels of HRM expression. Normal or standard values for HRM expression are established by combining body fluids or cell extracts taken from normal mammalian subjects, preferably human, with antibody to HRM under conditions suitable for complex formation. The amount of standard complex formation may be quantified by various methods, but preferably by photometric means. Quantities of HRM expressed in subject, control, and disease, samples from biopsied tissues are compared with the standard values. Deviation between standard and subject values establishes the parameters for diagnosing disease.

In another embodiment of the invention, the polynucleotides encoding HRM may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of HRM may be correlated with disease. The diagnostic assay may be used to distinguish between absence, presence, and excess expression of HRM, and to monitor regulation of HRM levels during therapeutic intervention.

In one aspect, hybridization with PCR probes which are capable of detecting polynucleotide sequences, including genomic sequences, encoding HRM or closely related molecules, may be used to identify nucleic acid sequences which encode HRM. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding HRM, alleles, or related sequences.

Probes may also be used for the detection of related sequences, and should preferably contain at least 50% of the nucleotides from any of the HRM encoding sequences. The hybridization probes of the subject invention may be DNA or RNA and derived from the nucleotide sequence of SEQ ID NOs:50–98 or from genomic sequence including promoter, enhancer elements, and introns of the naturally occurring HRM.

Means for producing specific hybridization probes for DNAs encoding HRM include the cloning of nucleic acid sequences encoding HRM or HRM derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding HRM may be used for the diagnosis of conditions, disorders, or diseases which are associated with either increased or decreased expression of HRM. Examples of such conditions or diseases include adenocarcinoma, leukemia, lymphoma, melanoma, myeloma, sarcoma, teratocarcinoma, and cancers of the adrenal gland, bladder, bone, brain, breast, cervix, gall bladder, ganglia, gastrointestinal tract, heart, kidney, liver, lung, bone marrow, muscle, ovary, pancreas, parathyroid, penis, prostate, salivary glands, skin, spleen, testis, thymus, thyroid, and uterus; and immune disorders such as AIDS, Addison's disease, adult respiratory distress syndrome, allergies, anemia, asthma, atherosclerosis, bronchitis, cholecystitus, Crohn's disease, ulcerative colitis, atopic dermatitis, dermatomyositis, diabetes mellitus, emphysema, atrophic gastritis, glomerulonephritis. gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and thyroiditis. The polynucleotide sequences encoding HRM may be used in Southern or northern analysis, dot blot, or other membrane-based technologies; in PCR technologies; or in dipstick, pin, ELISA-like assays or microarrays utilizing fluids or tissues from patient biopsies to detect altered HRM expression. Such qualitative or quantitative methods are well known in the art.

In a particular aspect, the nucleotide sequences encoding HRM may be useful in assays that detect activation or induction of various cancers, particularly those mentioned above. The nucleotide sequences encoding HRM may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding HRM in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of HRM, a normal or standard profile for expression is established. This may be accomplished by combining body fluids or cell extracts taken from normal subjects, either animal or human, with a sequence, or a fragment thereof, which encodes HRM, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding HRM may involve the use of PCR. Such oligomers may be chemically synthesized, generated enzymatically, or produced in vitro. Oligomers will preferably consist of two nucleotide sequences, one with sense orientation (5'→3') and another with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of HRM include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA-like format where the oligomer of interest is presented in various dilutions and a spectrophotometric or calorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously (to produce a transcript image), and to identify genetic variants, mutations and polymorphisms. This information may be used to determine gene function. understanding the genetic basis of disease, diagnosing disease, and in developing and in monitoring the activities of therapeutic agents.

In one embodiment, the microarray is prepared and used according to the methods described in PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference.

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray, it may be preferable to use oligonucleotides which are only 7–10 nucleotides in length. The microarray may contain oligonucleotides which cover the known 5', or 3', sequence, or contain sequential oligonucleotides which cover the full length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell or tissue type or to a normal, developmental, or disease state. In certain situations it may be appropriate to use pairs of oligonucleotides on a microarray. The "pairs" will be identical, except for one nucleotide which preferably is located in the center of the sequence. The second oligonucleotide in the pair (mismatched by one) serves as a control. The number of oligonucleotide pairs may range from 2 to one million.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. In one aspect, the oligomers are synthesized at designated areas on a substrate using a light-directed chemical process. The substrate may be paper, nylon or other type of membrane, filter, chip, glass slide, or any other suitable solid support.

In another aspect, the oligonucleotides may be synthesized on the surface of the substrate by using a chemical coupling procedure and an ink jet application apparatus, as described in PCT application WO95/25 1116 (Baldeschweiler et al.) which is incorporated herein in its entirety by reference. In another aspect, a "gridded" array analogous to a dot or slot blot (HYBRIDOT apparatus, Life Technologies) may be used to arrange and link cDNA fragments or oligonucleotides to the surface of a substrate using a vacuum system, thermal, UV, mechanical or chemical bonding procedures. In yet another aspect, an array may be produced by hand or using available devices, materials, and machines (including Brinkmann multichannel pipettors or robotic instruments) and may contain 8, 24, 96, 384, 1536 or 6144 oligonucleotides, or any other multiple from 2 to one million which lends itself to the efficient use of commercially available instrumentation.

In order to conduct sample analysis using the microarrays, polynucleotides are extracted from a biological sample. The biological samples may be obtained from any bodily fluid (blood, urine, saliva, phlegm, gastric juices, etc.), cultured cells, biopsies, or other tissue preparations. To produce probes, the polynucleotides extracted from the sample are used to produce nucleic acid sequences which are complementary to the nucleic acids on the microarray. If the microarray consists of cDNAs, antisense RNAs (aRNA) are appropriate probes. Therefore, in one aspect, mRNA is used to produce cDNA which, in turn and in the presence of fluorescent nucleotides, is used to produce fragment or oligonucleotide aRNA probes. These fluorescently labeled probes are incubated with the microarray so that the probe sequences hybridize to the cDNA oligonucleotides of the microarray. In another aspect, complementary nucleic acid sequences are used as probes and can also include polynucleotides, fragments, complementary, or antisense sequences produced using restriction enzymes, PCR technologies, and Oligolabeling or TransProbe kits (Pharmacia) well known in the area of hybridization technology.

Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. A detection system may be used to measure the absence, presence, and amount of hybridization for all of the distinct sequences simultaneously. This data may be used for large scale correlation studies or functional analysis of the sequences, mutations, variants, or polymorphisms among samples (Heller, R. A. et al., (1997) Proc. Natl. Acad. Sci. 94:2150–55).

In another embodiment of the invention, the nucleic acid sequences which encode HRM may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial P1 constructions or single chromosome cDNA libraries as reviewed in Price, C. M. (1993) Blood Rev. 7:127–134, and Trask, B. J. (1991) Trends Genet. 7:149–154.

Fluorescent in situ hybridization (FISH as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in various scientific journals or at Online Mendelian Inheritance in Man (OMIM). Correlation between the location of the gene encoding HRM on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, HRM, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between HRM and the agent being tested, may be measured.

Another technique for drug screening which may be used provides for high throughput screening of compounds having suitable binding affinity to the protein of interest as described in published PCT application WO84/03564. In this method, as applied to HRM large numbers of different small test compounds are synthesized on a solid substrate, such as plastic pins or some other surface. The test compounds are reacted with HRM, or fragments thereof, and washed. Bound HRM is then detected by methods well known in the art. Purified HRM can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HRM specifically compete with a test compound for binding HRM. In this manner, the antibodies can be used to detect the presence of any peptide which shares one or more antigenic determinants with HRM.

In additional embodiments, the nucleotide sequences which encode HRM may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

For purposes of example, the preparation and sequencing of the LNODNOT03 cDNA library, from which Incyte Clones 1572888, 1573677, 1574624, and 1577239 were isolated, is described. Preparation and sequencing of cDNAs in libraries in the LIFESEQTM database have varied over time, and the gradual changes involved use of kits, plasmids, and machinery available at the particular time the library was made and analyzed.

I LNODNOT03 cDNA Library Construction

The LNODNOT03 cDNA library was constructed from microscopically normal lymph node tissue excised from a 67-year-old Caucasian male with lung cancer during a segmental lung resection. This nontumorous tissue was associated with an invasive grade 3 squamous cell carcinoma of the lung. The patient history included hemangioma and tobacco use. The patient was taking Doxycycline, a tetracycline, to treat an infection.

The frozen tissue was homogenized and lysed using a Brinkmann Homogenizer Polytron PT-3000 (Brinkmann Instruments, Westbury, N.J.) in guanidinium isothiocyanate solution. The lysate was centrifuged over a 5.7 M CsCl cushion using a Beckman SW28 rotor in a Beckman L8–70M Ultracentrifuge (Beckman Instruments) for 18 hours at 25,000 rpm at ambient temperature. The RNA was extracted with acid phenol pH 4.7, precipitated using 0.3 M sodium acetate and 2.5 volumes of ethanol, resuspended in RNAse-free water, and treated with DNase at 37° C. Extraction and precipitation were repeated as before. The mRNA was isolated with the OLIGOTEX (Qiagen) and used to construct the cDNA library.

The mRNA was handled according to the recommended protocols in the SUPERSCRIPT Plasmid System for cDNA synthesis and plasmid cloning (Cat. #18248-013, Life Technologies). The cDNAs were fractionated on a SEPHAROSE CL4B column (Cat. #275105-01; Pharmacia), and those cDNAs exceeding 400 bp were ligated into pINCY 1. The plasmid pINCY 1 was subsequently transformed into DH5α competent cells (Cat. #18258-012; Life Technologies).

II Isolation and Sequencing of cDNA Clones

Plasmid DNA was released from the cells and purified using the REAL Prep 96 plasmid kit (Catalog #26173. QIAGEN, Inc.). This kit enabled the simultaneous purification of 96 samples in a 96-well block using multi-channel reagent dispensers. The recommended protocol was employed except for the following changes: 1) the bacteria were cultured in 1 ml of sterile Terrific Broth (Catalog #22711, Life Technologies) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975, J. Mol. Biol. 94:441f), using a Hamilton Micro Lab 2200 (Hamilton, Reno, Nev.) in combination with Peltier Thermal Cyclers (PTC200 from MJ Research, Watertown, Mass.) and Applied Biosystems 377 DNA Sequencing Systems; and the reading frame was determined.

III Homology Searching of cDNA Clones and Their Deduced Proteins

The nucleotide sequences and/or amino acid sequences of the Sequence Listing were used to query sequences in the GenBank, SwissProt, BLOCKS, and Pima II databases. These databases, which contain previously identified and annotated sequences, were searched for regions of homology using BLAST, which stands for Basic Local Alignment Search Tool (Altschul, S. F. (1993) J. Mol. Evol 36:290–300; Altschul, et al. (1990) J. Mol. Biol. 215:403–410).

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms such as the one described in Smith, T. et al. (1992, Protein Engineering 5:35–51), incorporated herein by reference, could have been used when dealing with primary sequence patterns and secondary structure gap penalties. The sequences disclosed in this application have lengths of at least 49 nucleotides, and no more than 12% uncalled bases (where N is recorded rather than A, C, G, or T).

The BLAST approach searched for matches between a query sequence and a database sequence. BLAST evaluated the statistical significance of any matches found and reported only those matches that satisfy the user-selected threshold of significance. In this application, threshold was set at $10^{-25}$ for nucleotides and $10^{-14}$ for peptides.

Incyte nucleotide sequences were searched against the GenBank databases for primate (pri), rodent (rod), and other mammalian sequences (mam); and deduced amino acid sequences from the same clones were then searched against GenBank functional protein databases, mammalian (mamp), vertebrate (vrtp), and eukaryote (eukp) for homology.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques use BLAST to search for identical or related molecules in nucleotide databases such as GenBank or the LIFESEQ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\% \text{ sequence identity} \times \% \text{ maximum BLAST score } 100$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding HRM occurs. Abundance and percent abundance are also reported. Abundance directly reflects the number of times a particular transcript is represented in a cDNA library, and percent abundance is abundance divided by the total number of sequences examined in the cDNA library.

V Extension of HRM Encoding Polynucleotides

The nucleic acid sequence of an Incyte Clone disclosed in the Sequence Listing was used to design oligonucleotide primers for extending a partial nucleotide sequence to full length. One primer was synthesized to initiate extension in the antisense direction, and the other was synthesized to extend sequence in the sense direction. Primers were used to facilitate the extension of the known sequence "outward" generating amplicons containing new, unknown nucleotide sequence for the region of interest. The initial primers were designed from the cDNA using OLIGO 4.06 (National Biosciences), or another appropriate program, to be about 22 to about 30 nucleotides in length, to have a GC content of 50% or more, and to anneal to the target sequence at temperatures of about 68° to about 72° C. Any stretch of nucleotides which would result in hairpin structures and primer—primer dimerizations was avoided.

Selected human cDNA libraries (Gibco/BRL) were used to extend the sequence. If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. Beginning with 40 pmol of each primer and the recommended concentrations of all other components of the kit, PCR was performed using the Peltier Thermal Cycler (PTC200; M.J. Research, Watertown, Mass.) and the following parameters:

| Step 1 | 94° C. for 1 min (initial denaturation) |
| --- | --- |
| Step 2 | 65° C. for 1 min |

-continued

| Step 3 | 68° C. for 6 min |
| --- | --- |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 µl aliquot of the reaction mixture was analyzed by electrophoresis on a low concentration (about 0.6–0.8%) agarose mini-gel to determine which reactions were successful in extending the sequence. Bands thought to contain the largest products were excised from the gel, purified using QIAQUICK kit (QIAGEN Inc., Chatsworth, Calif.), and trimmed of overhangs using Klenow enzyme to facilitate religation and cloning.

After ethanol precipitation, the products were redissolved in 13 µl of ligation buffer, 1 µl T4-DNA ligase (15 units) and 1 µl T4 polynucleotide kinase were added, and the mixture was incubated at room temperature for 2–3 hours or overnight at 16° C. Competent E. coli cells (in 40 µl of appropriate media) were transformed with 3 µl of ligation mixture and cultured in 80 µl of SOC medium (Sambrook et al., supra). After incubation for one hour at 370° C., the E. coli mixture was plated on Luria Bertani (LB)-agar (Sambrook et al., supra) containing 2× Carb. The following day, several colonies were randomly picked from each plate and cultured in 150 µl of liquid LB/2× Carb medium placed in an individual well of an appropriate, cornmercially-available, sterile 96-well microtiter plate. The following day, 5 µl of each overnight culture was transferred into a non-sterile 96-well plate and after dilution 1:10 with water, 5 µl of each sample was transferred into a PCR array.

For PCR amplification, 18 µl of concentrated PCR reaction mix (3.3×) containing 4 units of rTth DNA polymerase, a vector primer, and one or both of the gene specific primers used for the extension reaction were added to each well. Amplification was performed using the following conditions:

| Step 1 | 94° C. for 60 sec |
| --- | --- |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58 SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, and SEQ ID NO:98 are used to obtain 5' regulatory sequences using the procedure above, oligonucleotides designed for 5' extension, and an appropriate genomic library.

VI Labeling and Use of Individual Hybridization Probes

Hybridization probes derived from SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, and SEQ ID NO:98 are employed to screen cDNAs, genomic DNAs, or mRNAs. Although the labeling of oligonucleotides, consisting of about 20 base-pairs, is specifically described, essentially the same procedure is used with larger nucleotide fragments. Oligonucleotides are designed using state-of-the-art software such as OLIGO 4.06 (National Biosciences), labeled by combining 50 pmol of each oligomer and 250 $\mu$Ci of [$\gamma$-$^{32}$P] adenosine triphosphate (Amersham Pharmacia Biotech) and T4 polynucleotide kinase (DuPont NEN, Boston, Mass.). The labeled oligonucleotides are substantially purified with SEPHADEX G-25 superfine resin column (Amersham Pharmacia Biotech). An aliquot containing $10^7$ counts per minute of the labeled probe is used in a typical membrane-based hybridization analysis of human genomic DNA digested with one of the following endonucleases (Ase I, Bgl II, Eco RI, Pst I, Xba 1, or Pvu II; DuPont NEN).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR film (Eastman Kodak, Rochester, N.Y.) is exposed to the blots in a Phosphoimager cassette (Molecular Dynamics, Sunnyvale, Calif.) for several hours, hybridization patterns are compared visually.

VII Microarrays

To produce oligonucleotides for a microarray SEQ ID NOs:50–98 are examined using a computer algorithm which starts at the 3' end of the nucleotide sequence. The algorithm identified oligomers of defined length that are unique to the gene, have a GC content within a range suitable for hybridization, and lack predicted secondary structure that would interfere with hybridization. The algorithm identifies approximately 20 sequence-specific oligonucleotides of 20 nucleotides in length (20-mers). A matched set of oligonucleotides are created in which one nucleotide in the center of each sequence is altered. This process is repeated for each gene in the microarray, and double sets of twenty 20 mers are synthesized and arranged on the surface of the silicon chip using a light-directed chemical process (Chee, M. et al. PCT/WO95/11995, incorporated herein by reference).

In the alternative, a chemical coupling procedure and an ink jet device are used to synthesize oligomers on the surface of a substrate (Baldeschweiler, J. D. et al., PCT/WO95/25116, incorporated herein by reference). In another alternative, a "gridded" array analogous to a dot (or slot) blot is used to arrange and link cDNA fragments or oligonucleotides to the surface of a substrate using a vacuum system, thermal, UV, mechanical or chemical bonding procedures. A typical array may be produced by hand or using available materials and machines and contain grids of 8 dots, 24 dots, 96 dots, 384 dots, 1536 dots or 6144 dots. After hybridization, the microarray is washed to remove nonhybridized probes, and a scanner is used to determine the levels and patterns of fluorescence. The scanned image is examined to determine degree of complementarity and the relative abundance/expression level of each oligonucleotide sequence in the microarray.

VIII Complementary Polynucleotides

Sequence complementary to the sequence encoding HRM, or any part thereof, is used to detect, decrease or inhibit expression of naturally occurring HRM. Although use of oligonucleotides comprising from about 15 to about 30 base-pairs is described, essentially the same procedure is used with smaller or larger sequence fragments. Appropriate oligonucleotides are designed using Oligo 4.06 software and the coding sequence of HRM, SEQ ID NOs:50–98. To inhibit transcription, a complementary oligonucleotide is designed from the most unique 5' sequence and used to prevent promoter binding to the coding sequence. To inhibit translation, a complementary oligonucleotide is designed to prevent ribosomal binding to the transcript encoding HRM.

IX Expression of HRM

Expression of HRM is accomplished by subcloning the cDNAs into appropriate vectors and transforming the vectors into host cells. In this case, the cloning vector is also used to express HRM in *E. coli*. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of HRM into the bacterial growth media which can be used directly in the following assay for activity.

X Demonstration of HRM Activity

HRM can be expressed in a mammalian cell line such as DLD-1 or HCT116 (ATCC; Bethesda, Md.) by transforming the cells with a eukaryotic expression vector encoding HRM. Eukaryotic expression vectors are commercially available and the techniques to introduce them into cells are well known to those skilled in the art. The effect of HRM on cell morphology may be visualized by microscopy; the effect on cell growth may be determined by measuring cell doubling-time; and the effect on tumorigenicity may be assessed by the ability of transformed cells to grow in a soft agar growth assay (Groden, J. et al. (1995) Cancer Res. 55:1531–1539).

XI Production of HRM Specific Antibodies

HRM that is substantially purified using PAGE electrophoresis (Sambrook, supra). or other purification techniques, is used to immunize rabbits and to produce antibodies using standard protocols. The amino acid sequence deduced from SEQ ID NOs:50–98 is analyzed using LASERGENE software (DNASTAR Inc) to determine regions of high immunogenicity and a corresponding oligopeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radio iodinated, goat anti-rabbit IgG.

XII Purification of Naturally Occurring HRM Using Specific Antibodies

Naturally occurring or recombinant HRM is substantially purified by immunoaffinity chromatography using antibodies specific for HRM. An immunoaffinity column is constructed by covalently coupling HRM antibody to an activated chromatographic resin, such as CNBr-activated Sepharose (Amersham Pharmacia Biotech). After the coupling. the resin is blocked and washed according to the manufacturer's instructions.

Media containing HRM is passed over the immunoaffinity column. and the column is washed under conditions that allow the preferential absorbance of HRM (e.g. high ionic strength buffers in the presence of detergent). The column is eluted under conditions that disrupt antibody/protein binding (eg, a buffer of pH 2–3 or a high concentration of a chaotrope, such as urea or thiocyanate ion), and HRM is collected.

XIII Identification of Molecules Which Interact with HRM

HRM or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled HRM, washed and any wells with labeled HRM complex are assayed. Data obtained using different concentrations of HRM are used to calculate values for the number, affinity, and association of HRM with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide encoding the human regulatory molecule of SEQ ID NO:16.

2. An isolated and purified polynucleotide which is completely complementary to the polynucleotide of claim 1.

3. An isolated and purified polynucleotide comprising SEQ ID NO:65.

4. An isolated and purified polynucleotide which is completely complementary to the polynucleotide of claim 3.

5. A composition comprising the polynucleotide of claim 1.

6. A composition comprising the polynucleotide of claim 3.

7. An expression vector containing the polynucleotide of claim 1.

8. A host cell containing the vector of claim 7.

9. A method for producing a polypeptide, the method comprising:
   a) culturing the host cell of claim 8 under conditions for the expression of the polypeptide; and
   b) recovering the polypeptide from the host cell culture.

10. A method for detecting a polynucleotide encoding a human regulatory molecule of SEQ ID NO:16 in a biological sample, the method comprising the steps of:
    a) hybridizing the polynucleotide of claim 2 to nucleic acid material of a biological sample, thereby forming a hybridization complex; and
    b) detecting the hybridization complex, wherein the presence of the hybridization complex correlates with the presence of a polynucleotide encoding a human regulatory molecule of SEQ ID NO:16 in the biological sample.

11. The method of claim 10 wherein before hybridization, the nucleic acid material of the biological sample are amplified and labeled using the polymerase chain reaction.

12. A microarray containing the polynucleotide of claim 1.

13. A microarray containing the polynucleotide comprising SEQ ID NO:65.

14. A method for detecting expression level of a polynucleotide encoding a human regulatory molecule of SEQ ID NO:16 in a sample, the method comprising the steps of:
    a) hybridizing the microarray of claim 12 to labeled complementary polynucleotides derived from the sample, thereby forming hybridization complexes; and
    b) determining expression of polynucleotides encoding a human regulatory molecule of SEQ ID NO:16 in the sample by quantifying the presence of the hybridization complexes.

15. A method for detecting expression levels of a polynucleotide encoding a human regulatory molecule of SEQ ID NO:16 in a sample, the method comprising:
    a) hybridizing the microarray of claim 13 to labeled complementary polynucleotides derived from the sample, thereby forming hybridization complexes; and
    b) determining expression of polynucleotides encoding a human regulatory molecule of SEQ ID NO:16 in the sample by quantifying the hybridization complexes.

* * * * *